(12) United States Patent
Kakeda et al.

(10) Patent No.: US 8,809,045 B2
(45) Date of Patent: Aug. 19, 2014

(54) HUMAN ARTIFICIAL CHROMOSOME (HAC) VECTOR AND HUMAN CELL MEDICINE COMPRISING SAME

(75) Inventors: Minoru Kakeda, Tokyo (JP); Kazuma Tomizuka, Tokyo (JP); Mitsuo Oshimura, Tottori (JP); Yasuhiro Kazuki, Tottori (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 1064 days.

(21) Appl. No.: 12/307,879

(22) PCT Filed: Jul. 6, 2007

(86) PCT No.: PCT/JP2007/063944
§ 371 (c)(1),
(2), (4) Date: Jun. 30, 2009

(87) PCT Pub. No.: WO2008/013067
PCT Pub. Date: Jan. 31, 2008

(65) Prior Publication Data
US 2010/0011454 A1    Jan. 14, 2010

(30) Foreign Application Priority Data

Jul. 7, 2006  (JP) .................................. 2006-188392

(51) Int. Cl.
*C07H 21/04* (2006.01)
*C12N 15/09* (2006.01)
*C12N 15/00* (2006.01)

(52) U.S. Cl.
USPC ..................................... 435/320.1; 536/23.1

(58) Field of Classification Search
USPC ..................................... 435/320.1; 536/23.1
See application file for complete search history.

(56) References Cited

U.S. PATENT DOCUMENTS

2006/0185025 A1 * 8/2006 Oshimura et al. ................ 800/8

FOREIGN PATENT DOCUMENTS

| EP | 1 559 782 A1 | * | 3/2005 |
| EP | 1 559 782 A1 |   | 8/2005 |
| WO | WO 2004/031385 | * | 4/2004 |

OTHER PUBLICATIONS

Heilig et al. (2003) Nature, vol. 421, 601-607.*
Riethman et al. (2004) Genome Res., vol. 14, 18-28.*
Rodriguez et al. (2000) Nat. Genet., vol. 25, 139-140.*
Xianying Ren et al., "Human Artificial Chromosome Vectors meet Stem Cells New Prospect for Gene Delivery", Stem Cell Reviews, vol. 2, 2006, pp. 43-50.
B. Vissel et al., "Four distinct alpha satellite subfamilies shared by human chromosomes 13, 14 and 21", Nucleic Acids Research, vol. 19, No. 2, 1991, pp. 271-277.
Supplementary European Search Report EP 07 76 8413 dated Jul. 22, 2011.
Elena V. Linardopoulou et al., "Human subtelomeres are hot spots of interchromosomal recombination and segmental duplication", Nature, vol. 437, Sep. 1, 2005, pp. 94-100.
Kazuma Tomizuka et. al., "Double trans-chromosomic mice: Maintenance of two individual human chromosome fragments containing Ig heavy and k loci and expression of fully human antibodies", Proc. Natl. Acad. Sci. USA, 2000, 97(2): 722-727.
Yoshimi Kuroiwa et al., "Manipulation of human minichromosomes to carry greater than megabase-sized chromosome inserts", Nature Biotechnology, 2000, 18: 1086-1090.
Japanese Office Action issued in counterpart JP Patent Application No. 2008-526726 on Sep. 25, 2012.
Office Action dated Dec. 4, 2012, issued by the Japanese Patent Office in counterpart Japanese Patent Application No. 2008-526726.

* cited by examiner

*Primary Examiner* — Anne Marie S Wehbe
(74) *Attorney, Agent, or Firm* — Sughrue Mion, PLLC

(57) ABSTRACT

This invention relates to a human artificial chromosome (HAC) vector carrying a human chromosome-derived centromere, a subtelomere sequence, and a telomere sequence, to a human cell medicine or human cells comprising the HAC vector, to methods for preparing the HAC vector and human cells, and to methods for producing a therapeutic protein using the HAC vector.

18 Claims, 90 Drawing Sheets

(16 of 90 Drawing Sheet(s) Filed in Color)

Fig. 12
A
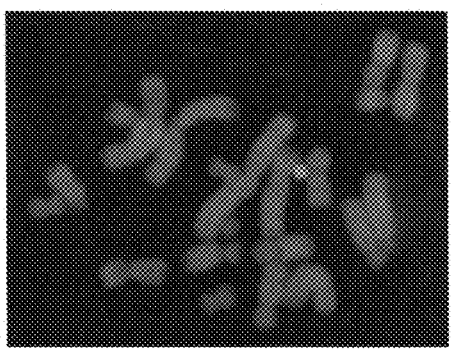
B
| Clones | Number of analyzed mitotic figures of diploids | HAC copy number per cell (Mitotic figures of diploids) | | | | Retention % Mitotic figure 1 copy | Retention % Mitotic figures Total | Insertion Transiocation |
|---|---|---|---|---|---|---|---|---|
| | | 0 | 1 | 2 | >3 | | | |
| 12t7S38-3 | 50 | 4 | 45 | 1 | 0 | 90% | 92% | 0 |
| 12t7S38-6 | 50 | 3 | 46 | 1 | 0 | 92% | 94% | 0 |
| 12t7S38-8 | 50 | 4 | 45 | 1 | 0 | 90% | 92% | 0 |
| 12t7S38-9 | 50 | 3 | 47 | 0 | 0 | 94% | 94% | 0 |
| 12t7S1-1 | 49 | 1 | 47 | 1 | 0 | 95.9% | 97.9% | 0 |
| 12t4S2-3 | 50 | 0 | 50 | 0 | 0 | 100% | 100% | 0 |
| 12t4S2-5 | 50 | 0 | 50 | 0 | 0 | 100% | 100% | 0 |
| 12t4S2-6 | 50 | 3 | 47 | 0 | 0 | 94% | 94% | 0 |

Fig. 13

| HAC | Number or duration of passage for cell population | HAC retention (%) | |
|---|---|---|---|
| | | Without drug selection | With drug selection |
| 21ΔqHAC | At the initiation of culture | — | 86.0 |
| | After 7 weeks of culture | 66.0 | 86.0 |
| 14AΔqHAC | At the initiation of culture | — | 94.0 |
| | 10 passages | 88.5 | 87.5 |
| 14NΔqHAC(G) | At the initiation of culture | — | 97.0 |
| | 10 passages | 97.5 | 98.5 |
| 14gNΔqHAC(g) | At the initiation of culture | — | 100.0 |
| | 10 passages | 99.0 | 98.0 |

Fig. 18

| Cell | Number of analyzed mitotic figures of diploids (N) | Copy number per cell (Mitotic figure of diploid) | | | | Insertion Translocation | Retention 1 copy (%) | Retention Total (%) 100* mitotic figures of diploids (1 copy of HAC+)/N | Retention Total Average 100* mitotic figures of diploids (HAC+)/N | Average amount of EPO production (IU/10$^6$ cells/24h) |
|---|---|---|---|---|---|---|---|---|---|---|
| | | 0 | 1 | 2 | >3 | | | | | |
| 6E25 P0+ | 50 | 3 | 45 | 2 | 0 | 0 | 90% | 94.0% | | 435 |
| 6E25 P10+1 | 65 | 1 | 64 | 0 | 0 | 0 | 98% | 98.5% | 97.8% | 393 |
| 6E25 P10+2 | 69 | 2 | 67 | 0 | 0 | 0 | 97% | 97.1% | | |
| 6E25 P10-1 | 68 | 3 | 62 | 3 | 0 | 0 | 91% | 95.6% | 95.5% | 427 |
| 6E25 P10-2 | 66 | 3 | 63 | 0 | 0 | 0 | 95% | 95.5% | | |
| 6E34 P0+ | 50 | 4 | 46 | 0 | 0 | 0 | 92% | 92.0% | | 414 |
| 6E34 P10+1 | 67 | 2 | 65 | 0 | 0 | 0 | 97% | 97.0% | 97.7% | 463 |
| 6E34 P10+2 | 65 | 1 | 62 | 2 | 0 | 0 | 95% | 98.5% | | |
| 6E34 P10-1 | 70 | 7 | 61 | 2 | 0 | 0 | 87% | 90.0% | 88.4% | 325 |
| 6E34 P10-2 | 68 | 9 | 59 | 0 | 4 | 0 | 87% | 86.8% | | |
| 8E5 P0+ | 50 | 1 | 49 | 0 | 0 | 0 | 98% | 98.0% | | 498 |
| 8E5 P10+1 | 68 | 3 | 65 | 0 | 0 | 0 | 96% | 95.6% | 97.8% | 520 |
| 8E5 P10+2 | 65 | 0 | 65 | 0 | 0 | 1 | 100% | 100.0% | | |
| 8E5 P10-1 | 69 | 3 | 62 | 0 | 0 | 1 | 90% | 95.7% | 94.2% | 240 |
| 8E5 P10-2 | 69 | 5 | 62 | 1 | 1 | 0 | 90% | 92.8% | | |

At the initiation of culture (P0)
After passage 10 (P10)

Underline: drug (+)
Double underline: drug (−)

Fig. 41

| Cells | Number of analyzed mitotic figures of diploids (N) | Copy number per cell (Mitotic figure of diploid) | | | | Insertion Translocation | 100* mitotic figure of diploid (1 copy HAC+)/N Retention 1 copy (%) | 100* mitotic figure of diploid (HAC+)/N Retention Total (%) | Retention Total Average | Average amount of EPO production (IU/10⁶ cells/24h) |
|---|---|---|---|---|---|---|---|---|---|---|
| | | 0 | 1 | 2 | >3 | | | | | |
| 13E4 P0+ | 50 | 0 | 49 | 1 | 0 | 0 | 98% | 100.0% | | 628 |
| 13E4 P10+1 | 83 | 4 | 78 | 1 | 0 | 0 | 94% | 95.2% | 95.2% | 279 |
| 13E4 P10+2 | 82 | 4 | 78 | 0 | 0 | 0 | 95% | 95.1% | | |
| 13E4 P10-1 | 83 | 10 | 72 | 1 | 0 | 0 | 87% | 88.0% | 89.7% | 224 |
| 13E4 P10-2 | 82 | 7 | 75 | 0 | 0 | 1 | 91% | 91.5% | | |
| 13E55 P0+ | 50 | 0 | 50 | 0 | 0 | 0 | 100% | 100.0% | | 577 |
| 13E55 P10+1 | 82 | 1 | 80 | 1 | 0 | 2 | 98% | 98.8% | 98.2% | 385 |
| 13E55 P10+2 | 81 | 2 | 79 | 0 | 0 | 2 | 98% | 97.5% | | |
| 13E55 P10-1 | 82 | 3 | 79 | 0 | 0 | 1 | 96% | 96.3% | 97.0% | 237 |
| 13E55 P10-2 | 85 | 2 | 82 | 1 | 0 | 0 | 96% | 97.6% | | |
| 1E6 P0+ | 50 | 1 | 47 | 2 | 0 | 0 | 94% | 98.0% | | 324 |
| 1E6 P10+1 | 82 | 0 | 77 | 5 | 0 | 1 | 94% | 100.0% | 100.0% | 355 |
| 1E6 P10+2 | 83 | 0 | 77 | 6 | 0 | 1 | 93% | 100.0% | | |
| 1E6 P10-1 | 85 | 2 | 81 | 2 | 0 | 0 | 95% | 97.6% | 97.6% | 209 |
| 1E6 P10-2 | 82 | 2 | 74 | 6 | 0 | 0 | 90% | 97.6% | | |
| 4E16 P0+ | 50 | 1 | 47 | 2 | 0 | 0 | 94% | 98.0% | | 307 |
| 4E16 P10+1 | 63 | 3 | 59 | 1 | 0 | 0 | 94% | 95.2% | 97.6% | 309 |
| 4E16 P10+2 | 64 | 0 | 64 | 0 | 0 | 0 | 100% | 100.0% | | |
| 4E16 P10-1 | 65 | 6 | 58 | 1 | 0 | 0 | 89% | 90.8% | 87.6% | 167 |
| 4E16 P10-2 | 64 | 10 | 53 | 1 | 0 | 1 | 83% | 84.4% | | |

At the initiation of culture (P0)
After passage 10 (P10)

Underline: drug (+)
Double underline: drug (-)

Fig. 43

| Clone # | | EPO AV (IU/10⁶ cells/24 h) | | |
|---|---|---|---|---|
| | | P0 | Passage | P10 |
| 14AΔneo | tΔ63H8 | 0.74 | ND | → |
| | tΔ63H13 | 1.64 | 8.06 | |
| | tΔ63H14 | 2.68 | 3.26 | |
| | tΔ63H15 | 1.72 | 2.56 | |
| | tΔ63H16 | 3.76 | 0.98 | |
| | tΔ63H32 | 2.65 | 2.86 | |
| | tΔ63H34 | 17 | 11.6 | |
| | tΔ38H2 | 1.48 | 2.05 | |
| | tΔ38H4 | 2.52 | 1.48 | |
| 14N telomere+ short subtelomere | G4H2 | 12.07 | 1.63 | P6 |
| | G16H17 | 1.11 | 5.34 | P11 |
| | G16H21 | 0.28 | 0.82 | P10 |
| | G55H7 | 10.1 | 19.1 | P6 |
| 14gN telomere+long subtelomere | g23H1 | 3.1 | 4.33 | P6 |
| | g62H26 | 6.42 | 0.8 | P10 |

A g7S9-11

B

| Clone | Number of analyzed mitotic figure of diploid | HAC copy number per cell (Mitotic figure of diploid) | | | | Retention % Mitotic figure 1 copy | Retention % Mitotic figure Total | Insertion Translocation |
|---|---|---|---|---|---|---|---|---|
| | | 0 | 1 | 2 | >3 | | | |
| g5S13-9 | 50 | 0 | 49 | 1 | 0 | 98% | 100% | 0 |
| g5S13-12 | 50 | 0 | 50 | 0 | 0 | 100% | 100% | 0 |
| g7S9-11 | 50 | 0 | 50 | 0 | 0 | 100% | 100% | 0 |
| g7S9-12 | 50 | 0 | 46 | 4 | 0 | 92% | 100% | 0 |
| g7S9-17 | 50 | 1 | 49 | 0 | 0 | 98% | 98% | 0 |

Fig. 58

| Cell | Number of analyzed mitotic figures of diploids (N) | Copy number per cell (Mitotic figure of diploid) 0 | 1 | 2 | >3 | Insertion Translocation | Retention 1 copy (%) 100* mitotic figure of diploid (1 copy HAC+)/N | Retention Total (%) 100* mitotic figure of diploid (HAC+)/N | Retention Total Average | Average amount of EPO produced (IU/10$^6$ cells/24h) |
|---|---|---|---|---|---|---|---|---|---|---|
| 11E28 P0+ | 50 | 0 | 50 | 0 | 0 | 0 | 100% | 100.0% | | 329 |
| 11E28 P10+1 | 70 | 1 | 68 | 1 | 0 | 2 | 97% | 98.6% | 97.9% | 424 |
| 11E28 P10+2 | 74 | 2 | 71 | 1 | 0 | 1 | 96% | 97.3% | | |
| 11E28 P10-1 | 81 | 9 | 68 | 4 | 0 | 0 | 84% | 88.9% | 90.4% | 244 |
| 11E28 P10-2 | 75 | 6 | 69 | 0 | 0 | 1 | 92% | 92.0% | | |
| 11E62 P0+ | 50 | 0 | 50 | 0 | 0 | 0 | 100% | 100.0% | | 455 |
| 11E62 P10+1 | 82 | 1 | 81 | 0 | 0 | 0 | 99% | 98.8% | 98.8% | 505 |
| 11E62 P10+2 | 80 | 1 | 79 | 0 | 0 | 0 | 99% | 98.8% | | |
| 11E62 P10-1 | 85 | 6 | 78 | 1 | 0 | 0 | 92% | 92.9% | 93.5% | 350 |
| 11E62 P10-2 | 84 | 5 | 79 | 0 | 0 | 0 | 94% | 94.0% | | |
| 12E23 P0+ | 47 | 0 | 47 | 0 | 0 | 0 | 100% | 100.0% | | 225 |
| 12E23 P10+1 | 61 | 0 | 60 | 1 | 0 | 1 | 98% | 100.0% | 100.0% | 477 |
| 12E23 P10+2 | 61 | 0 | 61 | 0 | 0 | 1 | 100% | 100.0% | | |
| 12E23 P10-1 | 61 | 6 | 55 | 0 | 0 | 1 | 90% | 90.2% | 90.0% | 340 |
| 12E23 P10-2 | 59 | 6 | 53 | 0 | 0 | 1 | 90% | 89.8% | | |

A

B

| | 4+0/2n | 4+1/2n | 8+2/4n | Translocation | Total | % |
|---|---|---|---|---|---|---|
| tΔ63H16 | 9 | 39 | 2 | | 50 | 80 |
| tΔ63H45 | 4 | 26 | | | 30 | 86 |
| tΔ63H32 | 2 | 46 | 2 | | 50 | 96 |
| tΔ63H34 | 2 | 25 | 1 | | 28 | 92 |
| tΔ63H27 | 5 | 25 | | 1 | 30 | 83 |
| tΔ63H42 | 6 | 43 | 1 | 2 | 50 | 88 |
| tΔ63H14 | 2 | 22 | 1 | | 25 | 92 |
| tΔ63H43 | 3 | 30 | | | 33 | 90 |

Fig. 90

| Es clone name | PCR evaluation | | | |
|---|---|---|---|---|
| | ○ | × | n | |
| #1(t11) | 12 | 0 | 12 | 14AΔq |
| #2(t11) | 8 | 0 | 8 | 14AΔq |
| #3(t11) | 11 | 0 | 11 | 14AΔq |
| #4(t11) | 9 | 0 | 9 | 14AΔq |
| #34(t24) | 11 | 0 | 11 | 14NΔq |
| #35(t24) | 8 | 0 | 8 | 14NΔq |
| #32(G1) | 6 | 1 | 7 | 14NΔq |
| #36(G5) | 16 | 0 | 16 | 14NΔq |
| #37(G5) | 13 | 0 | 13 | 14NΔq |
| total | 94 | 1 | 95 | |

```
SEQUENCE LISTING

<160> NUMBER OF SEQ ID NOS: 179

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agctagctca actggctcct gatttctctc                                          30

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atcttcctcg agtcaccaaa cttg                                                24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caagtttggt gactcgagga agat                                                24

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggatccttt caagtggaag agtgaggtcc                                          30

<210> SEQ ID NO 5
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 5
gcatgccttc aatgtgtgac                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagcagagcc aagatccagt                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tccacagttt caccagcatc                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aagtgggcgg ataacctgag                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cagccagtgt tttcctggat                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tctttgctct tctgcaacca                                                    20

<210> SEQ ID NO 11
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 11
cgatcagaat gggaaaccag                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgtcgctgg aatttgttga                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcaccatgat cgattgagtt                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcattgctgg gtcatatggt                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtgagataa gcagtggatg                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cttgtgctac tcccatcact                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 17
tggcttggca tacattttga                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agggagttcc tcacacagga                                              20

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gacagtgtcg acagtgagac ttgtaggcta caagaaaagg                        40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gacagtgtcg actctgataa tgcggaatga gtagggaggc                        40

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatggccggc ctggttggta aagattgcta cacttacggc a                      41

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cttaattaac aagagctcta caactgtcca tcgaaac                           37

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 23
gcagtgacag aagtccatgt tgaactgtac                                30

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cacagcaacc acagtgcttc ttgatgag                                  28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tccagaagtg ttggtaaaca gcccacaa                                  28

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tagtctctct ggatgaatat cagcaaaact                                30

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aagacaccag ggagtaacct                                           20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgaaccac taagggtgac                                           20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 29
ggaataggga ttaggaaatg                                           20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acatgaggtt tatttggtgg                                           20

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
actcagagat ccactgcacc aggatccaag ggagg                          35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctacaccaca gacaccattg ttggctactg ctgcc                          35

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agcccgggct taattaacac gtgggtac                                  28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccacgtgtta attaagcccg ggctgtac                                  28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
gcgtcgacgc aagcttaaat agtgttgc                                            28

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gagccaacca aagtggagaa                                                     20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcaccatgtt gaccaggcta                                                     20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agctcgagag gcactgaatc                                                     20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agggtcttca aaatgcctga                                                     20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gccatgtcct cagcctttag                                                     20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```

```
ctggagcatc ctcttcttgg                                              20

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cggaattccg ggagtgggtg gcataaac                                     28

<210> SEQ ID NO 43
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 cccgcatg                                                            8

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 cggggtac                                                            8

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cattcatggt agtcattggt gctgttctcc                                   30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acttcctgac tagggagga gtagaaggtg                                    30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agtgggcagt ttaccgtaaa tactccaccc                                   30
```

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tatggaaatc tgagatgtgc ccagcctcag                                    30

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtgggtcctg aggagaacaa                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttcttctcac ctccattggc                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cctaaagcac atacagcagc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tctccagggg aaatccaatc                                               20

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cccacgtgtt aattaagccc gggcatccgg                                    30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
atgcccgggc ttaattaaca cgtgggccgg         30

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
gacagtgtcg acagtgagac ttgtaggcta caagaaaagg         40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
gacagtgtcg actctgataa tgcggaatga gtagggaggc         40

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
aggccggccg ttggtaaaga ttgctacact tacggca         37

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
cttaattaac aagagctcta caactgtcca tcgaaac         37

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
gcagtgacag aagtccatgt tgaactgtac         30

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gacgtgctac ttccatttgt cacgtcct                                              28

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
cgtctgtggc tgccaaacac                                                       20

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
tagtctctct ggatgaatat cagcaaaact                                            30

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
aagacaccag ggagtaacct                                                       20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
gctgaaccac taagggtgac                                                       20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
ggaataggga ttaggaaatg                                                       20

<210> SEQ ID NO 66

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acatgaggtt tatttggtgg                                              20

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggaagtagca cgtctcacta gtctc                                        25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
atgtagtgta ttgaccgatt ccttg                                        25

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gatggccggc ctggttggta aagattgcta cacttacggc a                      41

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gatgcccggg ccaatagcca gtcaatcgag aaaccaagcc c                      41

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cattcatggt agtcattggt gctgttctcc                                   30

<210> SEQ ID NO 72
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cacagcaacc acagtgcttc ttgatgag                                        28

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tccagaagtg ttggtaaaca gcccacaa                                        28

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aagcagagct accatgcact gtaggataag                                      30

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcaaggactg tgagcctcct                                                 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgcactgaaa gccaattgaa                                                 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tccgttggag ttgatccttc                                                 20

<210> SEQ ID NO 78
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 78
acatgacaca gcaaggaacg                                                    20

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aggtacctta gagactttgt gaggcttatc ggct                                    34

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agggccctag ttagatctgg caagcctaaa gctg                                    34

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gactagtcgc ttgagtcgtc atcatcagat gagt                                    34

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aggaggatcc tttattgagt gcac                                               24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gtgcactcaa taaaggatcc tcct                                               24

<210> SEQ ID NO 84
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 84
cgatatcgat gctaagagat gccctaagaa atcc                                34

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tatggaggaa tggcagaggg tgacacaggc                                     30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
acttcctgac tagggagga gtagaaggtg                                      30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agtgggcagt ttaccgtaaa tactccaccc                                     30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctcttgaaga atctgagcca tctgtatgcc                                     30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aggtaccctg tctattatga ccagcatggc                                     30

<210> SEQ ID NO 90
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 90
aggtaccagc cgataagcct cacaaagtct                                           30

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctgaaaattt atctgcgtga                                                      20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agaaggaggg tcctttgcat                                                      20

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gatggccggc ctggttggta aagattgcta cacttacggc a                              41

<210> SEQ ID NO 94
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gatgcccggg ccaatagcca gtcaatcgag aaaccaagcc c                              41

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agcggtactg agaggcaatc tttcatgggc                                           30

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 96
accaaatatc ctgctcaaac tgtaaccc                                              28

<210> SEQ ID NO 97
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tggactagtc caggccggcc acgcgtgaag ttcctatact ttctagagaa taggaacttc         60
ggaataggaa cttcgctagc ggccggcctg gactagtcca                              100

<210> SEQ ID NO 98
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tggactagtc caggccggcc gctagcgaag ttcctattcc gaagttccta ttctctagaa         60
agtataggaa cttcacgcgt ggccggcctg gactagtcca                              100

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aactgcagcc caagcttcca ccatgccaca atttgg                                   36

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aactgcagtg acttgttgac aatatcgaaa ctcagc                                   36

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caaagctttg aagaaaaatg cgccttatcc                                          30

<210> SEQ ID NO 102
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 102
gatcatatgc atagtaccga gaaactagtg                                           30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gaccttcagg tgagaaaata gcatcatgtg                                           30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtgatatcag attgatgttt ttgtccattg                                           30

<210> SEQ ID NO 105
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
acctaaggtg cttgttcgtc agtttgtgga aaggtttgaa agaccttca                      49

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cgggatccct cgagcgagac atgataagat acattgatg                                 39

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gattttccac atacgttccc aagccactcc                                           30

<210> SEQ ID NO 108
<211> LENGTH: 35
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 108
actcagagat ccactgcacc aggatccaag ggagg                                35

<210> SEQ ID NO 109
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccgctcgagc ggctacacca cagacaccat tgttggctac tgctgcc                   47

<210> SEQ ID NO 110
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acctggaatt tcctaccatc ccccataa                                        28

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
atctctccag agggacagca tcataccc                                        28

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cctgcaagtt atgaccactg gggatttt                                        28

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ctgcagtgag ccgagatcat accactgt                                        28

<210> SEQ ID NO 114
<211> LENGTH: 28
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 114
aaatgcatca ccattctccc agttaccc                                          28

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggagatgagg aagaggagaa ca                                                22

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cctgttctat ggttccagcc tcacattg                                          28

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gaattcagcg agagcctgac                                                   20

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
caggcaactg taacacagtg gtaggta                                           27

<210> SEQ ID NO 119
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
aacagtagag caatttcagg caggtc                                            26

<210> SEQ ID NO 120
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued probe

<400> SEQUENCE: 120
cgcagctttt agctgaacta aggaga                                          26

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
gtgacacagg gatactctgt ccaaaa                                          26

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggagcaacag gacctctcat tccttgtt                                        28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ccaatgtcag gcactcctgc tctaaatg                                        28

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gatcctcctg aatgcctg                                                   18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtaaatgccc tttggacc                                                   18

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 126
ctgggcaata gagcaagacc                                                     20

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
acccatatta tctatggaca attga                                               25

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tggacaaata taaggcatgt tca                                                 23

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gtcaccttcc tctgcctttg                                                     20

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gaattcactc atcgtaactt cattt                                               25

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccttgtagga aggtatagac aatgg                                               25

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 132
ctgcaatctt tacctccctg gttcaagc                                     28

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ggccgctcta gaactagtgg atc                                          23

<210> SEQ ID NO 134
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcgttaatta aaccgattaa ctgttctttt ccagta                            36

<210> SEQ ID NO 135
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gcgctagcga agtcaaaaga agtaacttct ttctct                            36

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gacagtgtcg acaagtcaaa agaagtaact tctatc                            36

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gatgcccggg cgtttccatg aaggatatta atcagt                            36

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
caacagcatc cccatctctg                                          20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gctcaagatg cccctgttct                                          20

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gaatgtcccc cattgtcact tcatgttc                                 28

<210> SEQ ID NO 141
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggcaagctta gtccagttgg gaaactgatg ggttcat                       37

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggcgaattcg gattgagaga cacacatagc tggtca                        36

<210> SEQ ID NO 143
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgaattct gtcaacctgc cagttctcag gagttt                        36

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144

```
cattcatggt agtcattggt gctgttctcc                                    30

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
acttcctgac tagggagga gtagaaggtg                                     30

<210> SEQ ID NO 146
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ctggaagaca ctgagataac catgacc                                       27

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ctgagaagtt ccacaatagc ctgtctc                                       27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tggaggccat aaacaagaag ac                                            22

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ccccttgacc cagaaattcc a                                             21

<210> SEQ ID NO 150
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gacagtgtcg accggattga gagacacaca tagctg                             36
```

<210> SEQ ID NO 151
<211> LENGTH: 36
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 151
gatgcccggg cctgtcaacc tgccagttct caggag                               36

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 152
ttcggcttct ggcgtgtgac                                                 20

<210> SEQ ID NO 153
<211> LENGTH: 35
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 153
cgggatcccg tggcggcggg taattctttg ccaaa                                35

<210> SEQ ID NO 154
<211> LENGTH: 38
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 154
aagcggccgc gactctaggg atccgccctc tccctccc                             38

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 155
gacaccatgg ttgtggccat attatcatcg tg                                   32

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 156
gcatcgactt caaggaggac                                                 20

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cctgcagttc attcaggg                                                 18

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
acgtaaacgg ccacaagttc                                               20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtcctccttg aagtcgatgc                                               20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gcaaaacaat aactgttgtt                                               20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
catttatctt ctctggctta                                               20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cagccagtgt tttcctggat                                               20

```
<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tctttgctct tctgcaacca                                              20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ggaataggga ttaggaaatg                                              20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acatgaggtt tatttggtgg                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
aagacaccag ggagtaacct                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gctgaaccac taagggtgac                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gcatgccttc aatgtgtgac                                              20
```

```
<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cagcagagcc aagatccagt                                              20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gtgccctctg ctctcagact                                              20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tgagctgggt ttcacagttg                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gccatgtcct cagcctttag                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ctggagcatc ctcttcttgg                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ggtcttgtcc ttggctttca                                              20
```

```
<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
atggagtcag aggggggaaac                                                   20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gaccatgacc ccacctctaa                                                    20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ggtgggatgg aagagtcaga                                                    20

<210> SEQ ID NO 178
<211> LENGTH: 42
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 178
gtcgacgcta gcgatatcgc ccgggcttaa ttaaggccgg cc                           42

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 179
ggccggcctt aattaagccc gggcgatatc gctagcgtag ac                           42
```

HUMAN ARTIFICIAL CHROMOSOME (HAC) VECTOR AND HUMAN CELL MEDICINE COMPRISING SAME

FIELD OF THE INVENTION

The present invention provides a human artificial chromosome (HAC) vector comprising a human chromosome-derived centromere, the subtelomere sequence, and the telomere sequence. The present invention also provides a human cell medicine or human cells comprising the HAC vector. Such human cells (as medicines) are useful for gene therapy and regenerative medicine. The present invention also provides a method for preparing human cells comprising the HAC vector, the HAC vector, and a method for preparing the HAC vector. Further, the present invention provides a method for producing a therapeutic protein using the HAC vector.

BACKGROUND OF THE INVENTION

HAC Vector

Conventional vectors, such as plasmid, cosmid, bacteria artificial chromosome (BAC), yeast artificial chromosome (YAC), or virus vectors, which are commonly used when introducing genes into mammalian cells, suffer from the problem of transient expression of the introduced genes in the case of episomes. When genes are integrated into chromosomes of host cells, however, such conventional vectors suffer from a number of problems, such as the host chromosome genes being disrupted, the copy number of genes introduced not being regulated, the introduced genes being inactivated, or gene expression being affected by a control sequence of the host chromosome into which the genes have been integrated.

As a means for resolving such problems, the research group consisting of the present inventors constructed a novel HAC (21HAC) vector system with the use of human chromosome 21 as a starting material, from which unnecessary genes with apparent structures have been removed, and which is capable of easy introduction of foreign DNA (WO 2004/031385; Katoh et al., Biochem Biophys Res Commun; 321: 280-290, 2004). In these documents, the present inventors demonstrated that the 21HAC vector is capable of autonomous replication and distribution in mammalian host cells, including humans, the 21HAC vector is retained stably, and a given copy number of genes could be introduced, without disrupting host chromosomes. They also demonstrated that the 21HAC vector into which a therapeutic gene, human erythropoietin (hEPO), had been introduced as a model intended for ex vivo hormone-replacement gene therapy could be introduced into cultured normal primary human fibroblasts, EPO expression could be maintained for a long period of time, the expression level thereof would be suppressed to a level approximately $\frac{1}{1,000}$ of that in CHO cells, cultured normal primary human fibroblasts into which HAC had been introduced could be amplified from a single colony to a maximum of $3.8 \times 10^7$ cells, and 65.5% to 90.9% of the genes could be retained after 6- or 9-passage culture under non-selective conditions (WO 2004/031385; Kakeda et al., Gene Therapy; 12: 852-856, 2005).

In the case of a baboon model of ex vivo EPO-replacement gene therapy, it is reported that hypodermic transplantation of capsules of cultured primary baboon MSCs (0.81 to $6.6 \times 10^6$ cells/kg) into which hEPO genes had been introduced with the use of a retrovirus vector resulted in enhanced blood EPO level and recovery from anemia (Bartholomew, A. et al., Hum Gene Ther; 12: 1527-1541, 2001). For the purpose of gene therapy, however, further improvement is desired in expression levels per cell. From the viewpoint of the limit of division of cultured normal primary human fibroblasts, the number of instances of cell division is preferably small. In order to effectively amplify cells into which therapeutic HACs have been introduced that can exhibit effects in vivo, stability of vectors should be improved and enhanced.

An example of a means for resolving the aforementioned problem is to construct an HAC vector having a functional telomere, with the use of a highly stable human chromosome as a human chromosome that acts as a basic backbone of the vector.

It is known that expression of foreign genes is influenced by the chromatin structure or the presence or absence of the control sequence in the vicinity of the insertion site. It is also known that a functional telomere of a sufficient length is necessary in order to stably retain the chromosome (Smogorzewska, A. et al., Anuu. Rev. Biochem., vol. 73, pp. 177-208, 2004). While there is an example in which an insulator had been used in order to eliminate the influence of the chromatin structure or the control sequence on HAC (Otsuki et al., Biochem Biophys Res Commun; 329: 1018-1025, 2005), elimination of the influence of the chromatin structure or the control sequence has not yet been examined, and such insulator would not regulate the telomere sequence. Also, improvement of stability of HAC vectors by telomere sequence regulation, such as addition of a telomere sequence or restoration of telomere length with the aid of telomerase on HAC, has not yet been examined.

Improvement of Efficiency of Homologous Recombination

When introducing foreign genes, drug-resistant genes are generally introduced in order to select cells into which the genes of interest have been introduced. In many cases, drug-resistant genes are positioned in parallel with the target foreign genes in the same vector. When a plurality of gene expression units are arrayed in parallel, it is known that they interfere with each other and the expression levels of the foreign genes are lowered. Up to the present, a drug-resistant gene is positioned as an exon, spliced, and expressed to lower drug resistance, and a cell in which the introduced gene is expressed at a high level, is selected in order to elevate the expression levels, when constructing high-level expression/production cells (Barnett, R. S. et al., Antibody expression and engineering, Chapter 3, p. 27-40, American Chemical Society, 1995). However, there are no reports regarding significantly improved expression of foreign genes resulted from elimination of drug-resistant genes.

Removal of drug-resistant genes located downstream is known to improve the efficiency of homologous recombination in mouse ES cells, when knocking in a foreign gene in the antibody light-chain κ locus (JP Patent Publication (kokai) No. 2006-94849 (A)), although this is not intended to improve foreign gene expression.

Stability of Human Chromosome and Gene Expression

As a result of experiments involving mouse ES cells, it is known that a larger chromosome fragment introduced into a cell results in a lower contribution ratio of such cell in an individual chimera. The research group consisting of the present inventors demonstrated that an individual chimera could be prepared by introducing human chromosome 14, 2, and 22 fragments, including antibody genes, into mouse embryonic stem cells, the introduced antibody genes are functionally expressed in the individuals, human chromosome fragments are retained stably in an individual chimera, and such genes can be inherited by the following generation through a germ line (Tomizuka et al., Nature Genet., U.S.A., vol. 16, pp. 133-143, 1997; and Tomizuka et al., P.N.A.S., U.S.A., vol. 97, pp. 722-727, 2000). The naturally-occurring fragment, SC20, derived from human chromosome 14, which had been isolated so as to prepare a mouse carrying a human antibody heavy chain gene, and HAC prepared by cloning a human chromosome 22 region comprising an antibody light chain gene into SC20 were examined in terms of stability and germ-line transmission in a mouse (Kuroiwa et al., Nature Biotech., U.S.A., vol. 18, pp. 1086-1090, 2000). Further, the present inventors have demonstrated that the above SC20-derived HAC would be retained stably in a cloned bovine individual prepared by somatic nuclear transplantation and that the introduced antibody genes would be functionally expressed in individuals (Kuroiwa et al., Nature Biotech., U.S.A., vol. 20, pp. 889-894, 2002). The above human chromosome-14-derived naturally-occurring fragment and HAC have not yet been examined in terms of stability and expression in cultured normal primary human cells or in human cell lines. Further, other human chromosome-derived naturally-occurring fragments and HACs, except for human chromosome 21, have not yet been fully examined in terms of stability and expression in cultured normal primary human cells or in human cell lines. While there is an example of a report in which the human cell line retains minichromosomes derived from human chromosome X (Mills et al., Hum. Mol. Genet., U.K., vol. 8, pp. 751-761, 1999), such minichromosomes are found to result in a significant number of multicopies after subculture, and maintenance of a given number of copies still remains difficult.

Regulation of Expression and Stability by Telomere

A telomere is a repeat sequence located at the end of a chromosome, and it is conserved in a wide range of organism species from yeast cells to mammalian cells, including humans. In a normal human cell, repeats of TTAGGG reach a size of 15 to 0.4 kb. A telomere becomes shorter as cell division proceeds, and heterochromosomes (i.e., involving fusion, drop out, split, alteration of chromosome number, or the like) appear or increase as the telomere length becomes shorter. Thus, a telomere is considered to be necessary for protection and maintenance of stability of chromosomes (Smogorzewska, A. et al., Anuu. Rev. Biochem., vol. 73, pp. 177-208, 2004; and Ning, Y et al., Hum Mol Genet., vol. 12, pp. 1329-1336, 2003). Thus, a functional telomere structure of the sufficient length is considered to result in improved stability of chromosomes.

A telomere length can be artificially extended by forced expression of telomerase or deletion of a telomere-binding protein (POT•TRF2) (Crisrofari, C. et al., EMBO J, vol. 25, pp. 565-574, 2006; Smogorzewska, A. et al., Anuu. Rev. Biochem., vol. 73, pp. 177-208, 2004). These techniques verified the increased number of instances of cell division and prolonged life in cultured normal primary human cells and in human cell lines; however, whether or not chromosome stability can be restored and improved has not yet been elucidated. When endogenous telomerase activity was elevated after crisis and the shortened telomerase was extended and maintained at a given length, the frequency at which heterochromosomes appearing in immortalized cells was constant without increase or decrease (Counter, C. M. et al., EMBO J, vol. 11, pp. 1921-1929, 1992). In this case, however, restoration and improvement of chromosome stability were not achieved.

A subtelomere is a chromosome region of approximately 300 to 500 kb, which is located adjacent to the centromere side of the telomere (TTAGGG)n repeat sequence at the chromosome terminus, and which has a segmented/overlapped domain or a (TTAGGG)n-like repeat sequence. Because of the high degree of homology of the segmented/overlapped domain structure, it is known that displacement or recombination is highly likely to occur within the subtelomere of the same chromosome or between subtelomeres of different chromosomes (Mefford, H. C. et al., Nat Rev Genet., vol. 3, pp. 91-102, 2002; Riethman, H et al., Chromosome Res., vol. 13, pp. 505-515, 2005; Linardopoulou, E. V. et al., Nature, vol. 437, pp. 94-100, 2005). The subtelomere length of the long arm of human chromosome 14 is identified as a 499-bp segmented/overlapped domain, and the presence of an unidentified sequence of 20 kb or shorter between the telomere sequence (TTAGGG)n and the subtelomeric region is suggested (Riethman H et al., Genome Res., vol. 14, pp. 18-28, 2004). As subtelomere functions, for example, restoration and maintenance of the telomere via recombination acceleration utilizing high homology in the absence of telomerase, adaptation to a new environment due to subtelomere plasticity, and induction of displacement and deletion that cause diseases are suggested, although details thereof have not yet been elucidated.

Regarding the correlation between the telomere and gene expression or the correlation between the telomere and the subtelomere and gene expression, it is observed that expression of the introduced foreign gene in a proximal site of the telomere is affected by silencing by heterochromatinization (i.e., telomere position effect (TPE)) in cells having a chromosome in which the terminus has been substituted with the telomere sequence upon random insertion of the telomere sequence (Tham W H et al., Oncogene, vol. 21, pp. 512-521, 2002). Regarding TPE, it is reported that telomere extension is correlated with silencing (Baur J A et al., Science, vol. 292, pp. 2075-2077, 2001). Regarding expression of genes of endogenous telomeric regions, however, there was no correlation between a gene expression pattern and decrease in the telomere length or the distance from the telomere end in neonatal human foreskin fibroblasts before and after subculture (Ning Y et al., Hum Mol Genet., vol. 12, pp. 1329-1336, 2003). Thus, discussion regarding the correlation between the telomere and gene expression has not yet been concluded.

DISCLOSURE OF THE INVENTION

The present invention provides a human artificial chromosome (HAC) vector, which is retained stably in a cell and is capable of expressing foreign genes at high levels, and a method for preparing the same. Also, the present invention provides human cell medicines (or pharmaceuticals), which are useful for gene therapy and regenerative medicine and a method for producing the same. Further, the present invention provides a method for producing a protein for therapy.

In order to attain these objects, the present inventors have focused on a telomere sequence and a subtelomere sequence that are present in a human chromosome, and they have attempted to construct a human artificial chromosome vector comprising a telomere sequence and/or a subtelomere sequence at the artificial chromosome terminus.

As an example, the present inventors prepared a modified human chromosome (14HAC) vector by deleting almost all known genes from the long arm of human chromosome 14, except for the centromere region, the telomere sequence, and part of the subtelomere sequence, and inserting the loxP sequence in a long-arm proximal region in a site-directed manner (FIG. 1). They confirmed that long-term subculture of CHO hybrid cells carrying the 14HAC vectors under nonselective conditions would enable maintenance of a given copy number of 14HAC vectors without substantial drop out and that such subculture would realize significant improvement in stability of the 14HAC vectors, compared with the conventional 21HAC vectors (WO 2004/031385) (FIG. 13). Further, CHO hybrid cells carrying 14HAC vectors into which human erythropoietin (hEPO) genes, i.e., erythrocyte growth factors, had been introduced using the Cre/loxP system were found to exhibit enhanced hEPO expression, which was 2.5 times greater than that attained with conventional 21HAC vectors. Furthermore, cultured normal primary human fibroblasts carrying the 14HAC vectors into which the hEPO genes had been introduced were found to exhibit significantly enhanced hEPO expression, which was 11.7 times greater than that attained with conventional 21HAC vectors (FIG. 21).

For the purpose of inspecting the causes of such effects, the present inventors have compared the expression efficiency of the HAC vector comprising the telomere sequence and part of the human chromosome 14-derived subtelomere sequence. As a result, the HAC vector was found to enhance hEPO expression by approximately 4 times in human normal fibroblasts, compared with the HAC vector comprising only the telomere sequence at the terminus from which the long arm had been deleted. These HAC vectors were different from each other in terms of the subtelomere sequence at the terminus from which the long arm had been deleted, but they were identical to each other in terms of the chromosome basic skeleton and the site into which foreign genes (e.g., hEPO) were to be introduced. Thus, significant enhancement of expression described above was considered to result from modification of human chromosome 14, so as to comprise the subtelomere sequence at the terminus from which the long arm had been deleted.

The presence of the subtelomere sequence in the human artificial chromosome vector was found to enhance the expression levels of foreign genes or foreign DNA and to positively affect stable maintenance of the vectors in the transduced cells and enhancement of efficiency of inheritance. Such effects were found in the human artificial chromosome (HAC) vector, which had been also prepared from human chromosome 21, in addition to human artificial chromosome 14 vector. Accordingly, the HAC vector, which was prepared from any human chromosome other than human chromosome 14 or 21 in the same manner, can exhibit effects similar to those attained by the HAC vector derived from human chromosome 14 or 21.

Based on such findings, the present inventors discovered that the aforementioned objects could be attained with the use of a human chromosome-based HAC vector. This has led to the completion of the present invention.

In order to attain the above objects, the present inventors have further conducted concentrated studies for the purpose of constructing a chromosome vector that can express the genes introduced into normal human cells or human cell lines at high levels and that can be retained stably therein. It is known that a plurality of gene expression units arrayed in parallel would interfere with each other and the expression of units located downstream in the transcription direction is attenuated, when introducing foreign genes (Proudfoot, N. J. et al., Nature, vol. 332, pp. 562-565, 1986; Kadesch, T. et al., Mol Cell Biol, vol. 6, pp. 2593-2601, 1986). In the above 21HAC vector for hEPO introduction (WO 2994/031385), a neo-resistant gene expression unit is adjacent to a site downstream of the hEPO gene expression unit. As a means for enhancing hEPO gene expression, the neo-resistant gene expression unit adjacent to a site downstream of the hEPO gene expression unit may be removed from the HAC vector. More specifically, a modified chromosome was prepared from a human chromosome by deleting almost all known genes from the long arm thereof. The loxP sequence, the FRT sequence, and the hCMV promoter were inserted into a long-arm proximal region of the modified chromosome in a site-directed manner. The hEPO gene was introduced into the modified chromosome as a foreign gene using the Cre/loxP system in the CHO hybrid cell carrying the modified chromosome. The neo-resistant gene expression unit was removed using the FLPe/FRT system. Then, the resultants were introduced into the cultured normal primary human fibroblasts carrying the modified chromosomes into which hEPO had been introduced. As a result, the 14HAC vector of the present invention was found to exhibit improvement in hEPO expression by average 18.5 times, compared with conventional 21HAC vectors (FIG. 21). Based on such finding, the present inventors discovered that the above objects could be attained with the use of an HAC vector from which a resistant gene expression unit had been deleted. This has also led to the completion of the present invention.

Specifically, the present invention is summarized as follows.

In the first aspect, the present invention provides a human artificial chromosome vector comprising a human chromosome fragment, from which the long-arm and/or short-arm distal regions are deleted, and which comprises a human chromosome-derived centromere and a telomere sequence and/or a subtelomere sequence (preferably, a human chromosome-derived subtelomere sequence) added or bound to the deleted long-arm and/or short-arm distal ends.

In one embodiment, the present invention provides a human artificial chromosome (HAC) vector comprising a human chromosome 14 fragment, from which the long-arm and/or short-arm distal regions have been deleted, and which comprises (i) a centromere derived from a human chromosome 14, (ii) a telomere sequence, and (iii) a subtelomere sequence.

In another embodiment, the present invention provides a human artificial chromosome (HAC) vector comprising a human chromosome 21 fragment, from which the long-arm and/or short-arm distal regions are deleted, and which comprises (i) a centromere derived from a human chromosome 21, (ii) a telomere sequence, and (iii) a subtelomere sequence.

Throughout the present description, the HAC vector of the present invention does not always comprise a spontaneous human chromosome fragment or a naturally-occurring human chromosome fragment. When such fragment has the aforementioned properties and is artificially isolated, such fragment is construed to be within the scope of the present invention.

According to another embodiment, the HAC vector may comprise: (iv) a foreign DNA (or a foreign gene or nucleic acid) that is inserted into a given site.

In another embodiment of the present invention, the size of the human chromosome fragment is generally approximately 1 Mb or greater; for example, between approximately 1 Mb and approximately 19 Mb, preferably approximately 18 Mb or smaller, and further preferably approximately 17 Mb or smaller, although the size is not particularly limited thereto. Such size is influenced by the type of a human chromosome, the length of the long-arm proximal region remaining in the chromosome fragment after deletion of the long-arm distal region or the short-arm distal region, the length of the short-arm proximal region or the short arm, or the like.

According to another embodiment of the present invention, the long-arm distal region of the human chromosome may be deleted from a human chromosome fragment and the resulting chromosome fragment may comprise the long-arm proximal region and the short-arm. Alternatively, the human chromosome fragment may lack the short-arm distal region due to deletion and may comprise the short-arm proximal region. Alternatively, the human chromosome fragment may lack both the long-arm distal region and the short-arm distal region of the human chromosome due to deletion and may comprise the long-arm and short-arm proximal regions.

The long-arm and/or short-arm distal regions of the human chromosome fragment can be cleaved and deleted by designing a target sequence (i.e., a targeting vector) based on the nucleotide sequence of the target region of cleavage; for example, the nucleotide sequence stored in the online genome database of the U.S. National Center for Biotechnology information (NCBI), the Human Genome Resources, (http://www.ncbi.nlm.nih.gov/genome/guide/human/), and using the same.

According to another embodiment of the present invention, the long-arm distal region of the human chromosome fragment is deleted within the q11 region or between the q11 region and the q12 region of the long arm of the human chromosome.

According to a further embodiment of the present invention, the short-arm distal region of the human chromosome fragment is deleted within the q11 region or between the q11 region and the q12 region of the short arm of the human chromosome.

For example, the long-arm distal region of the human chromosome 14 is deleted within the 14q region, preferably within the 14q11 region, further preferably at AL391156 or at a more proximal site than AL391156, particularly between AL391156 and CR383659, further preferably between AL512310 and CR383659, further preferably between AL929601 and CR383659, further preferably between AL589182 and CR383659, further preferably between AL589743 and CR383659, further preferably between AL929602 and CR383659, further preferably between AL512624 and CR383659, further preferably between CR383657 and CR383659, and so further preferably at CR383659.

The short-arm distal region of the human chromosome 14 is deleted, for example, within the 14p region, preferably between the 14p11 region and the 14p12 region, further preferably between the 14p11.1 region and the 14p11.2 region, further preferably within the 14p11.1 region, and further preferably at any one position selected from the group consisting of RNR2 and PABPCP2.

As another example, the long-arm distal region of the human chromosome 21 is deleted, for example, in the 21q region, preferably within the 21q11 region, and further preferably between the 21q11.1 region and the 21q11.2 region. The position of deletion is, for example, at a more proximal region than NT_011512 of 21q11.1, preferably at a more proximal region than AL16202 within the NT_011512-containing region, and further preferably at a more proximal region than AP001657 or AP001657 within the AL16202-containing region.

Also, the short-arm distal region of the human chromosome 21 is deleted, for example, within the 21p region, preferably between the 21p11.1 region and the 21p11.2 region, further preferably within the 21p11.1 region, and further preferably at AL163201.

According to another embodiment, a telomere sequence is a nucleotide sequence having a repeat sequence such as TTAGGG. Examples of such sequence include, but are not particularly limited to, an artificially synthesized sequence and a sequence derived from the long arm or short arm of a mammalian chromosome, including that of a human. The telomere sequence is preferably derived from a human chromosome, and further preferably derived from the same chromosome as that of the subtelomere sequence.

According to another embodiment of the present invention, the length of the telomere sequence is approximately 0.4 to 50 kb, preferably approximately 0.4 to 25 kb, and further preferably approximately 0.4 to 15 kb.

According to another embodiment, the subtelomere sequence is derived from the long arm or the short arm of a human chromosome, and it is a subtelomere sequence derived from any human chromosome, such as human chromosome 14 or human chromosome 21. According to a concrete embodiment, the human chromosome fragment above comprises a subtelomere sequence derived from the long arm of the same or a different, and preferably the same, human chromosome at a site from which the long-arm distal region has been deleted.

According to a further embodiment of the present invention, the size of the subtelomere sequence is approximately 1 to 500 kb, preferably approximately 1 to 300 kb, further preferably approximately 1 to 100 kb, further preferably approximately 5 to 60 kb, further preferably 5 to 40 kb, further preferably approximately 25 to 60 kb, and still further preferably approximately 25 to 40 kb.

According to a preferable embodiment, a human chromosome 14 or 21 fragment comprises a telomere sequence and a subtelomere sequence derived from the long arm of human chromosome 14 or 21 at a site in the long-arm distal region, which had been deleted in the manner described above.

According to another embodiment, the subtelomere sequence and telomere sequence derived from human chromosome 14 is a sequence between a site in the 14q32 region and the 14q-tel region of human chromosome 14. Such sequence is preferably a sequence between the 14q32.33 region and the 14q-tel region of human chromosome 14, and further preferably a sequence between any marker selected from among AB019439, AB019438 and AB019437, and the 14q-tel region of human chromosome 14. It is particularly preferably a sequence between AB019437 and the 14q-tel region of human chromosome 14.

According to another embodiment, the subtelomere sequence and the telomere sequence derived from human chromosome 21 are sequences between the 21q22.3 region and the telomere end within the 21q-tel region and the telomere sequence of human chromosome 21. The subtelomere sequence is preferably a sequence between an arbitrary site and the telomere end within the 21q-tel region of human chromosome 21, and it is further preferably a sequence between NT_011515 and the telomere end within the 21q-tel region.

According to a further embodiment, the human artificial chromosome vector of the present invention can comprise a human chromosome fragment further comprising at least one recognition site for site-directed recombinant enzyme. For example, a recognition site for the site-directed recombinant enzyme is inserted into the long-arm proximal region and/or the short-arm proximal region of the human chromosome fragment.

According to a preferable embodiment, the recognition site for a site-directed recombinant enzyme is inserted into a site closer to the centromere side (i.e., a "proximal site") than a site at which the long arm or short arm is deleted from the human chromosome (or a deletion position).

In the case of human chromosome 14, for example, a recognition site for a site-directed recombinant enzyme is inserted into the 14q region preferably at a more proximal site than the deletion site in the 14q11 region of the long-arm proximal region of human chromosome 14, further preferably into a site between AL391156 and CR383659, further preferably into a site between AL512310 and CR383659, further preferably into a site between AL929601 and CR383659, further preferably into a site between AL589182 and CR383659, further preferably into a site between AL589743 and CR383659, further preferably into a site between AL929602 and CR383659, further preferably into a site between AL512624 and CR383659, further preferably into a site between CR383657 and CR383659, and further preferably at CR383659. According to another embodiment, a recognition site for a site-directed recombinant enzyme is inserted into a more proximal site than the deletion position; for example, in the short-arm 14p region of human chromosome 14, further preferably between the 14p11 region and the 14p 12 region of the short-arm proximal region of human chromosome 14, and further preferably in the 14p11 region of the short-arm proximal region of human chromosome 14.

In the case of human chromosome 21, for example, a recognition site for site-directed recombinant enzyme is inserted into a more proximal site than the deletion position in the 21q region, preferably into a more proximal site between the 21q11.1 region and the 21q11.2 region of the long-arm proximal region of human chromosome 21, for example, preferably into a more proximal site in the NT_011512 region of 21q11.1, a more proximal site in the AL16202 region in the NT_011512-containing region, and further preferably into a more proximal site in AP001657 or AP001657 within the AL16202-containing region. According to another embodiment, at least one recognition site for site-directed recombinant enzyme is inserted into a more proximal site than the deletion position in the short arm of human chromosome 21; for example, a site between the 21p11.1 region and the 21p11.2 region in the 21p region, further preferably at a site in the 21p11.1 region of the short-arm proximal region of human chromosome 21, and further preferably at AL163201.

According to a preferable embodiment, a site-directed recombinant enzyme is the enzyme Cre, and a recognition site for site-directed recombinant enzyme is the loxP sequence. According to the other preferable embodiment, a site-directed recombinant enzyme is the FLPe enzyme, and a recognition site for site-directed recombinant enzyme is the FRT sequence.

In another embodiment of the present invention, the human artificial chromosome vector of the present invention comprises a human chromosome fragment containing at least two types of recognition sites for site-directed recombinant enzymes. For example, at least two types of recognition sites for site-directed recombinant enzymes are inserted into the long-arm proximal region and/or the short-arm proximal region of the human chromosome. This enables the use of a site-directed recombinant enzyme recognition site for introduction of a foreign gene and the use of another site-directed recombinant enzyme recognition site for removal of a drug-resistant gene expression unit, which became unnecessary.

In such a case, a plurality of recognition sites for site-directed recombinant enzyme are inserted into a site closer to the centromere (i.e., a proximal site) than the deletion position of the long arm or the short arm of a human chromosome, as described above.

In the case of human chromosome 14, for example, a recognition site for site-directed recombinant enzyme is as described above. That is, it is inserted into the 14q region, preferably at a more proximal site than the deletion position in the 14q11 region of the long-arm proximal region of human chromosome 14, further preferably at a site between AL391156 and CR383659, further preferably at a site between AL512310 and CR383659, further preferably at a site between AL929601 and CR383659, further preferably at a site between AL589182 and CR383659, further preferably at a site between AL589743 and CR383659, further preferably at a site between AL929602 and CR383659, further preferably at a site between AL512624 and CR383659, further preferably at a site between CR383657 and CR383659, and further preferably at a site in CR383659. According to another embodiment, a recognition site for site-directed recombinant enzyme is preferably inserted into a more proximal site than the deletion position in the short arm of human chromosome 14, further preferably at a site between the 14p11 region and the 14p12 region of the short-arm proximal region of human chromosome 14, and further preferably a more proximal site than the deletion position in the 14p11 region of the short-arm proximal region of human chromosome 14, for example.

In the case of human chromosome 21, for example, a recognition site for site-directed recombinant enzyme is inserted into the 21q region, preferably at a more proximal site than the deletion position between the 21q11.1 region and the 21q11.2 region of the long-arm proximal region of human chromosome 21, such as a site in the NT_011512 region of 21q11.1, preferably at a site in the AL16202 region in the NT_011512-containing region, further preferably at a site of deletion of AP001657 in the AL16202-containing region, or a the deletion position in AP001657. According to another embodiment, a recognition site for site-directed recombinant enzyme is inserted in the short arm of human chromosome 21, for example, in the 21p region, preferably at a site between the 21p11. 1 region and the 21p11.2 region, further preferably at a site in the 21p11.1 region of the short-arm proximal region of human chromosome 21, and further preferably a more proximal site than the deletion position in AL163201.

According to a preferable embodiment, a site-directed recombinant enzyme is the Cre enzyme and/or the FLPe enzyme, and a recognition site for site-directed recombinant enzyme is the loxP sequence and/or the FRT sequence.

In the second aspect, the present invention provides a cell that carries the human artificial chromosome (HAC) vector. Examples of cells that can be used include mammalian cells, preferably human cells (such as embryonic and somatic stem cells, somatic cells, normal somatic cells, epidermic cells, nerve cells, fibroblasts, benign or malignant tumor cells, endothelial cells, dermal cells, basal cells, cardiac muscle cells, skeletal muscle cells, interstitial cells, myeloma cells, blood cells, adipose cells, bone cells, cartilage cells, hair cells, hepatocytes, pancreatic cells, renal cells, amniotic cells, visual cells, acoustic cells, olfactory cells), Chinese hamster ovary (CHO) cells, 3T3 cells, BHK cells, 293 cells, and A9 cells.

In the third aspect, the present invention provides a method for preparing a human artificial chromosome (HAC) vector comprising the following steps:

(a) obtaining a cell that carries a human chromosome or a human chromosome fragment;

(b) deleting long-arm and/or short-arm distal regions of the human chromosome or the human chromosome fragment;

(c) adding a telomere sequence at a site(s) where the long-arm and/or short-arm regions are deleted; and (d) adding a subtelomere sequence at a site(s) where the long-arm and/or short-arm regions are deleted.

When the vector was prepared using the telomere sequence and the subtelomere sequence as a single sequence, step (c) and step (d) may be carried out as a single step to add such sequence to the deletion site(s) of the long-arm and/or short-arm regions.

According to another embodiment of the present invention, step (a) involves the use of the cell that carries a human chromosome or a human chromosome fragment having high efficiency for homologous recombination. According to a preferable embodiment, a cell having high efficiency for homologous recombination is derived from a chicken DT40 cell.

According to another embodiment of the present invention, the long-arm and/or short-arm distal regions of the human chromosome or the human chromosome fragment can be deleted in step (b) with the use of a site-directed recombinant enzyme. For example, the long-arm and/or short-arm distal regions of the human chromosome or the human chromosome fragment can be deleted by substitution with a telomere sequence and/or a subtelomere sequence with the use of a site-directed recombinant enzyme.

According to a preferable embodiment, the long-arm distal region of human chromosome 14 or a human chromosome 14 fragment is deleted from the 14q region, and preferably between the 14q11 region and the 14q12 region, and the short-arm distal region is deleted within the 14p12 region. According to a further preferable embodiment, the long-arm distal region of human chromosome 14 or a human chromosome 14 fragment is deleted at AL391156 or at a more proximal site than AL391156, specifically between AL391156 and CR383659, further preferably between AL512310 and CR383659, further preferably between AL929601 and CR383659, further preferably between AL589182 and CR383659, further preferably between AL589743 and CR383659, further preferably between AL929602 and CR383659, further preferably between AL512624 and CR383659, further preferably between CR383657 and CR383659, and further preferably between CR383659 and CR383659. In another embodiment, the short-arm distal region of human chromosome 14 is deleted within, for example, the 14p region, preferably between the 14p11 region and the 14p12 region, further preferably between the 14p11.1 region and the 14p11.2 region, further preferably within the 14p11.1 region, and still further preferably at any site selected from the group consisting of RNR2 and PAB-PCP2.

According to another embodiment, the long-arm distal region of human chromosome 21 or a human chromosome 21 fragment is deleted from the 21q region, and preferably between the 21q11.1 region and the 21q11.2 region, and the short-arm distal region is deleted between the 21q11.1 region and the 21q11.2 region. The long-arm distal region of human chromosome 21 or a human chromosome 21 fragment is deleted from, for example, a region comprising NT_011512 of 21q11.1, preferably a region comprising AL16202 in the NT_011512-containing region, and further preferably at AP001657 in the AL16202-containing region or a more proximal site than AP001657. Also, the short-arm distal region of human chromosome 21 is deleted from, for example, the 21p region, preferably between the 21p11.1 region and the 21p11.2 region, further preferably at a site in the 21p11.1 region, and further preferably at AL163201.

According to a further embodiment of the present invention, the long-arm and/or short-arm distal regions of the human chromosome or the human chromosome fragment can be deleted by substitution with a telomere sequence, and the telomere sequence can be added to the human chromosome fragment in steps (b) and (c). According to another embodiment, in steps (b) and (c), the long-arm and/or short-arm distal regions of the human chromosome or the human chromosome fragment can be deleted by substitution with a telomere sequence and a human chromosome-derived subtelomere sequence, and the telomere sequence and the subtelomere sequence can be added to the human chromosome fragment. The human chromosome-derived subtelomere sequence is preferably derived from a human chromosome, such as human chromosome 14 or human chromosome 21, although the origin is not limited thereto.

According to a preferable embodiment, in step (b) and step (c), at least two sites of the long-arm and/or short-arm distal regions of the human chromosome or the human chromosome fragment may be cleaved, so that the long-arm and/or short-arm distal regions can be deleted, and a telomere sequence can be added to a site of the deleted long arm and/or the short arm.

According to the other preferable embodiment, in steps (b) to (d), at least two sites of the long-arm and/or short-arm distal regions of the human chromosome or the human chromosome fragment may be cleaved, so that the long-arm and/or short-arm distal regions can be deleted, and a telomere sequence and a subtelomere sequence derived from the human chromosome or the human chromosome fragment can be added to a site of the deleted long arm and/or the short arm.

According to a preferable embodiment, the telomere sequence and the subtelomere sequence are a sequence each comprising a region between a site in the 14q32 region and the 14q-tel region of human chromosome 14, further preferably a sequence each comprising a region between the 14q32.33 region and the 14q-tel region of human chromosome 14.

According to the other preferable embodiment, the subtelomere sequence and the telomere sequence derived from human chromosome 21 are a sequence comprising a region between the 21q22.3 region and the telomere end in the 21q-tel region and a telomere sequence of human chromosome 21. The subtelomere sequence is preferably a sequence comprising a region between an arbitrary site and the telomere end in the 21q-tel region of human chromosome 21, and further preferably a sequence comprising a region between NT_011515 and the telomere end in the 21q-tel region of human chromosome 21.

According to a concrete embodiment, a site-directed recombination system, such as the Cre-loxP or FLPe-FRT system, may be used to delete the long-arm and/or short-arm distal regions, while maintaining the starting materials that serve as the basic skeletons, i.e., a naturally-occurring telomere sequence and/or subtelomere sequence derived from the human chromosome. In steps (b) to (d), for example, the long-arm distal region is deleted from the q11 region or the q11-q12 region of the long arm of a human chromosome or a human chromosome fragment, and the telomere sequence and the subtelomere sequence of a human chromosome or a human chromosome fragment are added to the deletion site of the long arm. In the case of human chromosome 14, for example, the telomere sequence and the subtelomere sequence, each comprising a region between a site in the 14q32 region and the 14q-tel region, are added. In the case of human chromosome 21, for example, the telomere sequence and the subtelomere sequence, each comprising a region between a site in the 21q22.3 region and the 21q-tel region, are added.

The long-arm distal region of the human chromosome or the human chromosome fragment is deleted by, for example, inserting a recognition site for site-directed recombinant enzyme in the long-arm distal and proximal regions and deleting a space between these two recognition sites by site-directed recombination.

According to a preferable embodiment, a recognition site for site-directed recombinant enzyme is inserted into a more distal site than the 14q32 region of the long-arm distal region and a more proximal site than the 14q11 region of the long-arm proximal region of human chromosome 14 or a human chromosome 14 fragment, further preferably a more distal site than AB019437 of the long-arm distal region, and a more proximal site than AL391156 of the long-arm proximal region. According to another preferable embodiment, a recognition site for site-directed recombinant enzyme is inserted into a more distal site than the 21q22 region of the long-arm distal region and a more proximal site than the 21q11 region of the long-arm proximal region of human chromosome 21 or a human chromosome 21 fragment, further preferably a more distal site than 21q22.3 of the long-arm distal region, for example, at NT_011515, and a more proximal site than 21q11.2 of the long-arm proximal region, for example, at a more distal site than NT_011512, and preferably a more distal site than AL16202, for example, at NT_011515, and further preferably at AP001657 or a more distal site than AP001657.

According to the other preferable embodiment, a site-directed recombinant enzyme is the Cre enzyme, and a recognition site for site-directed recombinant enzyme is the loxP sequence. According to a further preferable embodiment, a site-directed recombinant enzyme is the FLPe enzyme, and a recognition site for site-directed recombinant enzyme is the FRT sequence.

Further, the short-arm distal region of a human chromosome or a human chromosome fragment is deleted by, for example, inserting a recognition site for site-directed recombinant enzyme into the short-arm distal and proximal regions and deleting a region between these two recognition sites by site-directed recombination. According to a preferable embodiment, the recognition site for site-directed recombinant enzyme is inserted at a more distal site than, for example, a site within the short arm p region of the short-arm distal region of a human chromosome or a human chromosome fragment, preferably at a more distal site than a site within the p11 region or at a more distal site than a site within the region between the p11 region and the p12 region, further preferably at a more distal site than a site within the p11 region and at a more proximal site than a site within the p11 region or a site within the region between the p11 region and the p12 region of the short-arm proximal region.

In the case of human chromosome 14 or a human chromosome 14 fragment, for example, the recognition site for site-directed recombinant enzyme is inserted at a more distal site than a site within the 14p region of the short-arm distal region, preferably at a more distal site than a site within the region between the 14p12 region and the 14p11 region, and further preferably at a more distal site than a site within the 14p11 region and at a more proximal site than a site within the region between the 14p12 region and the 14p11 region of the short-arm proximal region, preferably at a more proximal site than a site within the 14p11 region, further preferably at a more proximal site than a site within the region between the 14p11.2 region and the 14p11.1 region, further preferably at a more proximal site than a site within the 14p11.1 region, and further preferably at a more proximal site than a position selected from the group consisting of RNR2 and PABPCP2. In the case of human chromosome 21 or a human chromosome 21 fragment, the recognition site for site-directed recombinant enzyme is inserted at, for example, a more distal site than a site within the 21p region of the short arm of human chromosome 21, preferably at a more distal site than a site within the region between the 21p11.2 region and the 21p11.1 region, and further preferably at a more distal site than a site within the 21p11 region and at a more proximal site than a site within the region between the 21p12 region and the 21p11 region of the short-arm proximal region, preferably at a more proximal site than a site within the 21p11 region, further preferably at a more proximal site than a site within the region between the 21p11.2 region and the 21p11.1 region, further preferably at a more proximal site than a site within the 21p11.1 region, and further preferably at a more proximal site than the position of AL163201.

According to a preferable embodiment, the site-directed recombinant enzyme is the enzyme Cre, and the recognition site for site-directed recombinant enzyme is the loxP sequence. According to a further preferable embodiment, the site-directed recombinant enzyme is the FLPe enzyme, and the recognition site for site-directed recombinant enzyme is the FRT sequence.

According to another embodiment, the method for preparing the HAC vector of the present invention may further comprise a step (e) of inserting at least one recognition site for site-directed recombinant enzyme into the human chromosome or the human chromosome fragment.

According to another embodiment of the present invention, in step (e), a site-directed recombinant enzyme is the Cre enzyme, and a recognition site for site-directed recombinant enzyme is the loxP sequence. According to another embodiment, in step (e), a site-directed recombinant enzyme is the FLPe enzyme, and a recognition site for site-directed recombinant enzyme is the FRT sequence.

In a further embodiment, a recognition site for site-directed recombinant enzyme can be inserted into, for example, the deletion position at AL391156 of human chromosome 14 or a human chromosome 14 fragment or a more proximal site than AL391156, and further preferably a more proximal site than the deletion position in the 14p12 region of the short-arm proximal region of human chromosome 14 or a human chromosome 14 fragment.

A recognition site for site-directed recombinant enzyme can be inserted into, for example, the 14q region, preferably a more proximal site than the deletion position in the 14q11 region of the long-arm proximal region of human chromosome 14 or a human chromosome 14 fragment, further preferably at a more proximal site than the deletion position in AL391156, further preferably in AL512310, further preferably in AL929601, further preferably in AL589182, further preferably in AL589743, further preferably in AL929602, further preferably in AL512624, further preferably in CR383657, and further preferably in CR383659. The recognition site can also be inserted, for example, at a more proximal site than a deletion position within the 14p region of the short-arm proximal region of human chromosome 14 or a human chromosome 14 fragment, and further preferably at a more proximal site than a deletion position within the 14p12 region of the short-arm proximal region of human chromosome 14, and further preferably at a more proximal site than a deletion position within the 14p11 region of the short-arm proximal region of human chromosome 14.

According to another embodiment, a recognition site for site-directed recombinant enzyme can be inserted into, for example, the deletion position in AP001657 of human chromosome 21 or a human chromosome 21 fragment, or at a more proximal site than AP001657, and further preferably at a more proximal site than a deletion position between the 21p11 and the p12 regions of the short-arm proximal region of human chromosome 21 or a human chromosome 21 fragment.

Further, in the fourth aspect, the present invention provides a human artificial chromosome (HAC) vector prepared by the method described above.

Furthermore, in the fifth aspect, the present invention provides a method for preparing a human artificial chromosome vector comprising foreign DNA, comprising the following steps:

(a) obtaining a cell that carries the human chromosome or the human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting at least one recognition site for site-directed recombinant enzyme into the human chromosome or the human chromosome fragment; and (f) inserting foreign DNA into the human chromosome or the human chromosome fragment in the presence of a site-directed recombinant enzyme.

In the sixth aspect, the present invention provides a method for preparing a human artificial chromosome vector comprising foreign DNA, comprising the following steps:

(a) obtaining a cell that carries the human chromosome or the human chromosome fragment;

(b) deleting the long-arm and/or short-arm distal regions of the human chromosome or the human chromosome fragment;

(c) adding a telomere sequence or a telomere sequence in combination with a subtelomere sequence at a site(s) where the long-arm and/or short-arm regions are deleted;

(d) inserting at least two types of recognition sites for site-directed recombinant enzyme into the human chromosome or the human chromosome fragment;

(e) inserting foreign DNA into the human chromosome or the human chromosome fragment in the presence of a site-directed recombinant enzyme; and (f) removing a drug-resistant gene from the human chromosome or the human chromosome fragment in the presence of a site-directed recombinant enzyme different from that used in step (e).

According to a preferable embodiment, the human chromosome is human chromosome 14 or human chromosome 21.

According to another embodiment, at least two types of site-directed recombinant enzyme and recognition sites thereof are the Cre enzyme and the loxP sequence and the FLPe enzyme and the FRET sequence. According to another embodiment, the drug-resistant gene is a neomycin-resistant gene.

According to the fifth and the sixth aspects above, the insertion position of foreign DNA, i.e., the insertion position of a site-directed recombinant enzyme, is the same as that of the above-described site-directed recombinant enzyme. In the case of human chromosome 14, for example, it is a more proximal site than 14q11 of the long-arm proximal region, and preferably a more proximal site than the deletion position in AL391156 (GenBank Accession Number) of the long-arm proximal region. Also, it may be on the short arm of human chromosome 14, and preferably a more proximal site than the deletion position in the 14p12 region of the short-arm proximal region. It should be noted that the insertion position is not limited thereto. In the case of human chromosome 21, for example, it is a more proximal site than 21q11.2 of the long-arm proximal region, preferably a more proximal site than 21q11.1, further preferably a more proximal site than AL16202 (GenBank Accession Number) of the long-arm proximal region, and further preferably a more proximal position than the deletion region of AP001657 (GenBank Accession Number) or AP001657 of the long-arm proximal region. Also, it may be on the short arm of human chromosome 21, and preferably at a more proximal site than a deletion position in the 21p11.2 region of the short-arm proximal region. It should be noted that the insertion position is not limited thereto.

According to a preferable embodiment, the insertion position of foreign DNA is a region of approximately 1 to 500 kb, preferably approximately 1 to 300 kb, further preferably approximately 1 to 100 kb, further preferably approximately 5 to 60 kb, further preferably 5 to 40 kb, further preferably approximately 25 to 60 kb, and further preferably approximately 25 to 40 kb from the telomere sequence at the end of the human chromosome fragment.

In the seventh aspect, the present invention provides a human artificial chromosome vector comprising foreign DNA obtained by the above method.

In the eighth aspect, the present invention provides a cell that carries a human artificial chromosome vector comprising foreign DNA. Examples of cells that can be used include mammalian cells, preferably human cells (e.g., embryonic and somatic stem cells, somatic cells, normal somatic cells, epidermic cells, nerve cells, fibroblasts, benign or malignant tumor cells, endothelial cells, dermal cells, basal cells, cardiac muscle cells, skeletal muscle cells, interstitial cells, myeloma cells, blood cells, adipose cells, bone cells, cartilage cells, hair cells, hepatocytes, pancreatic cells, renal cells, amniotic cells, visual cells, acoustic cells, and olfactory cells), Chinese hamster ovary (CHO) cells, 3T3 cells, BHK cells, 293 cells, and A9 cells.

In the ninth aspect, the present invention provides a pharmaceutical composition comprising a cell that carries the HAC vector or the HAC vector comprising foreign DNA. In such a case, examples of foreign DNA include, but are not limited to, genes encoding, for example, erythropoietin (EPO), thrombopoietin (TPO), a blood clotting factor, a von Willebrand factor (vWF), dystrophin, dopamine synthetase, insulin, insulin-like growth factor (IGF), insulin-like growth factor binding protein (IGFBP), antibody, telomerase, granulocyte colony-stimulating factor, granulocyte macrophage colony-stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, α-1 antitrypsin, ornithine transcarbamylase, purine nucleotide phosphorylase, growth inhibitory factor (GIF), tumor necrosis factor (TNF), leukaemia inhibitory factor (LIF), oncostatin M, Flt3 ligand (Flt3L), stroma-derived factor (SDF), stem cell factor (SCF), fibroblast growth factor (FGF), epithelial growth factor (EGF), vascular endothelial growth factor (VEGF), angiopoietin, nerve growth factor (NGF), bone morphogenetic protein (BMP), activin, transforming growth factor (TGF), Wnt, R-spondin, monoclonal antibody, oligoclonal antibody, and polyclonal antibody.

In the tenth aspect, the present invention provides a method for introducing foreign DNA into a recipient cell comprising the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting at least one recognition site for site-directed recombinant enzyme into the human chromosome or the human chromosome fragment;

(f) inserting foreign DNA into the human chromosome or the human chromosome fragment in the presence of a site-directed recombinant enzyme;

(g) preparing a microcell from the donor cell that carries the human chromosome or the human chromosome fragment;

(h) allowing the microcell to be fused to the recipient cell; and (i) confirming the introduction of foreign DNA into the fused recipient cell.

According to another embodiment of the present invention, the recipient cell is an animal cell, and preferably a mammalian cell. The recipient cell may be a multipotent cell, such as an embryonic stem cell (ES cell), an interstitial stem cell, and a tissue stem/precursor cell.

In the eleventh aspect, the present invention provides a method for preparing a cell that expresses foreign DNA comprising the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions to be deleted;

(e) inserting a recognition site for site-directed recombinant enzyme into the human chromosome or the human chromosome fragment;

(f) inserting foreign DNA into the human chromosome or the human chromosome fragment under the expression of a site-directed recombinant enzyme;

(g) preparing a microcell from the donor cell that carries the human chromosome or the human chromosome fragment;

(h) allowing the microcell to be fused to the recipient cell; and (i) selecting a cell that expresses foreign DNA in the fused recipient cell.

According to another embodiment of the present invention, the recipient cell is an animal cell, and preferably a mammalian cell. The recipient cell may be a multipotent cell, such as an embryonic stem cell (ES cell), an interstitial stem cell, or a tissue stem/precursor cell.

In the twelfth aspect, the present invention provides a method for preparing a protein comprising the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting a recognition site for site-directed recombinant enzyme into the human chromosome or the human chromosome fragment;

(f) inserting foreign DNA encoding a protein into the human chromosome or the human chromosome fragment under the expression of a site-directed recombinant enzyme;

(g) preparing a microcell from the donor cell that carries the human chromosome or the human chromosome fragment;

(h) allowing the microcell to fuse to the recipient cell;

(i) culturing the fused recipient cell in a medium; and (j) sampling the protein from the resulting culture product.

According to another embodiment of the present invention, examples of the aforementioned protein include erythropoietin (EPO), thrombopoietin (TPO), a blood clotting factor, the eighth factor, the ninth factor, a von Willebrand factor (vWF), dystrophin, dopamine synthetase, insulin, insulin-like growth factor (IGF), insulin-like growth factor binding protein (IGFBP), antibody, telomerase, granulocyte colony-stimulating factor, granulocyte•macrophage colony-stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, α-1 antitrypsin, ornithine transcarbamylase, purine nucleotide phosphorylase, growth inhibitory factor (GIF), tumor necrosis factor (TNF), leukaemia inhibitory factor (LIF), oncostatin M, Flt3 ligand (Flt3L), stroma-derived factor (SDF), stem cell factor (SCF), fibroblast growth factor (FGF), epithelial growth factor (EGF), vascular endothelial growth factor (VEGF), angiopoietin, nerve growth factor (NGF), bone morphogenetic protein (BMP), activin, transforming growth factor (TGF), Wnt, R-spondin, monoclonal antibody, oligoclonal antibody, and polyclonal antibody.

The terms used in the present invention are defined as follows.

The term "human artificial chromosome vector" or "HAC vector" used herein refers to an artificial chromosome prepared based on a human chromosome.

Also, the term "human chromosome" used herein refers to a composite of human cell-derived naturally-occurring DNA and a protein. It is known that there are 23 pairs (46 chromosomes) of normal human chromosomes (24 types in case of a male) (i.e., autosomal chromosomes: chromosomes 1 to 22; and sex chromosomes: chromosomes X and Y), and that each chromosome comprises DNA of approximately 50 to 300 Mb. The term "human chromosome fragment" refers to a partial fragment of a chromosome that is capable of stable replication and distribution as an independent chromosome. The size of such fragment is generally 1 Mb or greater, and it is occasionally 1 Mb or smaller.

In the present description, the terms "long arm" and "short arm" of a chromosome refer to arms on both sides of a chromosome centromere, and such arms are referred to as long arms (q) or short arms (p) in accordance with their lengths. The terms "long-arm distal region" and "long-arm proximal region" of the human chromosome refer to regions located at a distance from the centromere of the long arm (i.e., on the telomere side; a distal region) and regions located adjacent to the centromere (a proximal region). In the case of human chromosome 14, specifically, the long-arm distal region is located closer to the telomere than AL359218, and the long-arm proximal region is located closer to the centromere than AL391156. In the case of human chromosome 21, the long-arm distal region is located closer to the telomere than 21q22.2, and the long-arm proximal region is 21q11.2. Further, the terms "short-arm distal region" and "short-arm proximal region" refer to a region located at a distance from the centromere of the short arm (a distant region) and a region located adjacent to the centromere (a proximal region), respectively. In the case of human chromosome 14, for example, there is a boundary in a ribosomal RNA region.

The terms "site-directed recombinant enzyme" and "recognition site for site-directed recombinant enzyme" are used regarding a phenomenon in which a given enzyme recognizes a given recognition site and causes DNA recombination specifically at such recognition site. Such terms indicate enzymes that cause recombination in a site-directed manner and sites to be recognized by such enzymes.

The term "telomere sequence" used herein refers to a sequence having a TTAGGG repeat sequence (TTAGGG)n. The length of the telomere sequence is approximately 0.4 to 50 kb, preferably approximately 0.4 to 25 kb, and further preferably approximately 0.4 to 15 kb. Such telomere sequence may be chemically synthesized, artificially generated, or derived from a chromosome.

The term "subtelomere sequence" used herein refers to a chromosome region of approximately 300 to 500 kb, which is located adjacent to the centromere of the telomere (TTAGGG)n repeat sequence at the chromosome end of an eukaryotic cell, and which has a segmented/overlapped domain or a (TTAGGG)n-like repeat sequence. The subtelomere sequence may be the whole or a part of a subtelomere sequence derived from an arbitrary chromosome. Alternatively, such sequence may be composed of a plurality of subtelomere sequences derived from an arbitrary chromosome bound to each other, or it may be composed of a subtelomere sequence derived from an arbitrary chromosome with another sequence added thereto. In the present invention, for example, addition of a telomere sequence or subtelomere sequence may be carried out by telomere truncation or translocation utilizing site-directed recombination.

The term "foreign DNA" used herein refers to DNA that is introduced into a target cell from the outside. The term refers to DNA encoding a gene, the expression of which is desired for the purpose of material production, disease treatment, function modification, functional analysis, or the like, or another functional sequence (e.g., a promoter sequence). Such DNA may be allogeneic or xenogeneic.

In the present description, the term "cell" refers to a cell derived from an individual organism or tissue. Examples thereof include somatic cells, normal somatic cells, germ cells, somatic stem cells, neoplastic cells, immortal cell lines, embryonic stem cells (ES cells), embryonic germ cells (EG cells), embryonic carcinoma cells (EC cells), and germline stem cells (GS cells). Cells may be allogeneic or xenogeneic, and the aforementioned human-derived cells (i.e., human cells) may be used.

The term "donor cell" and "recipient cell" refers to a cell that first carries the vector (i.e., a donor cell) and a cell into which the vector is to be introduced from the donor cell (i.e., a recipient cell), when a human artificial chromosome vector is to be transferred or introduced.

This description includes part or all of the contents as disclosed in the description and/or drawings of Japanese Patent Application No. 2006-188392, which is a priority document of the present application.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 12 shows the results of FISH analysis regarding a CHO hybrid cell into which a 14AΔqHAC vector has been introduced. FIG. 12A shows a FISH image, and FIG. 12B shows a karyotype of the 14AΔqHAC vector.

FIG. 13 shows the results of long-term stability analysis of 14ΔqHAC vectors (14AΔqHAC, 14NΔqHAC(G), and 14gNΔqHAC(g)) and a 21ΔqHAC vector in a CHO hybrid cell under non-selecting conditions.

FIG. 17A shows a FISH image, and FIG. 17B shows a karyotype of the hEPO-14AΔqHAC vector.

FIG. 18 shows the results of long-term expression/stability analysis of the hEPO-14AΔqHAC vector in the CHO hybrid cell.

FIG. 20A shows a FISH image, and FIG. 20B shows a karyotype of the hEPO-14AΔqHAC vector.

FIG. 30B: g/n1).

FIG. 32A shows the G94n56 cell, and FIG. 32B shows a FISH image of the G94n56Δp25 cell.

FIG. 37A shows a FISH image, and FIG. 37B shows a karyotype of the 14NΔqHAC vector.

FIG. 39A shows a FISH image, and FIG. 39B shows a karyotype of the hEPO-14AΔqHAC vector.

FIG. 41 shows the results of long-term expression and stability analysis of the hEPO-14NΔqHAC vector in the CHO hybrid cell.

FIG. 42A shows a FISH image, and FIG. 42B shows a karyotype of the hEPO-14NΔqHAC vector.

FIG. 43 shows long-term expression of hEPO genes in a human normal fibroblast into which the hEPO-14ΔqHAC vector has been introduced.

FIG. 50A shows a FISH image, and FIG. 50B shows a karyotype of the 14gNΔqHAC vector.

FIG. 54A shows a FISH image, and FIG. 54B shows a karyotype of the 14gNΔqHAC vector.

FIG. 56A shows a FISH image, and FIG. 56B shows a karyotype of the hEPO-14gΔqHAC vector.

FIG. 58 shows the results of long-term expression and stability analysis of the hEPO-14gNΔqHAC vector in the CHO hybrid cell.

FIG. 59A shows a FISH image, and FIG. 59B shows a karyotype of the hEPO-14gNΔqHAC vector.

FIG. 67A shows a FISH image, and FIG. 67B shows a karyotype of the hEPO-14AΔqF-HAC vector.

FIG. 70A shows a FISH image, and FIG. 70B shows a karyotype of the hEPO-14AΔqΔneo-HAC vector.

FIG. 87A shows red blood cell (RBC) counts, FIG. 87B shows the hemoglobin level (HGB) counts, and FIG. 87C represents hematocrit (HCT) values. In the figure, a rhombic shape indicates the average (N=3; week 28: N=2; week 32 and later: N=1) of CMV (CHO cell clones, t7S38-8E5, that carry the 14AΔqHAC vectors comprising the hEPO genes introduced into a site downstream of the cytomegalovirus promoter) and a square indicates the average of control samples (i.e., sham operation) (N=3; week 20, week 28, and week 44=2).

FIG. 88A shows the structure of the EGFP-14HAC vector resulting from introduction of a gene of an enhanced green fluorescent protein (EGFP) into the human chromosome 14 vector. FIG. 88B shows the presence or absence of a human marker on the centromere side and on the telomere side of the 14AΔq-HAC vector and the 14NΔq-HAC vector.

FIG. 90 shows the results of PCR inspecting whether or not chimera mice, which had been prepared from a variety of ES clones carrying the EGFP-14AΔq-HAC vector or the EGFP-14NΔq-HAC vector, carry HAC.

BEST MODES FOR CARRYING OUT THE INVENTION

Figure 1:
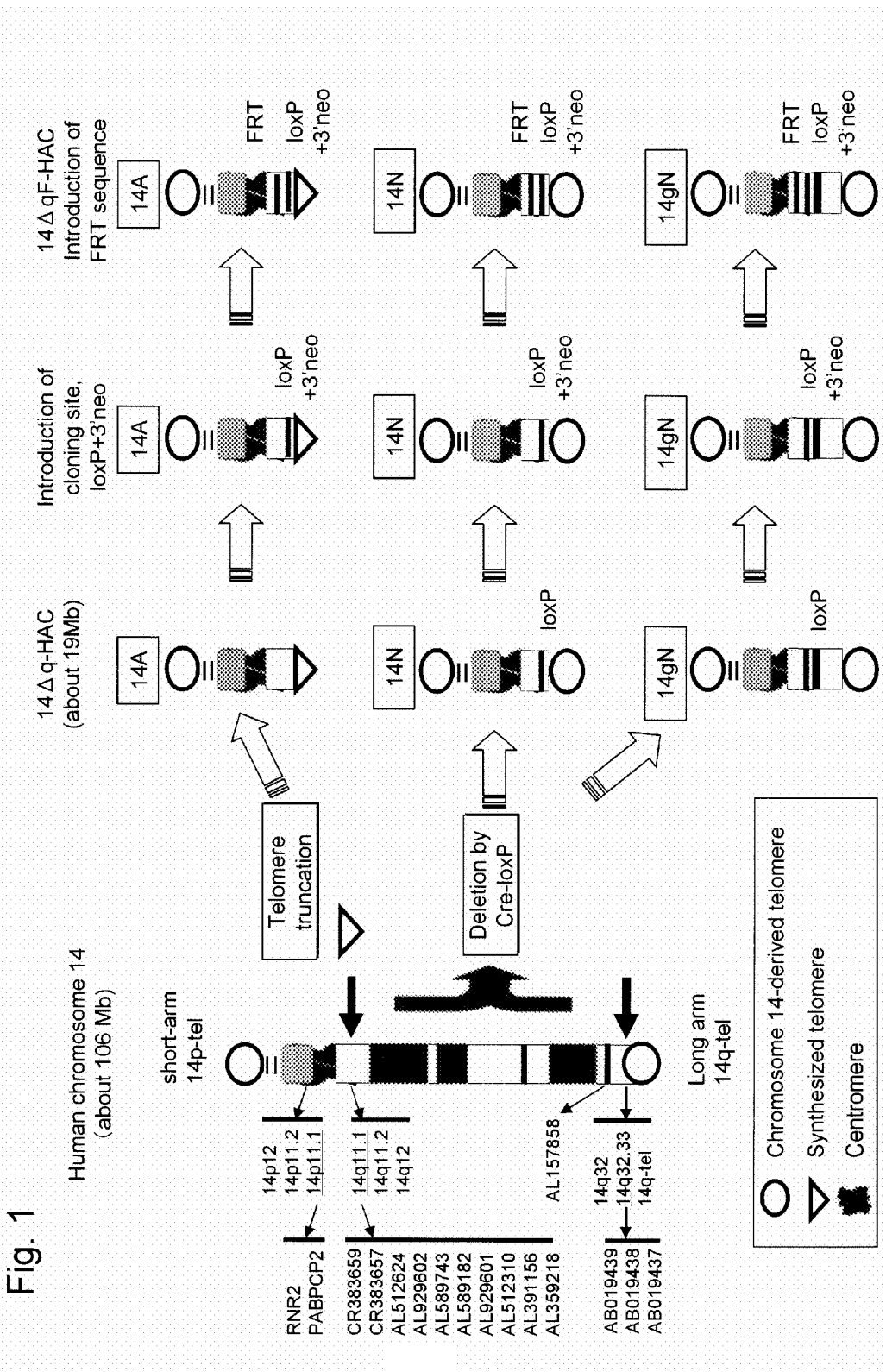
FIG. 1 schematically shows the structure of the HAC vector derived from human chromosome 14. In the figure, "14A" schematically represents an HAC vector with the deleted long-arm distal region of human chromosome 14, to which a telomere sequence has been added, "14N" schematically represents an HAC vector with the deleted long-arm distal region of human chromosome 14, which comprises a telomere sequence and a subtelomere sequence of approximately 25 kb derived from human chromosome 14, and "14gN" schematically shows an HAC vector with the deleted long-arm distal region of human chromosome 14, which comprises a telomere sequence and a subtelomere sequence of approximately 60 Kb derived from human chromosome 14.

Hereafter, the present invention is described in detail.

The present invention relates to a human artificial chromosome vector (which may be referred to as "the HAC vector" hereafter). The HAC vector comprises a human chromosome fragment, which is prepared based on a human chromosome with the deleted long-arm distal region and/or short-arm distal region and which comprises the telomere sequence and the subtelomere sequence, and particularly the subtelomere sequence.

In the present invention, a human chromosome type is not particularly limited, and a human chromosome is selected from the group consisting of human chromosomes 1 to 22, chromosome X, and chromosome Y. In the present invention, variations in polymorphisms or the like in a human chromosome are acceptable. In the examples below, human chromosome 14 and a human chromosome 21 are exemplified, and preparation of human artificial chromosome vectors from these human chromosomes or the human chromosome fragments is explained. The methods, means, and the like described therein may also be applied to other human chromosomes to realize preparation of the human artificial chromosome vector of the present invention.

Hereafter, preparation of the HAC vector, insertion of foreign DNA into a vector, and applications of the HAC vector are described.

1. Preparation of Human Artificial Chromosome (HAC) Vector

The HAC vector is prepared based on a human chromosome as described above. Preparation of the HAC vector comprises the following steps (a) to (d):

(a) obtaining a cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted; and (d) adding a subtelomere sequence at a site(s) where the long-arm and/or short-arm regions are deleted.

Preparation of the HAC vector may also comprise the following step (e):

(e) inserting at least one recognition site for site-directed recombinant enzyme into the human chromosome or the human chromosome fragment.

It should be noted that the order for performing the steps (b), (c), and (d) and that of the steps (b), (c), (d), and (e) are not particularly limited.

Step (a): Preparation of a Cell that Carries a Human Chromosome

When preparing the HAC vector, a cell that carries a human chromosome (for example, all human autosomal chromosomes, including human chromosome 14 and human chromosome 21) or a fragment thereof is prepared. A cell that exclusively carries a human chromosome or a fragment thereof and that has high efficiency for homologous recombination is preferable for convenience of subsequent operations. In the present invention, accordingly, a cell that satisfies such conditions is prepared.

A cell that carries a human chromosome can be prepared by, for example, selecting a clone carrying a human chromosome from a known library of mouse A9 hybrid cells comprising a human monochromosome, and introducing the chromosome into a cell exhibiting high efficiency for homologous recombination. The library of mouse A9 hybrid cells comprises human monochromosomes labeled with drug-resistant genes, and it is described in, for example, WO 00/10383, Tanabe, H. et al., (Chromosome Res., 8: 319-334, 2000). A mouse A9 hybrid cell carrying human chromosome 14, for example, is registered with the Japanese Collection of Research Bioresources (JCRB) under JCRB2214 (cell name: A9 (Hygro14)), and detailed information and a culture method thereof are also available.

Human chromosomes that are carried by the thus-obtained mouse A9 hybrid cells are introduced into a cell exhibiting high efficiency for homologous recombination. The term "a cell exhibiting high efficiency for homologous recombination" used herein refers to a cell exhibiting a high frequency of homologous recombination, when performing homologous recombination in the cell of interest. Examples of such cells include chicken DT40 cells (Dieken et al., Nature Genetics, 12: 174-182, 1996) and mouse ES cells (Shinichi Aizawa, Biomanual Series 8 Gene Targeting, Youdosha, 1995). In the present invention, use of chicken DT40 cells is particularly preferable, from the viewpoint of easy operability.

Chromosomes can be introduced in accordance with a method of chromosome introduction that is known in the art. An example of a method for introducing only one chromosome of interest is the microcell mediated chromosome transfer method described in Koi et al. (Jpn. J. Cancer Res., 80: 413-418, 1973). In this method, microcells that are induced by a drug inhibiting spindle formation in a given cell are separated, the separated microcells are fused to recipient cells, and a small number of chromosomes are thus introduced. A specific procedure for introducing a human chromosome by the microcell mediated chromosome transfer method is described in, for example, WO 97/07671 and WO 00/10383. Thus, a cell that carries a human chromosome can be prepared.

Alternatively, a cell that carries a partially fragmented chromosome instead of a full-length human chromosome, such as a partial fragment (SC20) of human chromosome 14, can be used in the present invention (SC20; Tomizuka et al., P. N. A. S., 97: 722-727, 2000). It is reported that SC20 lacks a major part of the long-arm distal region and the long-arm proximal region of human chromosome 14 (Tomizuka et al., P. N. A. S., 97: 722-727, 2000; Kuroiwa et al., Nature Biotech., U.S.A., vol. 18, pp. 1086-1090, 2000). Specifically, SC20 comprises a region including the telomere sequence to AL137229 (GenBank Accession Number) of the long arm of human chromosome 14, and a region from AL121612 (GenBank Accession Number), which is located closer to the centromere side than the former region, to a position 24 to 26-kb away from the telomere side of AL157858 (GenBank Accession Number). Also, SC20 lacks a region between AL137229 (GenBank Accession Number) and AL121612 (GenBank Accession Number) and a region between the 24-26 kb on the telomere side and the centromere of AL157858 (GenBank Accession Number). SC20 comprise the short arm region of human chromosome 14. Disadvantageously, SC20 comprises a plurality of genes in the 14q32 region of chromosome 14. However, miniaturization of SC20 by the method described in the present description enables preparation of an HAC vector, which is retained stably in various cell lines and which does not contain excessive genes. The chicken DT-49 cell (SC20) carrying the SC20 chromosome fragment is deposited internationally at the International Patent Organism Depositary of the National Institute of Advanced Industrial Science and Technology (Tsukuba Central 6, 1-1-1 Higashi, Tsukuba, Ibaraki, Japan) as of May 9, 2001 under the accession number: FERM BP-7583.

Step (b): Deletion of Long-Arm Distal Region and/or the Short-Arm Distal Region from the Human Chromosome
Step (c): Addition of a Telomere Sequence
Step (d): Addition of a Subtelomere Sequence When preparing the HAC vector, the long-arm and/or short-arm distal regions of the human chromosome or the human chromosome fragment is deleted from the cell that carries the human chromosome or the human chromosome fragment. The chromosome can be deleted in accordance with a method known in the art. For example, a site-directed recombinant enzyme system can be utilized. When preparing the HAC vector, a telomere sequence and a subtelomere sequence are added to the sites of the long arm and/or the short arm to be deleted from the human chromosome or the human chromosome fragment, and such addition can be carried out, for example, with the utilization of a site-directed recombinant enzyme system. Utilization of a site-directed recombinant enzyme system is well-known in the art, and a site-directed recombinant enzyme exemplified in step (e) described below and a recognition site thereof can be utilized, for example. According to a preferable embodiment, for example, a site-directed recombinant enzyme is the Cre enzyme, and a recognition site for site-directed recombinant enzyme is the loxP sequence. According to the other preferable embodiment, a site-directed recombinant enzyme is the FLPe enzyme, and a recognition site for site-directed recombinant enzyme is the FRT sequence.

The order for performing steps (b) to (d) is not particularly limited. For example, the long-arm and/or short-arm distal regions may be deleted, and a telomere sequence and a subtelomere sequence may then be added. Alternatively, the long-arm and/or short-arm distal regions may be deleted by substitution with a telomere sequence, and a subtelomere sequence may then be inserted. Also, the long-arm and/or short-arm distal regions may be deleted by substitution with a telomere sequence and a subtelomere sequence. These steps can be carried out in any order and arbitrarily repeated, provided that the target HAC vector can be eventually obtained.

The size of the human chromosome fragment resulting from deletion of the long-arm and/or short-arm distal regions is preferably approximately 18 Mb or smaller, and further preferably approximately 17 Mb or smaller, so that the size of the resulting human chromosome fragment would be approximately 1 Mb or greater in general, for example, between approximately 1 Mb and approximately 19 Mb, including the telomere sequence and the subtelomere sequence.

A telomere sequence to be added to the long-arm and/or short-arm regions of a human chromosome fragment may be any sequence, provided that it comprises a nucleotide sequence having a repeat sequence, such as TTAGGG A telomere sequence may be chemically synthesized based on, for example, a TTAGGG repeat sequence, or it can be prepared from an arbitrary chromosome (e.g., a human chromosome) by a known method. The length of the telomere sequence to be added is approximately 0.4 to 50 kb, preferably approximately 0.4 to 25 kb, and further preferably approximately 0.4 to 15 kb.

A subtelomere sequence to be added to the long-arm and/or short-arm regions of a human chromosome fragment is a mammalian chromosome-derived subtelomere sequence, preferably a human chromosome-derived subtelomere sequence, and further preferably a human autosomal chromosome-derived subtelomere sequence, such as a subtelomere sequence derived from human chromosome 14 or human chromosome 21. When a human chromosome-derived subtelomere sequence is used, a subtelomere sequence derived from the long arm and/or the short arm of an arbitrary chromosome can be used. A subtelomere of a human chromosome is described in detail in terms of a structure, a length, and the like in documents, such as Linardopoulou, E. V et al., Nature, vol. 437, pp. 94-100, 2005; Riethman, H. et al., Chromosome Res., vol. 13, pp. 505-515, 2005; or Mefford, H. C. et al., Nat Rev Genet., vol. 3, pp. 91-102, 2002. Those skilled in the art would be able to select and design an adequate subtelomere sequence based on such documents.

The length of the subtelomere sequence to be added is approximately 1 to 500 kb, preferably approximately 1 to 300 kb, further preferably approximately 1 to 100 kb, further preferably approximately 5 to 60 kb, further preferably 5 to 40 kb, further preferably approximately 25 to 60 kb, and still further preferably approximately 25 to 40 kb. A subtelomere sequence to be used may be the whole or a part of the subtelomeric region in an arbitrary human chromosome. For the HAC vector, preferably part of a subtelomere sequence of approximately 5 to 60 kb is used, from the viewpoint of stability in the cell. A subtelomere sequence can be obtained from an arbitrary human chromosome in accordance with a known technique, such as the use of a site-directed recombinant enzyme system. Preferably, a human chromosome fragment comprises a subtelomere sequence derived from the long arm of a human chromosome, which is the same with or different (preferably the same) from the human chromosome that had been added or bound to the site from which the long-arm distal region had been deleted.

According to a preferable embodiment, a human chromosome 14 fragment comprises a telomere sequence that has been added or bound to the site from which the long-arm distal region has been deleted from human chromosome 14 and a subtelomere sequence derived from the long arm of human chromosome 14. A subtelomere sequence derived from human chromosome 14 is, for example, a more distal region than the 14q32 region of human chromosome 14 (i.e., a region up to the 14q-tel region). Specifically, a subtelomere sequence is the 14q32.33 region of human chromosome 14, a region between AB019439 and AB019437 or a region between AB019438 and AB019437, and preferably a more distal region than AB019437 of human chromosome 14.

According to the other preferable embodiment, a human chromosome 21 fragment comprises a telomere sequence added or bound to a site of human chromosome 21 from which the long-arm distal region has been deleted and a subtelomere sequence derived from the long arm of human chromosome 21. The subtelomere sequence derived from human chromosome 21 is, for example, a more distal region than the 21q22.3 region of human chromosome 21, such as a sequence from NT_011515 to the telomere end within the 21q-tel region. The term "telomere end" refers to a region at the end of a telomere continuing from the chromosome, and this term is synonymous with the term "chromosome end." The telomere sequence naturally comprises a telomere end.

For example, the long-arm and/or short-arm distal regions can be deleted from the human chromosome or a fragment thereof by substitution with a telomere sequence (i.e., telomere truncation) as described in WO 00/10383. Also, the long-arm and/or short-arm distal regions can be deleted from the human chromosome or a fragment thereof by substitution with a telomere sequence. In steps (b) and (c), more specifically, the long-arm and/or short-arm distal regions of the human chromosome or a fragment thereof is substituted with a telomere sequence to add a telomere sequence to the long-arm and/or short-arm regions. More specifically, the long-arm and/or short-arm distal regions can be deleted by, for example, constructing a targeting vector comprising a telomere sequence in a cell that carries a human chromosome, obtaining a clone comprising a telomere sequence inserted into a desired position of a chromosome by homologous recombination, and obtaining a deletion mutant resulting from telomere truncation (see Itzhaki et al., Nature Genet., vol. 2, pp. 283-p 287, 1992; and Brown et al., P. N. A. S., vol. 93, pp. 7125-7130, 1996). The term "a desired position of a chromosome" refers to a site where the target long-arm distal region or short-arm distal region is cleaved, a telomere sequence is substituted and inserted at this position by homologous recombination, and the long-arm distal region or short-arm distal region is then deleted (i.e., telomere truncation). A desired position can be adequately determined by designing a target sequence at the time of construction of a targeting vector.

It is described with reference to, for example, deletion of the long arm sequence from intact human chromosome 14.

A target sequence is designed based on the nucleotide sequence in the 14q region, preferably the 14q11 region, and further preferably between AL391156 and CR383659 (GenBank Accession Number) of the long arm of human chromosome 14, and telomere truncation is induced at a site closer to the telomere side than the resulting target sequence. Thus, the long-arm distal region can be cleaved or deleted in the region where the target sequence has been designed. The target sequence is designed in such a manner that the long arm of human chromosome 14 is deleted at AL391156 or at a more proximal position than AL391156. Specifically, the target sequence is designed based on a nucleotide sequence between AL391156 and CR383659, further preferably between AL512310 and CR383659, further preferably between AL929601 and CR383659, further preferably between AL589182 and CR383659, further preferably between AL589743 and CR383659, further preferably between AL929602 and CR383659, further preferably between AL512624 and CR383659, further preferably between CR383657 and CR383659, and still further preferably at CR383659. When the short-arm distal region is to be deleted, for example, the target sequence can be designed based on a nucleotide sequence in, for example, the 14p region, preferably between the 14p11 region and the 14p12 region, preferably in the 14p11 region, further preferably at RNR2, and still further preferably at PABPCP2 (the online genome database of the National Center for Biotechnology Information (NCBI, U.S.A., http://www.ncbi.nlm.nih.gov/mapview/maps.cgi?ORG=hum&CHR=14&BEG=0.00&ENI) of human chromosome 14. The nucleotide sequence information of the whole long arm region excluding the centromere region of human chromosome 14 is disclosed in the above database (also see FIG. 1). Designing of the target sequence is not limited to the aforementioned regions, and those skilled in the art can adequately design the target sequence in a manner similar to that when preparing a desired HAC vector.

When the long arm sequence is deleted from human chromosome 14 at a region closer to the centromere than SC20, for example, a target sequence is designed based on the nucleotide sequence of AL157858, and telomere truncation is induced at a site closer to the telomere side than the target sequence. Thus, the long-arm distal region can be cleaved or deleted in the region where the target sequence has been designed. When the short-arm distal region is to be deleted, for example, a target sequence can be designed based on a nucleotide sequence in the 14p region, preferably between the 14p11 region and the 14p12 region, further preferably in the 14p11 region, further preferably between the 14p11.1 region and the 14p11.2 region, further preferably in the 14p11.1 region, further preferably RNR2, and still further preferably PABPCP2 (the online genome database of the National Center for Biotechnology Information (NCBI, U.S.A., http://www.ncbi.nlm.nih.gov/mapview/maps.cgi?ORG=hum&CHR=14&BEG=0.00&ENI) of human chromosome 14. Designing of the target sequence is not limited to the aforementioned regions, and those skilled in the art can adequately design the target sequence in a manner similar to that when preparing a desired HAC vector.

Alternatively, the long-arm and/or short-arm distal regions may be preferably deleted from the human chromosome or a fragment thereof in accordance with, for example, Zheng B. et al., Mol Cell Biol., vol. 20, pp. 648-p 655, 2000. That is, a region between two recognition sites for site-directed recombinant enzyme may be deleted, and the long-arm and/or short-arm distal regions are preferably deleted while allowing a subtelomere sequence derived from the starting human chromosome or a fragment thereof as a basic skeleton to remain and adding a telomere sequence. More specifically, in steps (b) and (c), at least two sites of the long-arm and/or short-arm distal regions of the human chromosome or the human chromosome fragment may be cleaved and deleted, so that the long-arm and/or short-arm distal regions can be deleted, and a telomere sequence can be added to the site of the deleted long arm and/or short arm. In steps (b) to (d), at least two sites of the long-arm and/or short-arm distal regions of the human chromosome or a fragment thereof may be cleaved and deleted, so that the long-arm and/or short-arm distal regions can be deleted from the human chromosome or the human chromosome fragment, and the telomere sequence or the telomere sequence and the human chromosome-derived subtelomere sequence can be added to the sites of the deleted long arm and/or short arm.

Specifically, the long-arm and/or short-arm distal regions are deleted by, for example, constructing a targeting vector carrying a recognition site for site-directed recombinant enzyme in a cell comprising the human chromosome or the human chromosome fragment, obtaining a clone comprising a recognition site for site-directed recombinant enzyme inserted into a desired position of the chromosome by homologous recombination, and obtaining a deletion mutant via recombination caused by a site-directed recombinant enzyme. The term "a desired position of the chromosome" used herein refers to a cleavage site of the long-arm distal region and the long-arm proximal region or the short-arm distal region and the short-arm proximal region to be deleted. A site-directed sequence is substituted and inserted into this position by homologous recombination, and the long-arm distal region or short-arm distal region is then deleted. A desired position can be adequately determined by designing a target sequence when constructing a targeting vector.

For example, the long-arm distal region is deleted from the human chromosome or a fragment thereof by inserting a recognition site for site-directed recombinant enzyme into the long-arm distal region and a proximal site, and deleting a region between these two recognition sites by site-directed recombination. According to another embodiment of the present invention, the long-arm and/or short-arm distal regions is deleted, so as to maintain a telomere sequence, or a telomere sequence and a subtelomere sequence which compose a basic skeleton derived from a starting chromosome. For example, the long-arm distal region is deleted from human chromosome 14 by inserting at least two recognition sites for site-directed recombinant enzyme into the long-arm distal region and the proximal site, and deleting a region between these two recognition sites by site-directed recombination. According to a preferable embodiment, such recognition sites for site-directed recombinant enzymes are inserted into a site which is more distal than the 14q32 region of the long-arm distal region of human chromosome 14 and more proximal than the 14q11 region of the long-arm proximal region, and further preferably into a site which is more distal than AB019437 of the long-arm distal region of human chromosome 14 and more proximal than AL391156 of the long-arm proximal region.

The short-arm distal region is deleted from human chromosome 14 by, for example, inserting the recognition sites for site-directed recombinant enzymes into the short-arm distal region and the proximal site, and deleting a region between these two recognition sites by site-directed recombination. According to a preferable embodiment, recognition sites for site-directed recombinant enzymes are inserted into human chromosome 14 at, for example, a more distal site than the 14p region, preferably a more distal site than the 14p12 region, and further preferably a more distal site than the 14p11 region of the short-arm distal region as well as at a more proximal site than the 14p12 region, further preferably a more proximal site than the 14p11 region, further preferably a more proximal site than the 14p11.2 region, further preferably a more proximal site than the 14p11.1 region, and still further preferably at a more proximal site than a position selected from the group consisting of RNR2 and PABPCP2 in the short-arm proximal region.

Further, recognition sites for site-directed recombinant enzymes can be inserted into, for example, a deletion site in AP001657 or a more proximal site than AP001657 of human chromosome 21 or the human chromosome 21 fragment, and further preferably a more proximal site than a deletion position in the 21p11-p 12 region of the short-arm proximal region of human chromosome 21 or the human chromosome 21 fragment.

As described above, a human chromosome fragment with the deleted long-arm distal region and/or short-arm distal region is prepared while maintaining a telomere sequence or a telomere sequence and a subtelomere sequence, and a cell carrying the same is obtained. By providing a telomere sequence or a telomere sequence and a subtelomere sequence at the end of the human chromosome fragment, enhanced expression levels and/or stability in cells can be achieved.

Further, a human chromosome fragment with the deleted long-arm distal region and/or short-arm distal region is prepared, and a cell carrying the same is obtained, as described above. Reduction of the chromosome size can result in enhanced stability in cells. In order to prevent adverse effects on cellular functions, multiplication, and the like of a cell carrying the HAC vector and a cell into which the HAC vector is to be introduced, chromosome regions that may adversely affect can be removed.

Step (e): Insertion of Recognition Site for Site-Directed Recombinant Enzyme

When preparing the HAC vector, a recognition site for site-directed recombinant enzyme is inserted into the human chromosome or the human chromosome fragment. Step (e) may be carried out before, between, or after steps (b), (c), and (d), and the order for performing these steps is not particularly limited. Specifically, the long-arm distal region and/or the long-arm distal region may be deleted from the human chromosome or the human chromosome fragment, the telomere sequence and the subtelomere sequence may be added, and a recognition site for site-directed recombinant enzyme may then be inserted. Alternatively, a recognition site for site-directed recombinant enzyme may be first inserted, the long-arm distal region and/or the long-arm distal region may then be deleted, and the telomere sequence and the subtelomere sequence may be added. Further, the long-arm distal region and/or the long-arm distal region may be first deleted, a recognition site for site-directed recombinant enzyme may be inserted, and the telomere sequence and the subtelomere sequence may then be added.

DNA recombination that takes place at a given recognition site specifically recognized by a given enzyme is known in the art. The present invention involves the use of such enzyme and such recognition site systems, although the types thereof are not particularly limited to those described below. An example of such system that is known is the Cre/loxP system (see, for example, Sauer, B. et al., P. N. A. S., 85: pp. 5166-5170, 1988). Cre is a bacteriophage P1-derived 38 KD protein that belongs to the integrase (Int) family of recombinases. This enzyme recognizes the loxP sequence, which is a recognition site of approximately 34 bp, and causes DNA recombination specifically at this site. Orientation of the loxP sequence is known to cause DNA deletion or translocation between two loxP sequences. Examples of other systems that recognize specific sequences and cause recombination include budding yeast-derived recombinase, FLP (Broach et al., Cell, 21: 501-508, 1980) and phage phiC31-derived integrase (Thorpe et al., P. N. A. S., 95: 5505-5510, 1998). It is reported that DNA recombination would be caused by these enzymes in mammalian cells (Koch et al., Gene, 249: 135-144, 2000; Thyagarajan et al., Mol. Cell. Biol., 21: 3926-3934, 2000).

A recognition site for site-directed recombinant enzyme can be inserted into the human chromosome by known gene recombination techniques, such as homologous recombination. A person skilled in the art can adequately determine the insertion position of a recognition site for site-directed recombinant enzyme while taking, for example, a position of an unnecessary gene into consideration. For example, a recognition site for site-directed recombinant enzyme is inserted into an arbitrary position of the long-arm proximal region or short-arm proximal region of the human chromosome. Examples of such insertion position include a more proximal site than the long-arm proximal region 14q11 of human chromosome 14, further preferably a more proximal site than the deletion site above in AL391156 (GenBank Accession Number) of the long-arm proximal region, and a more proximal site than the deletion site above in the 14p12 region of the short-arm proximal region of human chromosome 14, although the insertion position is not limited thereto. Examples thereof regarding human chromosome 21 include a more proximal site than the 21q11.2 region of the long-arm proximal region, preferably a more proximal site than the 21q11.1 region, preferably a more proximal site than AL16202, a more proximal site than the deletion site in AP001657 (GenBank Accession Number) of the long-arm proximal region or a more proximal site than AP001657, and a site on the short arm of human chromosome 21, and preferably a proximal site than the deletion position in the short-arm proximal region, 21p11.2, although such sites are not limited to these examples.

As the insertion position of foreign DNA described below, for example, the recognition site for site-directed recombinant enzyme can be used. Accordingly, examples of such insertion position include a more proximal site than 14q11 region of the long-arm proximal region of human chromosome 14, further preferably a more proximal site than the deletion site in AL391156 (GenBank Accession Number) of the long-arm proximal region, and a more proximal site than the deletion position in the 14p12 region of the short arm, and preferably the short-arm proximal region of human chromosome 14, although the position is not limited thereto. In the case of human chromosome 21, examples of such position include a more proximal site than the 21q11.2 region of the long-arm proximal region, preferably a more proximal site than the 21q11.1 region, preferably a more proximal site than AL16202, further preferably a more proximal site than the deletion position in AP001657 (GenBank Accession Number) or a more proximal site than AP001657 of the long-arm proximal region, and still further preferably a more proximal site than a deletion position in a short-arm proximal region of human chromosome 21, preferably a deletion position in the 21p11.2 region of the short arm, although the position is not limited thereto.

Subsequently, a reporter gene may be introduced in accordance with a method for introducing foreign DNA described below, and expression thereof may then be confirmed. Thus, whether or not a recognition site, which has been inserted into the human chromosome, is adequate can be examined by confirming that the positioning of a recognition site on the human chromosome.

A single type of a recognition site exemplified above may be inserted alone or in combinations of two or more. Alternatively, a plurality of recognition sites of different systems may be inserted. As described below, the HAC vector comprises a recognition site for site-directed recombinant enzyme. Thus, foreign DNA can be introduced in a site-directed manner, and a position at which foreign DNA is to be introduced can be determined by determining a recognition site. This maintains positions at which foreign DNA is to be introduced constant, and position effects can be avoided. Also, a procedure for foreign DNA introduction becomes simplified. Further, insertion of a plurality of recognition sites of different systems enables sequential insertion of a plurality of foreign DNAs. Use of recognition sites for a plurality of types of site-directed enzymes in combination enables introduction of foreign DNA with the utilization of a recognition site for a type of site-directed enzyme, followed by deletion/removal of unnecessary genes, such as drug-resistant genes, of the vector with the utilization of a recognition site for a different type of site-directed recombinant enzyme.

The HAC vector thus-prepared by modification of a human chromosome may comprise, inserted therein, a sequence or element that is generally inserted when constructing a vector, such as a promoter or drug-resistant gene, in addition to a recognition site for site-directed recombinant enzyme. Also, a sequence or element, which is involved in regulation of gene expression, cell function, tissue function, ontogenesis, and/or biofunction, such as an insulator (e.g., JP Patent Publication No. 2006-94849 A), a matrix attachment region (MAR), or a genomic region of a human or other organism species, may be inserted. Further, a gene that controls a cell life, such as telomerase, a suicide gene, such as thymidine kinase, and/or a gene involved in regulation of gene expression, cell function, tissue function, ontogenesis, and/or biofunction, may be inserted. Such sequence, element, and/or gene can be inserted into a desired position of the HAC vector by homologous recombination as described above.

Further, the present inventors had performed long-term subculture of the cells carrying the HAC vector prepared in the above manner in a medium containing no selection agent and tested the HAC vector retention by the FISH method with the elapse of time. As a result, they confirmed that the HAC vector could be retained stably in a host cell such as a CHO cell and that such stability was significantly enhanced from that of the conventional 21HAC vector. They also confirmed that dropout of the HAC vector is small and the introduced HAC vector could be retained stably without excessive increase/decrease in copy number during subculture.

Surprisingly, use of the HAC vector enables high-level expression of foreign DNA without being influenced by inhibition of foreign gene expression via the telomere position effects (TPE), which were reported in the past, even when foreign DNA was inserted into a site in the vicinity of the telomere sequence. The term "vicinity" used herein refers to a region of approximately 1 to 500 kb from the telomere end toward the centromere, and such region is preferably of approximately 1 to 300 kb, further preferably approximately 1 to 100 kb, further preferably approximately 5 to 60 kb, further preferably 5 to 40 kb, further preferably approximately 25 to 60 kb, and further preferably approximately 25 to 40 kb.

2. Introduction of Foreign DNA into HAC Vector (Step (f))

When preparing the HAC vector, step (f) of inserting foreign DNA in the presence of a site-directed recombinant enzyme can be carried out, so that foreign DNA can be introduced into the HAC vector. Step (f) is to be carried out following step (e); however, the order for carrying out steps (b), (c), and (d) in connection with step (f) is not particularly limited, and step (f) can be carried out before, between, or after steps (b), (c), and (d). It should be accordingly noted that the order of steps (b) to (f) is not limited to the order described herein.

The term "foreign DNA" refers to DNA that is introduced into a target cell from the outside and it is DNA encoding a gene and other functional sequence. In the present invention, foreign DNA to be introduced is not particularly limited, provided that such DNA encodes a gene, expression of which is desired for the purpose of material production, disease treatment, functional modification, or functional analysis, and other functional sequence. The term "other functional sequence" refers to a sequence that functions for gene expression, and examples thereof include promoter, enhancer, and signal sequences.

Foreign DNA can be introduced with the use of a site-directed recombinant enzyme system. For example, a targeting vector carrying the loxP sequence, which is a recognition site for the Cre enzyme, and foreign DNA is constructed. Subsequently, the Cre enzyme is expressed in a cell carrying the HAC vector (a human chromosome 14 fragment), and a region sandwiched between the loxP sequence and the telomere sequence is subjected to site-directed recombination with the targeting vector, so as to insert foreign DNA into the HAC vector (Kuroiwa et al., Nature Biotech., 18: 1086-1090, 2000).

Cyclic DNA that carries a recognition site for site-directed recombinant enzyme (the loxP sequence) can be inserted into the HAC vector. Thus, DNA cloned by an existing vector such as a plasmid, BAC, or PAC vector utilizing an *E. coli* host or a cyclic YAC vector utilizing a yeast host can be inserted. Since the vector has been prepared based on a human chromosome, the size of foreign DNA which can be introduced into the HAC vector is extended to 100 kb. In addition to cDNA that has been incorporated into a plasmid vector used for expression experiments in the past, genomic DNA comprising a gene expression regulatory region can be introduced.

As described above, the insertion position of foreign DNA can be the recognition site for site-directed recombinant enzyme, for example. Examples of such insertion position include, but are not particularly limited to, a more proximal site than the 14q11 region of the long-arm proximal region, further preferably a more proximal site than the deletion position of AL391156 (GenBank Accession Number) of the long-arm proximal region, and preferably a more proximal site than the deletion position within the 14p12 region of the short-arm proximal region in a region of the short arm of human chromosome 14. Examples of such insertion position on human chromosome 21 include, but are not particularly limited to, a more proximal site than the 21q11.2 region of the long-arm proximal region, preferably a more proximal site than the 21q11.1 region, preferably a more proximal site than AL16202, further preferably the deletion position of AP001657(GenBank Accession Number) of the long-arm proximal region or a more proximal site than AP001657, and preferably a more proximal region than the deletion position of the 21p11.2 region of the short-arm proximal region in a region of the short arm. Also, use of a plurality of recognition sites for site-directed recombinant enzymes enables removal of an unnecessary drug-resistant gene expression unit, a DNA element, and the like from the HAC vector. When removing a Neo-resistant gene unit located downstream of the foreign gene expression unit introduced using the Cre-loxP system, for example, a construct, which comprises a recognition site different from loxP (i.e., the FRT sequence) introduced downstream of the foreign gene expression unit of the targeting vector carrying foreign DNA and downstream of the Neo-resistant gene unit of the HAC vector, is constructed. The FLPe enzyme is expressed in a cell that carries the foreign DNA-introduced HAC vector, so that the region of the Neo-resistant gene unit sandwiched with the FRT sequence can be cleaved and removed by site-directed recombination (see, for example, FIG. 60).

Such drug-resistant gene can be removed when preparing a human artificial chromosome vector based on an arbitrary human chromosome, without being limited to human chromosomes 14 and 21. Accordingly, the present invention relates to a method for preparing a human artificial chromosome vector, including foreign DNA comprising the following steps:

(a) obtaining a cell that carries a human chromosome or a human chromosome fragment, (b) deleting the long-arm and/or short-arm distal regions of the human chromosome or the human chromosome fragment;

(c) adding a telomere sequence or a telomere sequence in combination with a subtelomere sequence at a site(s) where the long-arm and/or short-arm regions are deleted;

(d) inserting at least two types of recognition sites for site-directed recombinant enzymes into the human chromosome or the human chromosome fragment;

(e) inserting foreign DNA into the human chromosome or the human chromosome fragment in the presence of a site-directed recombinant enzyme; and (f) removing a drug-resistant gene from the human chromosome or the human chromosome fragment in the presence of a site-directed recombinant enzyme different from that used in step (e).

Figure 21:
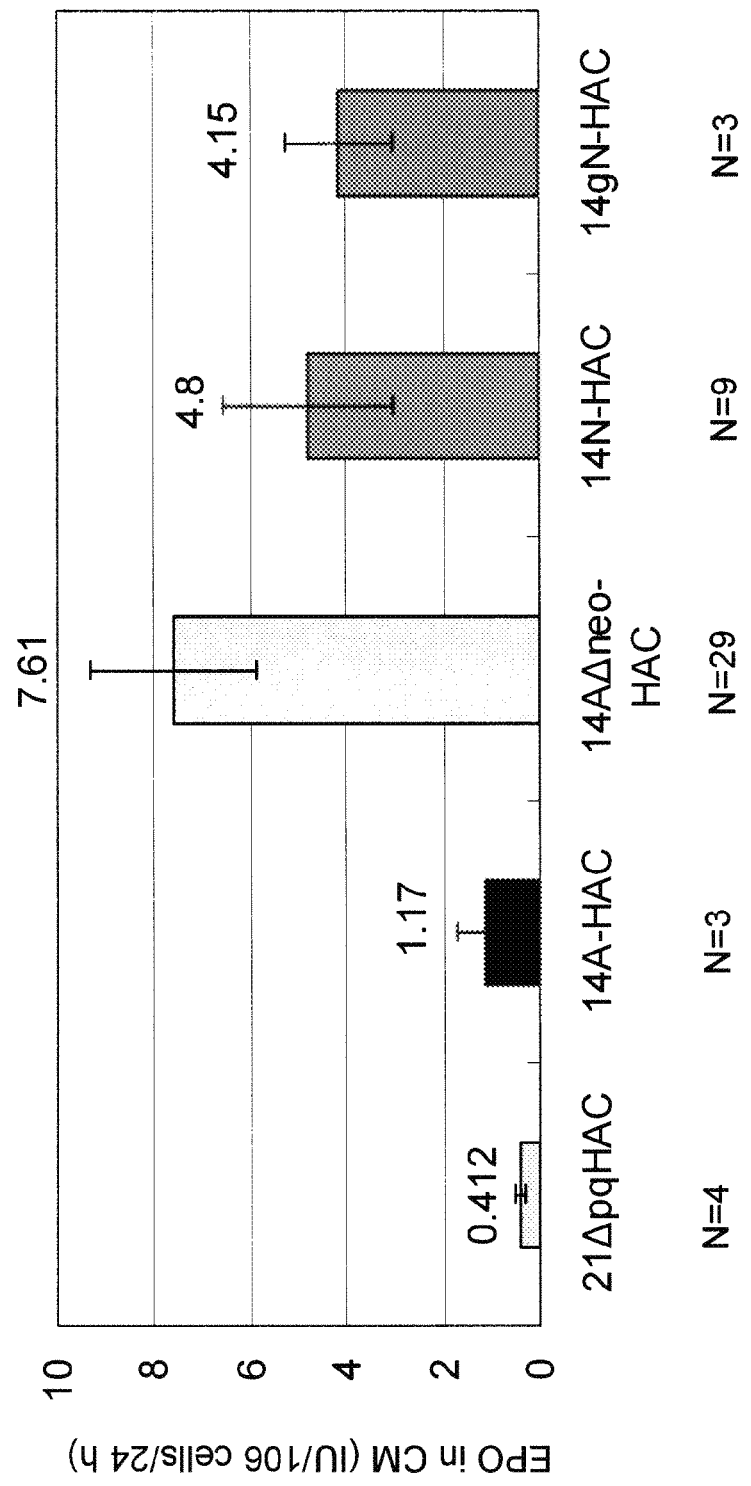
FIG. 21 shows expression of hEPO genes in the human normal fibroblast, HFL-1, into which the hEPO-14A/N/gNΔqHAC vector has been introduced.

The human artificial chromosome vector comprising foreign DNA prepared in accordance with the above method lacks a drug-resistant gene and it is thus capable of expressing foreign DNA at high levels (see, for example, FIG. 21 concerning a human chromosome 14 vector).

According to a conventional method for gene introduction utilizing a cDNA forced expression vector, side effects, such as cytotoxicity resulting from overexpression or growth inhibition, may occur, and cell lines in which transgenes are constitutively expressed cannot be often obtained. In order to overcome such drawbacks and artificially regulate expression levels while maintaining physiological expression patterns, it is preferable that a gene expression induction system utilizing tetracycline or the like be applied. To this end, the features of the HAC vector such that a size of an insert that can be inserted is large and a given copy gene number can be stably retained are suitable.

Tissue-specific/physiological gene expression is regulated at stages of transcription from the gene-encoding genomic region and revision, extranuclear transportation, and translation of a transcript. It is known that tissue-specific isoforms are expressed because of a plurality of promoters for a single gene which bring different transcription origins or variation in splicing. Cloned cDNA is just a variant of a plurality of transcripts derived from a single gene. In order to reproduce physiological gene expression, a gene region comprising the control sequence is preferably introduced as genomic DNA. Use of the HAC vector is suitable for such purposes.

According to a human genome project, genomic DNA was isolated as a BAC clone, and the nucleotide sequence thereof was determined. Thus, nucleotide sequences are registered in terms of BAC in an open database, such as GenBank. An example of a means for gene function analysis is preparation of a transgenic mouse. Insertion of BAC into the HAC vector platform enables gene expression analysis under conditions in which the insertion positions are always the same. Since many BAC vectors comprise the loxP sequence, a system that negatively selects insertion into the HAC vector may be used to easily insert the BAC having known nucleotide sequences into the HAC vector as a cassette.

In addition to the above, there are methods for introducing foreign DNA into the HAC vector and advantages in such introduction, and such methods and advantages are described below.

(1) Introduction of Partial Chromosome Fragment by Reciprocal Translocation

Site-directed recombination (e.g., site-directed recombination with the loxP sequence by the Cre enzyme) causes an insertion reaction in the case of a linear chromosome and a cyclic insert (i.e., foreign DNA); however, reciprocal translocation takes place between linear chromosomes. With the utilization thereof, a chromosome fragment of Mb or greater that cannot be cloned into a cyclic insert can be introduced into the HAC vector (Kuroiwa et al., Gene Ther., 9: 708-712, 2002).

(2) Method of Insert Selection

In the methods described in the examples of the present description, foreign DNA is inserted into the HAC vector by positive selection, which utilizes reconstruction of a drug-resistant gene as an indicator (see WO 00/10383 regarding positive selection of a recombinant). Alternatively, a vector comprising foreign DNA inserted therein can be obtained by negative selection of, for example, the thymidine kinase/ ganciclovir system. In such a case, cyclic DNA to be inserted may selectively comprise a recognition site for site-directed recombinant enzyme. Since a BAC library used for the genome project comprises the loxP sequence, establishment of such negative selection system would enable easy insertion of a genomic clone having a known sequence into the HAC vector.

(3) Insertion of a Plurality of Inserts

The loxP sequence that is preferably used in the present invention is a wild-type sequence derived from P1 phage, and insertion of a cyclic insert into the loxP sequence of the HAC vector by the Cre enzyme is reversible. In the examples of the present invention, Cre enzymes were expressed transiently, acquisition of drug resistance was employed as the indicator to select a site-directed recombinant, and a constitutive insert was then obtained. When a cyclic insert was inserted, two loxP sequences remained on the HAC vector. This may cause a reverse reaction (i.e., cleavage of a cyclic insert) upon re-expression of Cre enzymes, and further modification of the HAC vector, such as secondary insertion of an insert, becomes difficult. Meanwhile, there is a report such that the reaction orientation and reaction specificity can be limited in accordance with a combination of mutated loxP sequences, which had been subjected to nucleotide substitution (Hoess et al., Nucleic Acids Res., 14:2287-2300, 1986; Araki et al., Nucleic Acids Res., 25: 868-872, 1997; Lee et al., Gene, 216:55-65, 1998). Use of such mutated loxP sequences enables construction of a system that successively inserts a plurality of cyclic inserts without causing the reverse reaction described above.

(4) Copy-Number-Dependent Expression Regulation

According to a report of analysis of the correlation between the copy number of genes randomly inserted into host chromosomes using α-globin gene transgenic mice and the mRNA expression level (Sharpe et al., Proc Natl Acad Sci USA, 90: 11262, 1993), no correlation is observed between the expression level and the copy number of transgenes. This is considered to result from a phenomenon that is referred to as a position effect in which the expression levels of transgenes significantly differ due to transgenic animal lineages and expression that is inversely proportional to the copy number of transgenes occurs, and such phenomenon frequently occurs when introducing genes into transgenic animals. There is also a report regarding transgenic mice, in which a foreign DNA insertion position is designated at the recognition site for site-directed recombinant enzyme, which had been introduced into the host chromosome in advance (e.g., the loxP site), and a target DNA unit is introduced from a plasmid vector by site-directed recombination (e.g., the Cre-loxP system) (Garrick et al., Nature Genet., 18: 56-59, 1998), for the purpose of comparison while eliminating position effects of transgenes. However, copy-number-dependent expression regulation was not attempted herein.

While copy-number-dependent tyrosinase expression was observed in the introduced genomic region in a transgenic mouse, which had been prepared with the use of YAC comprising a tyrosinase genomic region introduced therein (Schedl et al., Nature, 362: 258-261, 1993), influence of a position effect is considered to be insignificant because of the use of a genome comprising a physiological expression regulation region. Thus, expression is not caused by multicopy of artificial gene expression units containing no physiologically regulation regions, unlike the present invention. Episome vectors are present independently from host chromosomes. Althogh the foreign DNA insertion position has already been determined, episome vectors cannot yet strictly regulate the copy number thereof in cells (Morlino et al., ppl Environ Microbiol., 65:4808-4013, 1999; Cooper et al., Proc Natl Acad Sci U.S.A., 94: 6450-6455, 1997).

In the present invention, multicopies of allogeneic and/or heterogenic target gene expression units are coupled and parallelly arranged, and the resultants are introduced into a predetermined site of the HAC vector (e.g., the loxP site). Thus, expression control can be carried out in a copy-number-dependent manner, without mutating a host chromosome.

Accordingly, the method of the present invention enables introduction of multicopies of target genes into desired cells as foreign DNAs and expression of the target genes in the cells in a copy-number-dependent manner. The method also enables copy-number-dependent expression of the target genes, which was difficult in the past, without influence of the position effect in transgenic animals prepared with the use of such cells.

3. Introduction of HAC Vector into Cell

The HAC vector or the HAC vector comprising foreign DNA that is retained in a cell can be transferred to another cell. Such cell is not particularly limited, and an example is an animal cell (e.g., a mammalian cell). In the present invention, it is preferable to use a Chinese hamster ovary (CHO) cell to which an undamaged human chromosome can be introduced (see WO 00/10383). A CHO cell is known to efficiently form a microcell (e.g., Koi et al., SCIENCE 260: 361-364, 1993), and thus, the HAC vector can further be transferred from the CHO cell to another cell (i.e., a cell other than CHO cell). According to the present invention, the HAC vector can be introduced into a multipotent cell. The term "multipotent cell" used herein refers to a cell that can be differentiated into specified cells or tissue upon a soecified treatment. Examples are cells that can be differentiated into two or more types of cells or tissue of a chimera animal via injection into a host embryo, formation of an aggregate embryo, or the like. Specific examples include embryonic stem cell (ES cell), embryonic germ cells (EG cells), embryonic carcinoma cells (EC cells), and germ stem cells (GS cells). Further examples include cells that can be differentiated into bone cells, cartilage cells, or adipose cells by culturing in an induction medium comprising, for example, a growth factor (e.g., a transforming growth factor (TGF)) added thereto. A specific example is a somatic stem cell (e.g., a mesenchymal cell).

The term "embryonic stem cell" used herein is also referred to as an "ES cell," and the term refers to a cultured cell derived from an early embryo, which can grow remaining undifferentiated (i.e., totipotent). Specifically, the embryonic stem cell is an established cell line which can keep growing with remaining undifferentiated during culture of an internal cell mass, which is an undifferentiated stem cell residing inside the blastocyst of an animal early embryo. The term "embryonic germ cells" is also referred to as an "EG cell," and the term refers to a cultured cell derived from a primordial germ cell, which has the ability substantially equivalent to that of the embryonic stem cell. The embryonic germ cell is an established cell line which can keep growing with remaining undifferentiated during culture of a primordial germ cell obtained from an embryo several days to several weeks after fertilization, for example, about 8.5 days after fertilization in the case of a mouse.

A cell that serves as a material for gene/cell therapy or tissue regeneration therapy targeting humans is preferably a normal cell instead of an immortalized cell, from the viewpoint of safety, i.e., for the purpose of prevention of canceration. In the present invention, the HAC vector derived from a human chromosome was found to be capable of introduction into a human normal fibroblast (HFL). The method of the present invention also enables introduction of a human chromosome 14-derived fragment or a human chromosome-derived HAC vector into a human normal somatic cell other than a fibroblast. Further, the human chromosome-derived HAC vector prepared in accordance with the method of the present invention can be introduced into a human normal somatic cell without being limited to a human chromosome.

The HAC vector can be introduced into a cell by the microcell mediated chromosome transfer method. The microcell mediated chromosome transfer method can be carried out in a manner described in "1. Preparation of a human artificial chromosome (HAC) vector" above.

Also, the HAC vector can be introduced into a cell by somatic cell nuclear transplantation. Somatic cell nuclear transplantation can be carried out in a manner described in Kuroiwa, Y. et al., Natute Biotech, vol. 20, pp. 889-894, 2002.

The human chromosome (HAC) vector can be introduced into a cell before, between, or after a step of modifying a cell carrying a human chromosome or chromosome fragment that was initially prepared to a human chromosome.

4. Applications of HAC Vector

An object of the present invention is to provide a basic tool, i.e., a vector, and a technique using the same. The present invention is deduced to make pervasive effects on very extensive areas from academic research to industry. The HAC vector is characterized in that: (i) it is independently maintained without being inserted into a host chromosome (free of a fear of mutation or canceration of a host gene); (ii) a given copy number thereof is stably retained for a long period of time (free of a fear of overexpression or quenching of expression); and (iii) the length of DNA that can be introduced is not limited (a gene or a plurality of genes containing a DNA element that assures normal expression regulation can be introduced simultaneously). These characteristics are deduced to realize many applications, which could not be attained with the use of conventional vectors. Major examples of applications of the HAC vector include, but are not limited to, (i) a vector used for analyzing gene functions in a cultured animal cell, (ii) a vector used for gene therapy of a human disease, (iii) a vector used for introducing a gene into a human organ stem cell or embryonic stem (ES) cell, and (iv) a vector used for preparing a transgenic animal (e.g., preparation of an animal model of a human disease, humanization of a given gene in combination with a KO animal). Hereafter, examples of applications of the HAC vector: (1) introduction of foreign DNA into a recipient cell; (2) preparation of a cell that expresses foreign DNA; (3) preparation of a protein; (4) a vector for analyzing gene functions; (5) a vector used for gene introduction into a stem cell; (6) a vector for preparing a culture feeder; (7) a vector used for treating human disease; and (8) a vector used for preparation of a transgenic animal, are described.

(1) Introduction of Foreign DNA in a Recipient Cell

The HAC vector is capable of inserting foreign DNA in a cell or capable of introducing the HAC vector comprising foreign DNA to the other cell. Thus, foreign DNA can be introduced into a desired recipient cell. Introduction of foreign DNA into a recipient cell comprises, for example, the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting at least one recognition site for site-directed recombinant enzyme into the human chromosome or the human chromosome fragment;

(f) inserting foreign DNA into the human chromosome or the human chromosome fragment in the presence of a site-directed recombinant enzyme;

(g) preparing a microcell from the donor cell that carries the human chromosome or the human chromosome fragment;

(h) allowing the microcell to be fused to the recipient cell; and (i) confirming the introduction of foreign DNA into the fused recipient cell.

Steps (a) to (f) can be carried out as described above, and the order for carrying out these steps is not limited.

In steps (g) and (h), a human chromosome or a fragment thereof is transferred from a donor cell carrying the same to a recipient cell by the microcell mediated chromosome transfer method. The human chromosome or a fragment thereof to be introduced can be of before, between, or after modification thereof in steps (b) to (f). In step (f), accordingly, before insertion of foreign DNA into the human chromosome or a fragment thereof, the human chromosome or a fragment thereof may be transferred from a donor cell carrying the same to a recipient cell by the microcell mediated chromosome transfer method, for example. Thereafter, a procedure for insertion of foreign DNA (i.e., step (f)) is carried out in a recipient cell, and the human chromosome or a fragment thereof comprising foreign DNA inserted therein can be retained in a recipient cell. These steps can be carried out in a different order, and the order for carrying out steps (f) to (h) is not limited to the above.

The microcell mediated chromosome transfer method can be carried out in a manner described in "1. Preparation of a human artificial chromosome (HAC) vector." A recipient cell used herein is not particularly limited, and an animal cell, and particularly a mammalian cell, such as a mouse or human cell, is preferable. Also, the multipotent cells described above, such as embryonic stem cells (ES cells), interstitial stem cells, and tissue stem/precursor cells, can be used as recipient cells.

In subsequent step (i), whether or not a recipient cell comprises foreign DNA transferred (transferred) therein is confirmed. Such confirmation can be made by a method known in the art, such as Southern blot analysis using probes corresponding to restriction enzyme sites of foreign DNA, so as to confirm introduction of foreign DNA.

Use of the HAC vector enables introduction and stable retention of foreign DNA of a greater size in a cell.

(2) Preparation of Cell Expressing Foreign DNA

As described above, the HAC vector is capable of inserting foreign DNA in a cell or capable of transferring the HAC vector comprising foreign DNA to another cell. Thus, a cell expressing foreign DNA can be prepared. Preparation of a cell expressing foreign DNA comprises, for example, the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting a recognition site for site-directed recombinant enzyme into the human chromosome or the human chromosome fragment;

(f) inserting foreign DNA into the human chromosome or the human chromosome fragment under the expression of a site-directed recombinant enzyme;

(g) preparing a microcell from the donor cell that carries the human chromosome or the human chromosome fragment;

(h) allowing the microcell to fuse to the recipient cell; and (i) selecting a cell that expresses foreign DNA in the fused recipient cell.

Steps (a) to (h) can be carried out as described above, and the order for carrying out these steps is not limited.

In step (i), expression of foreign DNA is observed in a recipient cell, and a cell expressing foreign DNA is selected. Foreign DNA expression can be confirmed by a method known in the art, and an example of such method is a Northern blot technique involving the use of a probe corresponding to foreign DNA. Alternatively, a protein encoded by foreign DNA may be detected using an antibody reacting with such protein or a means that is capable of detecting activity of such protein to confirm expression of foreign DNA.

Use of the HAC vector enables preparation of a cell that expresses foreign DNA of a greater size.

(3) Preparation of Protein

Use of the HAC vector enables introduction of foreign DNA into a cell or preparation of a cell that expresses foreign DNA, as described above. Thus, a protein encoded by such foreign DNA can be prepared. Preparation of a protein comprises, for example, the following steps:

(a) obtaining a donor cell that carries a human chromosome or a human chromosome fragment;

(b) deleting the long-arm and/or short-arm distal regions of the human chromosome or the human chromosome fragment;

(c) adding a telomere sequence at a site(s) where the long-arm and/or short-arm regions are deleted;

(d) adding a subtelomere sequence at a site(s) where the long-arm and/or short-arm regions are deleted;

(e) inserting a recognition site for site-directed recombinant enzyme into the human chromosome or the human chromosome fragment;

(f) inserting foreign DNA encoding a protein into the human chromosome or the human chromosome fragment under the expression of a site-directed recombinant enzyme;

(g) preparing a microcell from the donor cell that carries the human chromosome or the human chromosome fragment;

(h) allowing the microcell to be fused to the recipient cell;

(i) culturing the fused recipient cell in a medium; and (j) sampling the protein from the resulting culture product.

Steps (a) to (h) can be carried out as described above, and the order for carrying out these steps is not limited.

In step (i), the recipient cell fused in step (h) is cultured in a medium. A medium used for culturing the recipient cell may be a naturally-occurring or synthetic medium, provided that such medium comprises a carbon source, a nitrogen source, an inorganic salt, and the like and it is capable of efficient culture of the recipient cell. A person skilled in the art can optionally select a suitable medium and prepare a medium by adequate modification. Also, aerobic conditions, such as shake culture or aeration agitation culture, temperature, pH level, culture duration, and other conditions should be adequately determined.

After culture, a protein is sampled from the resulting culture product as described in step (j). The term "culture product" refers to either a cultured cell or a fragmented cell, in addition to a culture supernatant. After the completion of culture, a protein can be sampled from the culture product by convensional techniques of protein purification for example. When the culture product is secreted in a cell, for example, a cell is subjected to ultrasonic fragmentation, grinding, pressurized fragmentation, or the like, via conventional techniques to extract a protein. A protease inhibitor is added according to need. When the culture product is secreted in a culture supernatant, a culture medium can be used. This solution is then subjected to filtration, centrifugation, and other means to remove a solid component, and a nucleic acid is then removed by protamine treatment or other means, according to need.

Subsequently, ammonium sulfate, alcohol, acetone, and the like are added thereto for fractionation, a precipitate is sampled, and a solution of crude protein is obtained. The resulting protein solution is subjected to various chromatography techniques, electrophoresis, and the like to obtain a purified enzyme sample. For example, fractionation techniques, such as gel filtration involving the use of Sephadex, ultra gel, or bio gel, ion-exchange chromatography, electrophoresis using polyacrylamide gel, affinity chromatography, reversed-phase chromatography, or other means, are adequately selected or combined to obtain the target purified protein. It should be noted that these culture or purification methods are mere examples, and techniques are not limited thereto.

In the present invention, a protein to be prepared is not particularly limited, provided that preparation thereof is desired. Examples include erythropoietin (EPO), thrombopoietin (TPO), a blood clotting factor, a von Willebrand factor (vWF), dystrophin, dopamine synthetase, insulin, insulin-like growth factor (IGF), insulin-like growth factor binding protein (IGFBP), antibody, telomerase, granulocyte colony-stimulating factor, granulocyte-macrophage colony-stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, α-1 antitrypsin, ornithine transcarbamylase, purine nucleotide phosphorylase, growth inhibitory factor (GIF), tumor necrosis factor (TNF), leukaemia inhibitory factor (LIF), oncostatin M, Flt3 ligand (Flt3L), stroma-derived factor (SDF), stem cell factor (SCF), fibroblast growth factor (FGF), epithelial growth factor (EGF), vascular endothelial growth factor (VEGF), angiopoietin, nerve growth factor (NGF), bone morphogenetic protein (BMP), activin, transforming growth factor (TGF), Wnt, R-spondin, monoclonal antibody, oligoclonal antibody, and polyclonal antibody. Sequence information of a gene encoding such target protein (i.e., foreign DNA) can be obtained with the utilization of for example, a public gene database.

(4) Vector Used for Gene Function Analysis

Foreign DNA that has been inserted into the HAC vector is expressed in a cell in a copy-number-dependent and stable manner. Thus, the HAC vector can be used for analyzing gene functions.

A technique of inhibiting expression of a target gene by expressing double-stranded RNA (dsRNA) comprising sequences complementary to part of the nucleotide sequence encoding the target gene, i.e., RNA interference, is known (e.g., see Elbashir et al., Nature, 411:494-498, 2001; McCaffrey et al., Nature, 418: 38-39, 2002; and Shinagawa, T. et al., Genes & Development, 17: 1340-1345, 2003 regarding short-strand interference RNA (siRNA)). DNA encoding dsRNA may be introduced into the HAC vector with the gene expression induction system for conditional inhibition of functions of the target gene. Instead of the gene expression induction system, a genomic region may be utilized to inhibit functions at a tissue-specific/physiological site. Also, functional analysis of microRNA (miRNA) in the genome is feasible.

When analyzing effects of target molecules, the dose-dependence of the target molecule can be used as an indicator to perform analysis. In this technique, the copy number of the expression unit of genes encoding the target molecules may be changed and introduced into the HAC vector according to the method of the present invention, the resultant is introduced into a cell, including tissue and organisms, and dose-dependency can be analyzed based on copy-number-dependent regulation in such cell. Also, an expression induction system or a genomic region may be used for regulation of gene expression so as to perform conditional or tissue-specific/physiological functional analysis.

(5) Vector Used for Introducing Gene into Stem Cell

The HAC vector prepared by the method of the present invention can be used as a vector for introducing a gene into an embryonic stem (ES) cell or a mesenchymal stem cell (MSC). The HAC vector can stably remain in the ES cell or MSC for a long period of time.

Also, the HAC vector could be retained stably in tissue or cells that are induced to differentiate from ES cells into which the HAC vector prepared by the method of the present invention has been introduced.

In recent years, pluripotent cells derived from stem cells and bone marrow of various tissue have been identified (Yokota et al., Experimental Medicine (extra edition), vol. 19, No. 15, 2001, Yodosha Co., Ltd.; Okano et al., Experimental Medicine (extra edition), vol. 21, No. 8, 2003, Yodosha Co., Ltd.; Li et al., Nature Med., online: 31 Aug. 2003, doi: 10.1038/nm925). The HAC vector prepared by the method of the present invention can be used as a vector for introducing a gene into a pluripotent stem/precursor cell derived from a tissue stem/precursor cell, such as bone marrow, blood, nerve, muscle, liver, pancreas, skin, or inner ear cell.

When clinical application of ES cells, MSC, and tissue stem/precursor cells to humans is considered, it is required that cells in amounts necessary for therapy be amplified and provided in a differentiated state of interest. In the past, it was not easy to selectively mass-amplify stem cells while retaining multipotency, and such amplification is still an object to be attained (Hino et al., Experimental Medicine, vol. 19, No. 15, extra edition, 10, 2001, Yodosha Co., Ltd.). When hematopoietic stem cells or neural stem cells are sampled from biological tissue and cultured, for example, precursor cells or mature cells differentiated from stems cells are simultaneously amplified, in addition to stem cells. Thus, such cells are not suitable for clinical applications (Hideyuki Okano, Experimental Medicine, vol. 19, No. 15 (extra edition): 80-90, 2001, Yodosha Co., Ltd.).

In the present invention, the HAC vector into which DNA encoding factors associated with retention of multipotency, for example, transcription factors, such as activated Stat3, Oct-3/4, or Nanog, in the case of mouse ES cells (Niwa et al., Genes Dev., 12: 2048-2060, 1998; Matsuda et al., EMBO J., 18: 4261-4269, 1999; Niwa et al., Nature Genet., 24: 372-376, 2000; Mitsui et al., Cell, 113: 631-642, 2003; Chambers et al., Cell, 113:643-655, 2003) has been introduced, is prepared and introduced into the stem cells. Thus, the HAC vector can be used for easily amplifying stem cells while retaining multipotency without varying a host chromosome.

When regulating stem cell differentiation, it is important to control expression levels of molecules involved. For example, undifferentiated state is maintained when the physiological expression level is adjusted to 100% via differentiation regulation by Oct-3/4 in the mouse ES cell. When the expression level is 50% or lower, however, stem cells are differentiated to trophectoderms. At the expression level of 150% or higher, stem cells are differentiated to primitive endoderms (Niwa et al., Nature Genet., 24: 372-376, 2000). When differentiation is to be regulated in accordance with such changes in expression levels, the gene expression ON/OFF induction system (e.g., an expression induction system by tetracycline) can be introduced into the HAC vector prepared by the method of the present invention, so that the expression level can be strictly controlled.

Also, the gene expression ON/OFF induction system (e.g., an expression induction system by tetracycline) may be introduced into the HAC vector prepared by the method of the present invention in combination with a plurality of differentiation inducers, so as to switch the multipotent state with the differentiated state.

When tissue regeneration is intended with the use of stem cells, transplanted cells or regenerated tissue derived from a donor serve as part of a recipient for a long period of time (desirably over a lifelong period). Therefore, operation that might impart causes that would induce deviation from physiological regulation, such as canceration, to donor cells (e.g., genetic mutation) is preferably avoided as much as possible. Since the HAC vector can be present independently of a host chromosome, gene introduction can be performed without mutating a host chromosome. As described in the examples of the present description, the HAC vector can be stably present in a human cell, and it can thus stably express the target molecule for a long period of time.

In accordance with the method of the present invention, the HAC vector into which DNA comprising the genomic sequence, which comprises a genomic region of a gene physiologically expressed in differentiated tissue or a tissue-specific expression regulatory region, and the target gene fused thereto has been introduced is prepared, and a stem cell into which the HAC vector has been introduced is used. Thus, a target molecule can be expressed in the regenerated tissue in a physiological/tissue-specific manner.

After a stem cell that carries the HAC vector prepared by the method of the present invention is induced to differentiate, the HAC vector may occasionally become unnecessary if expression of the introduced gene is unnecessary. After differentiation is induced, the HAC vector-eliminated clones can be selected by using, for example, drug-resistance via selection culture as an indicator, although the method of selection is not particularly limited. Thus, unnecessary HAC vector can be eliminated.

(6) Vector Used for Preparing Culture Support Feeder Cell

As a method of cell culture, a method wherein target cells are plated in feeder cells of a culture support in which adhesive cells are spreaded at the bottom of the incubator and subjected to coculture is known (the Japanese Biochemical Society (ed.), New biochemical experiment course 14; Development, differentiation, and aging, 1992, TOKYO KAGAKU DOZIN CO., LTD.). When growth of hematopoietic precursor cells is intended, for example, necessary factors, such as SCF, Flt3L, TPO, IL-6, and sIL-6R, are prepared as recombinant proteins, and such proteins are added to the culture medium and then cultured (Ueda et al., J Clin Invest., 105: 1013-1021, 2000). Genes that have been added to the culture can be introduced into culture support feeder cell by a conventional technique. However, it is considered to be difficult to regulate the desired expression levels of all factors and supply them because of mutation/position effects resulting from random insertion into a host chromosome, inactivated expression, and attenuated expression of downstream genes because of parallel arrangement of multicopy expression units. The HAC vector into which all (or some) DNAs encoding such necessary factors have been introduced may be prepared by the method of the present invention, and the resulting HAC vector may then be introduced into the culture support feeder cell. Thus, all the necessary factors can be easily supplemented by coculture without a need of later addition of recombinant proteins or the like. Also, use of a gene expression induction system enables conditional expression control of such factors.

(7) Vector Used for Treating Human Diseases

Various types of virus or nonvirus vectors used for treating human diseases have been heretofore researched, and various problems, such as elicitation of immune reactions, size limitation of DNA to be introduced, mutation of a host chromosome, low introduction efficiency, low expression efficiency, and difficulty in expression level control (Yasufumi Kaneda, Clinical Immunology, vol. 39: 551-558, 2003, Kagaku-Hyoronsha Co., Ltd., Keiya Ozawa (ed.), Gene therapy, 1997, Yodosha, Co., Ltd.), have been pointed out. Such vectors are commonly required to achieve the same object; i.e., regulation of a desirable expression level with a desirable timing."

Examples of strategies for gene/cell therapy using the HAC vector include (i) supplement of enzymes or proteins that are primarily deficient, (ii) symptomatic therapy for supplementing metabolic products that are secondarily decreased, (iii) addition of new functions to cells to enhance cell survival (e.g., the HAC vector is capable of regulating physiological/tissue-specific gene expression by introducing the genome in tissue regeneration using modified cells. This enables prevention of side effects such as functional disorder resulting from overexpression or underexpression), and (iv) inhibition of degenerative disease that advances through a gain-of-function mechanism (e.g., GDNF supplementation on Parkinson's disease).

More specifically, the HAC vector can be used as a vector for treatment of human diseases, the HAC vector into which therapeutic foreign DNA has been introduced is introduced into the cells, such cells are prepared in the form of a pharmaceutical composition for administration thereof to patients, and gene therapy using the HAC vector is available. Such vectors for treatment of human diseases can be used for disease prevention, as well as disease treatment.

Hereafter, examples of applications of vectors for treatment of human diseases are demonstrated, although the applications are not particularly limited thereto.

(A) Use of Telomerase

Cells that are used for gene/cell therapy or tissue regeneration therapy are preferably normal cells instead of immortalized cells from the viewpoint of safety. Normal somatic cells, however, are known to stop multiplication/division after a given number of times of division and they eventually die, i.e., they age (Toshinori Ide, Experimental Medicine, vol. 16, No. 18 (extra edition): 18-24, 1998, Yodosha, Co., Ltd.). In order to prolong the therapeutic effects, therapeutic cells are required to be retained for a given period of time, and preferably over a lifetime of a patient. Telomerase, which is a repair enzyme of a telomere repeat sequence at the chromosome end, is known to overexpress in normal cells and thereby inhibits telomere shortening observed upon cell aging and to prolong the cell life (Bodnar et al., Science, 279: 349-352, 1998). It is also demonstrated that telomerase would not cause immortalization or canceration if it is overexpressed in a cell (Yoichi Shinkai, Experimental Medicine, vol. 16, No. 18 (extra edition): 25-30, 1998, Yodosha Co., Ltd.; Jiang et al., Nature Gent., 21:111-114, 1999). Thus, introduction of a gene encoding human telomerase (hTERT) into the HAC vector and introduction of the resultant to the target cell according to the method of the present invention enables prolongation of the life of the HAC-introduced cell and long-term maintenance of therapeutic effects without immortalization or canceration. Also, gene expression may be regulated with the use of an expression induction system or a genomic region, so that conditional or tissue-specific/physiological telomere expression can be realized.

(B) Inhibition of Generation of Autoantibody

When a recombinant protein preparation is developed, generation of autoantibodies (activity-neutralizing antibodies) at the time of administration is problematic (Li et al., Blood, 98: 3241-3248, 2001). A method for administering such preparation to a patient is not particularly limited. The HAC vector into which the genome encoding the target protein prepared by the method of the present invention has been introduced is first introduced into human cells, such as normal human cells of generative tissue, and the resultant is then transplanted to a patient. Generation of an autoantibody in a patient can be inhibited by allowing expression and providing target proteins from the HAC vector in a physiological/tissue-specific manner.

The tissue-specific microRNA (miRNA) target site can be added to the introduced genes (Brown, B. D. et al., Nature Medicine, vol. 12, pp. 585-591, 2006) to quench genes introduced into a given tissue/cells, and generation of autoantibodies and immune response against the introduced genes can be inhibited.

(C) Vector for Introducing Gene for Immunological Gene/Cell Therapy

As a treatment method of relapsed leukemia, a donor lymphocyte infusion method is known. This method takes advantages of the fact that grafted lymphocytes attack leukemia cells as tumor-specific cytotoxic T-cells via graft-versus-leukemia reactions (Kolb et al., Blood, 76: 2462-2465, 1990). A graft-versus-host disease in which grafted cells attack and damage recipient tissue is known as a side effect of such treatment. As means of overcoming such side effect, drug-inducible suicide genes are introduced into donor lymphocytes by a retrovirus vector and donor lymphocytes are removed by drug administration (Onodera et al., Genomic Medicine, vol. 3: 45, 2003 Medical Review). In such a case, mutation may disadvantageously occur in chromosomes of donor lymphocytes.

The HAC vector prepared by the method of the present invention can be used as a vector for introducing genes for immunological gene/cell therapy that would not mutate a host chromosome. Such HAC vector can also be used for gene introduction in treatment intended to accelerate antitumor activity, such as immunoactivation therapy of lymphoma using a CD40 ligand (Kato et al., Genomic Medicine, vol. 3, 53, 2003, Medical Review), and gene-based vaccination.

(D) Supplementation of Complete Human Monoclonal Antibody

In recent years, discovery of complete human monoclonal antibody medicine utilizing a human antibody-producing mouse has been attempted (Ishida et al., Bioventure, vol. 2: 44, 2002, Yodosha, Co., Ltd., Mori et al., Cell Death and Differentiation, in press, 2003, Proceedings of American Association for Cancer Research, Volume 44, 2nd Edition, July 2003, p1285, #6422). Application of such medicine to chronic disease, however, necessitates hospital visits for periodical administration of TPO, which could be an impediment to a patient's QOL. Also, production of recombinant protein preparations is very expensive, and high medical cost would be disadvantageously imposed upon a patient as a consequence.

A genomic region encoding a target antibody isolated from a hybridoma that produces the target antibody is introduced into the HAC vector prepared by the method of the present invention, the HAC vector is introduced into, for example, the hematopoietic stem cell or B cell of a patient, and the resultant is then transplanted to the patient again. Thus, a complete human antibody can be supplemented and supplied by physiological expression control. This also reduces the number of times of periodical visits to the hospital and improve a patient's QOL.

(E) Supplementation of Defect in Monogenic Disease (E-1) Hemophilia

Hemophilia A is a sex-linked, recessive hemorrhagic disease resulting from mutation in blood coagulation factor VIII, and hemophilia B is a sex-linked, recessive hemorrhagic disease resulting from mutation in blood coagulation factor IX. As a therapeutic method, supplementary therapy via administration of a concentrated preparation for factor VIII or IX is effective. However, administration after bleeding may disadvantageously cause serious complications, contamination of a concentrated preparation with a pathogen, generation of an autoantibody (activity-neutralizing antibody) due to repeated administration, lowered patient's QOL due to dealing with constant bleeding, a high medical cost, and other problems still remain, and resolution of such drawbacks by gene therapy has been deduced. Up to the present, vector-based gene therapy has been clinically studied; however, sufficient expression cannot be maintained for a long period of time, and significant therapeutic effects cannot be attained yet. In clinical study in which retrovirus and adeno-associated virus (AAV) vectors were directly administered, the vector gene was detected in the subject's semen, and a risk of gene introduction into the germ cell was pointed out (Mochizuki et al., Genomic Medicine, vol. 3: 25, 2003, Medical Review). The gene encoding factor VIII is of approximately 1.5 Mb in terms of the full-length genome and of approximately 7 kb in terms of cDNA. With the use of a nonvirus vector or adenovirus vector, full-length cDNA can be introduced, although the expression level is disadvantageously lowered. With the use of an AAV vector, the size of DNA to be introduced is limited to approximately 4.9 kb or smaller, and a full-length gene cannot be introduced disadvantageously.

The HAC vector into which DNA encoding blood coagulation factor VIII or factor IX has been introduced can be prepared by the method of the present invention. A method of administration to a patient is not particularly limited, and the HAC vector is, for example, first introduced into a human cell, the resultant is then transplanted to a patient, and supplementation can then be realized. A method of administration to a patient is not particularly limited, and the HAC vector into which the genomic region of blood coagulation factor VIII or factor IX has been introduced is, for example, first introduced into a human cell, the resultant is then transplanted to a patient, and such factor can then be supplemented by physiological/tissue-specific expression.

(E-2) X-SCID (X-Linked Severe Combined Immunodeficiency Disease)

Severe combined immunodeficiency disease (SCID) is caused by congenital disorder of humoral and cellular immunity. About a half of SCID is of X-linked (i.e., X-SCID), and mutation in the common γ-chain shared by the receptors of interleukin-2 family is known as a cause of such disease. As a therapeutic method, hematopoietic stem cell transplantation has been carried out; however, restoration of humoral immunity is insufficient, and periodical immunoglobulin administration becomes necessary. Thus, a resolution by gene/cell therapy in which a common γ-chain is introduced into the hematopoietic stem cell and the resultant is then introduced into the patient has been deduced. Since 1999, transplantation of hematopoietic stem cells into which the common γ-chain has been introduced by a retrovirus vector has been clinically studied, and a plurality of examples of conversion of transplanted cells into leukemia have been reported recently in France (Hacein-Bey-Abina et al., N Engl J Med., 348: 255-256, 2003; Marshall et al., Science, 299: 320, 2003). In any case, mutation resulting from insertion of a vector sequence was observed in a proto-oncogene in the gene-introduced cellular chromosome, i.e., the LMO2 gene region, and the correlation between LMO2 activation and tumorigensis has been suspected (Kume et al., Genomic Medicine, vol. 3: 9, 2003, Medical Review).

The HAC vector into which DNA encoding the common γ-chain has been introduced can be prepared by the method of the present invention. Also, use of the HAC vector as a vector for gene introduction enables prevention of mutation resulting from insertion of a vector sequence into a host chromosome. A method of administration to a patient is not particularly limited. The HAC vector is first introduced into a human cell (e.g., a human bone-marrow-derived normal hematopoietic stem cell), the resultant is transplanted to a patient, and deficient function of the common γ-chain can then be supplemented by physiological/tissue-specific expression.

(E-3) Duchenne Muscular Dystrophy (DMD)

Duchenne muscular dystrophy is caused by dysfunction of dystrophin because of mutation in the dystrophin gene, which is a X-linked, recessive, monogenic disorder (Hoffman et al., Cell, 51: 919-928, 1987). Since dystrophin is a cytoskeletal protein, DMD cannot be treated by supplementation via direct administration, and development of a gene therapy method has been deduced.

The dystrophin gene is of approximately 2.3 Mb in terms of the full-length genome, and it is of 14 kb in terms of cDNA. With the use of a nonvirus or adenovirus vector, full-length cDNA can be introduced, although the expression level is disadvantageously lowered (Liu et al., Mol. Ther., 4: 45, 2001; DelloRusso et al., Proc Natl Acad Sci, U.S.A., 99: 12979-12984, 2002). With the use of the AAV vector, the size of DNA to be introduced is limited to approximately 4.9 kb or smaller, and a full-length gene cannot be introduced. Disadvantageously, immune reactions were induced by an experiment of gene introduction into the cytoskeleton, and lowering was observed in expression of the introduced gene products (Yuasa et al., Gene Therapy, 9: 1576-1588, 2002).

In the experiment of gene introduction into the cytoskeleton using the AAV vector comprising the dystrophin minigene introduced under the control of a CMV promoter, which would induce ubiquitous expression, immune reactions were induced, and lowering was observed in expression of the introduced gene products. However, use of a cytoskeleton-specific MCK promoter resulted in improved immune responses (Yuasa et al., Gene Ther., 9: 1576-1588, 2002). This indicates that physiological/tissue-specific expression is necessary for dystrophin expression.

The HAC vector into which the genomic region encoding dystrophin has been introduced can be prepared by the method of the present invention. A method of administration to a patient is not particularly limited, the HAC vector is first introduced into a human cell (e.g., an autologous human normal sarcoblast, although examples are not limited thereto), the resultant is transplanted to a patient, and dystrophin can then be supplemented by physiological/tissue-specific expression.

(E-4) The diseases to be treated are not particularly limited, for example, monogenic disorders shown below can be treated: α-1 antitrypsin deficiency, cystic fibrosis transmembrane conductance regulator (CFTR), chronic granulomatous disease, familial hypercholesterolemia, Fanconi's anemia, Gaucher's disease, Hunter's syndrome, ornithine transcarbamylase deficiency, purine nucleotide phosphorylase deficiency, ADA-SCID, leukocyte adhesion deficiency, Canavan disease, callosal atrophy, Fabry's disease, amyotrophic lateral sclerosis, lysosomal disease, von Willebrand's disease, or thalassemia. The HAC vector into which the causal gene had been introduced is prepared by the method of the present invention, a method of administration to a patient is not particularly limited, for example, the HAC vector is introduced into a human cell, and the resultant is then transplanted to a patient. Thus, deficient molecules can be supplemented and complemented. Regarding information of disease-causing genes, a reference may be made to the online literature database of the U.S. National Center for Biotechnology Information (NCBI), PubMed (http://www.ncbi.nlm.nih.gov/entrez/query.fcgi?db=PubMed) or the OMIM™—Online Mendelian Inheritance in Man™ (http://www.ncbi.nlm.nih.gov/entrez/query.fcgi?db=OMIM).

(F) Other Diseases (F-1) Thrombopoietin (TPO) is a factor that plays a role in regulation of platelet production and in multiplication of hematopoietic stem/precursor cells. For example, application thereof to blood diseases such as aplastic anemia, hematopoietic recovery following chemotherapy, and the like is deduced. However, generation of activity-neutralizing antibodies at the time of TPO recombinant protein administration becomes an impediment to development of pharmaceutical products (Li et al., Blood, 98: 3241-3248, 2001). When TPO is applied to a chronic disease, accordingly, a patient is required to visit a hospital for periodical TPO administration, and this may become an impediment to a patient's QOL. Also, manufacture of recombinant protein preparations disadvantageously requires a high cost, which consequently and disadvantageously imposes a burden of a high medical cost upon a patient.

The HAC vector into which the TPO genome has been introduced is prepared by the method of the present invention, a method of administration to a patient is not particularly limited, the HAC vector is introduced into a human cell, such as a cell of generative tissue, TPO is expressed and supplied in a physiological/tissue-specific manner, and generation of autoantibodies can then be inhibited. This can reduce the number of times of periodical hospital visits and it can improve a patient's QOL.

(F-2) Erythropoietin (EPO) is an erythrocyte growth factor, which is commercially available as a therapeutic agent for renal anemia due to diabetes, renal disease, and the like. A patient having a chronic disease, such as renal anemia due to diabetes, is required to visit a hospital for periodical EPO administration, which deteriorates a patient's QOL. Also, manufacture of recombinant protein preparations disadvantageously requires a high cost, which consequently and disadvantageously imposes a burden of a high medical cost upon a patient. As described in Example 14 of the present invention, the HAC vector into which EPO cDNA has been introduced is introduced into the human normal fibroblasts, the resultant is transplanted to a patient, and EPO can then be expressed and supplied to the patient. Also, the HAC vector into which the hEPO genomic region has been introduced is prepared by the method of the present invention, the resulting HAC vector is introduced into a human cell, such as a cell of generative tissue, although a method of administration to a patient is not particularly limited. Thus, EPO can be expressed and supplied in a physiological/tissue-specific manner. This can reduce the number of times of periodical hospital visits and it can improve a patient's QOL.

(F-3) Parkinson's Disease

Parkinson's disease is a nervous disease in which the motor function is disturbed by progressive degeneration and dropout of dopamine-synthesizing cells of compact portions of the substantia nigra in the midbrain. An example of a therapeutic method is a L-DOPA administration method for the purpose of supplementing lost dopamine. Such method, however, is problematic in the following respects. In the case of moderate or advanced symptoms, drug efficacy is attenuated and side effects result in a restricted patient's QOL and a decreased dose. Such problems result from the fact that a dopamine concentration is inconstant in the striate body and that the administered L-DOPA acts outside the striate body. Thus, constant physiological expression of dopamines in the striate body is required (Takeda et al., Medical Science Digest, vol. 29; 20, 2003, New Sciences). At present, gene therapy using AAV vectors into which 3 types of enzymes associated with dopamine synthesis have been introduced, respectively, has been studied. Any of the resulting vectors, however, is not sufficient to regulate physiological expression. An example of a therapeutic method targeting inhibition of degeneration and dropout of dopamine-synthesizing cells is administration of a grial-cell derived neuronal factor (GDNF). While the effects thereof were observed as a result of continuous administration via indwelling catheters in the putamen (Gill et al., Nature Med., 9: 589-595, 2003), a risk of infection or a restricted patient's QOL remain problematic. Although the effects were exhibited by animal model-based research for AAV vector-based gene therapy (Wang et al., Gene Ther., 9: 381-389, 2002), this is not sufficient to regulate physiological expression.

The HAC vector into which enzymes associated with dopamine synthesis or the GDNF genomic region have been introduced can be prepared by the method of the present invention. A method of administration to a patient is not particularly limited, the HAC vector is introduced into a human cell (e.g., a human normal neural stem/precursor cell), the resultant is transplanted to a patient, and the introduced gene product can then be supplemented by physiological/tissue-specific expression.

(F-4) Diabetes

Insulin-dependent diabetes has been treated by administration of recombinant protein preparations. A patient having a chronic disease is required to visit a hospital for periodical administration, which damages a patient's QOL. Also, manufacture of recombinant protein preparations necessitates a high cost, which in turn incurs a high medical cost, disadvantageously. Since the range of optimal blood insulin levels is small, side-effects may occur at excessively high or low blood insulin levels, and insulin-dependent diabetes may occasionally become hazardous to life. While gene therapy has been studied, regulation of the insulin level in the body is an issue of concern (Moritani et al., Protein, Nucleic Acid, and Enzyme, vol. 40: 2764, 1995, Kyoritsu Shuppan Co., Ltd).

The HAC vector into which the insulin genome has been introduced is prepared by the method of the present invention. While a method of administration to a patient is not particularly limited, the HAC vector is introduced into a human cell, such as a cell of generative tissue, and such genome can be expressed and supplied in a physiological/tissue-specific manner. This can reduce the number of times of periodical visit to a hospital and improve a patient's QOL.

(F-5) Diseases to be treated are not particularly limited. For example, brain tumor, peripheral arterial disease (e.g., ischemia), chronic rheumatoid arthritis, artery restenosis, cubital tunnel syndrome, coronary artery disease, Alzheimer's disease, ulcer, pelvic fracture, renal disease, or malignant tumor can be treated in the following manner. The HAC vector into which a gene encoding a substance that is considered to be necessary to treat a disease has been introduced is prepared by the method of the present invention. While a method of administration to a patient is not particularly limited, for example, the HAC vector is introduced into a human cell, the resultant is transplanted to a patient, and defect molecules can the be supplemented and complemented.

(8) Vector for Preparing Transgenic Animal and Non-Human Animal Having HAC Vector The HAC vector prepared by the method of the present invention can be used as a vector for preparing a transgenic animal. In accordance with the method described in Tomizuka et al., Nature Genet., U.S.A., vol. 16, pp. 133-143, 1997, Tomizuka et al., P. N. A. S., U.S.A., vol. 97, pp. 722-727, 2000, or Kuroiwa et al., Nature Biotech., U.S.A., vol. 18, pp. 1086-1090, 2000, for example, the HAC vector comprising foreign genes may be introduced into a mouse embryonic stem cell to prepare a chimera individual. Also, the introduced foreign genes can be functionally expressed in an individual, and the HAC vector comprising foreign genes can be retained stably in a chimera individual and inherited to the next generation through a germ line. Further, the HAC vector comprising foreign genes is capable of preparation of a cloned bovine individual by somatic cell nuclear transplantation and stable retention and functional expression of introduced foreign genes in an individual in accordance with the method of Kuroiwa et al. (2002, as described above). Also, an animal carrying HAC of the present invention can be prepared by a known technique (e.g., a method involving the use of an embryonic stem cell or a method of nuclear transplantation disclosed in WO 97/07671, WO 03/041495, and WO 03/097812 filed by the present applicant). An animal species is not particularly limited, and it is preferably a mammalian animal, and particularly preferably bovine, goat, pig, sheep, dog, rat, mouse, monkey, or the like.

Examples

The present invention is described in greater detail with reference to the following examples, although the scope of the present invention is not limited thereto.

In Examples 1 to 5, HAC vectors were prepared by deleting the long-arm distal region of human chromosome 14, adding the telomere sequence to the long-arm distal region, and inserting a recognition site for site-directed recombinant enzyme (hereafter such HAC vectors may be referred to as the "telomere-type 14HAC" or "14AΔqHAC"). Safety thereof and expression of the introduced foreign gene were examined.

In Examples 6 to 11, HAC vectors were prepared by deleting the long-arm distal region of human chromosome 14, adding the telomere sequence and subtelomere sequence of approximately 25 Kb derived from human chromosome 14 to the long-arm distal region, and inserting a recognition site for site-directed recombinant enzyme (hereafter such HAC vectors may be referred to as the "telomere•short subtelomere-type HAC" or "14NΔqHAC"). Safety thereof and expression of the introduced foreign gene were examined.

In Examples 12 to 17, HAC vectors were prepared by deleting the long-arm distal region of human chromosome 14, adding the telomere sequence and the subtelomere sequence of approximately 60 Kb derived from human chromosome 14 to the long-arm distal region, and inserting a recognition site for site-directed recombinant enzyme (hereafter such HAC vectors may be referred to as the "telomere•long subtelomere-type HAC" or "14gNΔqHAC"). Safety thereof and expression of the introduced foreign gene were examined.

In Examples 18 to 22, the Neo-resistant gene units were removed from the above 3 types of HAC vectors.

In Examples 23 to 25, HAC vectors were prepared by deleting the long-arm distal region of human chromosome 21, adding the telomere sequence to the long-arm distal region, and inserting a recognition site for site-directed recombinant enzyme (hereafter such HAC vectors may be referred to as the "telomere-type 21HAC" or "21AΔqHAC"). Safety thereof and expression of the introduced foreign gene were examined.

In Examples 26 to 30, HAC vectors were prepared by deleting the long-arm distal region of human chromosome 21, adding the telomere sequence and the subtelomere sequence of approximately 8 Kb derived from human chromosome 21 to the long-arm distal region, and inserting a recognition site for site-directed recombinant enzyme (hereafter such HAC vectors may be referred to as the "telomere•subtelomere-type HAC" or "21NΔqHAC").

EXAMPLES

Example 1

Preparation of Telomere-Type 14HAC (14AΔqHAC) Vector by Deletion of the Long-Arm Distal Region of Human Chromosome 14

(1) Deletion of the Long Arm of Human Chromosome 14 by Telomere Truncation
(1-1) Construction of pTELpuro-t1 Vector for Telomere Truncation As a telomere truncation vector (a targeting vector) for deleting the long-arm distal region of human chromosome 14, pTELpuro (Kuroiwa et al., Nature Biotech., U.S.A., vol. 18, pp. 1086-1090, 2000) was used. Based on the nucleotide sequence (Accession No. AL391156) of the long-arm distal region of human chromosome 14 obtained from the GenBank database, a target sequence for inserting a telomere truncation vector was designed. Sequences of oligonucleotide primers comprising restriction enzyme recognition sequences added for amplifying the target sequence by PCR are shown below.

```
7791F NheI:
5'-AGCTAGCTCAACTGGCTCCTGATTTCTCTC     (SEQ ID NO: 1)

10680R (XhoI):
5'-ATCTTCCTCGAGTCACCAAACTTG           (SEQ ID NO: 2)

10657F (XhoI):
5'-CAAGTTTGGTGACTCGAGGAAGAT           (SEQ ID NO: 3)

14620R BamHI:
5'-GGGATCCTTTCAAGTGGAAGAGTGAGGTCC     (SEQ ID NO: 4)
```

Figure 2:
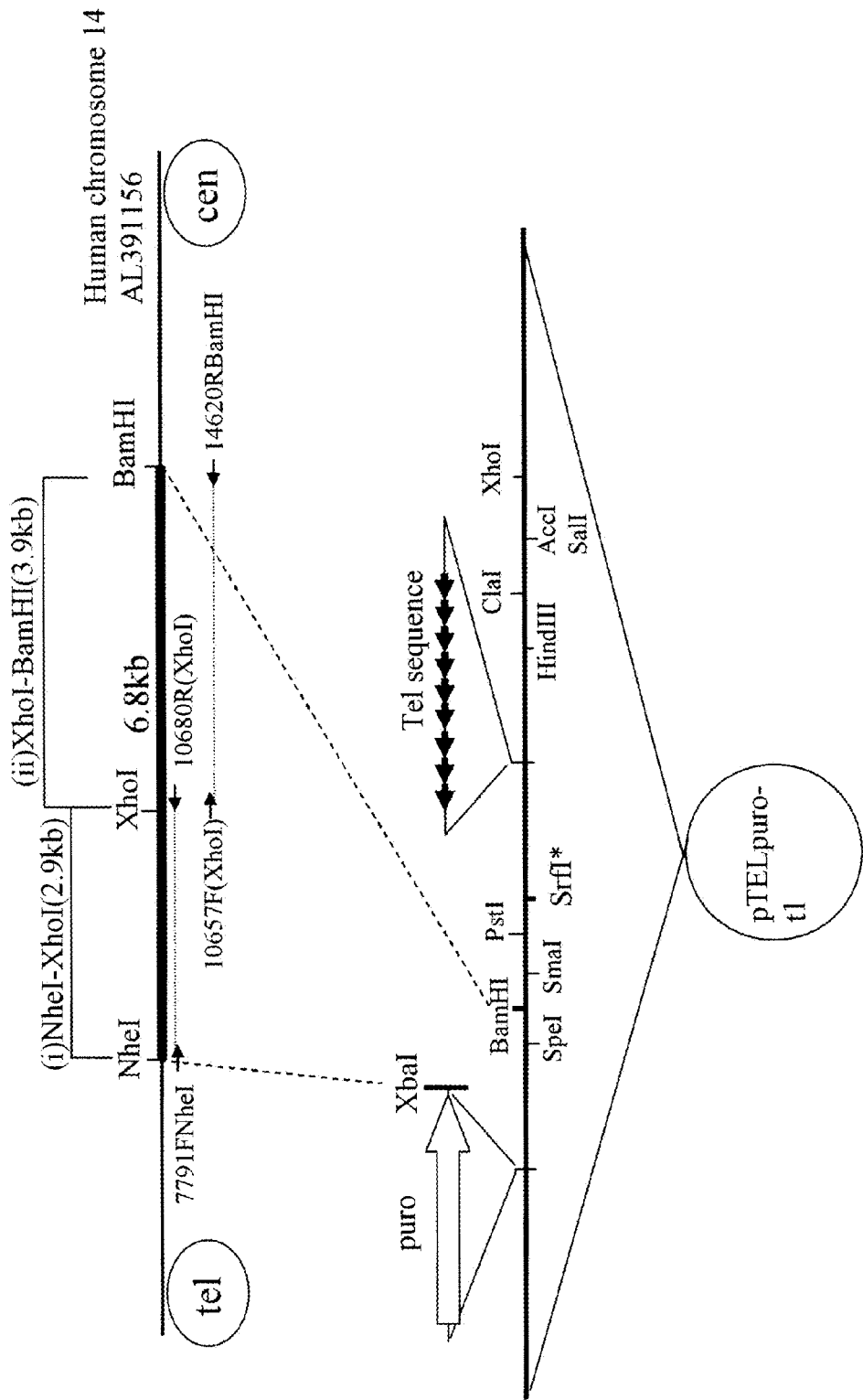
FIG. 2 shows the structure of the pTELpuro-t1 vector for telomere truncation. In the figure, "tel" indicates a telomere side and "cen" indicates a centromere side. Also, "puro" indicates a puromycin gene, "Tel sequence" indicates a telomere sequence, and a black arrow in the sequence indicates a repeat sequence.
Figure 3:
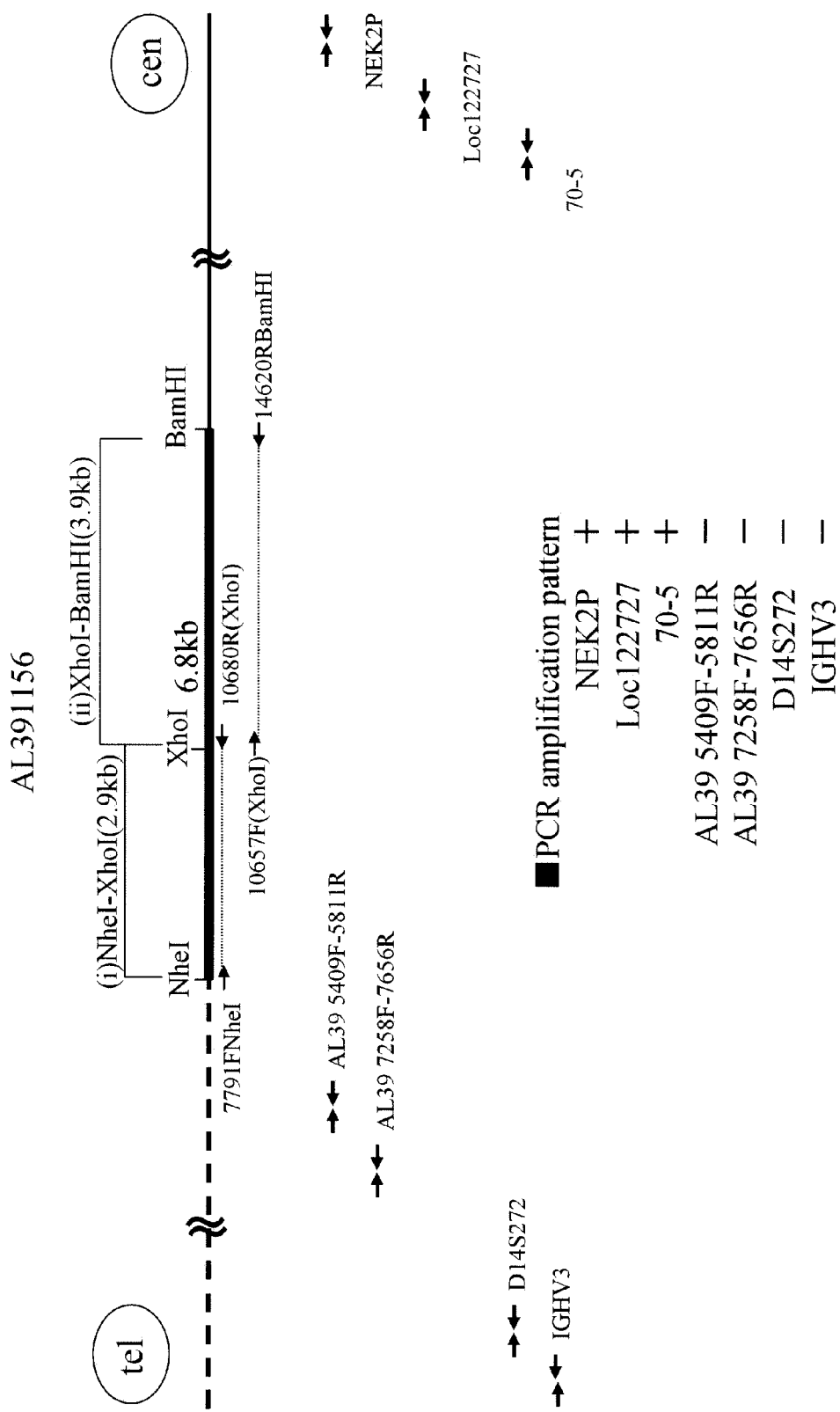
FIG. 3 shows the results of PCR analysis regarding introduction of a pTELpuro-t1 vector into human chromosome 14q.

Mouse A9 hybrid cells carrying human chromosome 14 (A9c11-14chr, Shinohara et al., Hum Mol Genet, 10: 1163-1175, 2001) were cultured, and genomic DNA was extracted from the cells using the Puregene DNA Isolation kit (Gentra System). The obtained genomic DNA was used as a template, and the target sequences to be recombined were amplified by PCR using the above primers. About 0.1 µg of genomic DNA was used as a template, and PCR was carried out in accordance with Innis et al. (PCR Experimental Manual, HBJ Press, 1991) using a GeneAmp9700 thermal cycler (Applied Biosystems). LA Taq polymerase (Takara Shuzo Co., Ltd.) was used, and the reactions were carried out at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 25 cycles of denaturation at 98° C. for 5 seconds followed by annealing/extension at 68° C. for 10 minutes, and extension at 72° C. for 10 minutes. The 2.9-kb product amplified with the use of 7791FNhe1/10680R(XhoI) was digested with restriction enzymes, NheI and XhoI, the 3.9-kb product amplified with the use of 10657F(XhoI)/14620RbamHI was digested with restriction enzymes, XhoI and BamHI (Roche), and DNA fragments having cohesive ends were separated by agarose gel electrophoresis, followed by purification. The resultant was cloned into the XbaI-BamHI site of the pTELpuro plasmid. The size of the final pTELpuro-t1 construct was approximately 12.8 kb. The telomere truncation vector, the target sequence, and a chromosome allele resulting from homologous recombination are shown in FIG. 2 and FIG. 3.
(1-2) Introduction of Telomere Truncation Vector into DT40 Cell Carrying Human Chromosome 14

The DT40 hybrid cells carrying human chromosome 14 were prepared by the microcell mediated chromosome transfer method using the above A9c11-14chr cells carrying human chromosome 14 as chromosome donor cells. Chromosome recipient cells, DT40, are registered under Accession No. JCRB2221 with the Japanese Collection of Research Bioresources (JCRB) and available therefrom. A method for preparing the same is hereafter briefly described.

At the outset, microcells were prepared from about $1\times10^8$ A9c11-14chr cells. A9c11-14chr cells that had been cultured to a cell density up to about 80% confluency in twelve 25-cm² centrifuge flasks (Nunc) were cultured for 48 hours in a culture medium (20% fetal bovine serum; FBS, 0.8 mg/ml G418, DMEM) containing colcemid (0.075 µg/ml, demecolcine, Wako Pure Chemical Industries Ltd.) to induce micronucleus formation. In Examples hereafter, DMEM manufactured by Nissui Pharmaceutical Co., Ltd. was used. After the medium was removed, the cytochalasin B (10 µg/ml in DMEM, Sigma) solution preheated to 34° C. was filled in the centrifuge flasks, and centrifugation was carried out at 34° C. and 8,000 rpm for 1 hour. The microcells were suspended in serum-free medium (DMEM), recovered, and purified by filtration using SWINNEX-25 (Millipore) equipped with filters (Whatman) having pore sizes of 8 µm, 5 µm, and 3 µm. The purified microcells were resuspended in 6 ml of DMEM. DT40 cells were cultured in RPMI 1640 culture medium containing 10% FBS, 1% CS (calf serum), and 0.1 mM 2-ME, washed twice with DMEM, and $1\times10^7$ cells were resuspended in 5 ml of DMEM. The microcell suspension was centrifuged at room temperature and 1,500 rpm for 5 minutes, the DT40 cell suspension was overlayered thereon, and centrifugation was carried out at room temperature and 1,500 rpm for 5 minutes, and the supernatant was then removed. The cells were subjected to fusion treatment using a polyethylene glycol (PEG)1:1.4 solution for 90 seconds (Tomizuka et al., Nature Genet., U.S.A., vol. 16, pp. 133-143, 1997). The fused cells were suspended in 60 ml of RPMI 1640 culture medium (Invitrogen) containing 10% FBS, 1% chicken serum (ChS), and 0.1 mM 2-mercaptoethanol (ME), the resulting suspension was plated in 6 96-well plates and cultured for 24 hours, and selection culture was carried out for about 2 weeks in a medium containing 1 mg/ml of G418. Drug-resistant colonies that had developed as a result of two microcell fusion experiments were isolated. Using PCR analysis, the presence of NEK2P, LOC122727, AL390798, AL121820, AL157858, AL137190, AL137229, IGIMC, IGHV3, and AB019437 regions on human chromosome 14 was confirmed, and fluorescence in situ hybridization (FISH) analysis using a human-specific probe, Cot1 (Gibco BRL), was further carried out to identify and obtain clones, DT40(-14)1-2 and DT40(-14)2-4, carrying a copy of human chromosome 14.

The pTELpuro-t1 construct was converted into linearized DNA by digestion with the SrfI restriction enzyme and then introduced into the DT40 hybrid cell that carries human chromosome 14. 1×10$^7$ DT40(-14)1-2 or DT40(-14)2-4 cells were suspended in 0.5 ml of RPMI medium, the suspension was allowed to stand in the presence of 30 μg of DNA at room temperature for 10 minutes, and electroporation was then carried out using the Gene Pulser II (Bio-Rad). A voltage of 550 V was applied to a condenser having a capacity of 25 μF and then discharged using an electroporation cell having 4 mm of an interelectrode distance. After the cells were allowed to stand at room temperature for 10 minutes, the electroporated cells were suspended in RPMI 1640 culture medium containing 10% FBS, 1% ChS, and 0.1 mM 2-ME, and the suspension was plated in twenty 96-well plates (Falcon). Twenty four hours later, puromycin (puromycin dihydrochloride, Sigma) was added to a final concentration of 0.3 μg/ml, and resistant colonies developed 2 to 3 weeks thereafter. A total of 276 drug-resistant colonies were isolated from DT40 (-14)1-2 cells by two transfection operations, a total of 294 drug-resistant colonies were isolated from DT40(-14)2-4 cells by 4 transfection operations, and the isolated colonies were grown and then subjected to subsequent analysis.

(1-3) PCR Analysis

Genomic DNA of the puromycin-resistant strain was used as a template to confirm by PCR the presence of a gene present on human chromosome 14, the STS marker, D14S272, and the 6 genes or the genomic regions shown below. The sequences of oligonucleotide primers of the STS marker are available on the online database UniSTS (http://www.ncbi.nlm.nih.gov/entrez/query.fcgi?db=unists) of the National Center for Biotechnology Information (U.S.A.). The accession number for the STS marker is UniSTS:45129. The position of the gene designed based on the nucleotide sequence obtained from the GenBank database or that of the oligonucleotide primer in the genomic region are shown in FIG. 3 (wherein a primer is indicated by an arrow), and the sequences thereof are shown below.

```
AL39 5409F:
5'-GCATGCCTTCAATGTGTGAC       (SEQ ID NO: 5)

AL39 5811R:
5'-CAGCAGAGCCAAGATCCAGT       (SEQ ID NO: 6)

AL39 7258F:
5'-TCCACAGTTTCACCAGCATC       (SEQ ID NO: 7)

AL39 7656R:
5'-AAGTGGGCGGATAACCTGAG       (SEQ ID NO: 8)

NEK2PF:
5'-CAGCCAGTGTTTTCCTGGAT       (SEQ ID NO: 9)
```

-continued
```
NEK2PR:
5'-TCTTTGCTCTTCTGCAACCA       (SEQ ID NO: 10)

LOC122727F:
5'-CGATCAGAATGGGAAACCAG       (SEQ ID NO: 11)

LOC122727R:
5'-TTGTCGCTGGAATTTGTTGA       (SEQ ID NO: 12)

70-5F:
5'-TCACCATGATCGATTGAGTT       (SEQ ID NO: 13)

70-5R:
5'-GCATTGCTGGGTCATATGGT       (SEQ ID NO: 14)

IGHV3F:
5'-AGTGAGATAAGCAGTGGATG       (SEQ ID NO: 15)

IGHV3R:
5'-CTTGTGCTACTCCCATCACT       (SEQ ID NO: 16)
```

A known primer was used for the STS marker, D14S282.

About 0.1 μg of genomic DNA was used as a template, and the above 6 types of genes or genomic regions and the D14S272 marker (7 types in total) were amplified by PCR (Innis et al., supra). Ex Taq polymerase (Takara Shuzo Co., Ltd.) was used, and the reactions were carried out at 94° C. for 5 minutes, followed by 35 cycles of denaturation at 94° C. for 15 seconds, annealing at 56° C. for 30 seconds, and extension at 72° C. for 30 seconds. When the long-arm distal region was deleted by telomere truncation, the resultant is deduced to comprise NEK2P, LOC122727, and 70-5, and the resultant is deduced to comprise neither of AL395409-AL395811, AL397258-397656, D14S272 marker, or IGHV3. After the primary screening in accordance with the presence or absence of AL397258-397656, the other markers were analyzed. Among 570 puromycin-resistant strains, the results of amplification as deduced were attained in 6 strains (5 clones derived from DT40(-14)1-2 and a clone derived from DT40 (-14)2-4).

(1-4) Southern Blot Analysis

Figure 4:
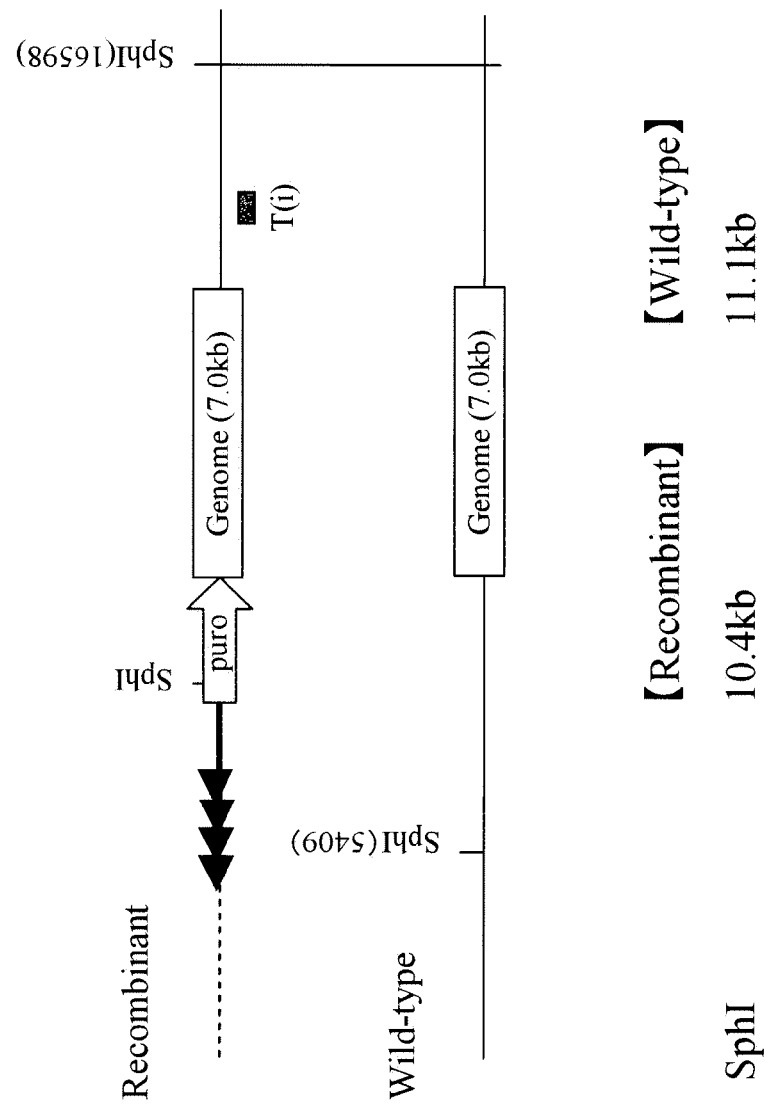
FIG. 4 shows an allele resulting from introduction of a pTELpuro-t1 vector into human chromosome 14q.

As a screening method for selecting a homologous recombinant, Southern blot analysis was carried out. Probes were designated in target sequences of homologous recombination (FIG. 4). In order to prepare probes, PCR was carried out using oligonucleotide primer pairs shown below and genomic DNA of A9c11-14chr cells comprising human chromosome 14 as a template, and the resultants were isolated, and purified.

```
AL39 15138F:
5'-TGGCTTGGCATACATTTTGA       (SEQ ID NO: 17)

AL39 15738R:
5'-AGGGAGTTCCTCACACAGGA       (SEQ ID NO: 18)
```

Figure 5:
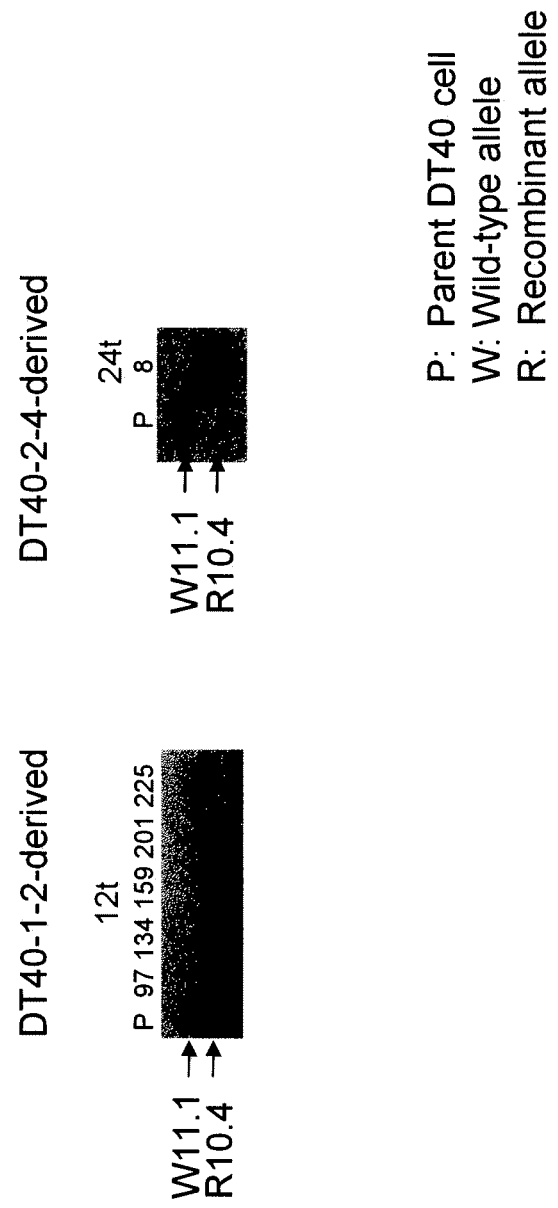
FIG. 5 shows the results of Southern analysis regarding a DT40 hybrid cell carrying a pTELpuro-t1 vector introduced into human chromosome 14q.

About 5 μg of genomic DNA extracted from the 6 strains obtained by primary screening was digested with the SphI restriction enzyme (Roche), and Southern blot analysis was carried out by the method described in Ausubel et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). Representative results are shown in FIG. 5. The length of the restriction enzyme fragment deduced from the nucleotide sequence is 10.4 kb in the form of a homologous recombinant, it is 11.1 kb in the form of a wild-type (i.e., a non-recombinant), and a total of 6 strains of homologous recombinant cells were confirmed from the candidate 6 strains.

(1-5) Fluorescence In Situ Hybridization (FISH) Analysis

Figure 6:
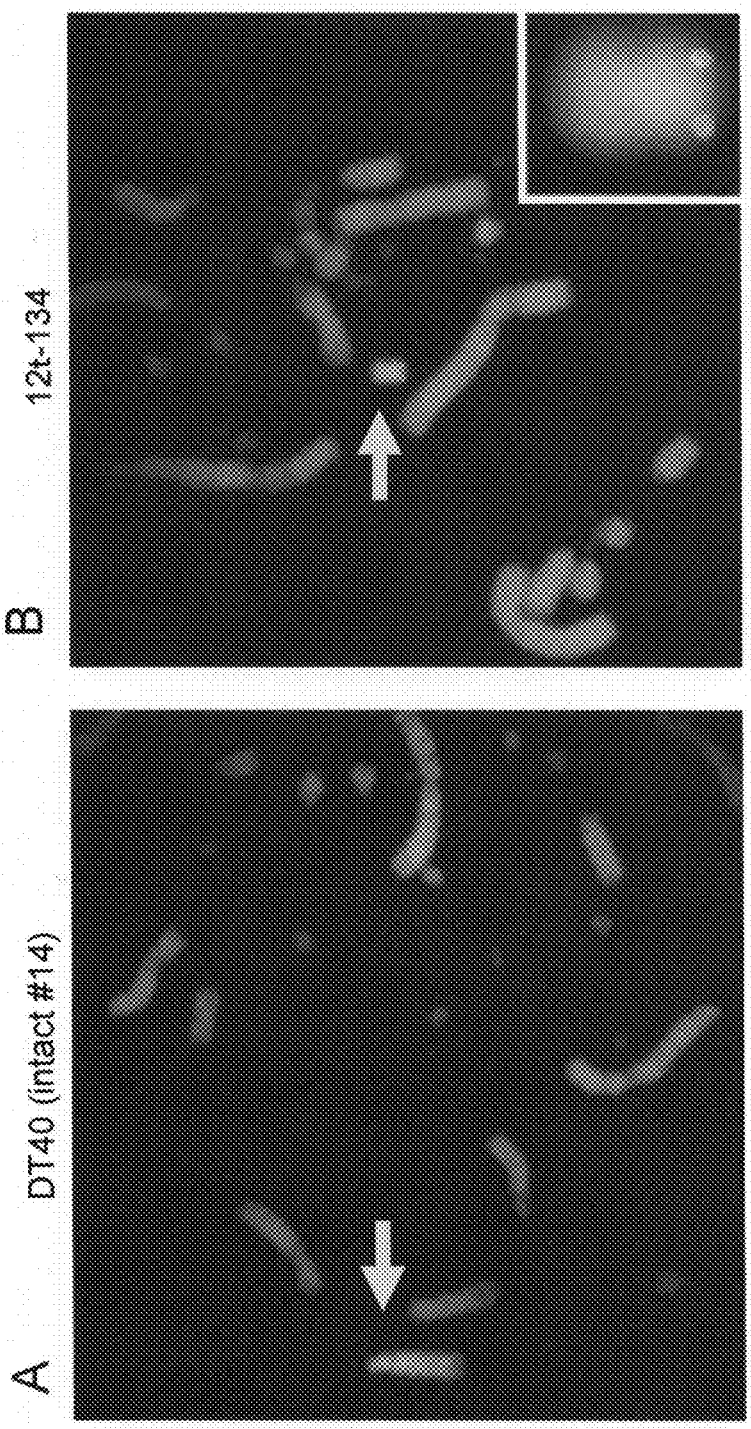
FIG. 6 shows the results of FISH analysis regarding a DT40 hybrid cell carrying a pTELpuro-t1 vector introduced into human chromosome 14q wherein: (A) represents a DT40 hybrid cell that carries human chromosome 14; and (B) represents a DT40 hybrid cell that carries a human chromosome 14 fragment with a deleted long arm.

FISH analysis was carried out in accordance with the method described in Matsubara et al. (FISH Experimental Protocol, Shujunsha Co. Ltd., 1994) using human-specific Cot1 (Invitrogen) and FITC-labeled PGK-puro fragment (prepared by cleaving from the pTELpuro vector) as probes. As a result, a shortened human chromosome 14 and two FITC signals at the long arm ends of a Cot1-stained shortened human chromosome 14 were detected in most of the observed mitotic figures. Representative FISH images are shown in FIG. 6a and FIG. 6b. In FIG. 6a, a white arrow indicates full-length human chromosome 14 before telomere truncation. In FIG. 6b, a white arrow indicates a human chromosome 14 fragment with the deleted long-arm distal region. Based on a size relative to a host DT40 cell chromosome, shortening of human chromosome 14 was confirmed.

Thus, it was confirmed that the six puromycin-resistant strains (i.e., 12t97, 12t134, 12t159, 12t201, 12t225, and 24t8) obtained as above carried an artificial chromosome (14AΔqHAC) derived from human chromosome 14 by means of deletion of the long arm and had at its end the telomere sequence.

(2) Introduction of a Cloning Site into Long-Arm Proximal Region of 14AΔqHAC (2-1) Construction of t1pSF1 Vector for Insertion of loxP and 3'neo Sequences As a basic plasmid for inserting loxP and 3'neo sequences into the human artificial chromosome (HAC) prepared in Example (1-1), pSF1 (Lifetech) was used. The nucleotide sequence of the long-arm proximal region of human chromosome 14 into which loxP and 3'neo sequences would be inserted was obtained from the GenBank database (Accession No. AL391156). Sequences of oligonucleotide primers used for amplifying two target sequences for homologous recombination are shown below.

```
49050F2longSalI:
                                  (SEQ ID NO: 19)
5'-GACAGTGTCGACAGTGAGACTTGTAGGCTACAAGAAAAGG 53978Rlong2SalI:
                                  (SEQ ID NO: 20)
5'-GACAGTGTCGACTCTGATAATGCGGAATGAGTAGGGAGGC 54023Flong2FseI:
                                  (SEQ ID NO: 21)
5'-GATGGCCGGCCTGGTTGGTAAAGATTGCTACACTTACGGCA 56084RlongPacI:
                                  (SEQ ID NO: 22)
5'-CTTAATTAACAAGAGCTCTACAACTGTCCATCGAAAC
```

Genomic DNA extracted from the A9c11-14chr cell carrying human chromosome 14 was used as a template, and two target sequences were amplified by PCR. About 5 kb of a DNA fragment was digested with the SalI restriction enzyme (Roche), about 2 kb of a DNA fragment was digested with FseI and PacI (Roche), and DNA fragments having cohesive ends were separated by agarose gel electrophoresis, followed by purification. The resultants were cloned into the SalI or FseI-PacI site of the pSF1③ plasmid. The pSF1③ vector was constructed in the following manner. That is, about 1.3 kb of a fragment of the blasticidin-resistant gene used for selecting a homologous recombinant was cleaved from pCMV/Bsd (Invitrogen) by digestion with restriction enzymes, XhoI (Roche) and SalI (Roche), inserted into the XhoI site of the pSF1 plasmid in the opposite transcription direction with the 3'neo sequence. Further, the pSF1 construct into which the blasticidin-resistant gene had been introduced was introduced into a blunt-ended region after digestion with ApaI (Roche), with the insertion of the SNESPF linker (SalI-NheI-EcoRV-SrfI-PacI-FseI). The DNA sequences of the SNESPF linkers are shown below.

```
SNESPFlinker S
                                  (SEQ ID NO: 178)
GTCGACGCTAGCGATATCGCCCGGGCTTAATTAAGGCCGGCC SNESPFlinker AS
                                  (SEQ ID NO: 179)
GGCCGGCCTTAATTAAGCCCGGGCGATATCGCTAGCGTAGAC
```

Figure 7:
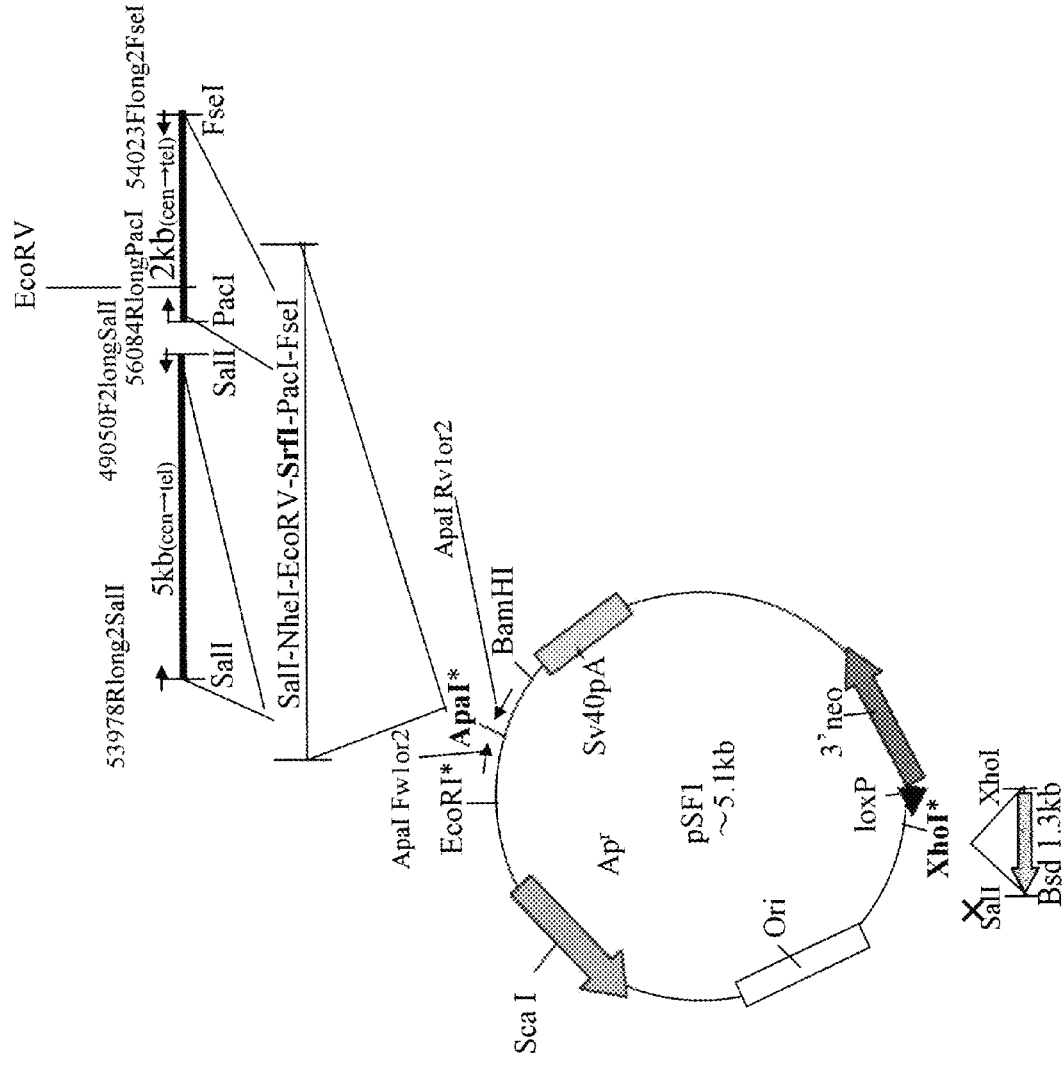
FIG. 7 shows the structure of the t1pSF1 vector for insertion of loxP and 3'neo sequences. In the figure, "Ori" indicates a replication origin, "Ap$^r$" indicates an ampicillin resistant gene, and "Sv40pA" indicates SV40 poly-A.
Figure 8:
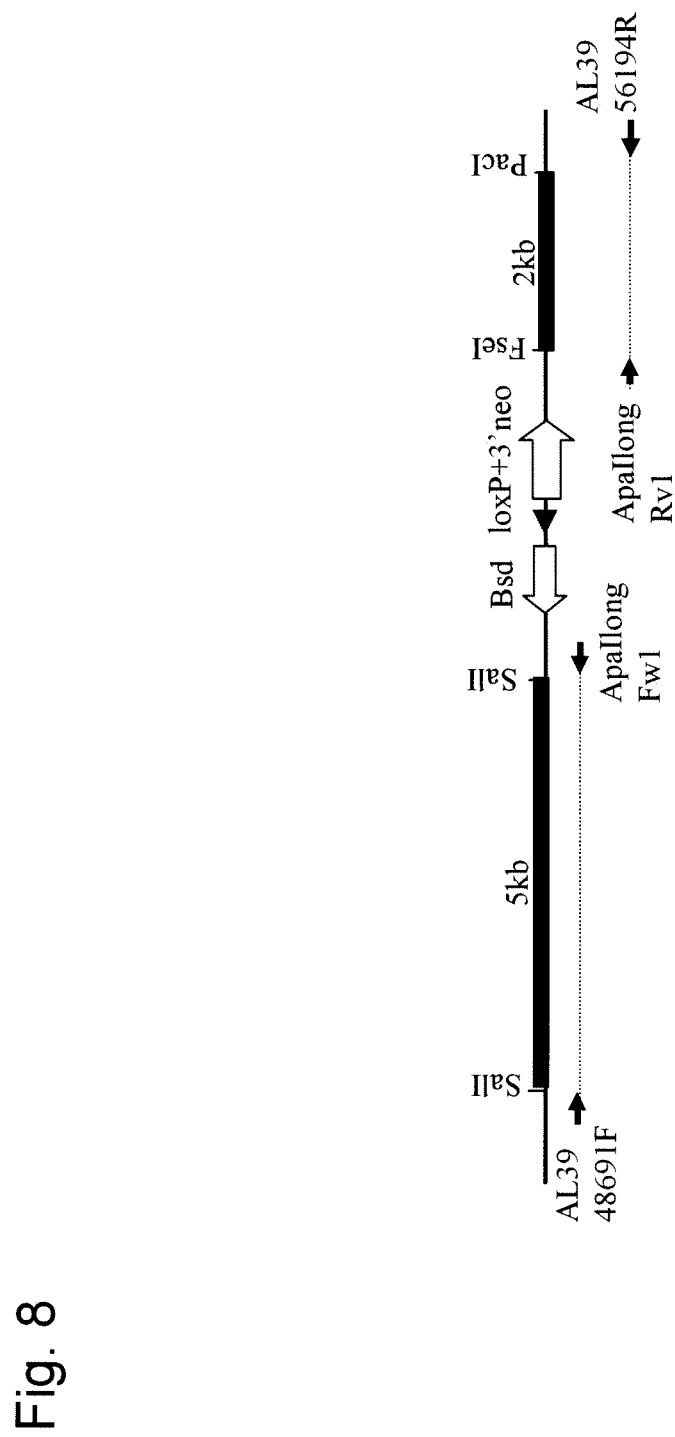
FIG. 8 shows the results of PCR analysis regarding introduction of a t1pSF1 vector into 14AΔqHAC.
Figure 9:
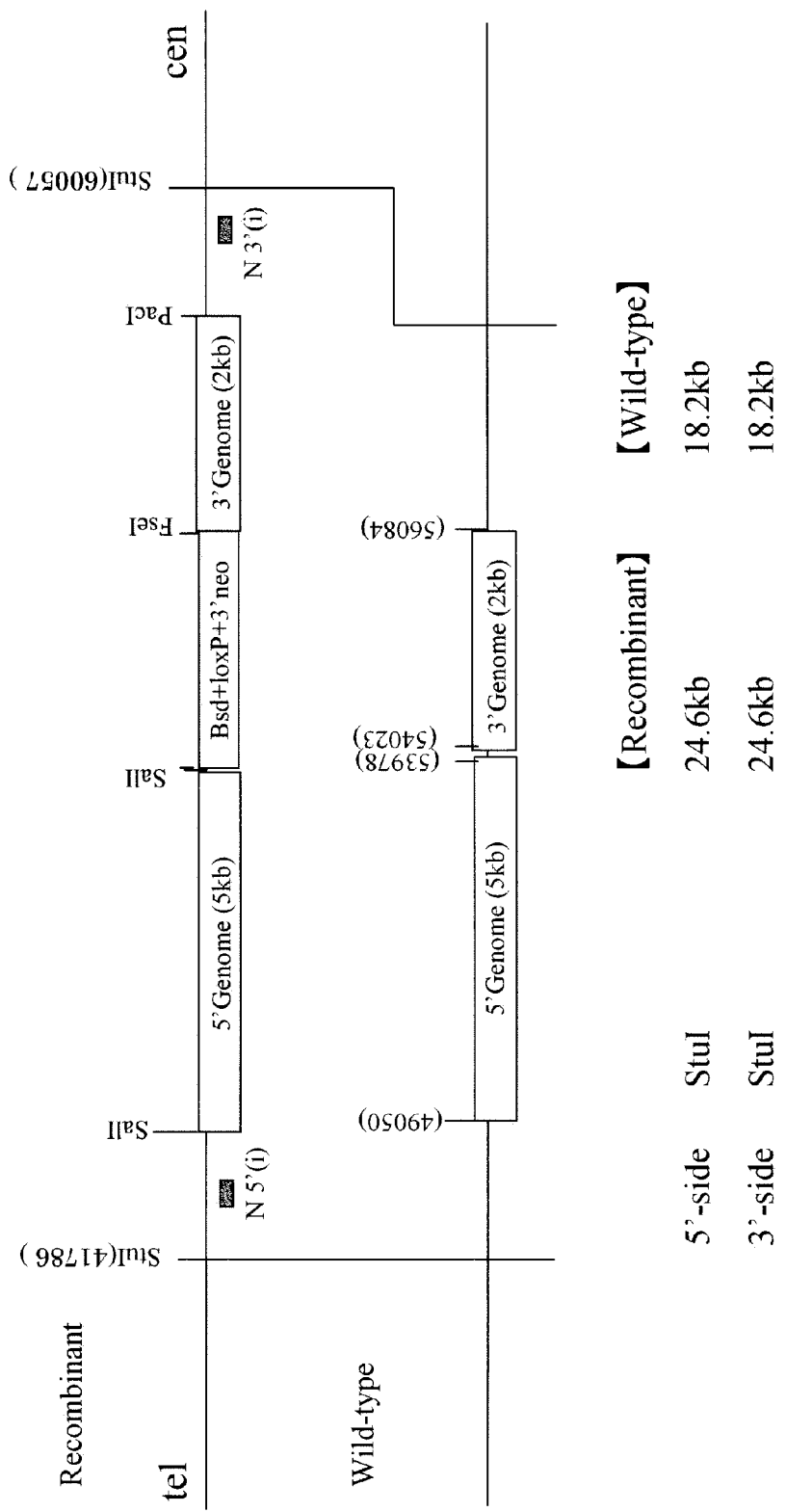
FIG. 9 shows an allele resulting from introduction of a t1pSF1 vector into 14AΔqHAC.

The size of the final construct is about 13.4 kb. The targeting vector, the target sequence, and a chromosome allele resulting from homologous recombination are shown in FIGS. 7 to 9. The thus-obtained construct is referred to as the t1pSF1 vector.

(2-2) Introduction of t1pSF1 vector into 14AΔqHAC-Carrying DT40 Cell

The t1pSF1 construct was linearized by digestion with the SrfI restriction enzyme (Roche) and introduced into DT40 hybrid cell carrying 14AΔqHAC with the deleted long-arm distal region. 1×10⁷ 12t97 or 12t134 cells were suspended in 0.5 ml of RPMI medium, the cells were allowed to stand at room temperature for 10 minutes in the presence of 30 μg of DNA, and electroporation was then carried out using the Gene Pulser II (Bio-Rad). A voltage of 550 V was applied to a condenser having a capacity of 25 μF and then discharged using an electroporation cell having 4 mm of an interelectrode distance. After the cells were allowed to stand at room temperature for 10 minutes, the electroporated cells were suspended in RPMI 1640 culture medium containing 10% FBS, 1% ChS, and 0.1 mM 2-ME, and the suspension was plated in twenty 96-well plates (Falcon). Twenty four hours later, blasticidin (blasticidin S hydrochloride, Funakoshi) was added to a final concentration of 8 μg/ml, and resistant colonies developed 2 to 3 weeks thereafter. A total of 56 drug-resistant colonies were isolated from 12t97 cells by two transfection operations, a total of 43 drug-resistant colonies were isolated from 12t134 cells by a single transfection operation, and the isolated colonies were grown and then subjected to subsequent analysis.

(2-3) PCR Analysis

Genomic DNA of a blasticidin-resistant strain was used as a template, and the presence of two target sequences (i.e., the 5' target sequence and the 3' target sequence) was detected by PCR. By sandwiching these two target sequences (in FIG. 7, these sequences are designated as the SalI-SalI sequence and the PacI-FseI sequence), oligonucleotide primer pairs were designed on the chromosome and on the targeting vector, respectively. Such positions are indicated by arrows in FIG. 8. The sequences are shown below.

```
AL39 48691F:
5'-GCAGTGACAGAAGTCCATGTTGAACTGTAC   (SEQ ID NO: 23)

ApaIlongFw1:
5'-CACAGCAACCACAGTGCTTCTTGATGAG     (SEQ ID NO: 24)

ApaIlongRv1:
5'-TCCAGAAGTGTTGGTAAACAGCCCACAA     (SEQ ID NO: 25)

AL39 56194R:
5'-TAGTCTCTCTGGATGAATATCAGCAAAACT   (SEQ ID NO: 26)
```

LA Taq polymerase (Takara Shuzo Co., Ltd.) was used, and the reaction was carried out under the conditions shown below. 5' genome analysis was carried out at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 25 cycles of denaturation at 98° C. for 5 seconds followed by annealing/extension at 68° C. for 10 minutes, and extension at 72° C. for 10 minutes. 3' genome analysis was carried out at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 6 minutes, and extension at 72° C. for 10 minutes. $MgSO_4$ (final concentration: 0.5 mM) was added to the PCR reaction solution.

Among 99 strains of the obtained blasticidin-resistant DT40 cells, 12 strains were found to produce amplification products having a size that could be deduced from the nucleotide sequence (5' genome: about 5 kb; 3' genome: about 2 kb).

(2-4) Southern Blot Analysis

As a screening method for selecting a homologous recombinant, Southern blot analysis was carried out. Two types of probes, N5'(i) and N3'(ii), were designated outside the target sequences of homologous recombination (FIG. 9). In order to prepare probes, PCR was carried out using oligonucleotide primer pairs shown below and genomic DNA of A9c11-14chr cells carrying human chromosome 14 as a template, and the resultants were, isolated, and purified.

```
AL39 46181F:
5'-AAGACACCAGGGAGTAACCT       (SEQ ID NO: 27)

AL39 46778R:
5'-GCTGAACCACTAAGGGTGAC       (SEQ ID NO: 28)

AL39 56451F:
5'-GGAATAGGGATTAGGAAATG       (SEQ ID NO: 29)

AL39 57026R:
5'-ACATGAGGTTTATTTGGTGG       (SEQ ID NO: 30)
```

Figure 10:
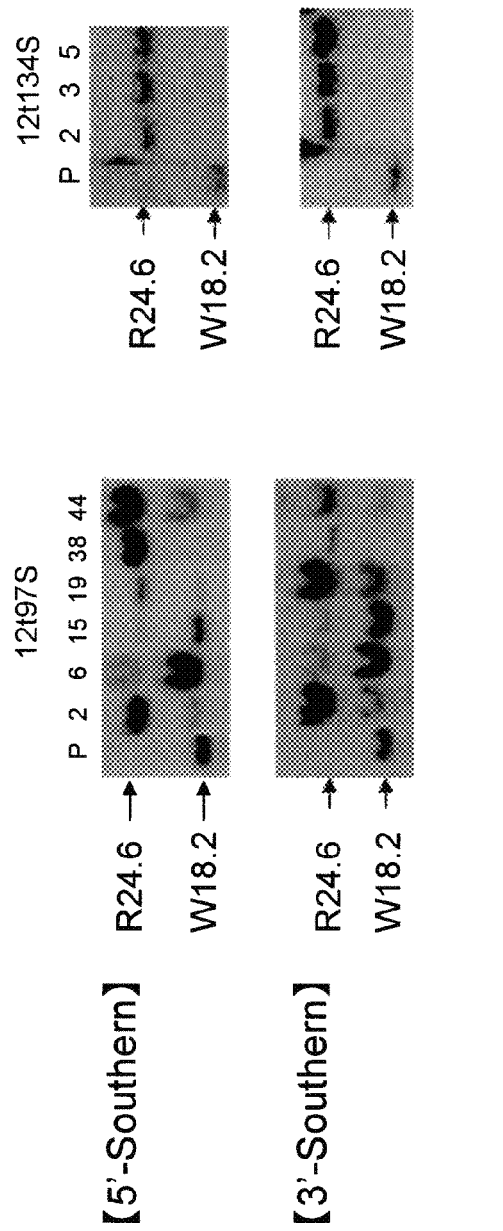
FIG. 10 shows the results of Southern analysis regarding a DT40 hybrid cell carrying a t1pSF1 vector introduced into 14AΔqHAC.

About 5 μg of genomic DNA extracted from 12 strains obtained by primary screening was digested with the StuI restriction enzyme (Roche), and Southern blot analysis was carried out by the method described in Ausubel et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). Representative results are shown in FIG. 10. The length of the restriction enzyme fragment deduced from the nucleotide sequence is 24.6 kb as a result of 5' genome analysis and 3' genome analysis in the form of a homologous recombinant, and it is 18.2 kb in the form of a wild-type (i.e., a non-recombinant). A total of 7 strains of homologous recombinants were confirmed from among 12 candidate blasticidin-resistant strains.

As a result of experiments (2-1) to (2-4) above, 7 strains of DT40 hybrid cells carrying the 14AΔqHAC vector into which the cloning site (i.e., the loxP sequence) had been inserted by homologous recombination (i.e., 12t97S1, 12t97S38, 12t134S1, 12t134S2, 12t134S3, 12t134S5, and 12t159S1) were obtained.

(3) Introduction of 14AΔqHAC Vector into CHO Cell (3-1) Introduction of 14AΔqHAC Vector into CHO Cell by Microcell Mediated Chromosome Transfer Method As chromosome donor cells, DT40 hybrid cells (12t97S1, 12t97S38, and 12t134S2) obtained in Example 1 (2), carrying the 14AΔqHAC vectors with the deleted long-arm distal regions into which the cloning sites (the loxP sequences) had been inserted were used. As the chromosome recipient cell, the Chinese hamster-derived cell line, CHO-K1 (Accession No. JCRB9018), was used.

At the outset, microcells were prepared from about $10^9$ DT40 hybrid cells. DT40 hybrid cells that had been cultured to a cell density of about 60 to 70% confluency were cultured in a culture medium (10% FBS, 1% ChS, and 0.1 mM 2-mercaptoethanol, RPMI 1640) containing colcemid (0.05 μg/ml, Invitrogen) for 13 to 18 hours to induce micronucleus formation. The cells were recovered by centrifugation, resuspended in serum-free DMEM, and plated in twelve 25-$cm^2$ centrifuge flasks (Nunc), which had been coated with poly-L-lysine in advance. The cells were allowed to stand at 37° C. for 1 hour, the culture medium was removed after the cells adhered, the cytochalasin B (10 μg/ml in DMEM, Sigma) solution preheated at 37° C. was filled in centrifuge flasks, the flask were inserted into the centrifuge, and centrifugation was carried out at 34° C. and 8,000 rpm for 1 hour. The microcells were suspended in serum-free medium (DMEM), recovered, purified by filtration using SWINNEX-25 (Millipore) equipped with filters (Whatman) having pore sizes of 8 μm, 5 μm, and 3 μm, and the resultant was suspended in 5 ml of DMEM. The microcell suspension was centrifuged at room temperature and 1,500 rpm for 5 minutes, about $10^7$ CHO-K1 cells, which had been washed twice with DMEM and then suspended in 5 ml of DMEM, were superposed thereon, and centrifugation was carried out at room temperature and 1,500 rpm for 5 minutes, and the supernatant was then removed. The cells were subjected to fusion treatment in a DMEM medium containing 45% polyethylene glycol 1500 (PEG1500, Roche) and 10% DMSO (Sigma) for 120 seconds, suspended in 120 ml of F12 medium (Invitrogen) containing 10% FBS, plated in five 48-well-plates (Falcon), and cultured in a selection medium (10% FBS, F12) containing blasticidin (8 μg/ml) 24 to 36 hours thereafter. After selection culture had been conducted for about 2 weeks, the developed drug-resistant colonies were isolated, and the subsequent analysis was performed. A total of 28 strains of blasticidin-resistant CHO strains (i.e., 9 12t97S1-derived strains, 10 12t97S38-derived strains, and 9 12t134S2-derived strains) were obtained through 6 micronuclear cell fusion operations.

(3-2) PCR Analysis

Genomic DNA of a blasticidin-resistant strain was used as a template, and the presence of two target sequences (i.e., the 5' target sequence and the 3' target sequence) was detected by PCR. PCR was carried out in accordance with Example 1 (2-3). Among the obtained 22 strains of blasticidin-resistant CHO cells, 20 strains were found to yield amplification products having a size deduced from the nucleotide sequence (i.e., about 5 kb; 5' genome region and about 2 kb; 3' genome region).

(3-3) Southern Blot Analysis

Figure 11:
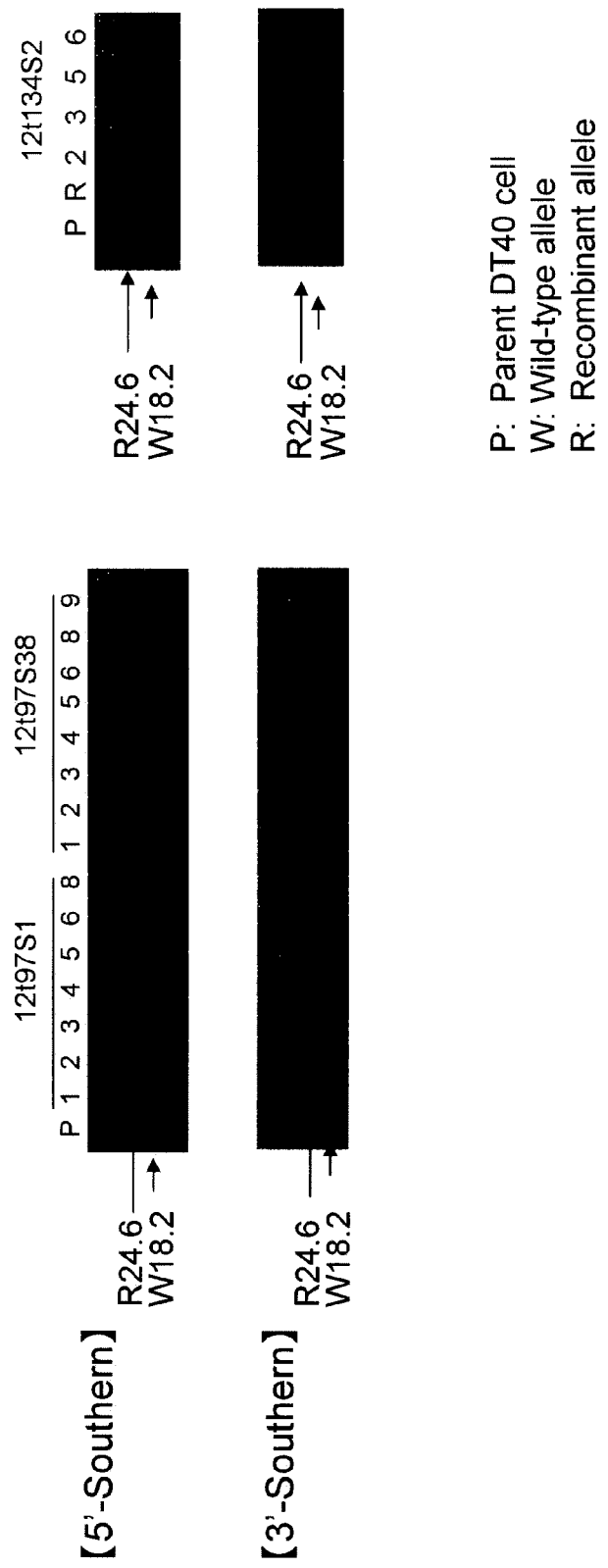
FIG. 11 shows the results of Southern analysis regarding a CHO hybrid cell into which a 14AΔqHAC vector has been introduced.

In order to confirm the structure of the introduced 14AΔqHAC vector, Southern blot analysis was carried out in the same manner as in Example 1 (2-4). Representative results are shown in FIG. 11. The length of the restriction enzyme fragment deduced from the nucleotide sequence is 24.6 kb as a result of 5' genome analysis and 3' genome analysis in the form of a homologous recombinant, and it is 18.2 kb in the form of a wild-type (i.e., a non-recombinant). A total of 19 strain of homologous recombinants were confirmed from among 20 candidate blasticidin-resistant strains (6 12t97S1-derived strains, 8 12t97S38-derived strains, and 5 12t134S2-derived strains).

(3-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of 17 strains of the blasticidin-resistant CHO strains, a total of 8 strains (i.e., 1 12t97S1-derived strain; 4 -1, 12t97S38-derived strains; 3 -3, -6, -8, -9, 12t134S2-derived strains; -3, -5, -6) were found to be of normal karyotypes, and a copy of Cot1-stained 14AΔqHAC vector was detected in most of the observed mitotic figures. Representative FISH images and the karyotype of the 14AΔqHAC vector are shown in FIG. 12A and in 12B.

Based on the experiments (3-1) to (3-4) above, the 8 strains of the obtained blasticidin-resistant CHO strains were found to carry the 14AΔqHAC vector.

Example 2

Analysis of Long-Term Stability of 14AΔqHAC Vector in CHO Cell (1) Long-Term Subculture Under Non-Selective Culture Conditions In order to confirm stability of the 14AΔqHAC vector in CHO cells, long-term subculture was carried out under non-selective culture conditions. Three of the CHO cell lines described in Example 1 (12t97S38-6, -8, and -9; hereafter 12t7S is abbreviated to "t7S38-6, -8, and -9") were used. The non-selection medium was F12 medium containing 10% FBS, and the selection medium contained said F12 medium and blasticidin added at 8 μg/ml. The $5.0 \times 10^5$ CHO cells were plated in a 10-cm dish, the cells that had been cultured to a cell density of about 80 to 90% confluency were counted, the $5.0 \times 10^5$ cells were plated again in a 10-cm dish, and subculture was continued up to the tenth passage. The number of cells was counted every passage to determine the population doubling level. The CHO strains were recovered after the tenth passage and FISH chromosome samples were prepared.

(2) FISH Analysis

FISH analysis was carried out in accordance with the method described in Matsubara et al. (FISH Experimental Protocol, Shujunsha Co. Ltd., 1994) using human-specific Cot1 probes (Invitrogen). The population doubling level and the HAC retention were measured in duplicate and the average values were determined. The results are shown in Table 1 and FIG. 13.

TABLE 1

Stability of 14AΔqHAC vector in CHO cell

| HAC | Cell population Number of subculture | HAC retention (%) Without drug selection | With drug selection |
|---|---|---|---|
| t7S38-6 | At the initiation of culture | — | 94 |
| | Ten passages | 93 | 90 |
| t7S38-8 | At the initiation of culture | — | 92 |
| | Ten passages | 72 | 82 |
| t7S38-9 | At the initiation of culture | — | 94 |
| | Ten passages | 84 | 84 |

In FIG. 13, "21ΔqHAC" indicates the results regarding a human chromosome 21-derived HAC vector (WO 2004/031385), "14AΔqHAC" indicates the results regarding an HAC vector prepared in Example 1 or 2, "14NΔqHAC(G)" indicates the results regarding an HAC vector prepared in Example 6 or 7, and "14gNΔqHAC(g)" indicates the results regarding an HAC vector prepared in Example 12 or 13.

The 14AΔqHAC vector was retained stably in CHO cells after long-term subculture. As a result of observation of images of metaphase chromosomes, 1 or 2 signals were detected per cell.

The Experiments (1) and (2) demonstrated that the 14AΔqHAC vector would be retained stably in CHO cells under non-selective culture conditions and that a copy number per cell would be maintained.

Example 3

Figure 14:
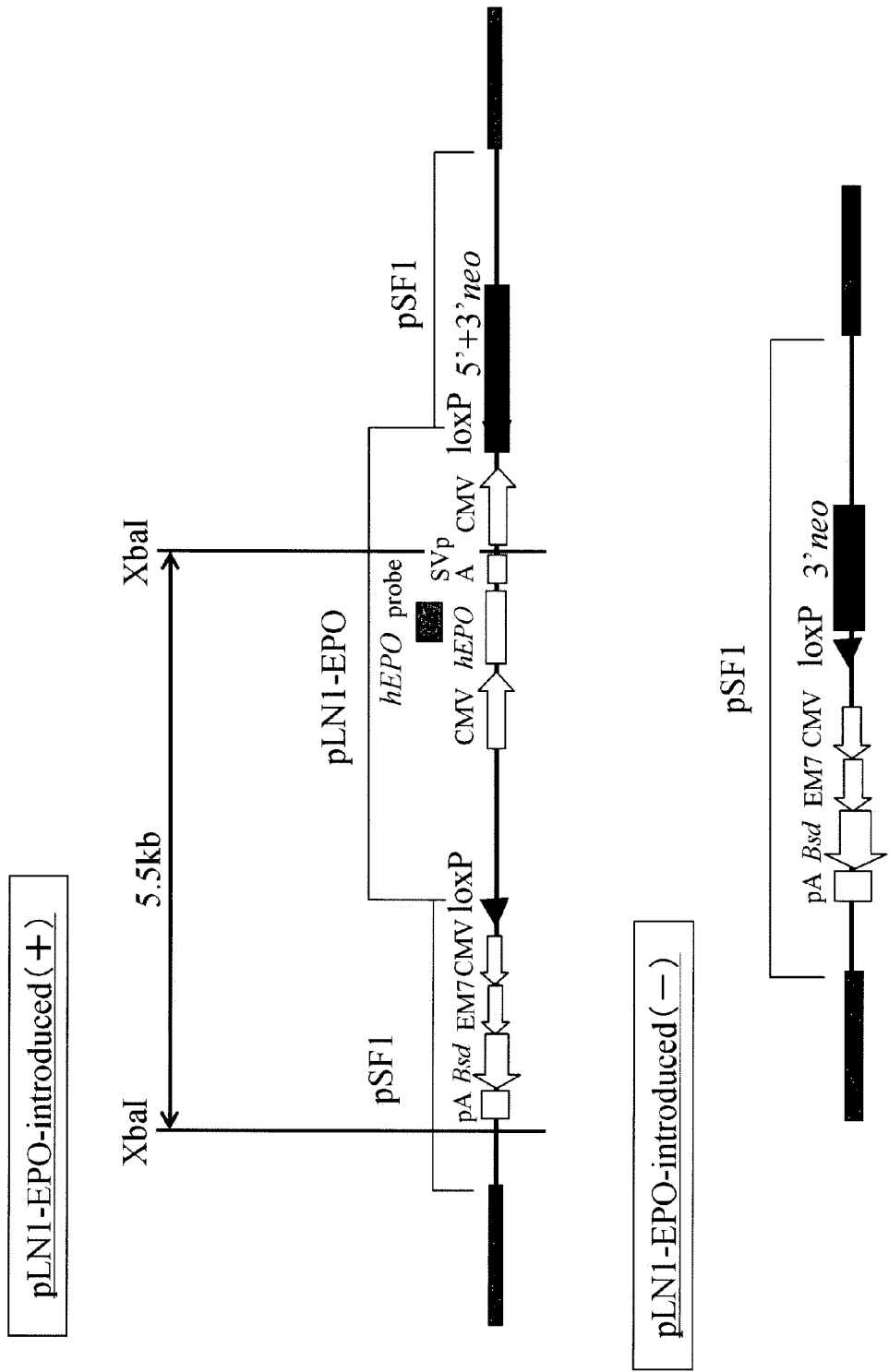
FIG. 14 shows an allele of the 14HAC vector resulting from introduction of the hEPO gene. In the figure, "hEPO" indicates a human erythropoietin gene, and CMV indicates a cytomegalovirus promoter.

Analysis of hEPO Gene Expression in CHO Hybrid Cell Comprising hEPO-14AΔqHAC Vector Introduced Therein (1) Construction of hEPO-14AΔqHAC Vector
(1-1) Introduction of hEPO Gene into 14AΔqHAC Vector The hEPO gene expression unit is inserted into the 14AΔqHAC vector constructed in Example 1. Specifically, the hEPO expression plasmid containing the loxP sequence was prepared, and the Cre recombinase was expressed transiently to insert the gene expression unit into an artificial chromosome by site-directed recombination between the loxP sequences. A recombinant comprising an insert was selected using the acquisition of G418 resistance (i.e., reconstruction of the promoter-fragmented neo-resistant gene expression unit) as an indicator. The outline is shown in FIG. 14.

The CHO hybrid cells carrying the 14AΔqHAC vectors (t7S1-1, t7S38-6, and t7S38-8) prepared in Example 1 were treated with trypsin, and $5 \times 10^6$ cells were suspended in 0.8 ml of the Hank's balanced salt solution (HBSS). In the presence of 10 μg of the hEPO expression plasmid containing the loxP sequence, pLN1-EPO (Kakeda et al., Gene Therapy; 12: 852-856, 2005), and 10 μg of the Cre enzyme expression vector, pBS185 (Life-Tech), electroporation was carried out using the Gene Pulser II (Bio-Rad). A voltage of 450 V was applied to a condenser having a capacity of 500 μF and then discharged using an electroporation cell having 4 mm of an interelectrode distance. The electroporated cells were plated in five 48-well tissue culture plastic petri-dishes (Falcon) containing F12 medium (Invitrogen) comprising 10% FBS added thereto. Two days later, a medium was exchanged with a medium containing G418 at 0.8 mg/ml (Geneticin, Invitrogen). G418-resistant colonies developed 2 to 3 weeks thereafter, a total of 113 colonies (6 t7S1-1-derived colonies, 70 t7S38-6-derived colonies, and 37 t7S38-8-derived colonies) were isolated, the isolated colonies were grown, and the subsequent analysis was performed.

(1-2) PCR Analysis

A recombinant comprising the hEPO gene expression unit inserted therein was selected by inspecting whether or not the hEPO gene expression unit had been inserted into a site of the loxP sequence of the 14AΔqHAC vector by PCR using the SVpANp1 and the Neo Rp2 primers, which had been designed on the pLN1-EPO vector and the 14AΔqHAC vector, so as to sandwich the site of the loxP sequence. Also, it was selected by inspecting amplification of the inserted hEPO gene by PCR using the M13RV and the Neo Rp2 primers of the pBS226 plasmid vector. Primer sequences and PCR conditions were determined in accordance with the method of Kakeda et al. (Kakeda et al., Gene Therapy; 12: 852-856, 2005). In the case of a recombinant comprising an insert, amplification of about 1.0 kbp is deduced with the use of the SVpANp1 and the Neo Rp2 primers and that of about 2.7 kbp is deduced with the use of the M13RV and the Neo Rp2 primers. As a result, amplification as deduced was observed in a total of 65 strains of the G418-resistant CHO hybrid cells obtained in (1-1) above (i.e., 6 t7S1-1-derived strains, 37 t7S38-6-derived strains, and 22 t7S38-8-derived strains).

Thus, these 65 strains of G418-resistant CHO hybrid cells were found to be recombinants comprising the hEPO gene expression units inserted in the loxP sequence.

(1-3) Southern Blot Analysis

Figure 15:
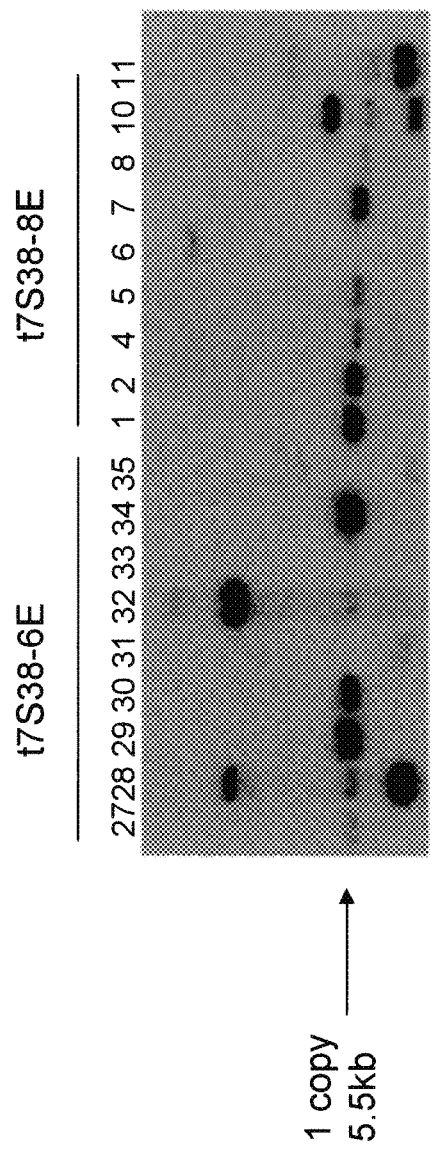
FIG. 15 shows the results of Southern analysis regarding a CHO hybrid cell into which the 14AΔqHAC vector comprising an hEPO gene introduced therein has been introduced.

Southern blot analysis was carried out in order to inspect whether or not the hEPO-14AΔqHAC vector properly carries the hEPO expression unit. The method was carried out in accordance with Kakeda et al. (Gene Therapy; 12: 852-856, 2005). Representative results are shown in FIG. 15. The length of the restriction enzyme fragment resulting from digestion with XbaI deduced from the nucleotide sequence is 5.5 kb, including the hEPO expression unit (FIG. 15). Bands having sizes as deduced were observed in a total of 33 strains from among 64 strains of the candidate G418-resistant CHO hybrid cells obtained in (1-2) (i.e., 4 t7S1-1-derived strains, 13 t7S38-6-derived strains, and 16 t7S38-8-derived strains).

(2) Expression of hEPO Genes Inserted into 14AΔqHAC Vector

Expression of hEPO genes was quantified by enzyme-linked immunosorbent assay (ELISA) of hEPO proteins generated in the culture supernatant.

Figure 16:
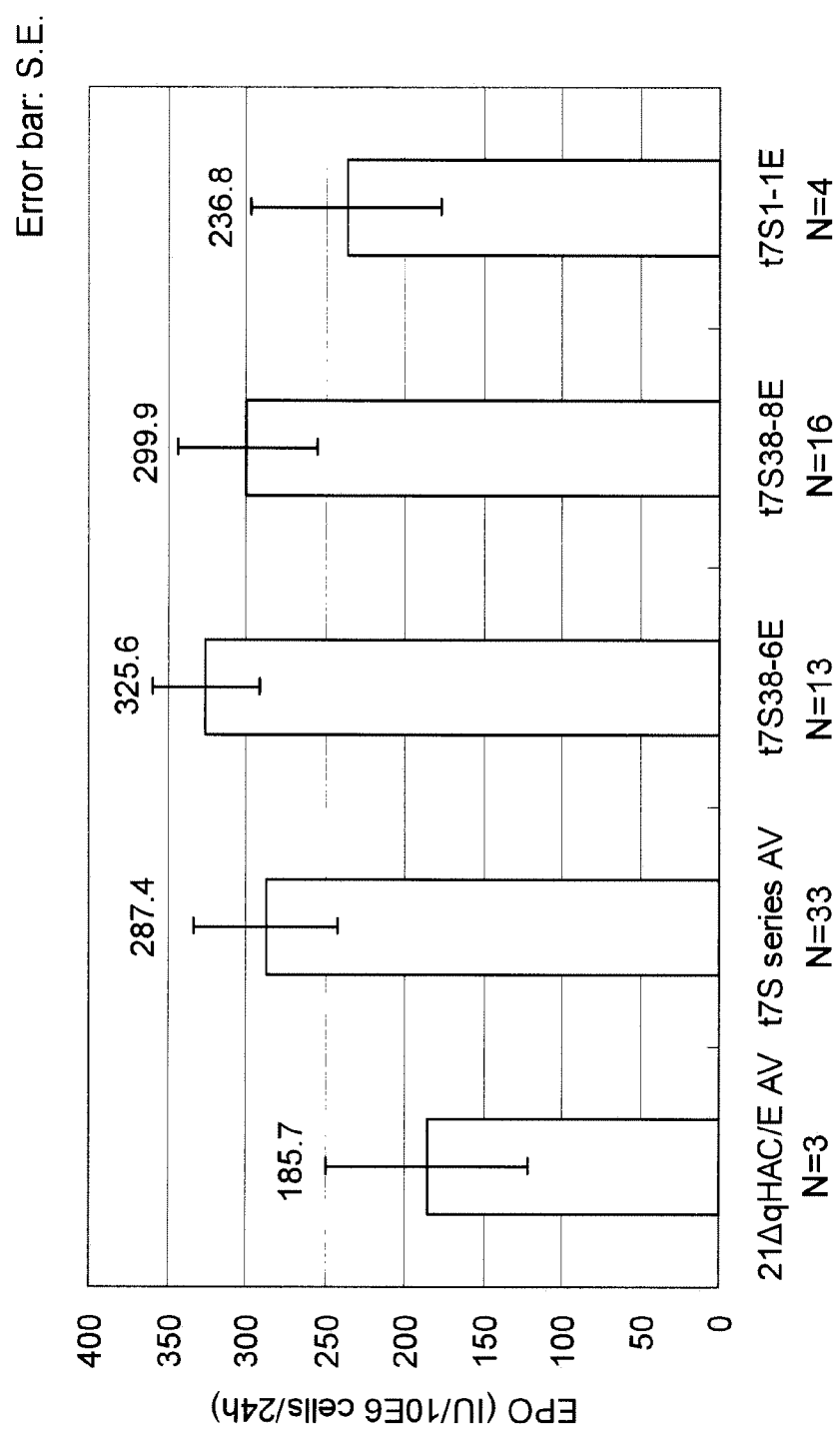
FIG. 16 shows expression of hEPO genes in the CHO hybrid cell that carries a hEPO-14AΔqHAC vector.

The 33 strains of the G418-resistant CHO hybrid cells carrying the hEPO-14AΔqHAC vector isolated in Example 3 (1-3) were plated in amounts of about $10^5$ cells on 12-well tissue culture plastic petri-dishes (Falcon) comprising 2 ml of F12 medium comprising G418 at 0.8 mg/ml containing 10% FBS. After the cells reached confluence, the medium was exchanged with 2 ml of F12 medium containing 10% FBS, culture was conducted for 2 days, the medium was exchanged again with 1 ml of F12 medium comprising 10% FBS added thereto, culture was carried out for an additional 24 hours, the supernatant was recovered, and the cell counts were determined. The hEPO ELISA kit (Quantikine IVD Human EPO Immunoassay, R&D Systems) was used to quantify hEPO in the culture supernatant. The average of experimental results that had been carried out in duplicate is shown in FIG. 16.

Thus, hEPO expression was observed in all 33 strains of the G418-resistant CHO hybrid cells carrying the hEPO-14AΔqHAC vector. The expression level thereof was higher than that of the EPO-21ΔqHAC vector with the deleted long arm.

(3) FISH Analysis

Figure 17:
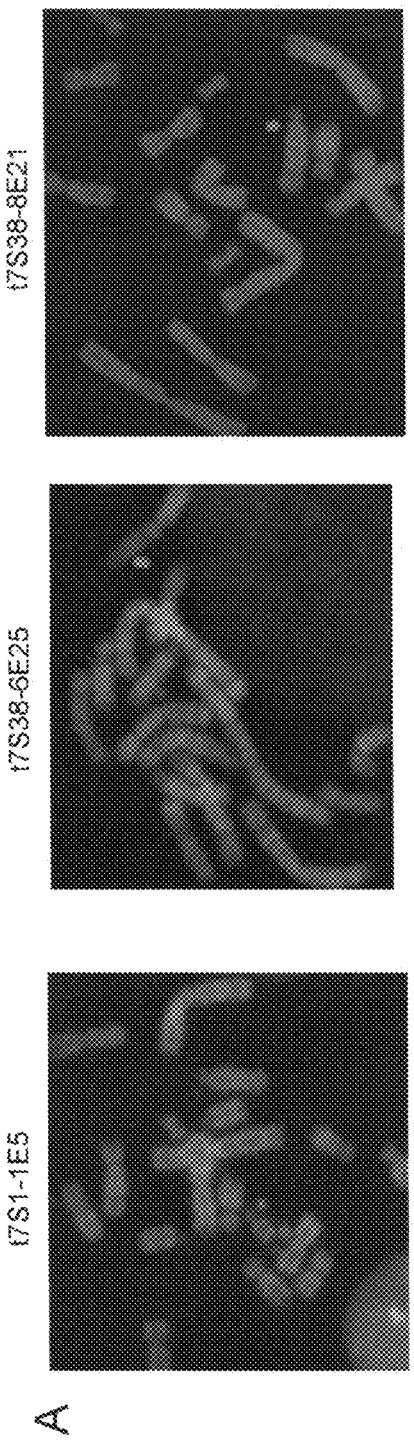
FIG. 17 shows the results of FISH analysis regarding the CHO hybrid cell that carries a hEPO-14AΔqHAC vector.

FISH analysis was carried out in accordance with the method described in Matsubara et al. (FISH Experimental Protocol, Shujunsha Co. Ltd., 1994) using human-specific Cot1 (Invitrogen) probes. Among the G418-resistant CHO hybrid cells obtained in (1-3), 14 strains were subjected to analysis. As a result, a normal karyotype and a copy of Cot1-stained hEPO-14AΔqHAC vector were detected in most observed mitotic figures of a total of 9 strains (i.e., 3 t7S 1-1-derived strains: E4, E5, and E6; 3 t7S38-6-derived strains; E25, E30, and E34; and 3 t7S38-8-derived strains; E5, E7, E21). Representative FISH images and the karyotype of the hEPO-14AΔqHAC vector are shown in FIGS. 17A and 17B.

The experiment (1) demonstrated that the resulting 9 G418-resistant strains were CHO cells of normal karyotypes carrying the hEPO-14AΔqHAC vectors.

Example 4

Analysis of Long-Term Stability of hEPO-14AΔqHAC Vector in CHO Hybrid Cell (1) Long-Term Subculture Under Non-Selective Culture Conditions In order to confirm stability of the hEPO-14AΔqHAC vector in CHO cells, long-term subculture was carried out under non-selective culture conditions and under selective culture conditions (the control group). The 3 strains of the CHO hybrid cells obtained in Example 3 (t7S38-6E25, t7S38-6E34, and t7S38-8E5) were used. A non-selection medium was F12 medium containing 10% FBS, and a selection medium comprised such F12 medium and blasticidin added thereto at 8 µg/ml. The $5.0\times10^5$ CHO cells were plated in a 10-cm dish, the cells that had been cultured to a cell density of about 80 to 90% confluency were counted, the $5.0\times10^5$ cells were plated again in a 10-cm dish, and subculture was continued up to the tenth passage. The number of cells was counted every passage to determine the population doubling level. The CHO strains were recovered after the tenth passage, and hEPO gene expression analysis and FISH analysis were carried out.

(2) hEPO Gene Expression after Long-Term Subculture

Expression of hEPO genes was quantified by enzyme-linked immunosorbent assay (ELISA) of hEPO proteins generated in the culture supernatant. The 3 strains of the CHO hybrid cells carrying the hEPO-14AΔqHAC vectors that had been subjected to long-term subculture in (1) above were analyzed in accordance with the method of Example 3 (2). As a result, hEPO expression was observed after long-term subculture in all the 3 strains of the CHO hybrid cells carrying the hEPO-14AΔqHAC vectors. The average of the results of experiments carried out in duplicate is shown in FIG. 18. Clones 6E25, 6E34, and 8E5 shown in FIG. 18 each indicate t7S38-6E25, t7S38-6E34, and t7S38-8E5.

(3) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate and the average values were determined. The results regarding the above 3 strains are shown in Table 2 and FIG. 18.

TABLE 2

Stability of hEPO-14AΔqHAC vector in CHO cell

| | | HAC retention (%) | |
|---|---|---|---|
| HAC | Cell population Number of subculture | Without drug selection | With drug selection |
| t7S38-6E25 | At the initiation of culture | — | 94.0 |
| | Ten passages | 95.5 | 97.8 |
| t7S38-6E34 | At the initiation of culture | — | 92.0 |
| | Ten passages | 88.4 | 97.7 |
| t7S38-8E5 | At the initiation of culture | — | 98.0 |
| | Ten passages | 94.2 | 97.8 |

The hEPO-14AΔqHAC vector was retained stably in CHO cells after long-term subculture. As a result of observation of images of metaphase chromosomes, 1 or 2 signals were detected per cell.

The above experiments (1) to (3) demonstrated that the hEPO-14AΔqHAC vector would be retained stably in CHO cells after long-term subculture under non-selective culture conditions, that a copy number per cell would be maintained, and that hEPO gene expression would be maintained.

Example 5 hEPO Gene Expression in Human Normal Fibroblasts Comprising hEPO-14AΔqHAC Vector Introduced Therein (1) Preparation of hEPO-14AΔqHAC Vector-Introduced Human Normal Fibroblasts (1-1) Introduction of hEPO-14AΔqHAC Vector into Human Normal Fibroblasts, HFL-1, by Micronuclear Fusion As chromosome donor cells, among the CHO cells carrying the hEPO-14AΔqHAC vectors obtained in Example 3, clones having the high capacity of forming micronucleus (t7S38-6E25, t7S38-6E34, and t7S38-8E5) were used. As chromosome recipient cells, human normal fibroblasts, HFL-1 (obtained from the Cell Engineering Division of the RIKEN BioResource Center; Accession No. RCB0521) were used. At the outset, microcells were prepared from about $10^7$ cells of t7S38-6E25 or t7S38-8E5. Specifically, t7S38-6E25 or t7S38-8E5 cells that had been cultured to a cell density of about 80 to 90% confluency in twenty four 25-cm$^2$ centrifuge flasks (Nunc) were cultured for 3 days in a medium (F12 medium containing 20% FBS and G418 at 0.8 mg/ml) containing colcemid (0.1 μg/ml, Invitrogen) to induce micronucleus formation. After the medium was removed, the cytochalasin B (10 μg/ml in DMEM, Sigma) solution preheated to 37° C. was filled in centrifuge flasks, centrifuge flasks were inserted into a centrifuge, and centrifugation was carried out at 34° C. and 8,000 rpm for 1 hour. The microcells were suspended in serum-free medium (DMEM), recovered, and purified by filtration using SWINNEX-25 (Millipore) equipped with filters (Whatman) having pore sizes of 8 μm, 5 μm, and 3 μm. The purified microcells were resuspended in 2 ml of DMEM containing Phytohemagglutinin P (Difco) at 50 μg/ml. The purified micronuclear cells were added to two 25-cm$^2$ culture flasks (Falcon) in which HFL-1 cells had been cultured to 90% confluency, the cells were allowed to stand at 37° C. for 15 minutes, and the cells were then subjected to fusion in a DMEM solution containing 45% polyethylene glycol 1500 (PEG1500, Roche) and 10% DMSO (Sigma) for 1 minute. After the cells were cultured in DMEM medium containing 20% FBS for 24 hours, the cells were dispersed by trypsin treatment, and the resultants were plated in two collagen-I-coated 48-well tissue culture plastic plates (Falcon). On the following day, the medium was exchanged with a selection medium (DMEM containing 20% FBS) containing blasticidin (3 μg/ml). Selective culture was carried out for about 4 weeks. The developed drug-resistant colonies were isolated, and the subsequent analysis was performed. As a result of 28 micronuclear cell fusion operations (13 operations for t7S38-6E25; 2 operations for t7S38-6E34; and 13 operations for t7S38-8E5), 138 drug-resistant colonies were obtained (56 colonies derived from t7S38-6E25, 26 colonies derived from t7S38-6E34, and 56 colonies derived from t7S38-8E5). Among such colonies, cells obtained with the use of the t7S38-6E25 cells as chromosome donor cells and cells obtained with the use of the t7S38-8E5 cells are hereafter referred to as "t25H cells" and "t5H cells", respectively (1-2) PCR Analysis Whether or not a human chromosome carries the hEPO-14AΔqHAC vector was inspected by PCR amplification using the SVpANp1 and Neo Rp2 primers of Example 3 (1-2) and the STS marker, i.e., the D2S1334 primer, in accordance with the method of Kakeda et al. (Gene Therapy; 12: 852-856, 2005). Also, inclusion of chromosome donor CHO cells was inspected by PCR amplification using the CHO furin gene-specific primers, furin3'subF and furinEx6-28R. The sequences of the designed primers are shown below.

```
furin3'subF:
                                  (SEQ ID NO: 31)
5'-ACTCAGAGATCCACTGCACCAGGATCCAAGGGAGG furinEx6-28R_short
                                  (SEQ ID NO: 32)
CTACACCACAGACACCATTGTTGGCTACTGCTGCC
```

The reactions were carried out at 94° C. for 5 minutes, followed by 32 cycles of denaturation at 94° C. for 20 seconds followed by annealing/extension at 68° C. for 3 minutes. When the hEPO-14AΔqHAC vector-carrying HFL-1 cells do not include the chromosome donor CHO cells, amplification of about 1.0 kbp is deduced with the use of the SVpANp1 and the Neo Rp2 primers, amplification of about 0.6 kbp is deduced with the use of the D2S1334 primer, and no amplification is deduced with the use of furin3'subF and furinEx6-28R. As a result, amplification as deduced was observed in a total of 7 strains from among the 138 blasticidin-resistant strains obtained in (1-1) above (i.e., t5H3, 4, 26, 27, 28, 29, and t25H2 cells).

Figure 19:
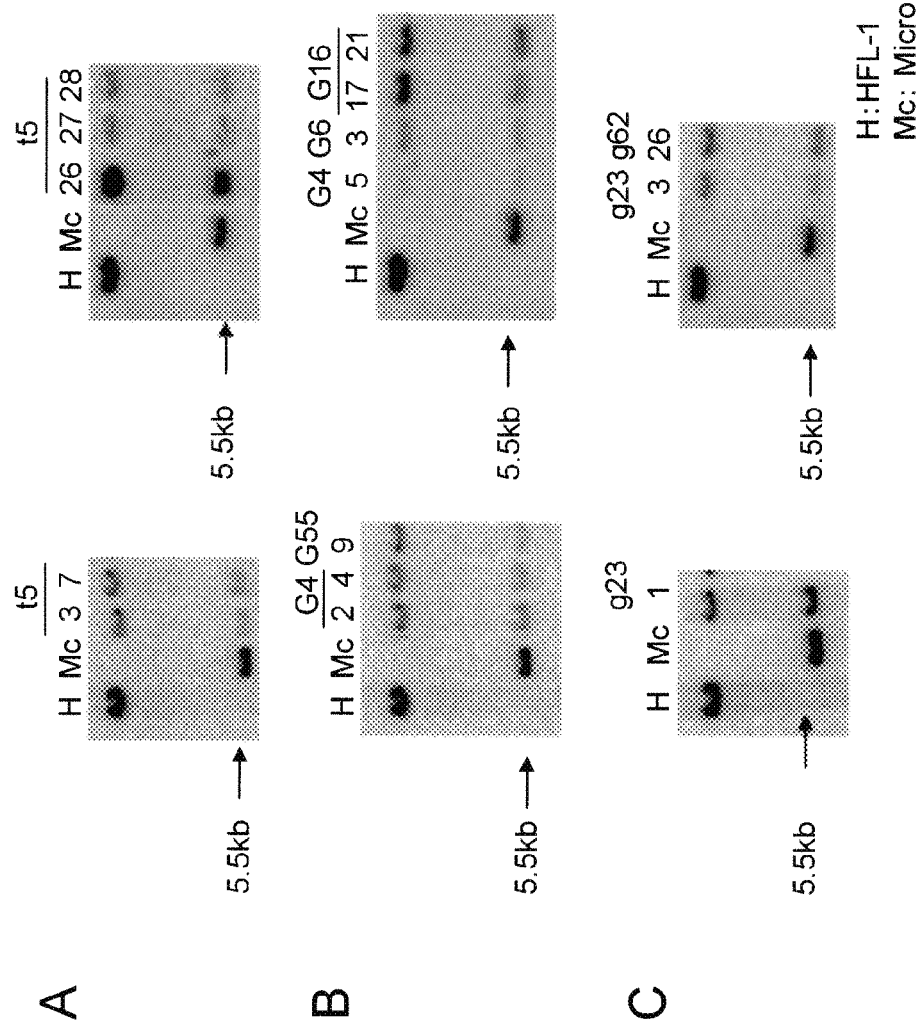
FIG. 19 shows the results of Southern analysis regarding a human normal fibroblast into which the hEPO-14A/N/gNΔqHAC vector has been introduced wherein: (A) indicates hEPO-14AΔqHAC; (B) indicates hEPO-14NΔqHAC; and (C) indicates hEPO-14gNΔqHAC.
Figure 20:
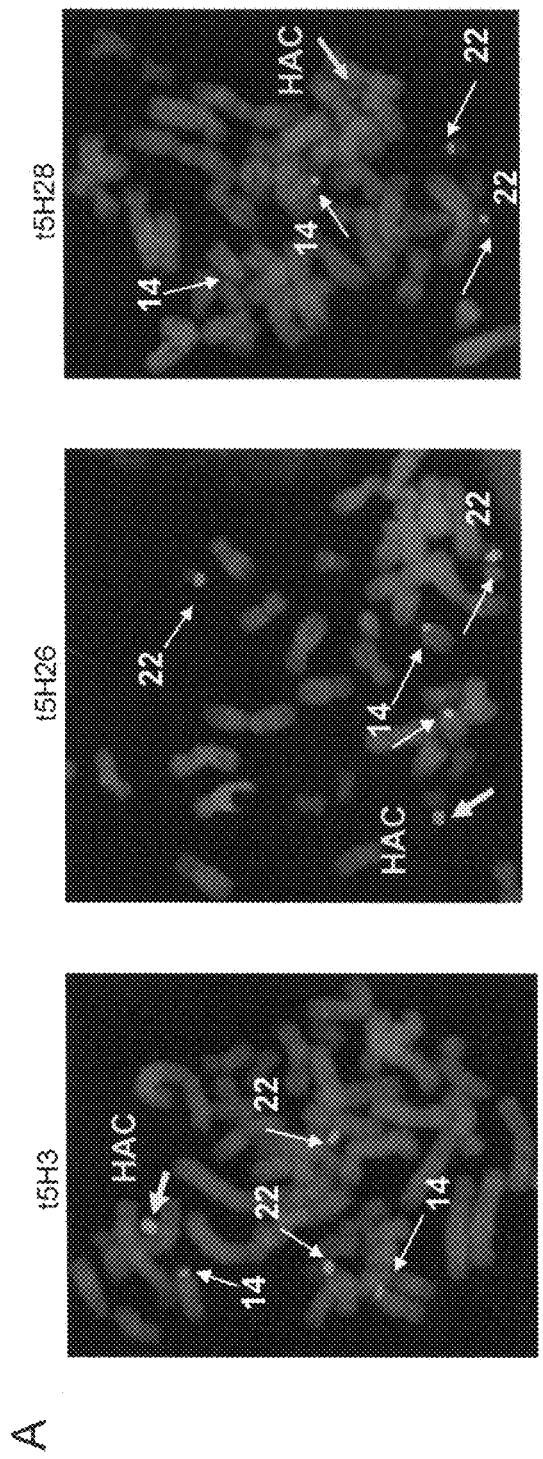
FIG. 20 shows the results of FISH analysis regarding a human normal fibroblast into which the hEPO-14AΔqHAC vector has been introduced.

Thus, the 6 blasticidin-resistant strains were confirmed to be the hEPO-14AΔqHAC vector-carrying HFL-1 cells.
(1-3) Southern Blot Analysis In order to inspect whether or not the hEPO-14AΔqHAC vector properly carries the hEPO expression unit, 5 strains (i.e., t5H3, 7, 26, 27, and 28 cells) from among the above blasticidin-resistant strains were subjected to Southern blot analysis. The method was carried out in accordance with Kakeda et al. (Gene Therapy; 12: 852-856, 2005). Representative results are shown in FIG. 19A. The length of the restriction enzyme fragment resulting from digestion with XbaI deduced from the nucleotide sequence is 5.5 kb, including the hEPO expression unit. As a result, a band of a deduced size was found in all the 5 hEPO-14AΔqHAC vector-carrying blasticidin-resistant strains obtained in (1-2) above.
(1-4) FISH Analysis FISH analysis was carried out in accordance with the method described in Matsubara et al. (FISH Experimental Protocol, Shujunsha Co. Ltd., 1994). Human chromosome 14- and human chromosome 22-specific α-satellite DNA probe (Q-Biogene, Funakoshi) were used. As a result of analysis of 3 strains (t5H3, 26, and 28) among the blasticidin-resistant strains, the 3 strains (t5H3, 26, and 28) were found to be of the normal karyotype, and signals were detected in 4 sites in the centromere region of a pair of human chromosome 14 and human chromosome 22 derived from a host cell and in a site derived from a copy of 14AΔqHAC vector in most of the observed mitotic figures. The results are shown in FIG. 20A and FIG. 20B.

The experiments (1-1) to (1-4) demonstrated that the obtained 3 blasticidin-resistant strains s were HFL-1 cells carrying the hEPO-14AΔqHAC vector and having the normal karyotypes.
(2) hEPO Gene Expression in hEPO-14AΔqHAC Vector-Carrying HFL-1 Cells Expression of hEPO genes was quantified by enzyme-linked immunosorbent assay (ELISA) of hEPO proteins generated in the culture supernatant.

The 4 hEPO-14AΔqHAC vector-carrying blasticidin-resistant HFL-1 strains isolated in (1) above were plated in amounts of about $10^5$ cells each on collagen-I-coated 24-well tissue culture plastic petri-dishes (Falcon) comprising 1 ml of selection medium (20% FBS, DMEM) containing blasticidin (3 μg/ml). After the cells reached confluence, the cells were cultured for 7 days, the medium was exchanged with a fresh medium, culture was carried out for an additional 24 hours, the supernatant was recovered, and the number of cells was counted. hEPO in the culture supernatant was quantified using the hEPO ELISA kit (Quantikine IVD Human EPO Immunoassay, R&D System). The results thereof are shown in "14A-HAC" in FIG. 21.

Thus, hEPO expression was observed in all the 3 HFL-1 strains carrying hEPO-14AΔqHAC vectors.

Example 6

Construction of 14HAC (14NΔqHAC) Vector by Deletion of the Long-Arm Distal Region from Human Chromosome 14

The loxP sequences were inserted into the long-arm distal region and the long-arm proximal region by homologous recombination, so that the HAC vector would comprise the telomere sequence and the short subtelomere sequence (about 5 kb) at the end of human chromosome 14, and a region between two sites of the loxP sequence was cleaved and deleted by site-directed recombination by Cre to construct an artificial chromosome vector with the deleted long-arm distal region (14NΔqHAC).

(1) Deletion of Long Arm from Human Chromosome 14 by Site-Directed Recombination (1-1) Construction of ploxpPGK-14qtel Vector for Inserting the Telomere-Side loxP Sequence into the Long-Arm Distal Region of Human Chromosome 14

As a vector for inserting the loxP sequence (i.e., the targeting vector), ploxpPupBSD-PGK prepared by inserting the KpnI* (a sequence for abolishing the site)-SrfIPacI-PmlI-KpnI linker into the KpnI site of ploxPupBSD (WO 00/10383) was used. The nucleotide sequences of the KpnI*-SrfI-PacI-PmlI-KpnI linker are shown below.

```
Loxpupbsd kpnI S
5'-AGCCCGGGCTTAATTAACACGTGGGTAC    (SEQ ID NO: 33)

Loxpupbsd kpnI AS
5'-CCACGTGTTAATTAAGCCCGGGCTGTAC    (SEQ ID NO: 34)
```

Based on the nucleotide sequence (Accession No. AB019437) of the long-arm distal region of human chromosome 14 obtained from the GenBank database, two target sequences for insertion of the ploxpPGK-14qtel vectors were designed. The Tel-side target sequences (about 9.5 kb in total) was amplified by PCR while being divided into 4 fragments using the A9/#14 genome as a template, the resultant was cloned into pUC18, and the 5'- and 3'-target sequence fragments were cleaved by digestion with restriction enzymes.

The fragment (i) of 0 kb-2.9 kb (comprising the SalI site at the 5' end and the BamHI site at the 3' end) was amplified by LA-PCR, digested with SalI and BamHI restriction enzymes, and then introduced into the SalI-BamHI site of pUC18. Sequences of oligonucleotide primers for amplifying the same by PCR are shown below.

```
AB019437 0 kb Fw (SalI):
5'-GCGTCGACGCAAGCTTAAATAGTGTTGC    (SEQ ID NO: 35)

AB019437 2.9 kb Rv:
5'-GAGCCAACCAAAGTGGAGAA            (SEQ ID NO: 36)
```

The fragment (ii) of 2.3 kb-5.4 kb (comprising the BamHI site at the 5' end and the AccI site at the 3' end) was amplified by LA-PCR, digested with BamHI and AccI restriction enzymes, and then introduced into the BamHI-AccI site of pBluescript. Sequences of oligonucleotide primers for amplifying the same by PCR are shown below.

```
AB019437 2.3 kb Fw:
5'-TCACCATGTTGACCAGGCTA    (SEQ ID NO: 37)

A1019437 5.4 kb Rv:
5'-AGCTCGAGAGGCACTGAATC    (SEQ ID NO: 38)
```

The fragment (iii) of 4.5 kb-6.7 kb (comprising the AccI site at the 5' end and the KpnI site at the 3' end) was amplified by LA-PCR, digested with AccI and KpnI restriction enzymes, and then introduced into the AccI-KpnI site of pBluescript comprising the fragment (ii). Sequences of oligonucleotide primers for amplifying the same by PCR are shown below.

```
AB019437 4.5 kb Fw:
5'-AGGGTCTTCAAAATGCCTGA    (SEQ ID NO: 39)

IGHV7-81Fw:
5'-GCCATGTCCTCAGCCTTTAG    (SEQ ID NO: 40)
```

The fragment (iv) of 6.3 kb-9.5 kb (comprising the KpnI site at the 5' end and the EcoRI site at the 3' end) was amplified by LA-PCR, digested with KpnI and EcoRI restriction enzymes, and then introduced into KpnI-EcoRI of pUC18 containing the fragment (i). Sequences of oligonucleotide primers for amplifying the same by PCR are shown below.

```
IGHV7-81Rv
5'-CTGGAGCATCCTCTTCTTGG        (SEQ ID NO: 41)

AB019437 9.5 kb Rv(EcoRI):
5'-CGGAATTCCGGGAGTGGGTGGCATAAAC (SEQ ID NO: 42)
``` pBluescript comprising the fragments (ii) and (iii) was digested with BamHI and KpnI restriction enzymes, and introduced into the BamHI-KpnI site of pUC18 comprising the fragments (i) and (iv), followed by cloning of the Tel-side target sequence (about 9.5 kb in total). PCR was carried out in accordance with the method of Example 1 (1-1), genomic DNA of human chromosome 14-carrying mouse A9 hybrid cells (A9c11-14chr) was used as a template, the above primers and LA Taq polymerase (Takara Shuzo Co., Ltd.) were used, and the reactions were carried out at 94° C. for 1 minute, followed by 30 cycles of denaturation at 94° C. for 30 seconds, annealing at 60° C. for 30 seconds, and extension at 72° C. for 3 min and extension at 70° C. for 10 minutes.

A 5' region (tel side) of 4.4 kb was cloned into the KpnI-ApaI site of the ploxPupBSD-PGK vector by linearizing pUC18 containing the above Tel-side target sequence (about 9.5 kb in total) by digestion with the SphI restriction enzyme, adding the KpnI-SphI linker, and digesting the same with KpnI and ApaI restriction enzymes, followed by purification. The sequences of the KpnI-SphI linker are shown below.

```
KS linker S:  5'-[Phosp]CCCGCATG    (SEQ ID NO: 43)

KS linker AS: 5'-[Phosp]CGGGGTAC    (SEQ ID NO: 44)
```

Figure 22:
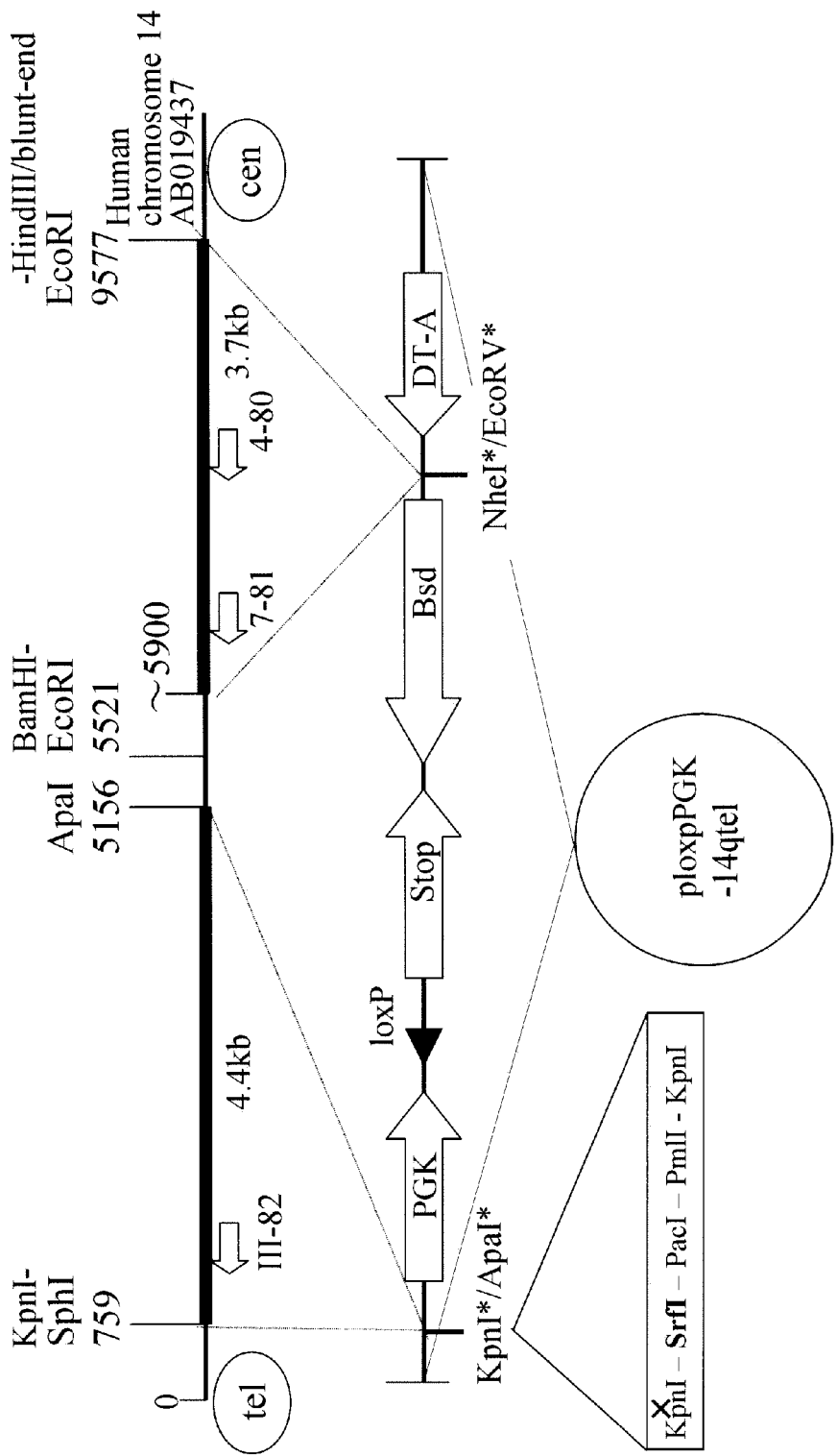
FIG. 22 shows the structure of the ploxpPGK-14qtel vector for insertion of the loxP sequence on the telomere side of the long-arm distal region of human chromosome 14.
Figure 23:
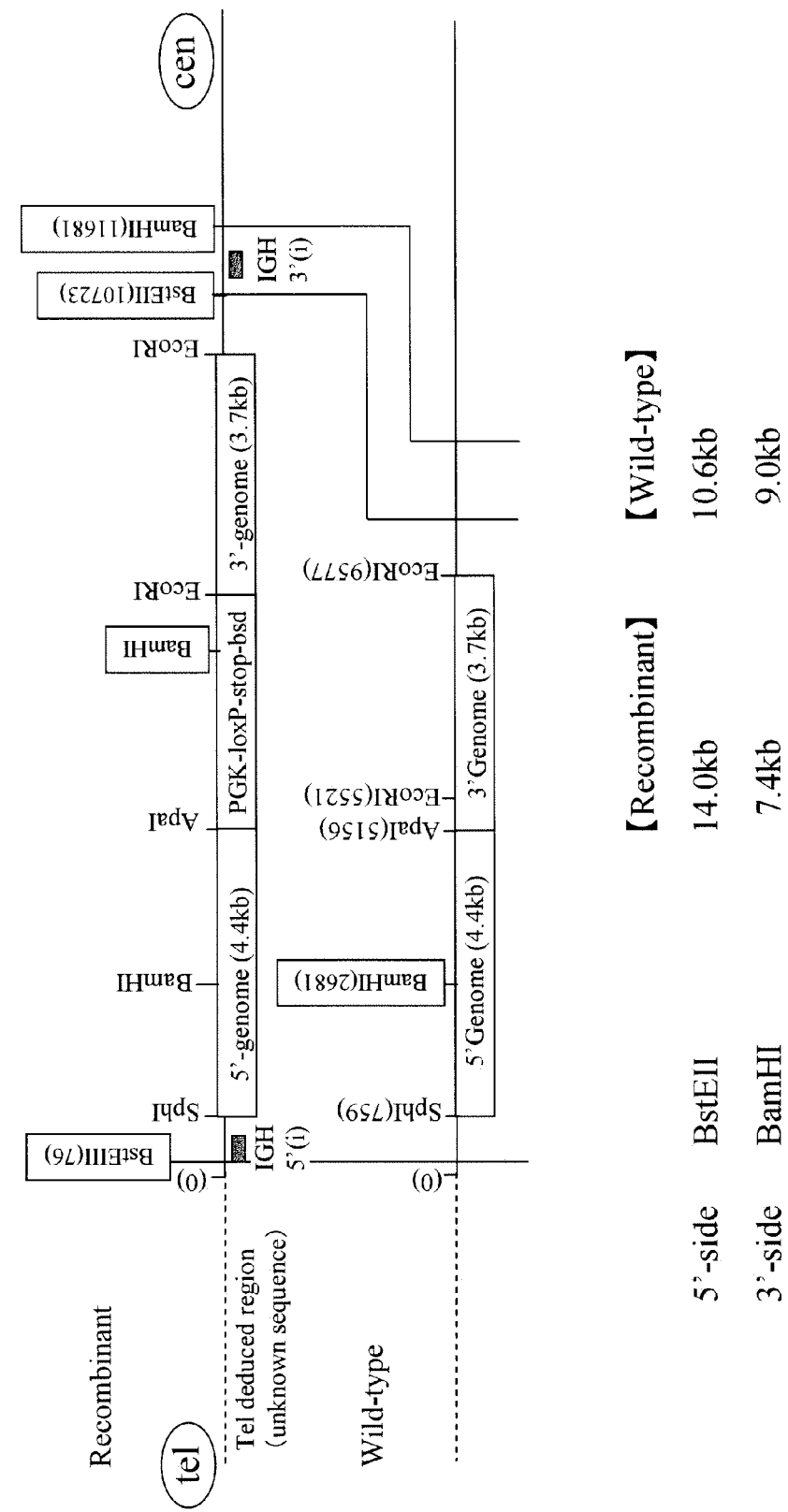
FIG. 23 shows an allele resulting from introduction of a ploxpPGK-14qtel vector into human chromosome 14q.

A 3' region (cen side) of 4.0 kb was cleaved from pUC18 containing the Tel-side target sequence (about 9.5 kb in total) by digestion with the EcoRI, subcloned into the EcoRI site of pBluescript, digested with the HindIII restriction enzyme, blunt-ended, further digested with the BamHI restriction enzyme, purified, and then cloned into the NheI-EcoRV site of the ploxPupBSD-PGK vector containing the 5' region (tel side) of 4.4 kb. The size of the final ploxpPGK-14qtel construct is about 15.7 kb. FIG. 22 shows the ploxpPGK-14qtel vector and FIG. 23 shows the target sequence and a chromosome allele resulting from homologous recombination.

(1-2) Introduction of ploxpPGK-14qtel Vector for Inserting the loxP Sequence into the Long-Arm Telomeric Distal Region of DT40 Cell Carrying Human Chromosome 14

The ploxpPGK-14qtel construct was converted into linearized DNA by digestion with the SrfI restriction enzyme in accordance with the method of Example 1 (1-2). The construct was introduced into DT40(#14)2-4 hybrid cell carrying human chromosome 14. Selection culture was carried out using blasticidin (final concentration: 8 ug/ml), and drug-resistant colonies developed 2 to 3 weeks thereafter. A total of 480 blasticidin-resistant colonies obtained through two transfection operations were isolated, grown, and then subjected to the subsequent analysis.

(1-3) PCR Analysis

Figure 24:
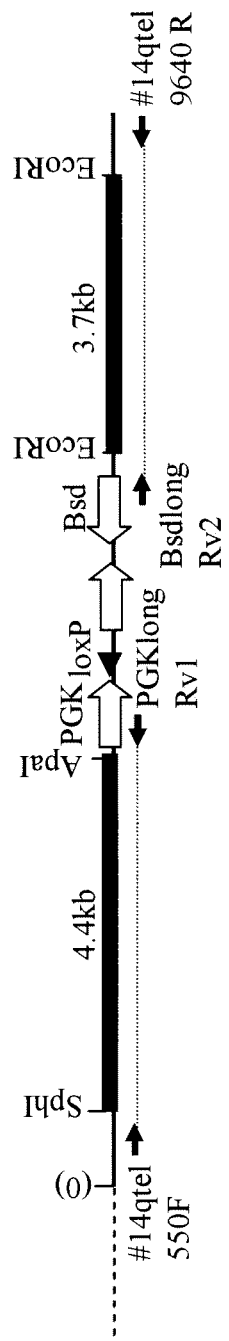
FIG. 24 shows the results of PCR analysis regarding introduction of the ploxpPGK-14qtel vector into human chromosome 14q.

Genomic DNA of a blasticidin-resistant strain was used as a template, and the presence of two target sequences (i.e., the 5' target sequence and the 3' target sequence) was detected by PCR in accordance with the method of Example 6 (1-1). By sandwiching these two target sequences (indicated as the "5' genome" and "3' genome" in FIG. 23), oligonucleotide primer pairs were designed on the chromosome and on the targeting vector, respectively. Such positions are indicated by arrows in FIG. 24. The sequences are shown below.

```
                                            (SEQ ID NO: 45)
14qtel 550F:   5'-CATTCATGGTAGTCATTGGTGCTGTTCTCC (SEQ ID NO: 46)
PGK longRv1:    5'-ACTTCCTGACTAGGGGAGGAGTAGAAGGTG (SEQ ID NO: 47)
Bsd longRv2:    5'-AGTGGGCAGTTTACCGTAAATACTCCACCC (SEQ ID NO: 48)
14qtel 9640R:  5'-TATGGAAATCTGAGATGTGCCCAGCCTCAG
```

From among the above 480 blasticidin-resistant strains, the presence of two target sequences (i.e., the 5' target sequence and the 3' target sequence) was observed in 3 strains.

(1-4) Southern Blot Analysis

As a screening method for selecting a homologous recombinant, Southern blot analysis was carried out. Probes were designated outside the two target sequences (i.e., the 5' target sequence and the 3' target sequence) of homologous recombination (IGH5' and IGH3') (FIG. 23). In order to prepare probes, PCR was carried out using oligonucleotide primer pairs shown below and genomic DNA of A9c11-14chr cells carrying human chromosome 14 as a template, and the resultants were isolated, and purified.

```
14qtel 5'probe1Fw:
5'-GTGGGTCCTGAGGAGAACAA        (SEQ ID NO: 49)

14qtel 5'probe1Rv:
5'-TTCTTCTCACCTCCATTGGC        (SEQ ID NO: 50)

14qtel 3probe1Fw:
5'-CCTAAAGCACATACAGCAGC        (SEQ ID NO: 51)

14qtel 3'probe1Rv:
5'-TCTCCAGGGGAAATCCAATC        (SEQ ID NO: 52)
```

Figure 25:
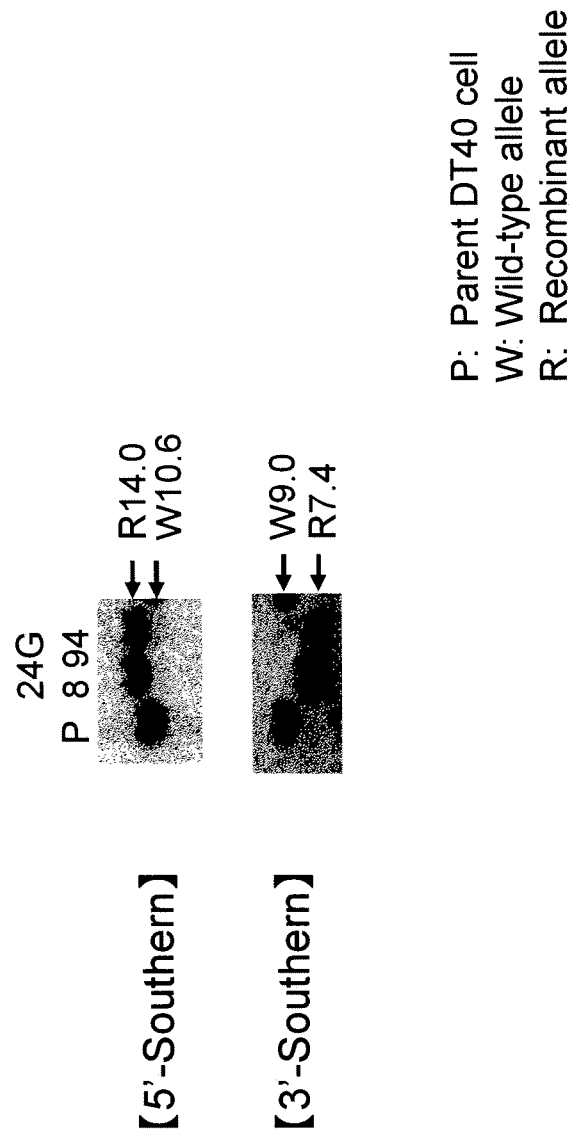
FIG. 25 shows the results of Southern analysis of a DT40 hybrid cell that carries the ploxpPGK-14qtel vector introduced into human chromosome 14q.

About 5 μg of genomic DNA extracted from the 3 strains obtained by primary screening was digested with the restriction enzyme, BstEII (5'-side) or BamHI (3'-side) (Roche), and Southern blot analysis was carried out by the method described in Ausubel et al. (Current Protocols in Molecular Biology, John Wiley & Sons, Inc., 1994). The signal to which the labeled probe had hybridized was detected by the Typhoon9210 image analyzer (Molecular Dynamics). Representative results are shown in FIG. 25. The length of the restriction enzyme fragment deduced from the nucleotide sequence is 14.0 kb in the form of a homologous recombinant, and it is 10.6 kb in the form of a wild-type (i.e., a non-recombinant), for 5'-target sequence. Such length is 7.4 kb in the form of a homologous recombinant, and it is 9.0 kb in the form of a wild-type (i.e., a non-recombinant), for 3'-target sequence. A total of two strains of homologous recombinants (24G8 and 24G94) were identified from among the 3 candidate strains.

(2) Insertion of the loxP Sequence into the Centromeric Long-Arm Proximal Region of Human Chromosome 14

(2-1) Construction of ploxPHYGOR/n1 Vector for Inserting the loxP Sequence into the Centromeric Long-Arm Proximal Region of Human Chromosome 14

As a vector for inserting the loxP sequence (i.e., a targeting vector), ploxPdownPURO-HYG prepared by inserting the FseI* (a sequence for abolishing a site)-PmlI-PacI-SrfI-FseI linker into the FseI site of ploxPdownPURO (WO 00/10383) was used. The nucleotide sequences of the FseI*-PmlI-PacI-SrfI-FseI linker are shown below.

```
Loxpdownhyg fseI S:
5'-CCCACGTGTTAATTAAGCCCGGGCATCCGG      (SEQ ID NO: 53)

Loxpdownhyg fseI AS:
5'-ATGCCCGGGCTTAATTAACACGTGGGCCGG      (SEQ ID NO: 54)
```

Based on the nucleotide sequence (Accession No. AL391156) of the long-arm distal region of human chromosome 14 obtained from the GenBank database, two target sequences for inserting the ploxPHYGOR/n1 vector were designed. Sequences of oligonucleotide primers comprising restriction enzyme recognition sequences added thereto for amplifying the same by PCR are shown below.

```
For 5'-target sequences:
49050F2longSalI:
                                            (SEQ ID NO: 55)
5'-GACAGTGTCGACAGTGAGACTTGTAGGCTACAAGAAAAGG 53978R2long2SalI:
                                            (SEQ ID NO: 56)
5'-GACAGTGTCGACTCTGATAATGCGGAATGAGTAGGGAGGC For 3'-target sequences:
54023FlongFseI:
                                            (SEQ ID NO: 57)
5'-AGGCCGGCCGTTGGTAAAGATTGCTACACTTACGGCA 56084R1longPacI:
                                            (SEQ ID NO: 55)
5'-CTTAATTAACAAGAGCTCTACAACTGTCCATCGAAAC
```

Figure 26:
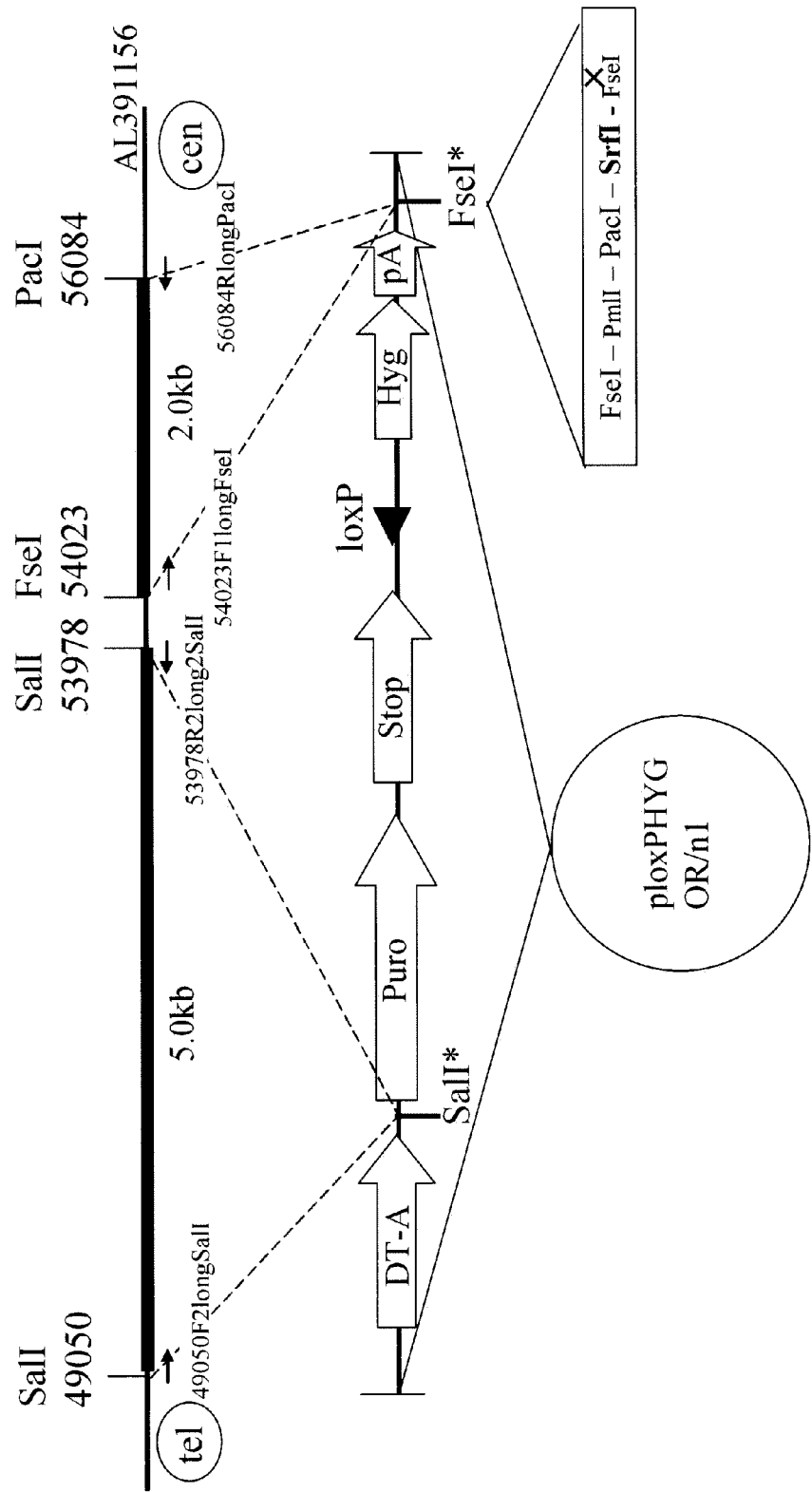
FIG. 26 shows the structure of the ploxPHYGOR/n1 vector for insertion of the loxP sequence on the centromere side of the long-arm proximal region of human chromosome 14.
Figure 27:
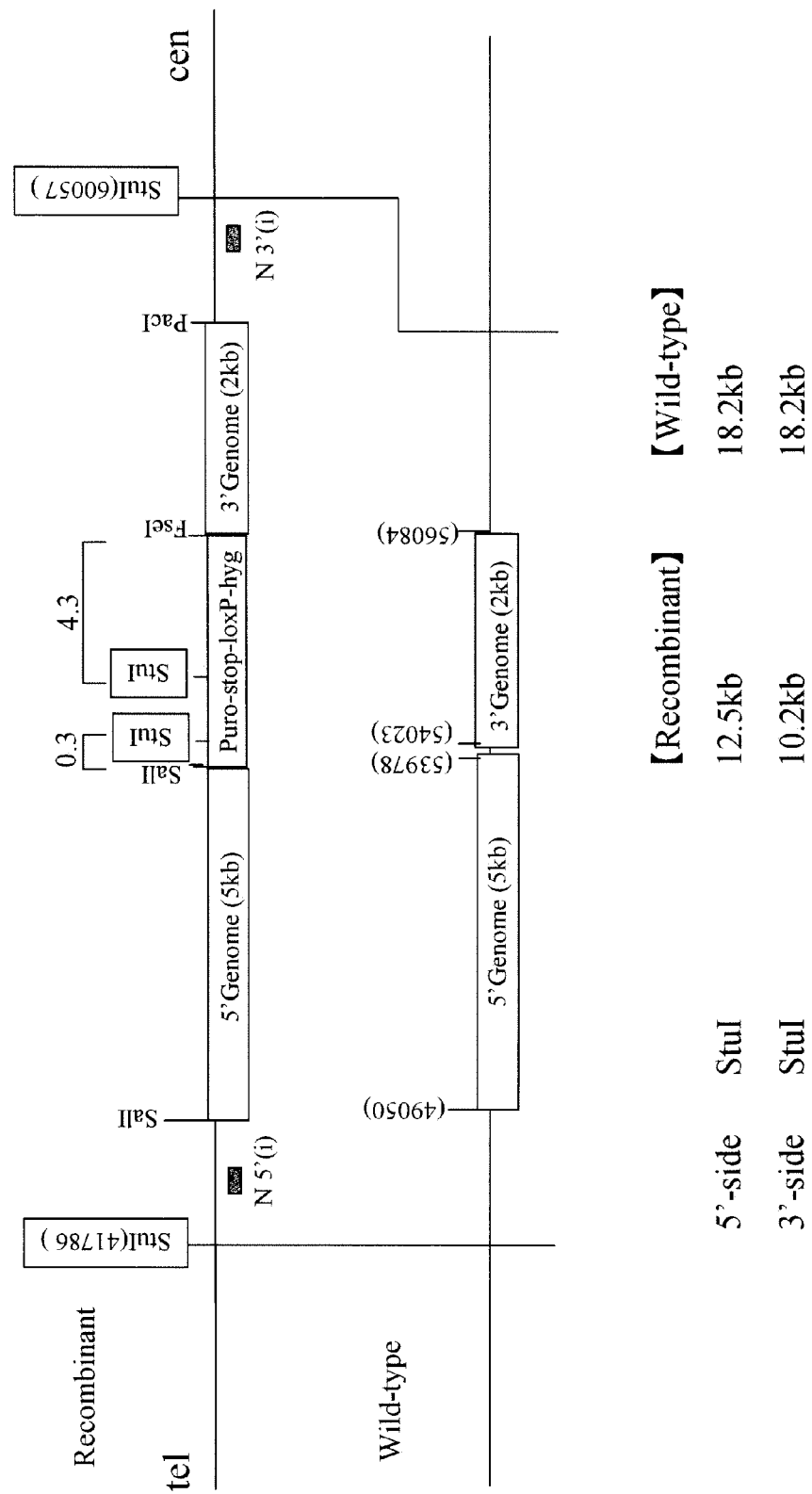
FIG. 27 shows an allele resulting from introduction of the ploxPHYGOR/n1 vector into human chromosome 14q.

In accordance with the method of Example 1 (1-1), genomic DNA of the mouse A9 hybrid cell (A9c11-14chr) carrying human chromosome 14 was used as a template, and the above primers were used to amplify the two target sequences for recombination, i.e., the 5' target sequence and the 3' target sequence, by PCR. LA Taq polymerase (Takara Shuzo Co., Ltd.) was used. The 5'-target sequences were subjected to the reactions at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 30 cycles of denaturation at 98° C. for 5 seconds followed by annealing/extension at 68° C. for 10 minutes, and extension at 70° C. for 10 minutes. The 3'-target sequences were subjected to the reactions at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 6 minutes, and extension at 70° C. for 10 minutes. The 2.0-kb-amplification product for the 3'-target sequences was digested with FseI and PacI and then cloned into the FseI-PacI site of the ploxPdownPURO-HYG vector. Also, the 5.0-kb-amplification product of the 5'-target sequences was digested with the SalI restriction enzyme and then cloned into the SalI site of the ploxPdownPURO-HYG vector comprising the aforementioned 2.0-kb target sequences. The size of the final ploxPHYGOR/n1 construct is about 16.1 kb. FIG. 26 shows the ploxPHYGOR/n1 vector and FIG. 27 shows the target sequences and a chromosome allele resulting from homologous recombination.

(2-2) Introduction of ploxPHYGOR/n1 Vector for Inserting the loxP Sequence of the Centromeric Long-Arm Proximal Region into DT40 Cell Carrying Human Chromosome 14 into which ploxpPGK-14qtel has been Introduced In accordance with the method of Example 1 (1-2), the ploxPHYGOR/n1 construct was converted into linearized DNA by digestion with the SrfI restriction enzyme, and the resultant was introduced into the DT40 hybrid cells, 24G8 and 24G94, that carry human chromosome 14 into which ploxpPGK-14qtel prepared in Example 7 (1-4) had been introduced. Selection culture was carried out with the use of puromycin (final concentration: 0.3 ug/ml), and drug-resistant colonies developed 2 to 3 weeks thereafter. A total of 230 puromycin-resistant colonies (50 colonies derived from 24G8 and 180 colonies derived from 24G94) were isolated through 6 transfection operations, grown, and then subjected to the subsequent analysis.

(2-3) PCR Analysis

Figure 28:
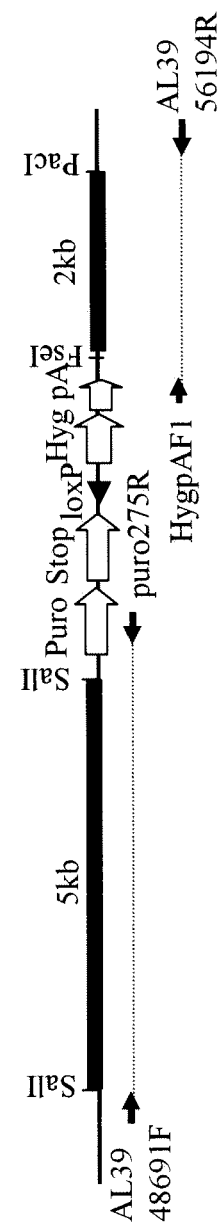
FIG. 28 shows the results of PCR analysis regarding introduction of the ploxPHYGOR/n1 vector into human chromosome 14q.

Genomic DNA of the puromycin-resistant strain was used as a template, and the presence of two target sequences (i.e., the 5' target sequence and the 3' target sequence) was detected by PCR in accordance with the method of Example 6 (2-1). By sandwiching these two target sequences (indicated as the 5' genome and the 3' genome in FIG. 27), oligonucleotide primer pairs were designed on the chromosome and on the targeting vector, respectively. Such positions are indicated by arrows in FIG. 28. The sequences are shown below.

```
                                      (SEQ ID NO: 59)
AL39 48691F: 5'-GCAGTGACAGAAGTCCATGTTGAACTGTAC (SEQ ID NO: 60)
Puro275R: 5'-GACGTGCTACTTCCATTTGTCACGTCCT (SEQ ID NO: 61)
HygpAF1: 5'-CGTCTGTGGCTGCCAAACAC (SEQ ID NO: 62)
AL39 56194R: 5'-TAGTCTCTCTGGATGAATATCAGCAAAACT
```

From among the above 230 blasticidin-resistant strains (14 strains derived from 24G8 and 20 strains derived from 24G94), the presence of the two target sequences (i.e., the 5' target sequence and the 3' target sequence) was observed in 34 strains.

(2-4) Southern Blot Analysis

As a screening method for selecting a homologous recombinant, Southern blot analysis was carried out. Probes were designated outside the two target sequences of homologous recombination (i.e., the 5' target sequence and the 3' target sequence; N5'(i) and N3'(i)) (FIG. 27). In order to prepare probes, PCR was carried out using oligonucleotide primer pairs shown below and genomic DNA of A9c11-14chr cells carrying human chromosome 14 as a template, and the resultants were isolated, and purified.

```
AL39 46181F:
5'-AAGACACCAGGGAGTAACCT    (SEQ ID NO: 63)

AL39 46778R:
5'-GCTGAACCACTAAGGGTGAC    (SEQ ID NO: 64)

AL39 56451F:
5'-GGAATAGGGATTAGGAAATG    (SEQ ID NO: 65)

AL39 57026R:
5'-ACATGAGGTTTATTTGGTGG    (SEQ ID NO: 66)
```

Figure 29:
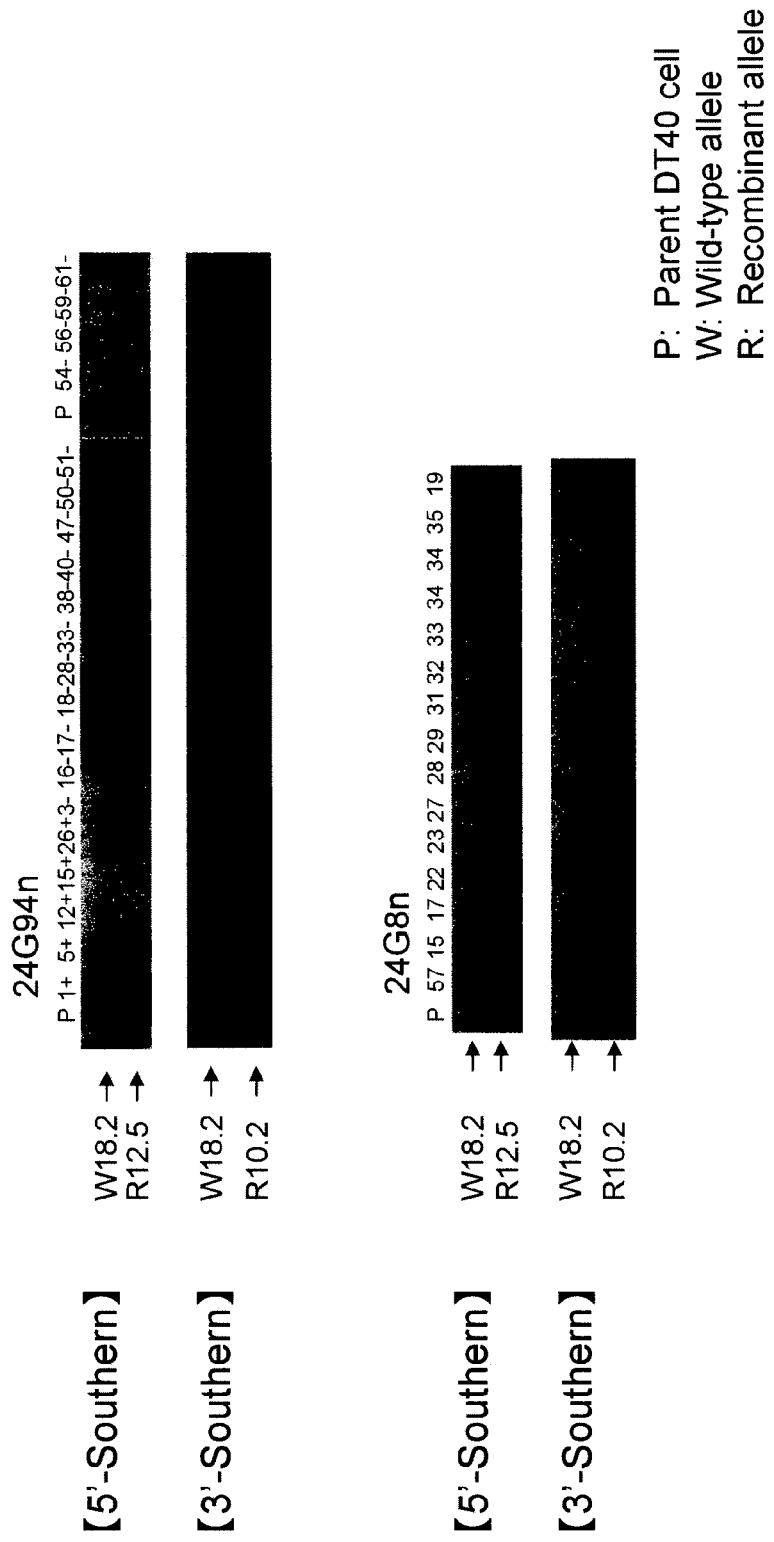
FIG. 29 shows the results of Southern analysis of a DT40 hybrid cell that carries ploxPHYGOR/n1 and ploxpPGK-14qtel vectors introduced into human chromosome 14q.

Genomic DNA (about 5 μg) extracted from the 34 strains obtained by primary screening was digested with the StuI restriction enzyme (Roche) and analyzed in the same manner as in Example 6 (1-4). Representative results are shown in FIG. 29. The length of the restriction enzyme fragment deduced from the nucleotide sequence is 12.5 kb in the form of a homologous recombinant, and it is 18.2 kb in the form of a wild-type (i.e., a non-recombinant), for 5'-target sequence. Such length is 10.2 kb in the form of a homologous recombinant, and it is 18.2 kb in the form of a wild-type (i.e., a non-recombinant), for 3'-target sequence. A total of 22 strains of homologous recombinants (14 strains derived from 24G8 and 8 strains derived from 24G94) were identified from among the candidate 34 strains. Among them, 24G8-derived clone 24G8n7 and 24G94-derived clones 24G94n18 and 24G94n56 were subjected to the subsequent step (3).

(3) Deletion of the Long-Arm Distal Region by Cre-loxP Site-Directed Recombination (3-1) Introduction of Cre Expression Vector into DT40 Hybrid Cell Carrying Human Chromosome 14 into which the loxP Sequences have been Introduced at the Long-Arm Distal and Proximal Regions In accordance with the method of Example 1 (1-2), Cre expression vector pCAGGS-Cre was introduced into the 24G8n7, 24G94n18, and 24G94n56 cells obtained in Example 6 (2). Selection culture was carried out with the use of hygromycin (final concentration: 1.25 mg/ml), and drug-resistant colonies developed 2 to 3 weeks thereafter.

In the 24G8n7 cells, a total of 54 hygromycin-resistant colonies obtained through 2 transfection operations were isolated, grown, and then subjected to the subsequent analysis. In the 24G94n18 and 24G94n56 cells, 10 clones were gathered as a pool, 20 pools were grown, and the subsequent analysis was then carried out.

(3-2) PCR Analysis

Genomic DNA of hygromycin-resistant strains was used as a template, and deletion between the two loxP sequences was confirmed by PCR. By sandwiching the loxP sequence remaining after the deletion of the long-arm distal region, oligonucleotide primer pairs were designed on the chromosome and on the targeting vector, respectively. Such positions are indicated by arrows in FIG. 30A. The sequences are shown below.

```
B.D PGK Fw1:
5'-GGAAGTAGCACGTCTCACTAGTCTC    (SEQ ID NO: 67)

B.D Hyg Rv1:
5'-ATGTAGTGTATTGACCGATTCCTTG    (SEQ ID NO: 68)
```

Ex Taq polymerase (Takara Shuzo Co., Ltd.) was used, and the reactions were carried out at 94° C. for 1 minute, followed by 35 cycles of denaturation at 94° C. for 15 seconds, annealing at 60° C. for 30 seconds, and extension at 72° C. for 1 minute. When the long-arm distal region was removed by deletion of a region between the loxP sequences, amplification of about 0.8 kb is deduced. In 16 strains from among the 54 hygromycin-resistant strains derived from the 24G8n7 cells and in each of the 20 pools derived from 24G94n18 and 24G94n56 cells, amplification products as deduced were consequently observed.

(3-3) Southern Blot Analysis

Figure 30:
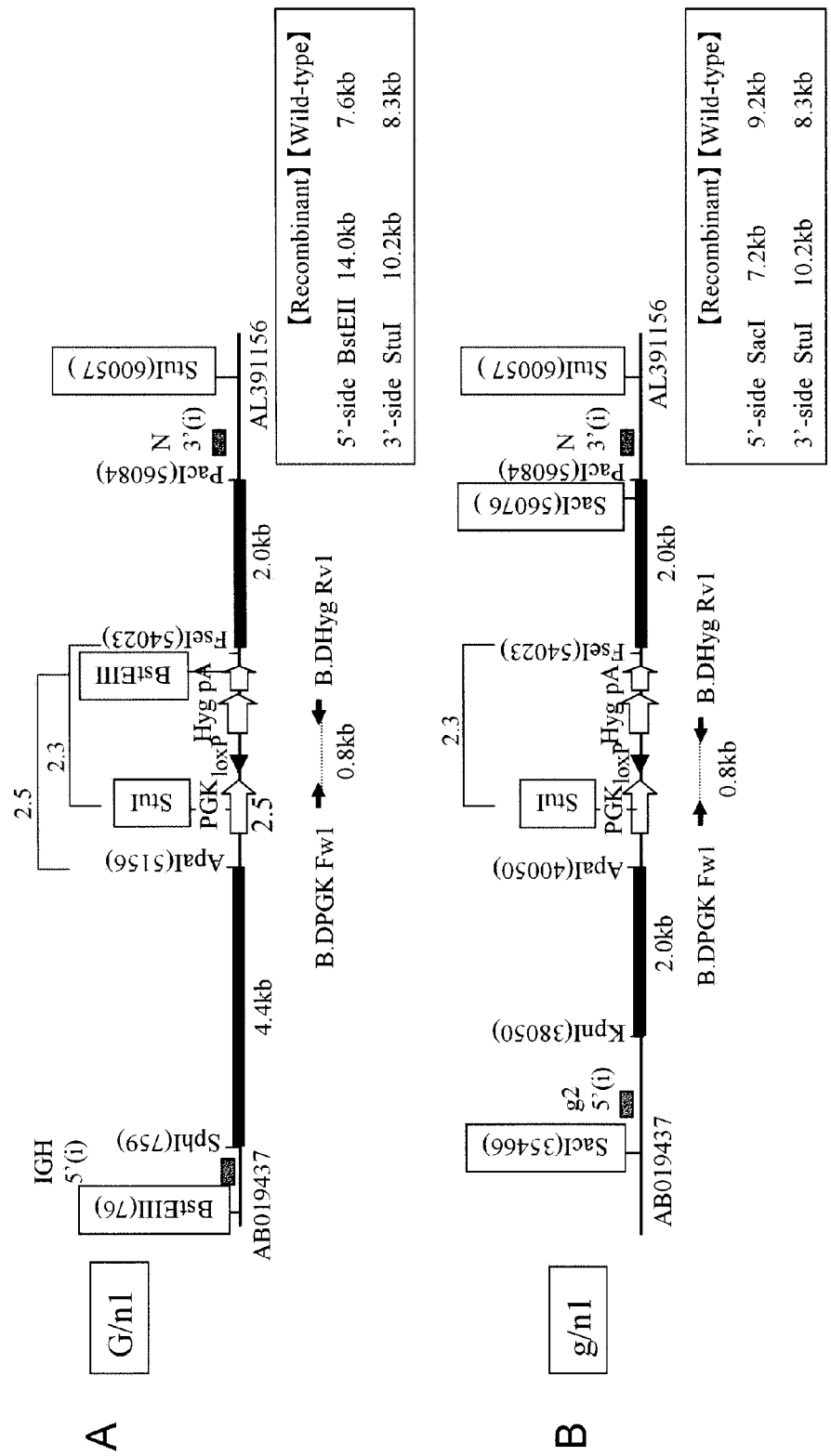
FIG. 30 shows a chromosome allele resulting from deletion of a distal site of human chromosome 14q by Cre-loxP site-directed recombination (FIG. 30A: G/n1.

Southern blot analysis was carried out to confirm and select the structure with the deleted long-arm distal region. The positions of the target sequences, the chromosome alleles, and the probes resulting from deletion of the long-arm distal region are shown in FIG. 30A and in FIG. 30B. Probes were designated outside the two target sequences of homologous recombination (i.e., the 5' target sequence and the 3' target sequence; IGH5'(i) and N3'(i)).

Figure 31:
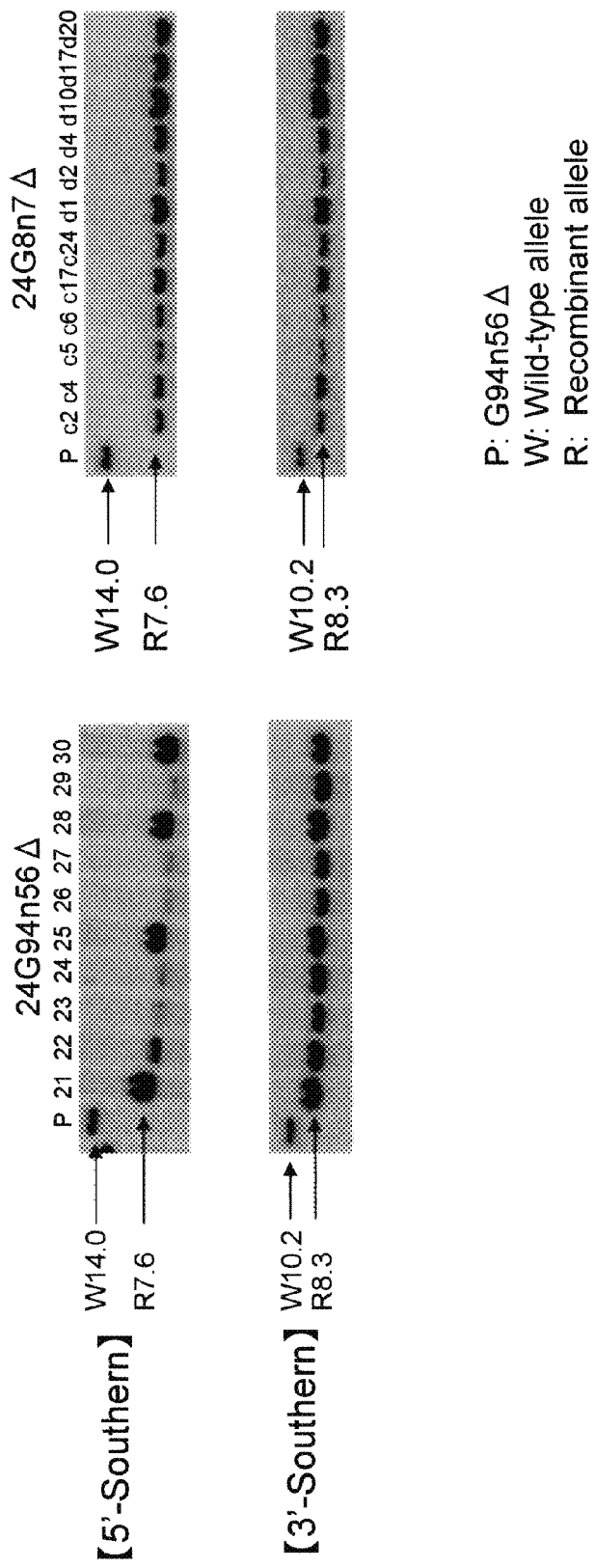
FIG. 31 shows the results of Southern analysis of a DT40 hybrid cell that carries 14NΔqHAC.

Genomic DNAs were extracted from 16 strains derived from 24G8n7 cells, 20 pools of cells derived from the 24G94n18 cells, and 10 pools of cells derived from 24G94n56 cells obtained by primary screening and analyzed in the same manner as in Example 6 (1-4). Digestion with restriction enzymes (Roche) was carried out with the use of BstEII (5'-side) and StuI (3'-side). Representative results are shown in FIG. 31. The length of the restriction enzyme fragment deduced from the nucleotide sequence is 7.6 kb in the form of a homologous recombinant, and it is 14.0 kb in the form of a wild-type (i.e., a non-recombinant), for 5'-target sequence. Such length is 8.3 kb in the form of a homologous recombinant, and it is 10.2 kb in the form of a wild-type (i.e., a non-recombinant), for 3'-target sequence. As a result, chromosomes with the deleted long-arm distal regions were observed in the 12 strains derived from the 24G8n7 cells and in 10 pools of cells derived from the 24G94n56 cells.

(3-4) FISH Analysis

Figure 32:
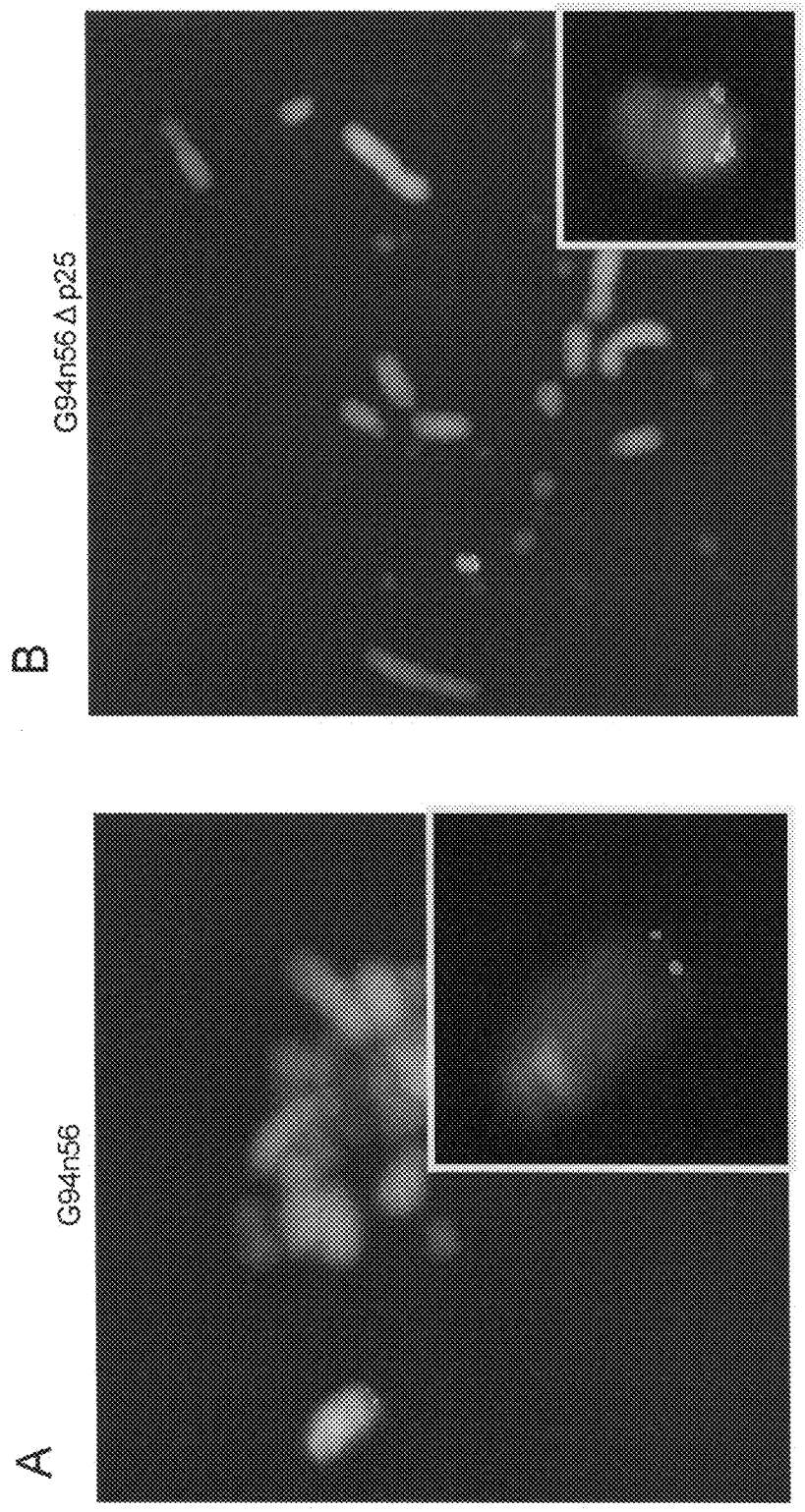
FIG. 32 shows the results of FISH analysis of a DT40 hybrid cell that carries 14NΔqHAC.

FISH analysis was carried out in accordance with the method described in Matsubara et al. (FISH Experimental Protocol, Shujunsha Co. Ltd., 1994). Human-specific Cot1 (Invitrogen) and a 5'-target sequence fragment of about 4.2 kb prepared from the ploxpPGK-14qtel vector prepared in Example 6 (1-1) by digestion with the HindIII restriction enzyme, cleavage, and purification were used as probes. The 4 clones derived from the 24G8n7 cells obtained in (3-3) above (i.e., G8n7Δc2, c5, d1, and d4) and the 4 pools of cells derived from the 24G94n56 cells (i.e., G94n56Δp21, p25, p28, and p30) were analyzed. As a result, all the clones were found to be of a normal karyotype and a copy of Cot1-stained signal and two signals at the ends of the shortened long arm were detected in most of the observed mitotic figures. Representative FISH images are shown in FIG. 32A and in 32B.

The experiments (3-1) to (3-4) demonstrated that the obtained hygromycin-resistant DT40 hybrid cell carries a human chromosome 14 fragment (14NΔqHAC) with the deleted long-arm distal region, while maintaining the telomere sequence.

(4) Introduction of Cloning Site into Long-Arm Proximal Region of 14NΔqHAC (4-1) Construction of pSF(G+n1) Vector for Inserting loxP and 3'neo Sequences As a basic plasmid for inserting the loxP and 3'neo sequences into the human artificial chromosome (HAC) prepared in Example 6 (3), pSF1(3) prepared in Example 1 (2-1) was used. The 5'-target sequences for homologous recombination where loxP and 3'neo would be inserted were designed based on the sequence used for the ploxpPGK-14qtel vector obtained in Example 7 (1-1). The 3'-target sequences were designed based on the nucleotide sequence (Accession No. AL391156) of the long-arm proximal region of human chromosome 14 obtained from the GenBank database. Sequences of oligonucleotide primers for amplifying the same by PCR are shown below.

```
54023Flong2FseI:
                                        (SEQ ID NO: 69)
5'-GATGGCCGGCCTGGTTGGTAAAGATTGCTACACTTACGGCA 58830RlongSrfI:
                                        (SEQ ID NO: 70)
5'-GATGCCCGGGCCAATAGCCAGTCAATCGAGAAACCAAGCCC
```

Figure 33:
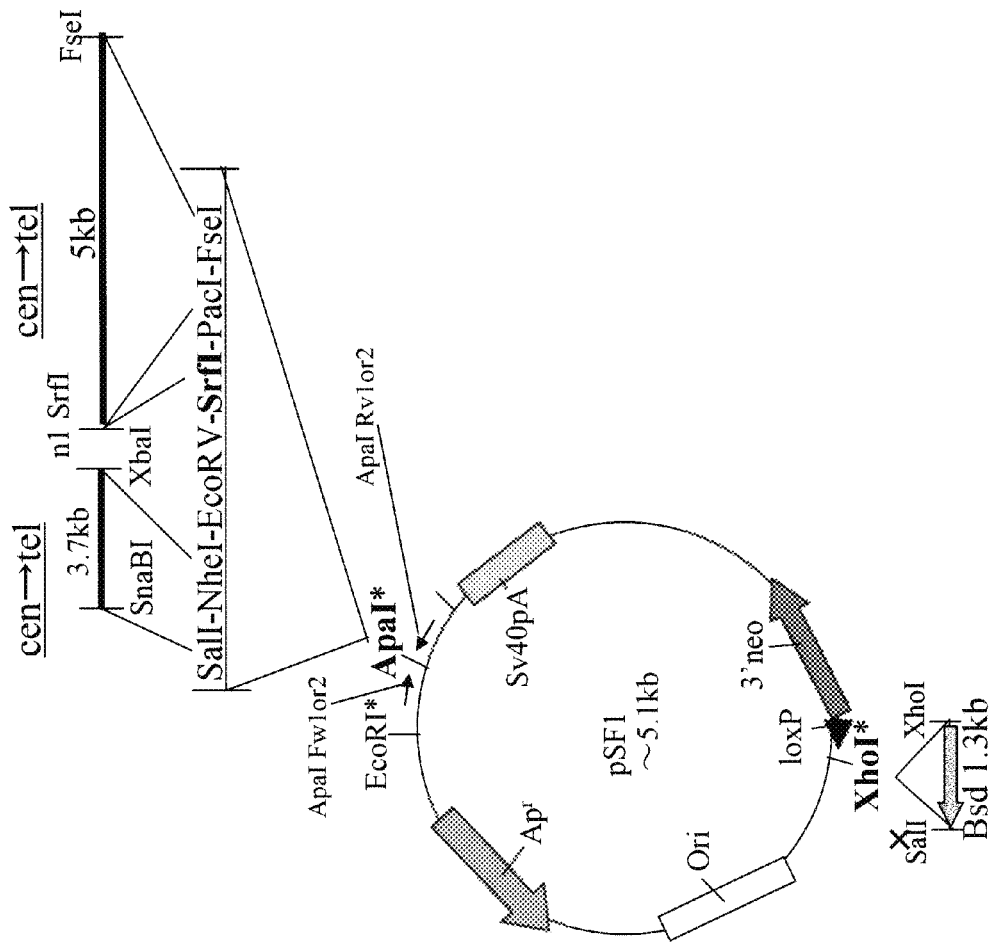
FIG. 33 shows the structure of the pSF1(G+n1) vector for insertion of loxP and 3'neo sequences.

The 5'-target sequence was cleaved from the ploxpPGK-14qtel vector by digestion with XbaI and SnaBI (Roche), separated and purified by agarose gel electrophoresis, and then cloned into the NheI-SalII site of the pSF1(3) plasmid. The 3'-target sequence was amplified by PCR using, as a template, genomic DNA extracted from the A9c11-14chr cell carrying human chromosome 14. This DNA fragment of about 5.0 kb was digested with the FseI restriction enzyme (Roche), separated and purified by agarose gel electrophoresis, and then cloned into the FseI site of the pSF1(3) plasmid into which the 5'target sequence had been inserted. The size of the final pSF1(G+n1) construct is about 15.0 kb. The targeting vector is shown in FIG. 33 and the target sequence and a chromosome allele resulting from homologous recombination are shown in FIG. 34A.

(4-2) Introduction of pSF(G+n1) Vector into 14NΔqHAC-Carrying DT40 Cell

The pSF(G+n1) constructs were linearized by digestion with the SrfI restriction enzyme (Roche) and then introduced into 6 types of DT40 hybrid cells (G94n56Δp21/p25/p28/p30, G8n7Δc2/c5) comprising 14NΔqHAC with the deleted long-arm distal region. The method was carried out in accordance with Example 1 (2-2). Blasticidin-resistant colonies developed 2 to 3 weeks thereafter. A total of 321 drug-resistant G94n56Δp21/p25/p28/p30 colonies obtained through 2 transfection operations (117, 153, 46, and 7 colonies) were isolated, and a total of 191 G8n7Δc2/c5 drug-resistant colonies obtained through a single transfection operation (96 and 95 colonies) were isolated, and the subsequent analysis was performed.

(4-3) PCR Analysis

Genomic DNA of the blasticidin-resistant strain was used as a template, and the presence of two target sequences (i.e., the 5' target sequence and the 3' target sequence) was detected by PCR. By sandwiching these two target sequences (indicated by the 5'genome and the 3'genome in FIG. 34), oligonucleotide primer pairs were designed on the chromosome and on the targeting vector, respectively. Such positions are indicated by arrows in FIG. 34. The sequences are shown below.

```
550F:
5'-CATTCATGGTAGTCATTGGTGCTGTTCTCC      (SEQ ID NO: 71)

ApaIlongFw1:
5'-CACAGCAACCACAGTGCTTCTTGATGAG         (SEQ ID NO: 72)

ApaIlongRv1:
5'-TCCAGAAGTGTTGGTAAACAGCCCACAA         (SEQ ID NO: 73)

58950R:
5'-AAGCAGAGCTACCATGCACTGTAGGATAAG       (SEQ ID NO: 74)
```

LA Taq polymerase (Takara Shuzo Co., Ltd.) was used, and the PCR solution comprised $MgSO_4$ (final concentration: 0.5 mM). The reactions were carried out at 94° C. for 1 minute, followed by 3 cycles of denaturation at 98° C. for 5 seconds followed by annealing/extension at 72° C. for 8 minutes, 2 cycles of denaturation at 98° C. for 5 seconds followed by annealing/extension at 70° C. for 8 minutes, 30 cycles of denaturation at 98° C. for 5 seconds followed by annealing/extension at 68° C. for 8 minutes, and extension at 72° C. for 10 minutes.

Among the obtained blasticidin-resistant strains, 12 strains (7 strains in total; i.e., 2 G94n56Δp21, 1p25, 2p28, and 2p30-derived strains; and 5 strains in total (1 G8n7Δc2 and 4 c5-derived strains) were found to produce amplified products of sizes deduced from the nucleotide sequences (i.e., the 5' genome sequence: about 4.5 kb; the 3' genome sequence: about 5.0 kb).

(4-4) Southern Blot Analysis

Figure 34:
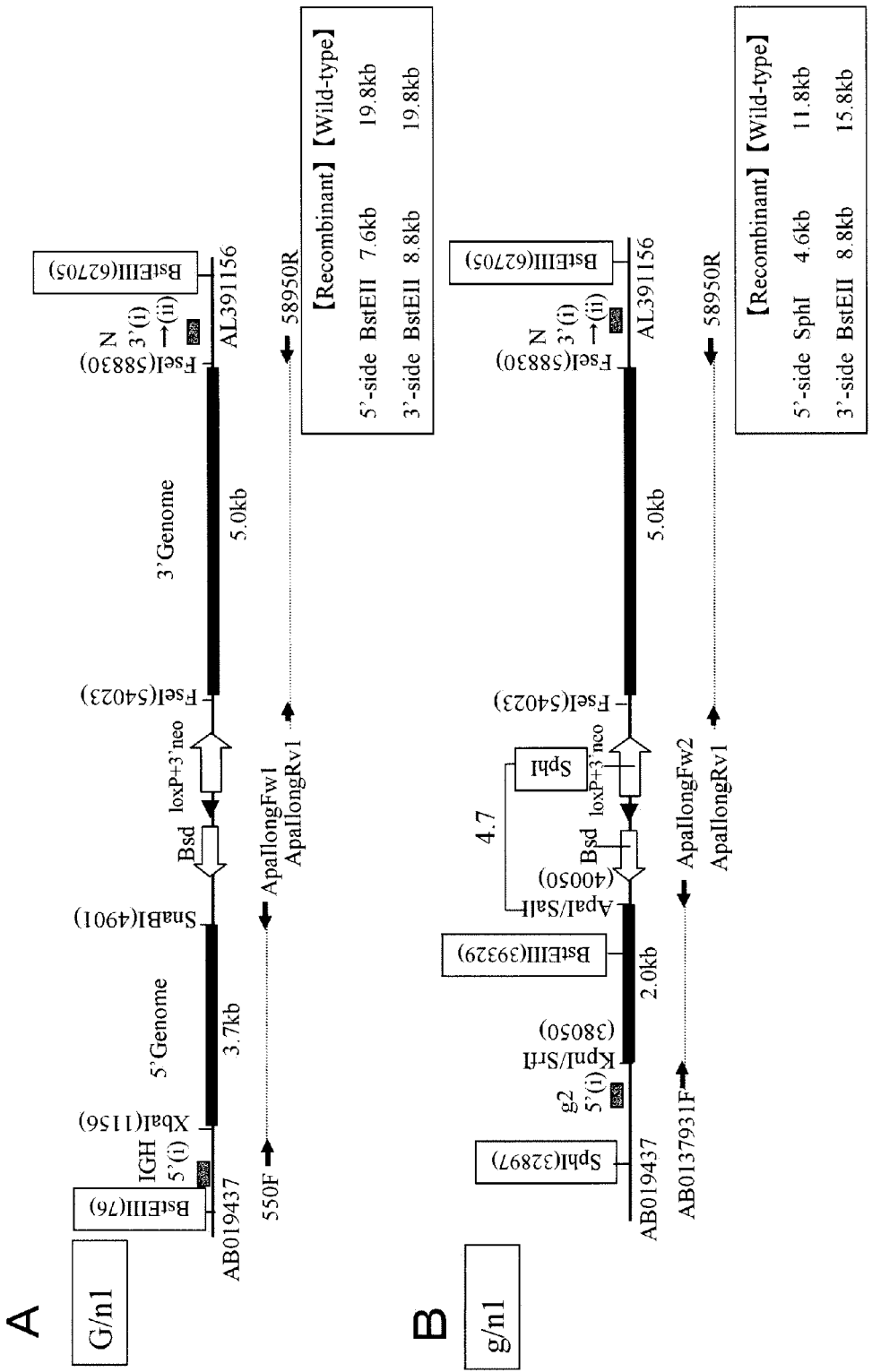
FIG. 34 shows alleles resulting from (A) introduction of a pSF1(G+n1) or GnpSF1-FRT vector into 14NΔqHAC and (B) introduction of a pSF1(g+n1) or gnpSF1-FRT vector into 14gNΔqHAC.

Southern blot analysis was carried out to select homologous recombinants. Probe IGH5'(i) (Example 6 (1-4)) was designated outside the target sequence of homologous recombination and probe N3'(ii) was designated outside the 3'-target sequence (FIG. 34). In order to prepare probe N3'(ii), PCR was carried out using oligonucleotide primer pairs shown below and genomic DNA of A9c11-14chr cells carrying human chromosome 14 as a template, and the resultants were isolated, and purified.

```
AL39 60781F:
5'-TCAAGGACTGTGAGCCTCCT          (SEQ ID NO: 75)

AL39 61387R:
5'-TGCACTGAAAGCCAATTGAA          (SEQ ID NO: 76)
```

Figure 35:
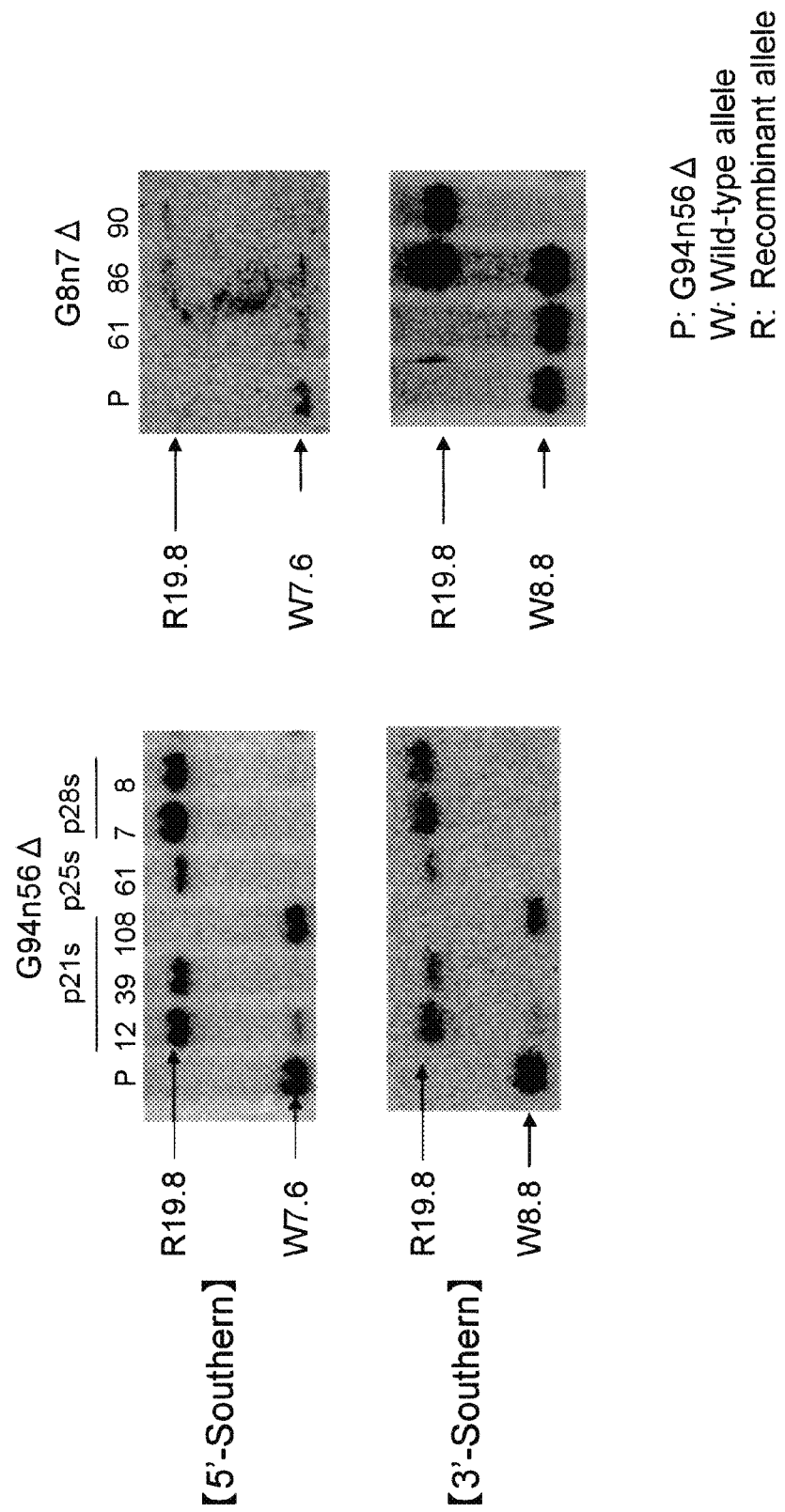
FIG. 35 shows the results of Southern analysis of a DT40 hybrid cell that carries a pSF1(G+n1) vector introduced into 14NΔqHAC.

Genomic DNA (about 5 μg) extracted from the 12 strains obtained by primary screening was digested with the BstEII restriction enzyme (Roche), and Southern blot analysis was carried out by the method described in Ausubel et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). Representative results are shown in FIG. 35. The length of the restriction enzyme fragment deduced from the nucleotide sequence is 19.8 kb in the form of a homologous recombinant, and it is 7.6 kb in the form of a wild-type (i.e., a non-recombinant), as a result of 5' genome analysis. Such length of a homologous recombinant is 19.8 kb, and it is 8.8 kb in the form of a wild-type (i.e., a non-recombinant), as a result of 3' genome analysis. A total of 5 strains of homologous recombinants were identified from among the 12 candidate blasticidin-resistant strains.

Through experiments (4-1) to (4-4) above, 5 strains of DT40 hybrid cells (i.e., G94n56Δp21S39, G94n56Δp25S61, G94n56Δp28S7, 8, G8n7Δc2S202, and G8n7Δc5S90) carrying 14NΔqHAC vectors into which cloning sites (i.e., the loxP and 3'neo sequences) had been inserted by homologous recombination were obtained. Among them, 4 strains, i.e., G94n56Δp21S39, G94n56Δp25S61, G8n7Δc2S202, and G8n7Δc5S90 (hereafter abbreviated to G4S39, G4S61, G8S202, and G8S90, respectively) were subjected to the subsequent step.

(5) Introduction of 14NΔqHAC Vector into CHO Cell
(5-1) Introduction of 14NΔqHAC Vector into CHO Cell by the Microcell Mediated Chromosome Transfer Method As chromosome donor cells, the 14NΔqHAC vector-carrying DT40 hybrid cells (G4S39, G4S61, G8S202, and G8S90) obtained in Example 6 (4) with the deleted long-arm distal regions into which cloning sites (i.e., the loxP and 3'neo sequences) had been inserted were used. As chromosome recipient cells, Chinese hamster-derived CHO-K1 cells (Accession No. JCRB9018) were used. The method in accordance with Example 1 (3-1) was employed. After selection culture had been carried out for about 2 weeks, developed blasticidin-resistant colonies were isolated, and the subsequent analysis was performed. A total of 92 blasticidin-resistant CHO strains (19 G4S61-derived strains, 23 G4S39-derived strains, 22 G8S90-derived strains, and 28 G8S202-derived strains) were obtained through 8 micronuclear cell fusion operations (twice for G4S39; twice for G4S61; twice for G8S202; and twice for G8S90).

(5-2) PCR Analysis

Genomic DNA of a blasticidin-resistant strain was used as a template, and the presence of two target sequences (i.e., the 5' target sequence and the 3' target sequence) was detected by PCR. The method in accordance with Example 6 (4-3) was employed. In order to inspect inclusion of DT40 cells, chicken β-actin detection primers were designed based on the nucleotide sequence of the chicken β-actin gene (Accession No. X00182) obtained from the GenBank database. Sequences of oligonucleotide primers for amplifying the same by PCR are shown below.

```
Ggbeta-actin1933F:
5'-TCCGTTGGAGTTGATCCTTC         (SEQ ID NO: 77)

Ggbeta-actin2536R:
5'-ACATGACACAGCAAGGAACG         (SEQ ID NO: 78)
```

Ex Taq polymerase (Takara Shuzo Co., Ltd.) was used, and the reactions were carried out at 94° C. for 1 minute, followed by 35 cycles of denaturation at 94° C. for 15 seconds, annealing at 56° C. for 30 seconds, and extension at 72° C. for 30 seconds. Among the obtained blasticidin-resistant CHO strains, amplification products having sizes deduced from the nucleotide sequence (5' genome: about 4.5 kb; 3' genome: about 5.0 kb) were observed in 67 strains (15 G4S61-derived strains, 23 G4S39-derived strains, 20 G8S90-derived strains, and 9 G8S202-derived strains) and no inclusion of DT40 cells was observed.

(5-3) Southern Blot Analysis

Figure 36:
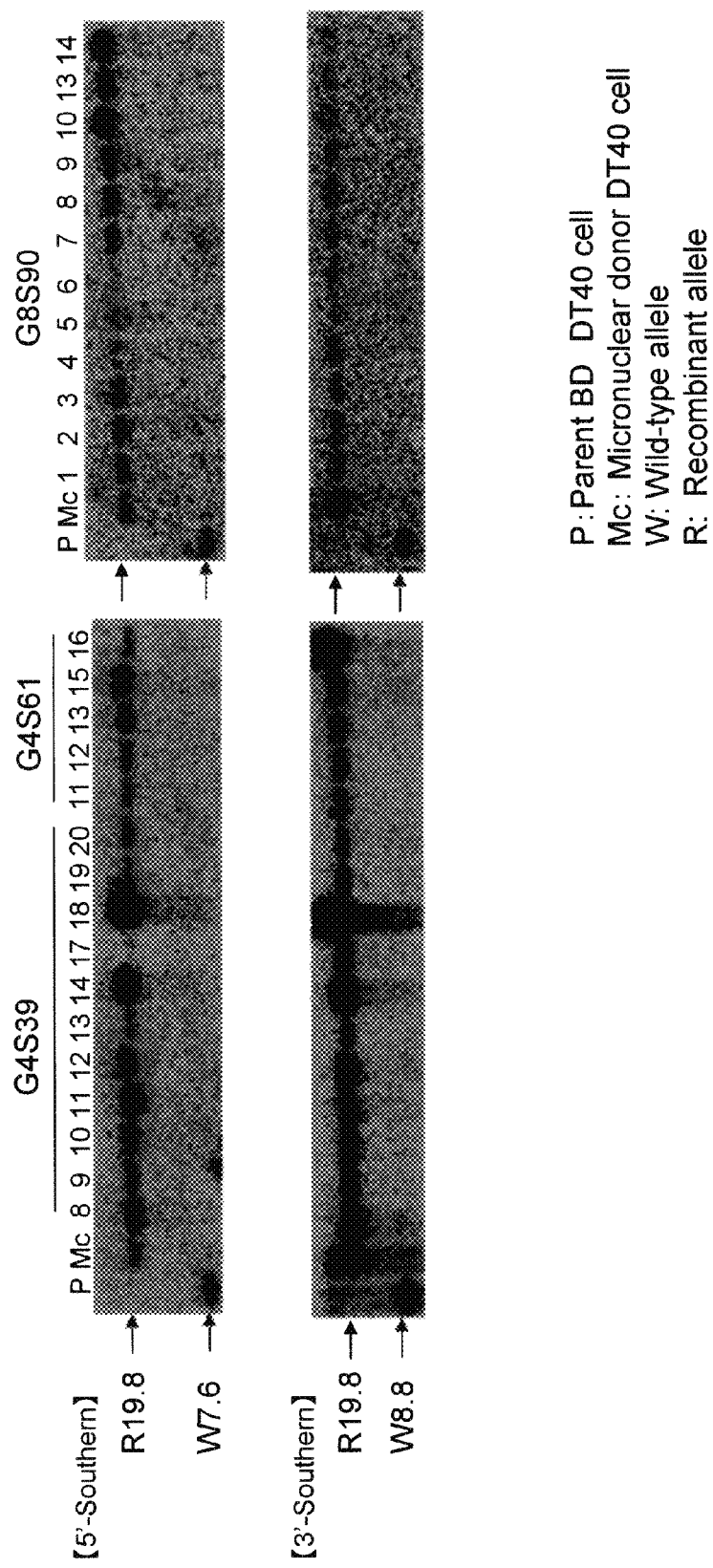
FIG. 36 shows the results of Southern analysis of a CHO hybrid cell into which the 14NΔqHAC vector has been introduced.

Southern blot analysis was carried out in the same manner as in Example 6 (4-4) in order to inspect the structure of the introduced 14NΔqHAC vector. Representative results are shown in FIG. 36. The length of the restriction enzyme fragment deduced from the nucleotide sequence is 19.8 kb in the form of a homologous recombinant and it is 7.6 kb in the form of a wild-type (i.e., a non-recombinant), as a result of the 5'-genome analysis. Such length is 19.8 kb in the form of a homologous recombinant and it is 8.8 kb in the form of a wild-type (i.e., a non-recombinant), as a result of the 3'-genome analysis. From among the 74 candidate blasticidin-resistant strains (i.e., 14 G4S61-derived strains, 16 G4S39-derived strains, 20 G8S90-derived strains, and 24 G8S202-derived strains), a total of 52 homologous recombinants (i.e., 14 G4S61-derived strains, 16 G4S39-derived strains, 15 G8S90-derived strains, and 7 G8S202-derived strains) were identified.

(5-4) FISH Analysis

Figure 37:
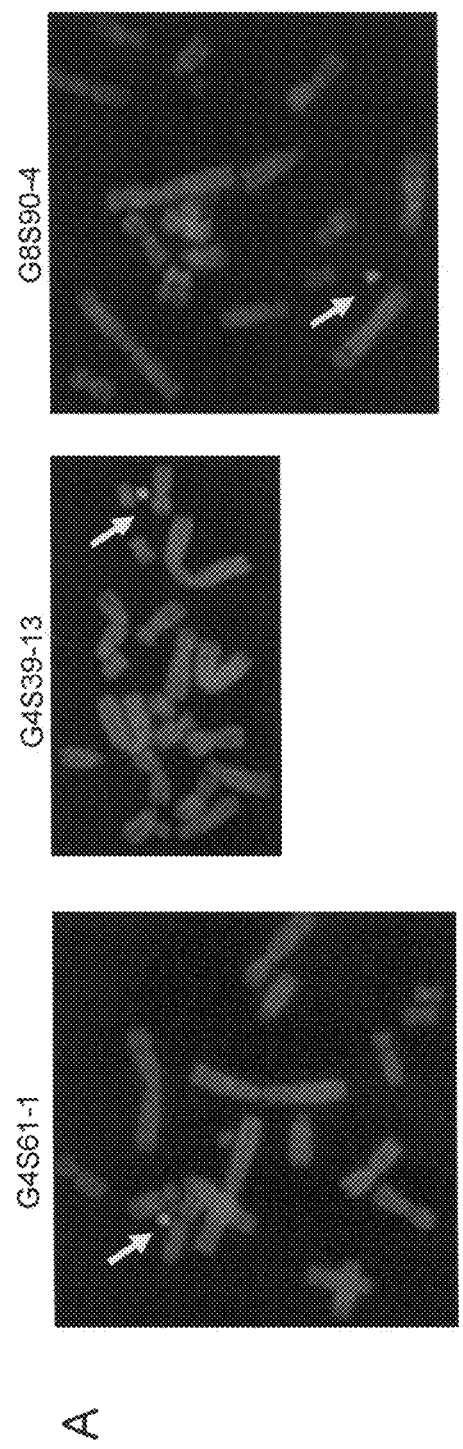
FIG. 37 shows the results of FISH analysis of the CHO hybrid cell into which the 14NΔqHAC vector has been introduced.

FISH analysis was carried out in accordance with the method described in Matsubara et al. (FISH Experimental Protocol, Shujunsha Co. Ltd., 1994) using human-specific Cot1 (Invitrogen) probes. 23 strains (i.e., 7 G4S61-derived strains, 11 G4S39-derived strains, 1 G8S202-derived strains, and 4 G8S90-derived strains) among the blasticidin-resistant CHO strains were analyzed. As a result, a total of 9 strains (G4S61-1, 6, 8, 9, 11, 12, G4S39-13, G8S90-2,4) were found to be of a normal karyotype and a copy of Cot1-stained 14NΔqHAC vector were detected in most of the observed mitotic figures. Representative FISH images and the karyotypes of the 14NΔqHAC vectors are shown in FIGS. 37A and 37B.

Experiments (5-1) to (5-4) demonstrated that the resulting 9 blasticidin-resistant CHO strains carry the 14NΔqHAC vectors.

Example 7

(7-1) Analysis of Long-Term Stability of 14NΔqHAC Vector in CHO Hybrid Cell
(1) Long-Term Subculture Under Non-Selective Culture Conditions In order to confirm stability of the 14NΔqHAC vector in CHO hybrid cells, long-term subculture was carried out under non-selective culture conditions. The two CHO strains carrying the 14NΔqHAC vector described in Example 6 (G4S39-

13 and G4S61-1) were used. A non-selection medium was F12 medium containing 10% FBS, and a selection medium comprised such F12 medium and blasticidin added thereto at 8 μg/ml. The $5.0 \times 10^5$ CHO cells were plated in a 10-cm dish, the cells that had been cultured to a cell density of about 80 to 90% confluency were counted, the $5.0 \times 10^5$ cells were plated again in a 10-cm dish, and subculture was continued up to the tenth passage. The number of cells was counted every passage to determine the population doubling level. The CHO cells were recovered after the tenth passage and FISH chromosome samples were prepared.

(2) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate and the average values were determined. The results regarding such two strains are shown in Table 3 and FIG. 13. In FIG. 13, the results are shown in the item of "14ΔqHAC(G)."

TABLE 3

Stability of 14NΔqHAC vector in CHO cell

| HAC | Cell population Number of subculture | HAC retention (%) Without drug selection | With drug selection |
|---|---|---|---|
| 12G4S39-13 | At the initiation of culture | — | 96 |
|  | Ten passages | 99 | 99 |
| 12G4S61-1 | At the initiation of culture | — | 98 |
|  | Ten passages | 96 | 98 |

The 14NΔqHAC vector was retained stably in CHO cells by the end of the tenth passage. As a result of observation of images of metaphase chromosomes, 1 or 2 signals were detected per cell.

The Experiments (1) and (2) demonstrated that the 14NΔqHAC vector would be retained stably in CHO cells under non-selective culture conditions and that a copy number per cell would be maintained.

Figure 87:
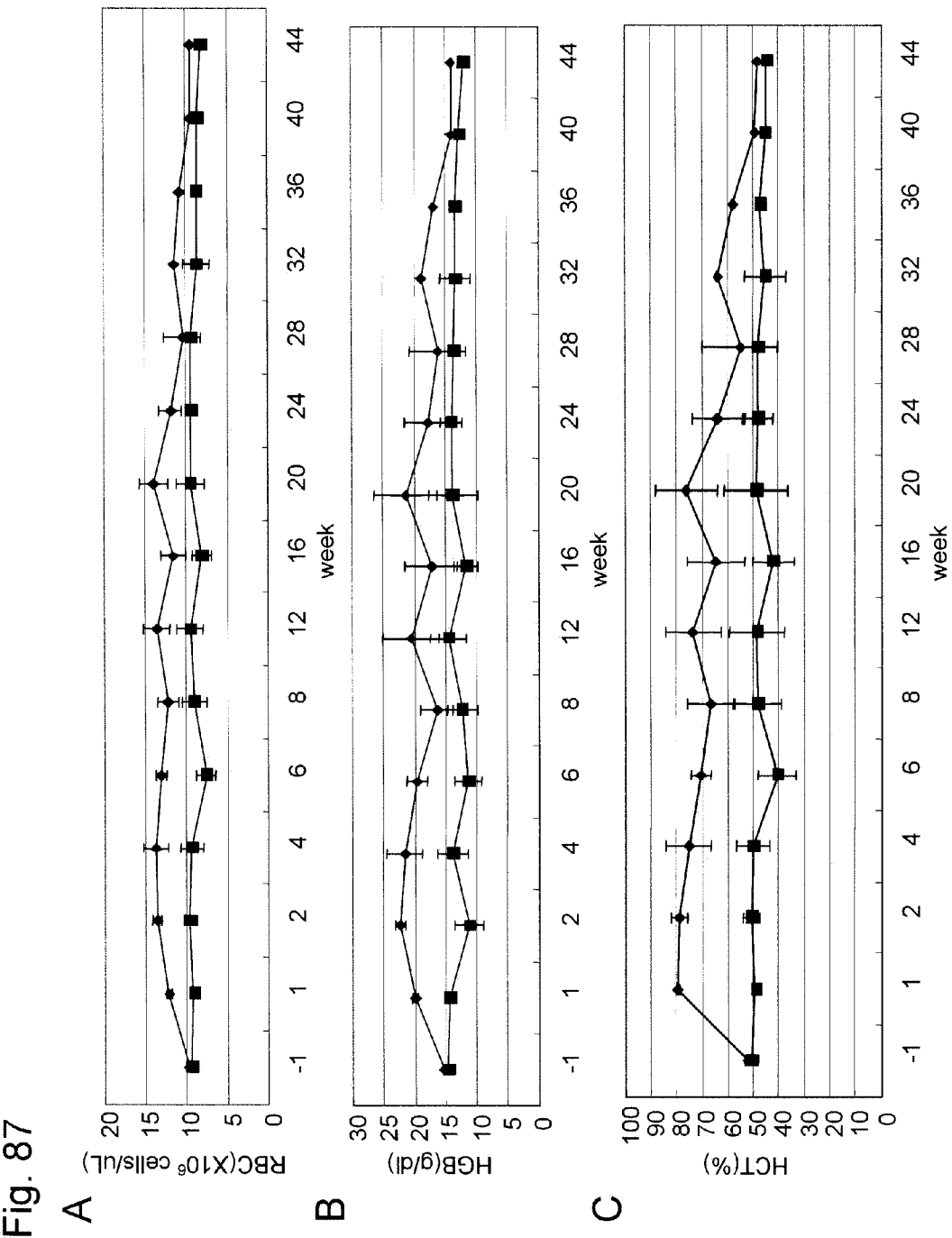
FIG. 87 is a chart showing changes of efficacy of EPO in vivo with the elapse of time.

(7-2) In Vivo EPO Efficacy Caused by Transplantation of CHO Cell Carrying EPO-Introduced 14AΔqHAC Vector t7S38-8E5 clones of the EPO-introduced 14AΔqHAC vector-carrying CHO cells prepared in Example 3 were sealed in immunocyte-blocking capsules, the resultants were transplanted subcutaneously to the Igμ-/- knockout mice that are incapable of antibody production due to B-cell defect (Tomizuka, K., et al., PNAS, 97, 722-727, 2000), and the red blood cell counts, the hemoglobin levels, and hematocrit values in the peripheral blood were analyzed. Thus, efficacy of EPO in vivo supplied from the t7S38-8E5 cells was evaluated. If the above 3 values are elevated compared with those of the group to which cell capsules have been transplanted, efficacy of EPO can be approved.

t7S38-8E5 clones of CHO cells carrying the EPO-introduced 14AΔqHAC vectors were cultured in accordance with the method of Example 3, $1 \times 10^6$ cells were sealed in immunocyte-blocking capsules, the TheraCyte immunoisolation device with 40 μl capacity (TheraCyte Inc., Irvine, Calif.), in accordance with the included protocol. The capsules were transplanted subcutaneously into the Igμ-/- knockout mice through their left backs under avertin anesthesia, the blood was drawn from the orbit with the elapse of time, and the red cell counts, the hemoglobin levels, and hematocrit values in the peripheral blood were measured using ADVIA120 (Bayer medical). As a control group, a group which had been subjected to surgery without capsules was analyzed. The results are shown in FIG. 87.

The red blood cell counts, the hemoglobin levels, and the hematocrit values began to elevate in the group to which the cell capsule had been transplanted from 2 weeks after transplantation, and the elevated values were maintained up to the 44th week. Thus, the in vivo long-term EPO efficacy was demonstrated by transplantation of CHO cells carrying EPO-14AHAC.

(7-3) In vivo EPO Efficacy Caused by Transplantation of Human Normal Fibroblasts Carrying EPO-Introduced 14HAC Vector tΔ63H15 selected from among tΔ63H clones of human normal fibroblasts, i.e., HFL-1 cells, carrying the EPO-introduced 14AΔqΔneoHAC vector prepared in Example 19 or tΔ471427, 30, and 37 clones of HFL-1 cells prepared in the same manner as in the case of tΔ63H15 were sealed in immunocyte-blocking capsules, transplanted subcutaneously to the Igμ-/- knockout mice incapable of antibody production due to B cell defect, and the red blood cell counts, the hemoglobin levels, and the hematocrit values in the peripheral blood were analyzed. Thus, the in vivo efficacy of EPO supplied from the HFL-1 clones was evaluated. If these three values of the group into which the cell capsule had been transplanted are elevated compared with the control group, EPO efficacy can be approved.

tΔ63H15 or tΔ47H27, 30, or 37 clones of HFL-1 cells carrying EPO-introduced 14-HAC were cultured in accordance with the method of Example 19, the $10^6$ cells were sealed in the immunocyte-blocking capsule, the TheraCyte immunoisolation device with 40 μl capacity (TheraCyte Inc., Irvine, Calif.), with collagen I beads (KOKEN) in accordance with the included protocol. The cells and beads were encapsulated by mounting an adaptor for silicon sealing to a 1-ml syringe (Telmo), connecting the resultant to a capsule port (i.e., an inlet), and introducing the resultant into the capsule. The capsule was cultured for 2 to 6 weeks on a 6-well plate using DMEM-20% FBS medium at 37° C. in the presence of 6.5% $CO_2$, exchanging a medium with human bFGF (0 or 10 ng/ml) two days before and on the day of transplantation with, and culture was further conducted. In the same manner as in (7-2), the capsules were transplanted subcutaneously to the Igμ-/- knockout mice at the left back, and the blood was sampled from the orbit with the elapse of time to measure the red blood cell counts, the hemoglobin level, the hematocrit value using ADVIA120 (Bio Medical).

Thus, long-term EPO's efficacy in vivo can be realized via transplantation of human normal fibroblasts carrying EPO-14HAC.

(7-4) Transmission of 14HAC Vector to Mouse Offspring

In order to examine stability of the 14HAC vector in vivo and transmission thereof to offspring, the EGFP-introduced 14HAC vector was prepared, the resultant was introduced into the mouse ES cell by the microcell mediated chromosome transfer method, and chimeric mice were prepared and subjected to crossing to analyze the HAC retention in the mouse somatic cells.

(1) Construction of EGFP-14HAC Vector

The pLN1-IRES-EGFP plasmid comprising the EGFP gene under the control of the CAG promoter was prepared, and the EGFP gene expression units were introduced into the 14AΔq-HAC and 14NΔq-HAC vectors by the Cre-loxP system in CHO cells.

(1-1) Preparation of EGFP Expression Plasmid, pLN1-IRES-EGFP

Prior to the preparation of pLN1-IRES-EGFP, pLN1-PGK-EGFP was prepared in two steps. In step 1, the CMV promoter in the CMV-5'neo region of pLN1-EPO (Kakeda et al., Gene Therapy; 12: 852-856, 2005) was replaced with the PGK promoter to prepare the pLN1-PGKEPO plasmid, the resulting plasmid was digested with SalI and blunt-ended, and the EPO expression unit was then removed by digestion with EcoRI. pEGFP-N1 (Clontech) was digested with AflII, blunt-ended, and further digested with EcoRI to prepare the EGFP-Sv40polyA unit, and the resultant was introduced thereto. In step 2, an early CAG promoter prepared by digestion of pCAGGS-Cre (Araki et al., PNAS, 92, 160-164, 1995) with SalI and with XbaI and a late CAG promoter prepared by PCR amplification with the use of the pCAGGS-Cre template and digestion with XbaI and with BamHI were simultaneously introduced into a region, which had been digested with SalI and with BamHI in step 1. The primer sequences used for PCR are shown below.

```
pCAGGSCre 2362F:
                                    (SEQ ID NO: 152)
5'-TTCGGCTTCTGGCGTGTGAC pCAG R1 BamHI:
                                    (SEQ ID NO: 153)
5'-CGGGATCCCGTGGCGGCGGGTAATTCTTTGCAAA
```

Subsequently, pLN1-IRES-EGFP was prepared. pLN1 (Kakeda et al., Gene Therapy; 12: 852-856, 2005) was digested with EcoRI and with NcoI, and the CMV promoter and Sv40polyA were removed. To this site, a fragment containing the CAG promoter and EGFP prepared by digestion of pLN1-PGK-EGFP with EcoRI and with NotI and the IRES fragment prepared by digestion of a DNA fragment which was amplified by PCR using, as a template, the IRES sequence derived from pcDNA3.0 (Invitrogen) with NotII and with NcoI were simultaneously introduced. The primer sequences used for PCR are shown below.

```
EGFP-IRESFw1:
                                    (SEQ ID NO: 154)
5'-AAGCGGCCGCGACTCTAGGGATCCGCCCTCTCCCTCCC

FGFP-IRESRv1:
                                    (SEQ ID NO: 155)
5'-GACACCATGGTTGTGGCCATATTATCATCGTG
```

The size of the final pLN1-IRES-EGFP construct is about 5.7 kb.

(1-2) Introduction of EGFP Gene Expression Unit into 14AΔqHAC Vector

The EGFP gene expression unit comprising the EGFP sequence was inserted into the 14AΔqHAC and 14NΔqHAC vectors. The EGFP expression plasmid, pLN1-IRES-EGFP, comprising the loxP sequence was prepared, and the Cre recombinase is expressed transiently to insert the gene expression unit into an artificial chromosome by site-directed recombination between the loxP sequences. A recombinant comprising an insert was selected using the acquisition of G418 resistance (i.e., reconstruction of the promoter-fragmented neo-resistant gene expression unit) as an indicator. The 14AΔqHAC vector-carrying CHO cells, t7S38-6, and the 14NΔqHAC vector-carrying CHO cells, G4S39-13 (Example 8), were used and analyzed in accordance with the method of Example 3 or 8. G418-resistant colonies developed 2 to 3 weeks thereafter, a total of 80 colonies (40 1t7S38-6-derived colonies and 40 G4S39-13-derived colonies) were isolated, the isolated colonies were grown, and the subsequent analysis was performed.

(1-3) PCR Analysis

Figure 88:
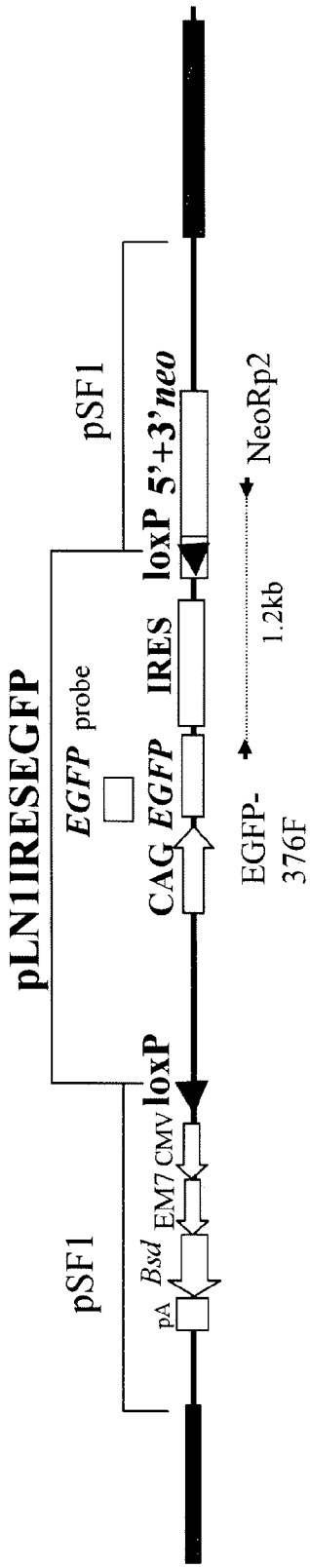
FIG. 88 schematically shows the results of PCR analysis of the EGFP-14HAC vector.

Recombinants into which the EGFP gene expression unit had been inserted were selected by inspecting whether or not such expression unit had been inserted into the site of the loxP sequence of the 14AΔq-HAC and 14NΔq-HAC vectors by PCR amplification using the EGFP374F and the Neo Rp2 primers designed on the pLN1-IRES-EGFP vector and on the 14AΔqHAC and the 14NΔq-HAC vectors so as to sandwich the site of the loxP sequence. The outline is shown in FIG. 88.

```
EGFP 374F:
5'-GCATCGACTTCAAGGAGGAC        (SEQ ID NO: 156)

Neo Rp2:
5'-CCTGCAGTTCATTCAGGG          (SEQ ID NO: 157)
```

In the case of a recombinant comprising an insert, amplification of about 1.2 kbp is deduced with the use of the EGFP 374F and the Neo Rp2 primers. As a result, amplification as deduced was observed in a total of 80 strains (i.e., 40 t7S38-6-derived strains and 40 G4S39-13-derived strains) from among the G418-resistant CHO hybrid cells obtained in (1-2) above. Thus, these 80 strains of G418-resistant CHO hybrid cells were confirmed to be recombinants comprising the EGFP gene expression unit inserted into the loxP sequence.

(1-4) Southern Blot Analysis

Southern blot analysis was carried out in order to inspect whether or not the EGFP-14AΔq-HAC and EGFP-14NΔq-HAC vectors properly comprise the EGFP expression unit. The method was carried out in accordance with Kakeda et al. (Gene Therapy; 12: 852-856, 2005). Probes were prepared by amplifying a 318-bp region from nucleotides 78 to 395 in the EGFP coding region by PCR. The primer sequences used are shown below.

```
EGFP-78F:
ACGTAAACGGCCACAAGTTC           (SEQ ID NO: 158)

EGFP-395R:
GTCCTCCTTGAAGTCGATGC           (SEQ ID NO: 159)
```

Figure 89:
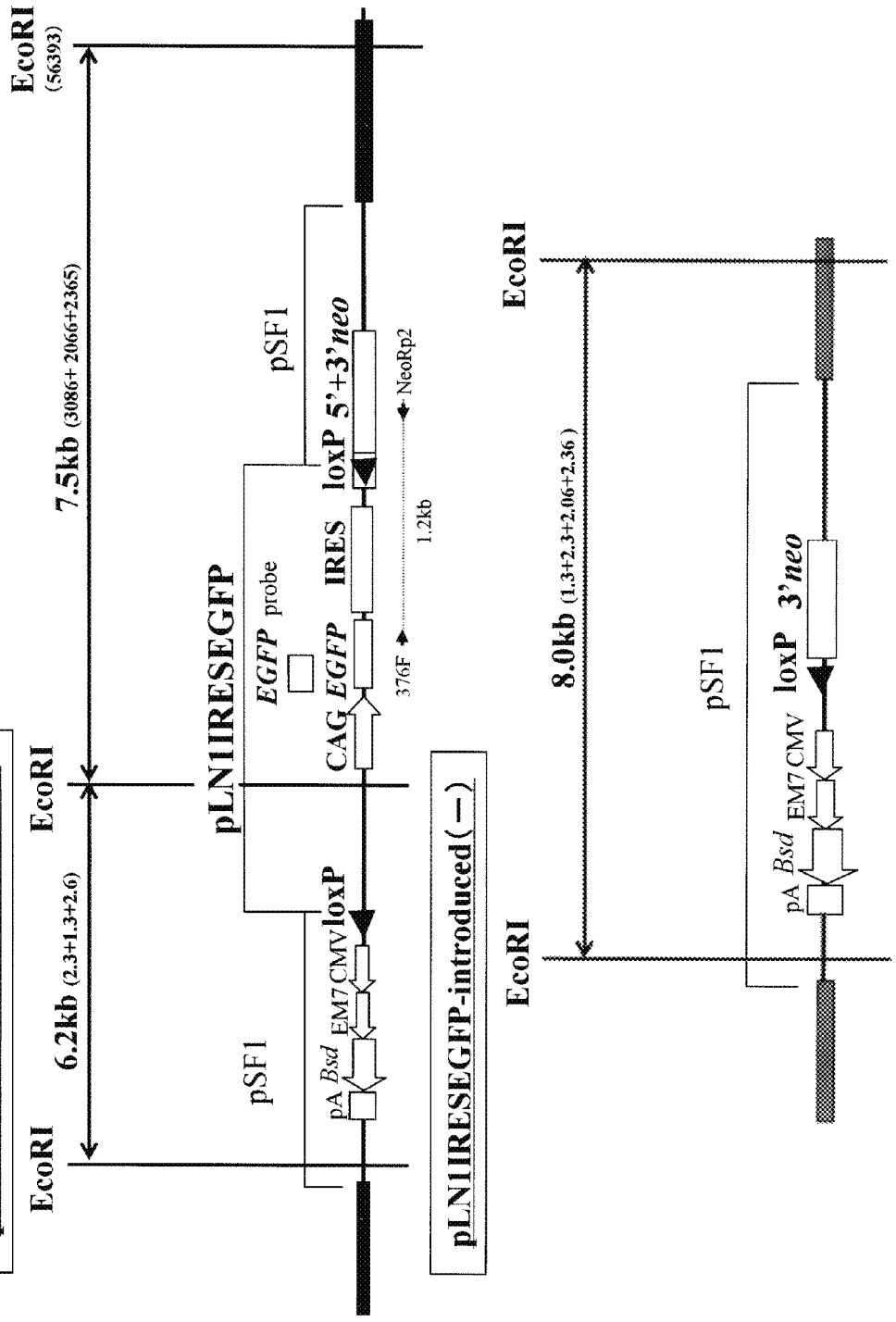
FIG. 89 shows the correlation between fragment size and the position on the vector inspected by Southern analysis, when pLN1IRESEGFP is introduced into CHO hybrid cell lines (+) or when pLN1IRESEGFP is not introduced (−).

The length of the restriction enzyme fragment resulting from digestion with EcoRI, which is deduced from the nucleotide sequence, is 7.5 kb, including the EGFP expression unit. The outline is shown in FIG. 89.

Bands having sizes as deduced were observed in a total of 70 strains (i.e., 34 t7S38-6-derived strains and 36 G4S39-13-derived strains) from among 80 strains of the candidate G418-resistant CHO hybrid cells obtained in (1-3) above.

(1-5) FISH Analysis

FISH analysis was carried out in accordance with the method described in Matsubara et al. (FISH Experimental Protocol, Shujunsha Co. Ltd., 1994) using human-specific Cot1 (Invitrogen) probes. 15 strains among the G418-resistant CHO hybrid cells obtained in (1-4) above (i.e., 8 t7S38-6-derived strains and 7 G4S39-13-derived strains) were analyzed. As a result, a normal karyotype and a copy of Cot1-stained EGFP-14AΔqHAC and EGFP-14NΔq-HAC vectors were observed in most observed mitotic figures of a total of 11 strains (i.e., 6 t7S38-6-derived strains; t6EGI-2, 6, 9, 11, 24, and 30; 5 G4S39-13-derived strains; G13EGI-1, 5, 15, 17, and 20).

The experiments (1-1) to (1-5) demonstrated that the obtained 11 G418-resistant strains were CHO cells having a normal karyotype and carrying the EGFP-14AΔq-HAC vectors (t6EGI-2, 6, 9, 11, 24, and 30) and CHO cells having a normal karyotype and carrying the EGFP-14NΔq-HAC vectors (G13EGI-1, 5, 15, 17, and 20).

(2) Preparation of Mouse ES Cell into which EGFP-14AΔqHAC or EGFP-14NΔqHAC Vector has been Introduced (2-1) Introduction of EGFP-14HAC Vector into Mouse ES Cell, TT2F CHO clones, t6EGI-11, t6EGI-24, G13EGI-1, and G13EGI-5 prepared in (1) above (hereafter referred to as t11, t24, G1, and G5, respectively) were used as HAC donor cells, and the EGFP-14AΔq-HAC vector or the EGFP-14NΔq-HAC vector was introduced into the mouse ES cell, TT2F, by the microcell mediated chromosome transfer method (Tomizuka et al., Nature Genetics, 16, 133-143, 1997). As a result, G418-resistant colonies developed 1 to 2 weeks thereafter, a total of 12 colonies were isolated, the isolated colonies were grown, and the subsequent analysis was performed.

(2-2) PCR Analysis

PCR analysis was carried out in accordance with the method of (7-4) (1-3) in order to select clones into which the EGFP-14AΔqHAC and EGFP-14NΔqHAC vectors have been introduced. As a result, amplification as deduced was observed in all G418-resistant mouse ES hybrid colonies isolated in (2-1) above. Thus, the 12 strains of the G418-resistant mouse ES hybrid cells were confirmed to carry the EGFP-14AΔqHAC and EGFP-14NΔqHAC vectors.

(2-3) Southern Blot Analysis

Southern blot analysis was carried out in the same manner as in (7-4) (1-4) above, in order to inspect whether or not the EGFP-14AΔq-HAC and EGFP-14NΔq-HAC vectors properly comprised the EGFP expression unit. As a result, bands having sizes as deduced were observed in a total of 11 strains among the 12 strains of the candidate G418-resistant mouse ES hybrid strains obtained in (2-2) above.

(2-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. From among the G418-resistant mouse ES hybrid cells obtained in (1-4) above, 8 strains (1-t11, 2-t11, 3-t11, 4-t11, 32-G1, 33-t24, 34-t24, and 35-t24) were analyzed. As a result, a normal karyotype and a copy of Cot1-stained EGFP-14AΔqHAC and EGFP-14NΔq-HAC vectors were detected in most of the observed mitotic figures of a total of 6 strains.

The experiments (2-1) to (2-4) demonstrated that the obtained 5 strains of the G418-resistant mouse ES hybrid cells (1-t11, 2-t11, 3-t11, 33-t24, and 34-t24) were mouse ES cells carrying the EGFP-14AΔq-HAC and the EGFP-14NΔq-HAC vectors and having normal karyotypes.

(3) 14HAC Vector Retention in Chimeric Mouse

The G418-resistant mouse ES hybrid cells carrying EGFP-14HAC obtained in (2) were used to obtain chimeric mice in accordance with the method of Tomizuka et al. (Nature Genetics, 16, 133-143, 1997). In order to confirm that chimeric mice carry the 14HAC vectors, PCR analysis was carried out in accordance with the methods of (7-4) (2-2) with the use of the set of primers shown below (schematically shown in FIG. 88).

```
Cen-side
(i) CR383659
CR38_7343SF    GCAAAACAATAACTGTTGTT  (SEQ ID NO: 160)
CR38_74060R    CATTTATCTTCTCTGGCTTA  (SEQ ID NO: 161)

(ii)
AL512320
NEK2PFw        CAGCCAGTGTTTTCCTGGAT  (SEQ ID NO: 162)
NEK2PRv        TCTTTGCTCTTCTGCAACCA  (SEQ ID NO: 163)

(iii)
AL39 1156-1
AL39_56451F    GGAATAGGGATTAGGAAATG  (SEQ ID NO: 164)
AL39_57026R    ACATGAGGTTTATTTGGTGG  (SEQ ID NO: 165)

(iv)
AL39 1156-2
AL39_46181F    AAGACACCAGGGAGTAACCT  (SEQ ID NO: 166)
AL39_46778R    GCTGAACCACTAAGGGTGAC  (SEQ ID NO: 167)

(v)
AL39 5409
AL39_5409F     GCATGCCTTCAATGTGTGAC  (SEQ ID NO: 168)
AL39_5811R     CAGCAGAGCCAAGATCCAGT  (SEQ ID NO: 169)

Tel-side
(i)
AB019437-1
IGHV3-79Fw     GTGCCCTCTGCTCTCAGACT  (SEQ ID NO: 170)
IGHV3-79Rv     TGAGCTGGGTTTCACAGTTG  (SEQ ID NO: 171)

(ii)
AB019437-2
IGHV7-81Fw     GCCATGTCCTCAGCCTTTAG  (SEQ ID NO: 172)
IGH7-81Rv      CTGGAGCATCCTCTTCTTGG  (SEQ ID NO: 173)

(iii)
AB019437-3
IGHVIII-82Fw   GGTCTTGTCCTTGGCTTTCA  (SEQ ID NO: 174)
IGHIII-82Rv    ATGGAGTCAGAGGGGGAAAC  (SEQ ID NO: 175)

(iv)
AB019437-4
AB01_to 1.5    GACCATGACCCCACCTCTAA  (SEQ ID NO: 176)
kbFw
AB01_0 to      GGTGGGATGGAAGAGTCAGA  (SEQ ID NO: 177)
1.5 kbRv
```

As a result, amplification as deduced was observed in the resulting chimeric mice. The summary is shown in FIG. 90. Thus, the somatic cells of the chimeric mice were found to comprise the EGFP-14AΔq-HAC and the EGFP-14NΔq-HAC vectors.

(4) Transmission of the EGFP-14AΔq-HAC and EGFP-14NΔq-HAC Vectors to Offspring

The chimeric mice (female) and the C57BL6 mice (male) obtained in (3) above were subjected to crossing to inspect the transmission of the EGFP-14AΔqHAC and the EGFP-14NΔqHAC vectors to offspring. PCR analysis was carried out in the same manner as in (7-4) (3) above, and the results were evaluated using HAC retention as an indicator. As a result, the EGFP-14AΔqHAC vector was found to have been amplified as deduced in 46.6% (N=133) in F1 mouse individuals and in 36.9% (N=84) F2 mouse individuals. Also, the EGFP-14NΔqHAC vector was found to have been amplified as deduced in 59.4% (N=79) of F1 mouse individuals. Thus, transmission of the EGFP-14AΔqHAC and the EGFP-14NΔqHAC vectors to offspring was confirmed.

Further, the F1 mice (males) and (females) carrying the EGFP-14AΔqHAC vectors obtained above were subjected to crossing. Tail fibroblasts of the offspring mice were sampled, cultured, fixed in the Carnoy's solution, and then subjected to FISH analysis in accordance with the method of Matsubara et al. (FISH Experimental Protocol, Shujunsha Co. Ltd., 1994) using human-specific Cot1 (Invitrogen) probes. As a result, individuals carrying two copies of EGFP-14AΔqHAC vectors in the tail fibroblasts were found.

Example 8

Analysis of hEPO Gene Expression in CHO Hybrid Cell Comprising hEPO-14NΔqHAC Vector (1) Construction of hEPO-14NΔqHAC Vector (1-1) Introduction of hEPO Gene into 14NΔqHAC Vector The hEPO gene expression unit was inserted into the 14NΔqHAC vector constructed in Example 6. The hEPO expression plasmid containing the loxP sequence was prepared, and the Cre recombinase was expressed transiently to insert the gene expression unit into an artificial chromosome by site-directed recombination between the loxP sequences.

A recombinant comprising an insert was selected using the acquisition of G418 resistance (i.e., reconstruction of the promoter-fragmented neo-resistant gene expression unit) as an indicator. With the use of the 14NΔqHAC vector-carrying CHO hybrid cells prepared in Example 6 (G4S61-1, 9, G4S39-13, and G8S90-4), the hEPO gene expression unit was inserted in the same manner as in Example 3 (1-1). G418-resistant colonies developed 2 to 3 weeks thereafter, a total of 246 colonies (61 G4S61-1-derived colonies, 75 G4S61-9-derived colonies, 73 G4S39-13-derived colonies, and 37 G8S90-4-derived colonies) were isolated, the isolated colonies were grown, and the subsequent analysis was performed.

(1-2) PCR Analysis

A recombinant comprising the hEPO gene expression unit inserted therein was selected by inspecting whether or not the hEPO gene expression unit had been inserted into a site of the loxP sequence of the 14NΔqHAC vector by PCR using the SVpANp1 and the Neo Rp2 primers, which had been designed on the pLN1-EPO vector and the 14NΔqHAC vector, so as to sandwich the site of the loxP sequence. Also, it was selected by inspecting amplification of the inserted hEPO gene by PCR using the M13RV and the Neo Rp2 primers of the pBS226 plasmid vector. Primer sequences and PCR conditions were determined in accordance with the method of Kakeda et al. (Kakeda et al., Gene Therapy; 12: 852-856, 2005). In the case of a recombinant comprising an insert, amplification of about 1.0 kbp is deduced with the use of the SVpANp1 and the Neo Rp2 primers and that of about 2.7 kbp is deduced with the use of the M13RV and the Neo Rp2 primers. As a result, amplification as deduced was observed in a total of 116 strains of the G418-resistant CHO hybrid cells obtained in (1-1) above (i.e., 31 G4S61-1-derived strains, 34 G4S61-9-derived strains, 35 G4S39-13-derived strains, and 16 G8S90-4-derived cells). Thus, the above 116 strains of the G418-resistant CHO hybrid cells were found to be recombinants comprising the hEPO gene expression units inserted into the loxP sequence.

(1-3) Southern Blot Analysis

Figure 38:
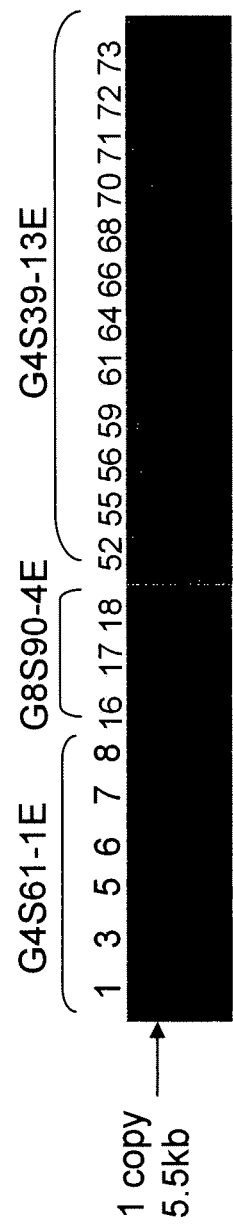
FIG. 38 shows the results of Southern analysis of the CHO hybrid cell into which the hEPO-introduced 14NΔqHAC vector has been introduced.

Southern blot analysis was carried out in order to inspect whether or not the hEPO-14NΔqHAC vector properly carries the hEPO expression unit. The method was carried out in accordance with Kakeda et al. (Gene Therapy; 12: 852-856, 2005). Representative results are shown in FIG. 38. The length of the restriction enzyme fragment resulting from digestion with XbaI deduced from the nucleotide sequence is 5.5 kb, including the hEPO expression unit. Bands having sizes as deduced were observed in a total of 60 strains (i.e., 13 G4S61-1-derived strains, 18 G4S61-9-derived strains, 19 G4S39-13-derived strains, and 10 G8S90-4-derived strains) from among 130 strains of the candidate G418-resistant CHO hybrid cells obtained in (1-2) (i.e., 36 G4S61-1-derived strains, 40 G4S61-9-derived strains, 35 G4S39-13-derived strains, and 19 G8S90-4-derived strains).

(1-4) FISH Analysis

Figure 39:
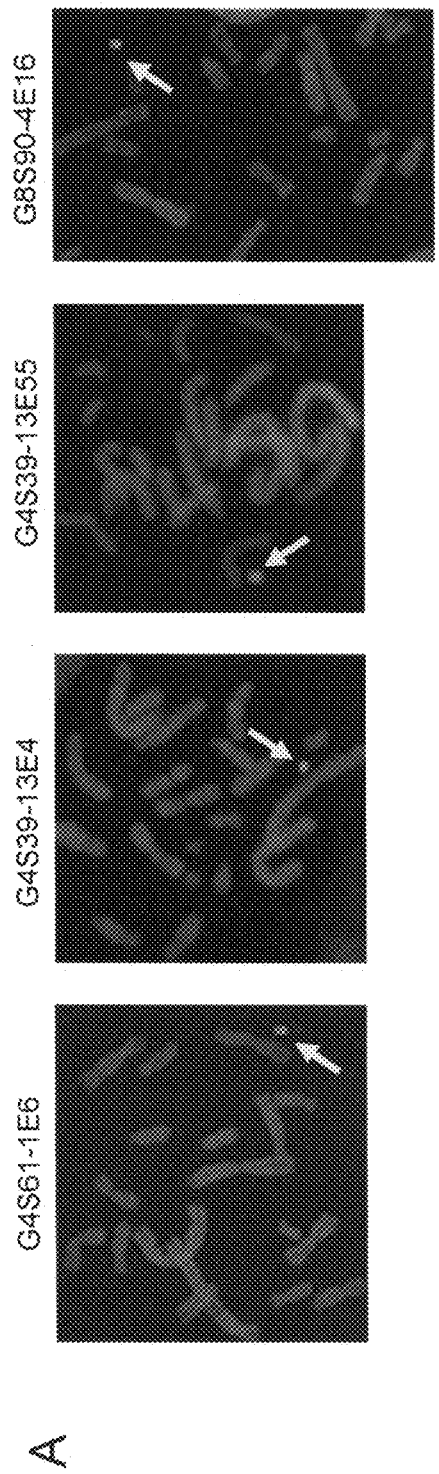
FIG. 39 shows the results of FISH analysis of the CHO hybrid cell that carries the hEPO-14AΔqHAC vector.

FISH analysis was carried out in accordance with the method described in Matsubara et al. (FISH Experimental Protocol, Shujunsha Co. Ltd., 1994) using human-specific Cot1 (Invitrogen) probes. 23 strains of the G418-resistant CHO hybrid cells obtained in (1-3) were analyzed. As a result, a normal karyotype and a copy of Cot1-stained hEPO-14NΔqHAC vector were observed in most of the observed mitotic figures of a total of 15 strains (hereafter referred to as G4S61-1E6, 9, G4S61-9E28, 34, 35, 65, G4S39-13E3, 4, 5, 16, 55, 61, 71, G8S90-4E16, and 18, respectively). Representative FISH images are shown in FIG. 39A, and karyotypes are shown in FIG. 39B and in FIG. 41. In FIG. 41, 13E4, 13E55, 1E6, and 4E16 represent G4S39-13E4, G4S39-13E56, G4S61-1E6, and G8S90-4E16, respectively.

The experiments (1-1) to (1-4) demonstrated that the obtained 15 strains of the G418-resistant CHO hybrid cells were CHO cells carrying the hEPO-14NΔqHAC vectors and having a normal karyotype.

(2) Expression of hEPO Genes Inserted into 14NΔqHAC Vector

Expression of hEPO genes was quantified by enzyme-linked immunosorbent assay (ELISA) of hEPO proteins generated in the culture supernatant.

Figure 40:
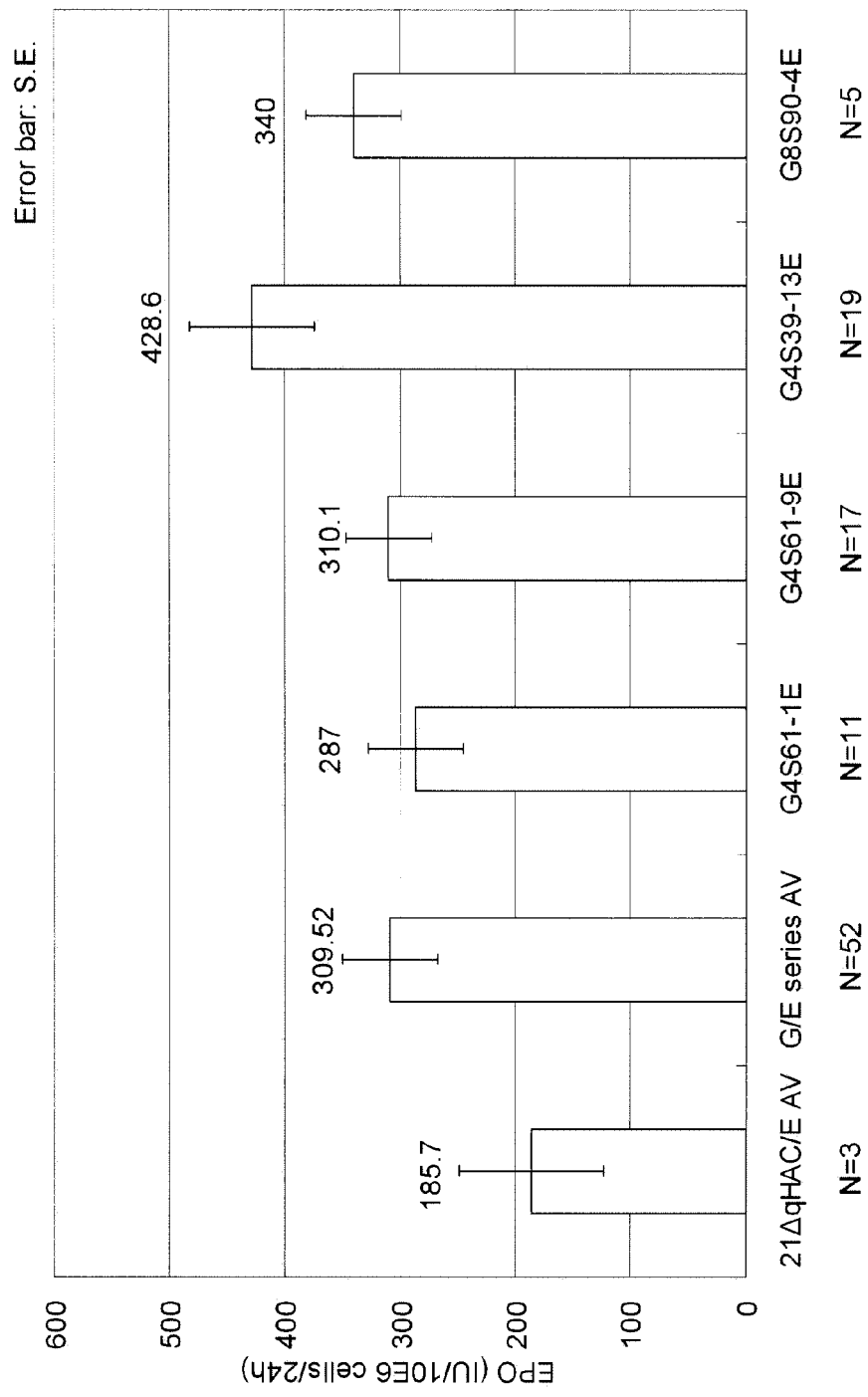
FIG. 40 shows expression of hEPO genes in the CHO hybrid cell that carries the hEPO-14NΔqHAC vector.

48 strains of the G418-resistant CHO hybrid cells carrying the hEPO-14NΔqHAC vector isolated in (1-3) above (i.e., 11 G4S61-1E-derived strains, 16 G4S61-9E-derived strains, 19 G4S39-13-derived strains, and 5 G8S90-4-derived strains) were plated in amounts of about $10^5$ cells in 12-well tissue culture plastic petri-dishes (Falcon) comprising 2 ml of F12 medium containing 10% FBS and G418 added thereto at 0.8 mg/ml. After the cultured cells reached confluence, the medium was exchanged with 2 ml of F12 medium containing 10% FBS, culture was conducted for 2 days, the medium was exchanged with 1 ml of F12 medium containing 10% FBS, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in FIG. 40. Based on the above results, hEPO expression was observed in all the G418-resistant CHO hybrid cells carrying the hEPO-14NΔqHAC vectors.

Example 9

Analysis of Long-Term Stability of hEPO-14NΔqHAC Vector in CHO Cells (1) Long-Term Subculture Under Non-Selective Culture Conditions In order to confirm stability of the hEPO-14NΔqHAC vector in CHO hybrid cells, long-term subculture was carried out under non-selective culture conditions. 4 strains of the CHO hybrid cells obtained in Example 8 (G4S61-1E6, G4S39-13E4, 55, and G8S90-4E16) were used. A non-selection medium was F12 medium containing 10% FBS, and a selection medium comprised such F12 medium and G418 added thereto at 0.8 mg/ml. The $5.0 \times 10^5$ CHO cells were plated in a 10-cm dish, the cells that had been cultured to a cell density of about 80 to 90% confluency were counted, the $5.0 \times 10^5$ cells were plated again in a 10-cm dish, and subculture was continued up to the tenth passage. The number of cells was counted every passage to determine the population doubling level. The CHO cells were recovered after the tenth passage, hEPO gene expression analysis and FISH analysis were carried out.

(2) hEPO Gene Expression After Long-Term Subculture

Expression of hEPO genes was quantified by enzyme-linked immunosorbent assay (ELISA) of hEPO proteins generated in the culture supernatant. The G4S61-1E6, G4S39-13E4, 55, and G8S90-4E16 strains were analyzed in accordance with the method of Example 8 (2). The average values of the results of experiments conducted in duplicate are shown in FIG. 41. Thus, hEPO expression was observed after long-term subculture in all the 4 strains of the CHO hybrid cells carrying the hEPO-14NΔqHAC vectors.

(3) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate and the average values were determined. The results regarding the above 4 strains are shown in Table 4 and in FIG. 41.

TABLE 4

Stability of hEPO-14NΔqHAC vector in CHO cell

| HAC | Cell population Number of subculture | HAC retention (%) Without drug selection | HAC retention (%) With drug selection |
|---|---|---|---|
| G4S61-1E6 | At the initiation of culture | — | 98 |
|  | Ten passages | 97.6 | 100 |
| G4S39-13E4 | At the initiation of culture | — | 100 |
|  | Ten passages | 89.7 | 95.2 |
| G4S39-13E55 | At the initiation of culture | — | 100 |
|  | Ten passages | 97 | 98.2 |
| G8S90-4E16 | At the initiation of culture | — | 98 |
|  | Ten passages | 87.6 | 97.6 |

The hEPO-14NΔqHAC vector was retained stably in CHO cells by the end of the tenth passage. As a result of observation of images of metaphase chromosomes, 1 or 2 signals were detected per cell.

The above experiments (1) to (3) demonstrated that the hEPO-14NΔqHAC vector would be retained stably in CHO cells after long-term subculture under non-selective culture conditions, that a copy number per cell would be maintained, and that hEPO gene expression would be maintained.

Example 10 hEPO Gene Expression in Human Normal Fibroblasts Comprising hEPO-14NΔqHAC Vector (1) Preparation of hEPO-14NΔqHAC Vector-Introduced Human Normal Fibroblasts
(1-1) Introduction of hEPO-14NΔqHAC Vector into Human Normal Fibroblasts, HFL-1, by the Microcell Mediated Chromosome Transfer Method Clones having the high capacity of forming micronucleus (G4S61-1E6, G4S39-13E4, 55, and G8S90-4E16) were selected from among the hEPO-14NΔqHAC vector-carrying CHO cells obtained in Example 9 and used as chromosome donor cells. As chromosome recipient cells, the human normal fibroblasts, HFL-1 (obtained from the Cell Engineering Division of the RIKEN BioResource Center; Accession No. RCB0521), were used. Micronuclear cell fusion was carried out in the same manner as in Example 5 (1). After selection culture was carried out for about 4 weeks, the developed drug-resistant colonies were isolated and then subjected to the subsequent analysis. As a result of 32 micronuclear cell fusion operations (8 times×4 strains), 47 drug-resistant colonies were obtained. Among the above colonies, cells obtained with the use of G4S61-1E6 cells as chromosome donor cells are hereafter referred to as the G6H cells, cells obtained with the use of G4S39-13E4 cells are hereafter referred to as the G4H cells, cells obtained with the use of G4S39-13E55 cells are hereafter referred to as the G55H cells, and cells obtained with the use of G8S90-4E16 cells are hereafter referred to as the G16H cells.

(1-2) PCR Analysis

Whether or not a human chromosome carries the hEPO-14NΔqHAC vector was inspected by PCR amplification using the SVpANp1 and the Neo Rp2 primers of Example 3 (1-2) and the STS marker, the D2S1334 primer, in accordance with the method of Kakeda et al. (Kakeda et al., Gene Therapy; 12: 852-856, 2005). Also, inclusion of chromosome donor CHO cells was inspected by PCR amplification using the CHO furin gene-specific primers, furin3'subF and furinEx6-28R. The method in accordance with Example 5 (1-2) was employed.

When the HFL-1 cells carrying the hEPO-14NΔqHAC vector did not include the chromosome donor CHO cells, amplification of about 1.0 kbp is deduced with the use of the SVpANp1 and the Neo Rp2 primers, amplification of about 0.6 kbp is deduced with the use of the D2S1334 primer, and no amplification is deduced with the use of furin3'subF and furinEx6-28R. As a result, amplification as deduced was observed in a total of 17 strains from among the 47 blasticidin-resistant strains obtained in (1-1) above (i.e., 2 G6H strains, 4 G4H strains, 6 G55H strains, and 5 G16H strains).

Thus, the above 17 blasticidin-resistant strains were found to be the HFL-1 cells carrying the hEPO-14NΔqHAC vectors.
(1-3) Southern Blot Analysis In order to inspect whether or not the hEPO-14NΔqHAC vector properly carries the hEPO expression unit, 13 strains of the above blasticidin-resistant cells were subjected to Southern blot analysis. The method was carried out in accordance with Kakeda et al. (Gene Therapy; 12: 852-856, 2005). Representative results are shown in FIG. 19B. The length of the restriction enzyme fragment resulting from digestion with XbaI deduced from the nucleotide sequence is 5.5 kb, including the hEPO expression unit. As a result, bands having sizes as deduced were observed in the 9 blasticidin-resistant strains carrying the hEPO-14NΔqHAC vector obtained in (1-2) above (i.e., G4H2, 4, 5, G6H3, G16H17, 21, 23, G55H7, and 9).

(1-4) FISH Analysis

Figure 42:
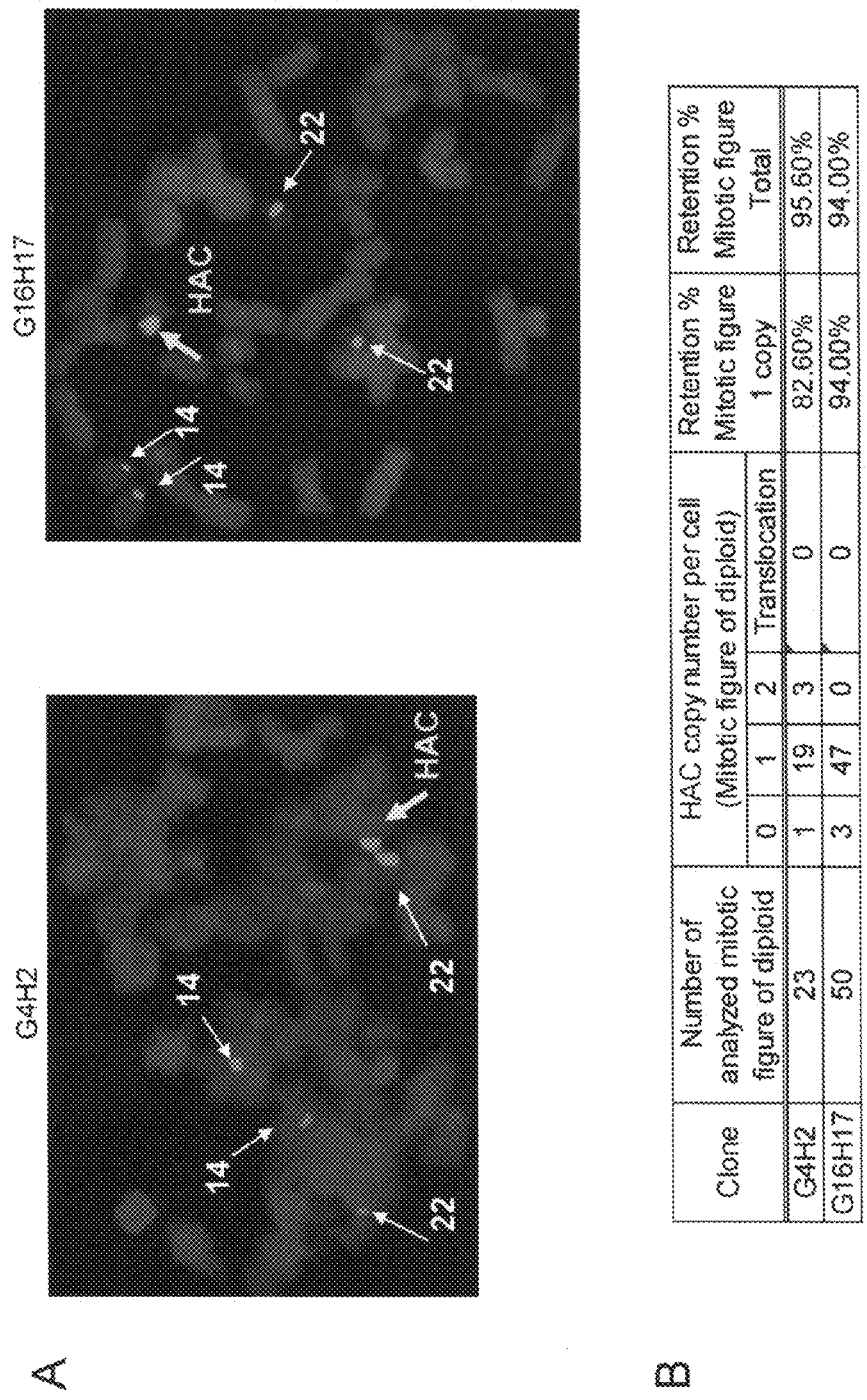
FIG. 42 shows the results of FISH analysis of a human normal fibroblast into which the hEPO-14NΔqHAC vector has been introduced.

FISH analysis was carried out in accordance with the method described in Matsubara et al. (FISH Experimental Protocol, Shujunsha Co. Ltd., 1994). Human chromosome 14- and human chromosome 22-specific α-satellite DNA probes (Q-biogene, Funakoshi) were used. As a result of analysis of 3 strains of blasticidin-resistant strains (G4H2, G16H17, and G55H7), a normal karyotype and signals in 4 sites in the centromeric regions of a pair of human chromosome 14 and human chromosome 22 derived from a host cell and in a site derived from a copy of 14NΔqHAC vector were detected in most of the observed mitotic figures of a total of 3 strains. The results are shown in FIG. 42A and in FIG. 42B.

The experiments (1-1) to (1-4) demonstrated that the obtained 3 strains of the blasticidin-resistant strains were HFL-1 cells carrying the hEPO-14NΔqHAC vector and having normal karyotypes.
(2) hEPO Gene Expression in hEPO-14NΔqHAC Vector-Carrying HFL-1 Cells Expression of hEPO genes was quantified by enzyme-linked immunosorbent assay (ELISA) of hEPO proteins generated in the culture supernatant.

9 strains of the blasticidin-resistant HFL-1 cells carrying the hEPO-14NΔqHAC vectors isolated in (1) above (G4H2, 4, 5, G6H3, G16H17, 21, 23, G55H7, and 9) were plated in amounts of about $10^5$ cells each in collagen-I-coated 24-well tissue culture plastic petri-dishes (Falcon) comprising 1 ml of selection medium (DMEM medium containing 20% FBS) containing blasticidin (3 μg/ml). After the cultured cells reached confluence, culture was conducted for 7 days, the medium was exchanged with a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The results are shown in the item of "14N-HAC" in FIG. 21.

Thus, hEPO expression was observed in all the HFL-1 cells carrying the hEPO-14NΔqHAC vectors.

Example 11

Long-Term EPO Expression in Human Normal Fibroblasts using hEPO-14NΔqHAC Vector (1) Long-Term Subculture Under Non-Selective Culture Conditions In order to confirm stability of the hEPO-14NΔqHAC vector in human normal fibroblasts, HFL-1, long-term subculture was carried out under non-selective culture conditions. 4 strains of the HFL-1 cells carrying the hEPO-14NΔqHAC vectors obtained in Example 10 (G4H2, G16H17, G16H21, and G55H7) were used. A non-selection medium was DMEM medium containing 20% FBS, and a selection medium comprised such DMEM medium and blasticidin added thereto at 3 μg/ml. The HFL-1 strains carrying the hEPO-14NΔqHAC vectors were plated in amounts of 1 to 3×10$^5$ cells in a collagen-I-coated T-25 flask (Falcon), the cells were cultured to a cell density of about 90% confluency, the 1 to 3×10$^5$ cells were plated again, and subculture was continued up to the sixth to the tenth passages. The number of cells was counted every passage to determine the population doubling level. The cells were recovered before and after the fifth passage and after the tenth passage, and hEPO gene expression analysis and FISH analysis were carried out.

(2) hEPO Gene Expression After Long-Term Subculture

Expression of hEPO genes was quantified by enzyme-linked immunosorbent assay (ELISA) of hEPO proteins generated in the culture supernatant.

The 4 strains of the HFL-1 cells carrying the hEPO-14NΔqHAC vectors that had been subjected to long-term subculture in (1) above were plated in amounts of about 10$^4$ cells in collagen-I-coated 24-well tissue culture plastic petri-dishes (Falcon) comprising 2 ml of DMEM medium containing 20% FBS. After the cultured cells reached confluence, culture was conducted for 7 days, the medium was exchanged with 1 ml of a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in FIG. 43.

Thus, hEPO expression was observed after long-term subculture in all the 4 strains of the HFL-1 cells carrying the hEPO-14NΔqHAC vectors.

The above experiment demonstrates that the hEPO-14NΔqHAC vector would retain hEPO gene expression in the HFL-1 cells after long-term subculture.

Example 12

Construction of 14HAC (14gNΔqHAC) Vector Comprising a Subtelomeric Region

The loxP sequences are inserted into the long-arm distal and proximal regions by homologous recombination, so that the HAC vector comprises a telomere sequence and a subtelomeric region of about 60 kb at the end of human chromosome 14. A region between the 2 loxP sequences is cleaved by site-directed recombination by Cre and deleted to construct an artificial chromosome (14gNΔqHAC) vector with the deleted long-arm distal region.

(1) Deletion of the Long Arm of Human Chromosome 14 by Site-Directed Recombination (1-1) Construction of ploxpPGK-14qtel-2 Vector for Inserting the loxP Sequence into the Telomeric Long-Arm Distal Region of Human Chromosome 14

The ploxPupBSD-PGK vector of Example 6 (1-1) was used as a vector for inserting the loxP sequence (i.e., a targeting vector). Based on the nucleotide sequence (Accession No. AB019437) of the long-arm distal region of human chromosome 14 obtained from the GenBank database, two target sequences for inserting the ploxpPGK-14qtel-2 vectors were designed. Sequences of oligonucleotide primers comprising restriction enzyme recognition sequences added thereto for amplifying the same by PCR are shown below.

```
AB01 38KpnIFw:
                                    (SEQ ID NO: 79)
5'-AGGTACCTTAGAGACTTTGTGAGGCTTATCGGCT

AB01 40ApaIRv:
                                    (SEQ ID NO: 80)
5'-AGGGCCCTAGTTAGATCTGGCAAGCCTAAAGCTG

AB01 42SpeIFw:
                                    (SEQ ID NO: 81)
5'-GACTAGTCGCTTGAGTCGTCATCATCAGATGAGT

AB01 45R:
                                    (SEQ ID NO: 82)
5'-AGGAGGATCCTTTATTGAGTGCAC

AB01 45F:
                                    (SEQ ID NO: 83)
5'-GTGCACTCAATAAAGGATCCTCCT

AB01 47EcoRV:
                                    (SEQ ID NO: 84)
5'-CGATATCGATGCTAAGAGATGCCCTAAGAAATCC
```

Figure 44:
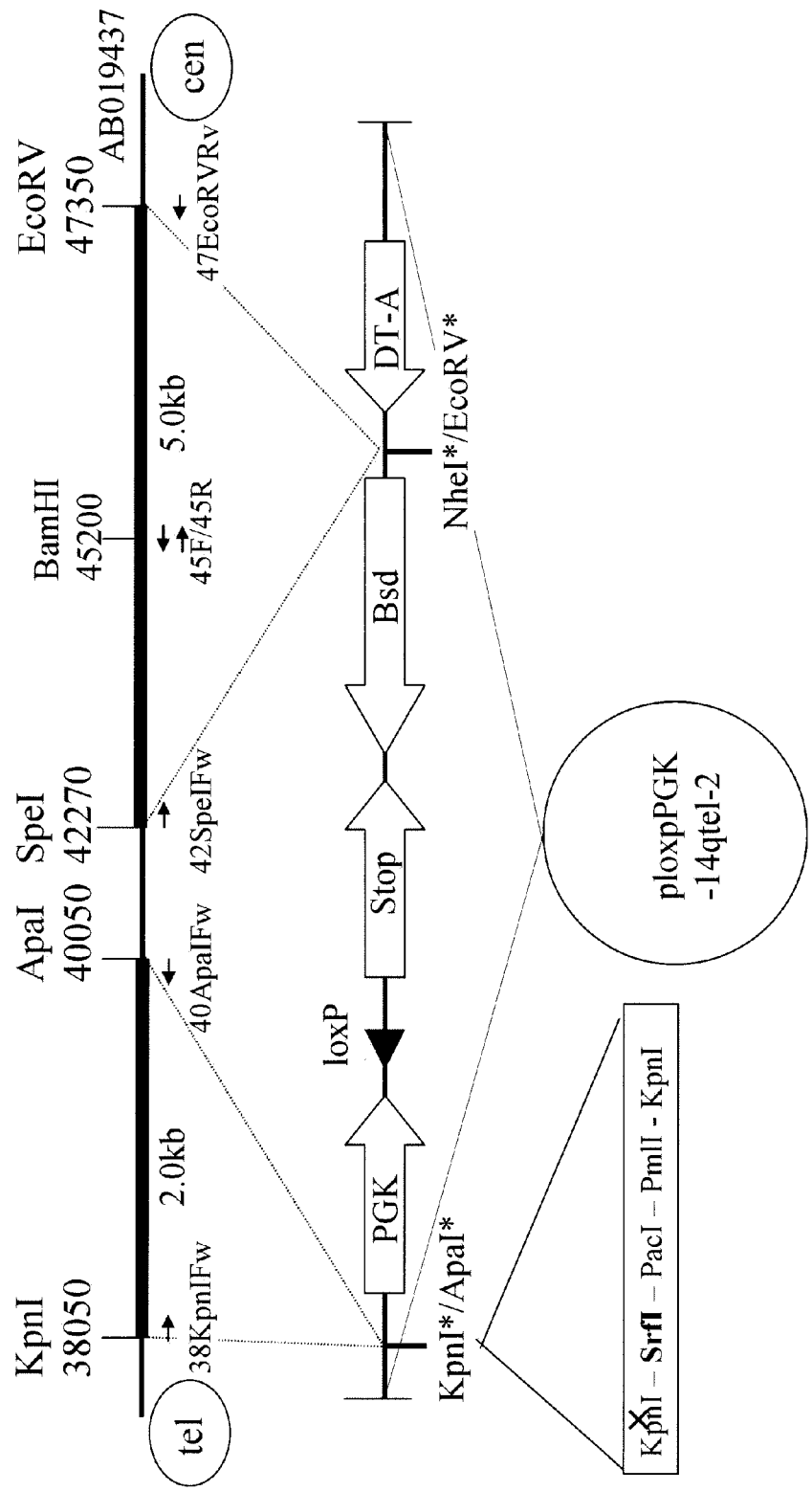
FIG. 44 shows the structure of the ploxpPGK-14qtel-2 vector for insertion of the loxP sequence on the telomere side of the long-arm distal region of human chromosome 14.

In accordance with the method of Example 1 (1-1), genomic DNA of the mouse A9 hybrid cell (A9c11-14chr) carrying human chromosome 14 was used as a template, and two target sequences of recombination (i.e., the 5'-target sequence and the 3'-target sequence) were amplified by PCR using the above primers. LA Taq polymerase (Takara Shuzo Co., Ltd.) was used, and the reactions were carried out using AB01 38KpnIFw/AB01 40ApaIFw at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 6 minutes, and extension at 70° C. for 10 minutes. Also, the reactions were carried out using AB01 42SpeIFw/AB01 47EcoRV at 94° C. for 1 minute, followed by 3 cycles of denaturation at 98° C. for 5 seconds followed by annealing/extension at 72° C. for 8 minutes, 2 cycles of denaturation at 98° C. for 5 seconds followed by annealing/extension at 70° C. for 8 minutes, 30 cycles of denaturation at 98° C. for 5 seconds followed by annealing/extension at 68° C. for 8 minutes, and extension at 70° C. for 10 minutes. The 2.0-kb-amplification product obtained with the use of AB01 38KpnIFw/AB01 40ApaIFw was digested with the restriction enzymes, KpnI and ApaI, and then cloned into the KpnI-ApaI site of the ploxPupBSD-PGK vector. Also, the 3.0-kbamplification product obtained with the use of AB01 42SpeIFw/AB01 45R was digested with the restriction enzymes, SpeI and BamHI, the 2.0-kb-amplification product obtained with the use of AB01 45F/AB01 47EcoRV was digested with the restriction enzymes, BamHI and EcoRV, these two fragments were subcloned into the pBluescript vector, the resultant was digested with SpeI and EcoRV, and the resultant was then cloned into the NheI-EcoRV site of the ploxPupBSD-PGK vector comprising the above 2.0-Kb target sequences. The size of the final ploxpPGK-14qtel-2 construct is about 12.1 kb. The ploxpPGK-14qtel-2 vector, the target sequence, and a chromosome allele resulting from homologous recombination are shown in FIG. 44 and in FIG. 45.

(1-2) Introduction of ploxpPGK-14qtel-2 Vector for Inserting the loxP Sequence into the Telomeric Long-Arm Distal Region of DT40 Hybrid Cell Carrying Human Chromosome 14

In accordance with the method of Example 1 (1-2), the ploxpPGK-14qtel-2 construct was converted into linearized DNA by digestion with the SrfI restriction enzyme, and the resultant was introduced into the DT40 hybrid cells carrying human chromosome 14, DT40(-14)1-2 and DT40(-14)2-4. Selection culture was carried out using blasticidin (final concentration: 8 ug/ml), and drug-resistant colonies developed 2 to 3 weeks thereafter. In the case of DT40(-14)1-2, a total of 1738 blasticidin-resistant colonies obtained through 6 transfection operations were isolated. In the case of DT40(-14)2-4, a total of 618 blasticidin-resistant colonies obtained through 4 transfection operations were isolated. These isolated colonies were then grown and then subjected to the subsequent analysis.

(1-3) PCR Analysis

Genomic DNA of a blasticidin-resistant strain was used as a template, and the presence of two target sequences (i.e., the 5' target sequence and the 3' target sequence) was detected by PCR in accordance with the method of Example 12 (1-1). By sandwiching these two target sequences (indicated as "5'-genome" and "3'-genome" in FIG. 45), oligonucleotide primer pairs were designed on the chromosome and on the targeting vector, respectively. Such positions are indicated by arrows in FIG. 46. The sequences are shown below.

```
AB01 37774F:
5'-TATGGAGGAATGGCAGAGGGTGACACAGGC (SEQ ID NO: 85)

PGKlongRv2:
5'-ACTTCCTGACTAGGGGAGGAGTAGAAGGTG (SEQ ID NO: 86)

BsdlongRv2:
5'-AGTGGGCAGTTTACCGTAAATACTCCACCC (SEQ ID NO: 87)

AB01 47441R:
5'-CTCTTGAAGAATCTGAGCCATCTGTATGCC (SEQ ID NO: 88)
```

The presence of the two target sequences (i.e., the 5' target sequence and the 3' target sequence) was observed in 2 strains among the 1738 blasticidin-resistant strains derived from DT40(-14)1-2 and in 5 strains among the 618 blasticidin-resistant strains derived from DT40(-14)2-4.

(1-4) Southern Blot Analysis

Figure 45:
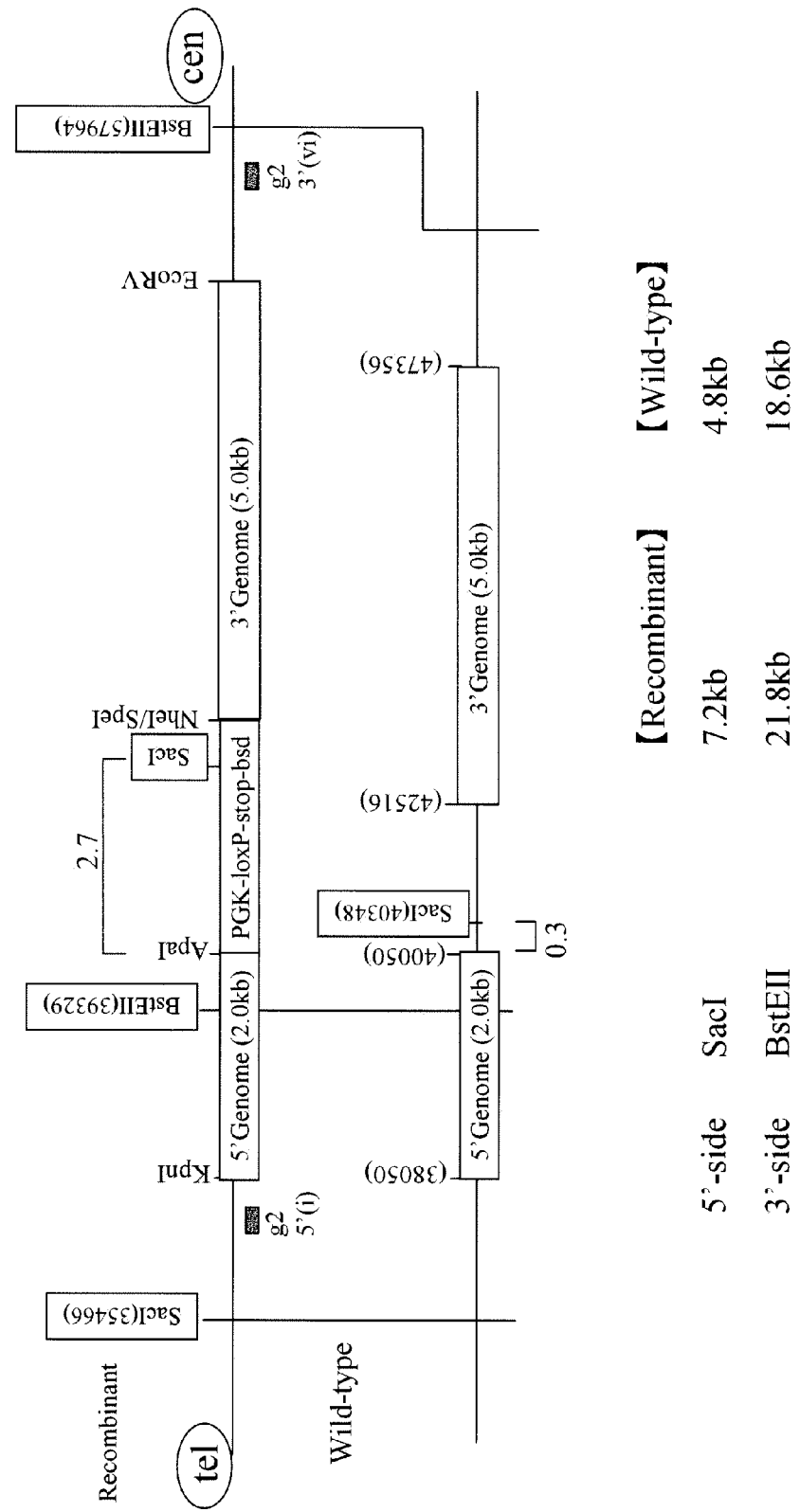
FIG. 45 shows an allele resulting from introduction of the ploxpPGK-14qtel-2 vector into human chromosome 14q.
Figure 46:
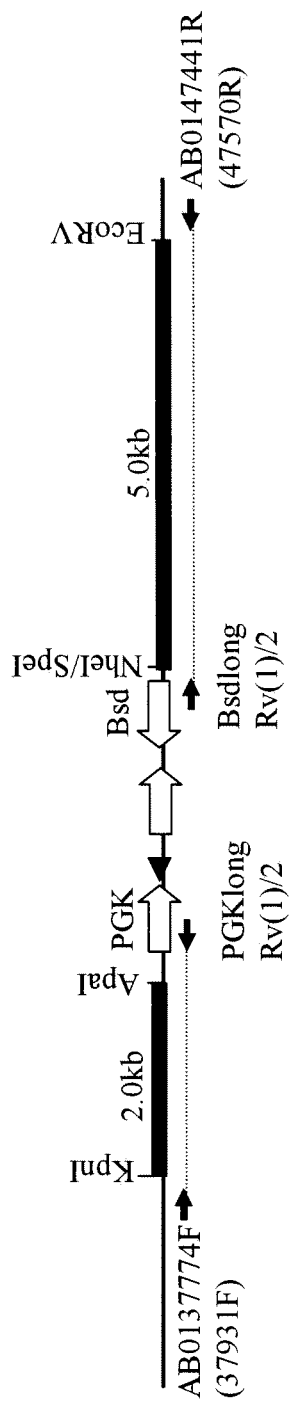
FIG. 46 shows the results of PCR analysis regarding introduction of the ploxpPGK-14qtel-2 vector into human chromosome 14q.

As a screening method for selecting a homologous recombinant, Southern blot analysis was carried out. Probes (g2-5' and g2-3') were designated outside the two target sequences (i.e., the 5' target sequence and the 3' target sequence) of homologous recombination (FIG. 45). In order to prepare probes, PCR was carried out using oligonucleotide primer pairs shown below and genomic DNA of A9c11-14chr cells carrying human chromosome 14 as a template, and the resultants were isolated, and purified.

```
AB01 37 kbKpnIFw:
5'-AGGTACCCTGTCTATTATGACCAGCATGGC (SEQ ID NO: 89)

AB01 38 kbKpnIRv:
5'-AGGTACCAGCCGATAAGCCTCACAAAGTCT (SEQ ID NO: 90)

AB01 56561F:
5'-CTGAAAATTTATCTGCGTGA (SEQ ID NO: 91)

AB01 57054R:
5'-AGAAGGAGGGTCCTTTGCAT (SEQ ID NO: 92)
```

Figure 47:
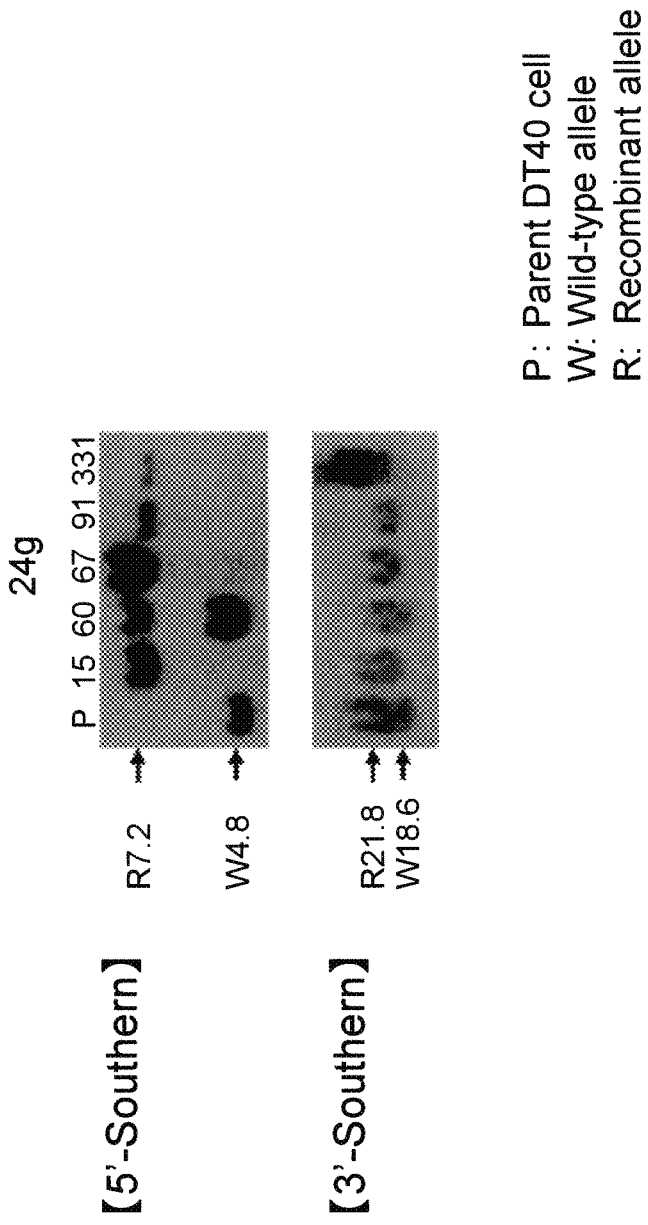
FIG. 47 shows the results of Southern analysis of the DT40 hybrid cell that carries the ploxpPGK-14qtel-2 vector introduced into human chromosome 14q.

Genomic DNA (about 10 μg) extracted from blasticidin-resistant strains obtained by primary screening was digested with the restriction enzymes, SacI (5'-side) or BstEII (3'-side) (Roche), and Southern blot analysis was carried out by the method described in Ausubel et al. (Current Protocols in Molecular Biology, John Wiley & Sons, Inc., 1994). The signal to which the labeled probes had hybridized was detected by the Typhoon9210 image analyzer (Molecular Dynamics). Representative results are shown in FIG. 47. The length of the restriction enzyme fragment deduced from the nucleotide sequence is 7.2 kb in the form of a homologous recombinant, and it is 4.8 kb in the form of a wild-type (i.e., a non-recombinant), for 5'-target sequence. Such length is 21.8 kb in the form of a homologous recombinant, and it is 18.6 kb in the form of a wild-type (i.e., a non-recombinant), for 3'-target sequence. One strain of homologous recombinant (12g5) was identified from among the two candidate DT40(-14)1-2-derived strains, and a total of 3 strains of the homologous recombinant strains (24g15, 24g67, and 24g91) were identified from among the 5 candidate DT40(-14)2-4-derived strains.

(2) Insertion of the loxP Sequence into the Centromeric Long-Arm Proximal Region of Human Chromosome 14

(2-1) Introduction of a ploxPHYGOR/n1 Vector for Inserting the loxP Sequence into the Centromeric Long-Arm Proximal Region of DT40 Cell Carrying Human Chromosome 14 into which ploxpPGK-14qtel has been Introduced The ploxPHYGOR/n1 construct prepared in Example 6 (2-1) was converted into linearized DNA by digestion with the SrfI restriction enzyme, and the resultant was introduced into the DT40 hybrid cells carrying human chromosome 14, i.e., 12g5, 24g15, and 24g67, into which ploxpPGK-14qtel-2 prepared in Example 13 (1-4) had been introduced. The method in accordance with Example 1 (1-2) was employed. After selection culture had been carried out for 2 to 3 weeks, puromycin-resistant colonies developed. As a result of a total of 6 transfection operations (two times for each cell), a total of 252 puromycin-resistant colonies (i.e., 78 12g5-derived colonies, 128 24g15-derived colonies, and 46 24g67-derived colonies) were isolated and then subjected to the subsequent analysis.

(2-2) PCR Analysis

Genomic DNA of the puromycin-resistant strain obtained (2-1) above was used as a template, and the presence of two target sequences (i.e., the 5' target sequence and the 3' target sequence) was detected by PCR in accordance with the method of Example 7 (2-1). By sandwiching these two target sequences (indicated as "5'-genome" and "3'-genome" in FIG. 27), oligonucleotide primer pairs were designed on the chromosome and on the targeting vector, respectively. Such positions are indicated by arrows in FIG. 28. The presence of the two target sequences (i.e., the 5' target sequence and the 3' target sequence) was observed in the 39 strains (i.e., 13 12g5- derived strains, 24 24g15-derived strains, and 2 24g67-derived strains) from among the above puromycin-resistant strains.

(2-3) Southern Blot Analysis

Figure 48:
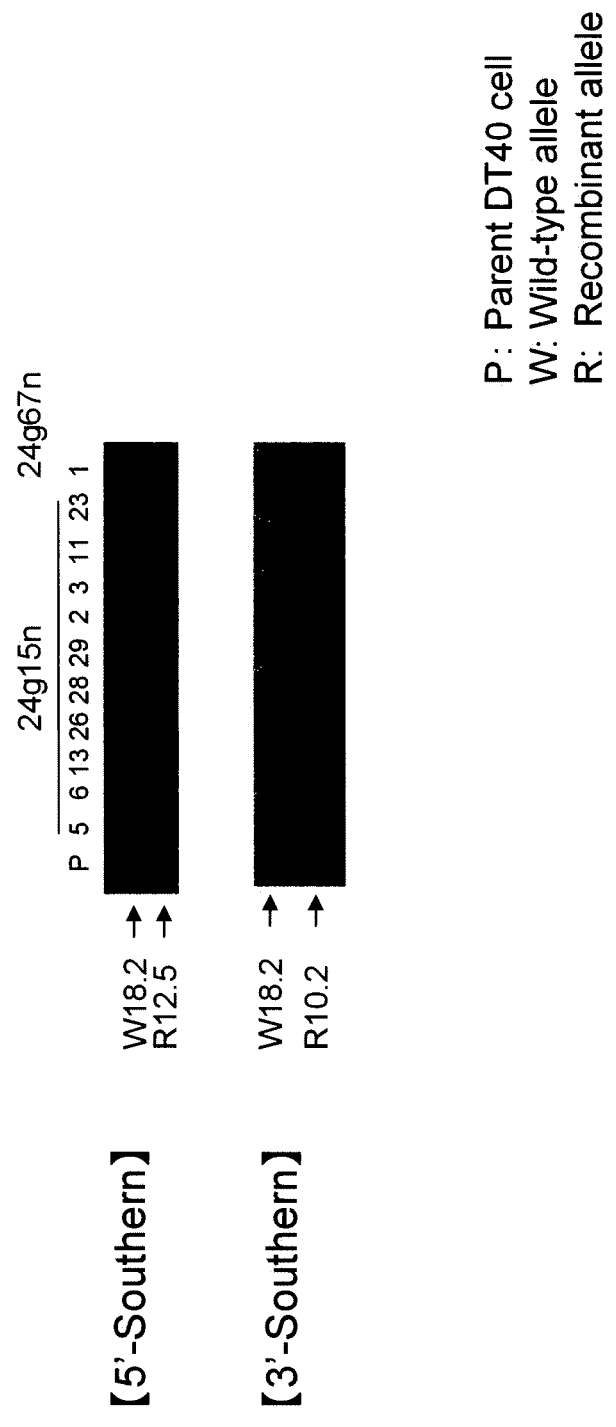
FIG. 48 shows the results of Southern analysis of the DT40 hybrid cell that carries ploxPHYGOR/n1 and ploxpPGK-14qtel-2 vectors introduced into human chromosome 14q.

As a screening method for selecting a homologous recombinant, Southern blot analysis was carried out in accordance with the method of Example 6 (2-4). Representative results are shown in FIG. 48. The length of the restriction enzyme fragment deduced from the nucleotide sequence is 12.5 kb in the form of a homologous recombinant, and it is 18.2 kb in the form of a wild-type (i.e., a non-recombinant), for 5'-target sequence. Such length is 10.2 kb in the form of a homologous recombinant, and it is 18.2 kb in the form of a wild-type (i.e., a non-recombinant), for 3'-target sequence. From among the 25 candidate strains obtained in (2-2) above, 23 strains of the homologous recombinants (i.e., 11 12g5-derived strains, 10 24g15-derived strains, and 2 24g67-derived strains) in total were identified. Among them, 24g15-derived clone, 24g15n28 (hereafter referred to as "g5n8"), and 24g67-derived clone, 24g67n19 (hereafter referred to as "g7n9"), were subjected to the following step (3).

(3) Deletion of the Long-Arm Distal Region by Cre-loxP Site-Directed Recombination (3-1) Introduction of Cre Expression Vector into DT40 Hybrid Cell Carrying Human Chromosome 14 Comprising the loxP Sequences Inserted into the Long-Arm Distal and Proximal Regions In accordance with the method of Example 1 (1-2), the Cre expression vector, pCAGGSCre, was introduced into the g5n8 and g7n9 cells obtained in Example 12 (2). Selection culture was carried out using hygromycin (final concentration: 1.25 mg/ml), and drug-resistant colonies developed 2 to 3 weeks thereafter. As a result of a total of 4 transfection operations (two times for each cell), a total of 16 hygromycin-resistant colonies (11 g5n8-derived colonies and 5 g7n9-derived colonies) were isolated and then subjected to the subsequent analysis.

(3-2) PCR Analysis

Genomic DNA of the hygromycin-resistant strains was used as a template, and deletion of a region between the two loxP sequences was confirmed by PCR in accordance with the method of Example 6 (3-2). By sandwiching the loxP sequence remaining after deletion of the long-arm distal region, oligonucleotide primer pairs were designed on the chromosome and on the targeting vector. Such positions are indicated by arrows in FIG. 28. As a result, amplification products as deduced were observed in the 12 strains (7 g5n8-derived strains and 5 g7n9-derived strains) among the above 16 hygromycin-resistant strains.

(3-3) Southern Blot Analysis

Figure 49:
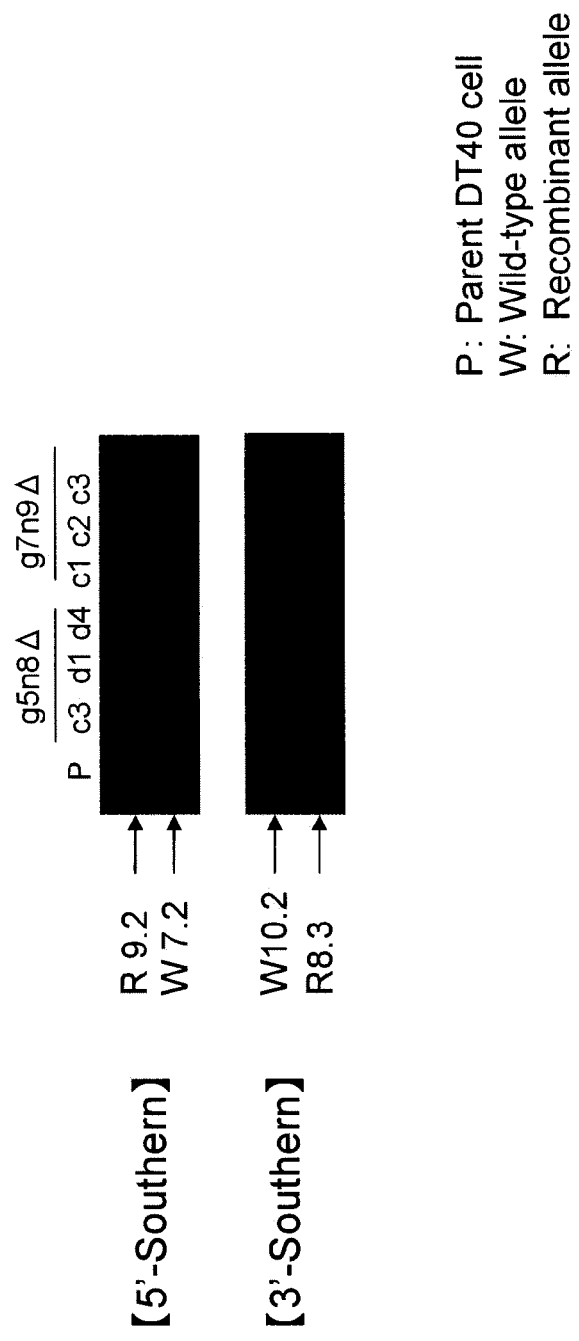
FIG. 49 shows the results of Southern analysis of the DT40 hybrid cell that carries 14gNΔqHAC.

Southern blot analysis was carried out in order to identify the structure of a chromosome with the deleted long-arm distal region and select the chromosome with the deleted long-arm distal region. The positions of the target sequence, the chromosome allele, and the probe resulting from deletion of the long-arm distal region are shown in FIG. 30B. Probes (g2-5'(i) and N3'(i)) were designated outside the two target sequences (the 5' target sequence and the 3' target sequence) of homologous recombination (FIG. 30B). Genomic DNA was extracted from 9 strains of the hygromycin-resistant strains obtained in Example 13 (3-2) (i.e., 5 g5n8-derived strains and 4 g7n9-derived strains) in the same manner as in Examples 13 (1-4) and (2-4). Digestion with a restriction enzyme (Roche) involved the use of SacI (5'-side) or StuI (3'-side). Representative results are shown in FIG. 49. The length of the restriction enzyme fragment deduced from the nucleotide sequence is 9.2 kb in the form of a homologous recombinant, and it is 7.2 kb in the form of a wild-type (i.e., a non-recombinant), for 5'-target sequence. Such length is 8.3 kb in the form of a homologous recombinant, and it is 10.2 kb in the form of a wild-type (i.e., a non-recombinant), for 3'-target sequence. As a result, chromosomes with the deleted long-arm distal regions were observed in a total of 5 strains (3 g5n8-derived strains and 2 g7n9-derived strains).

(3-4) FISH Analysis

Figure 50:
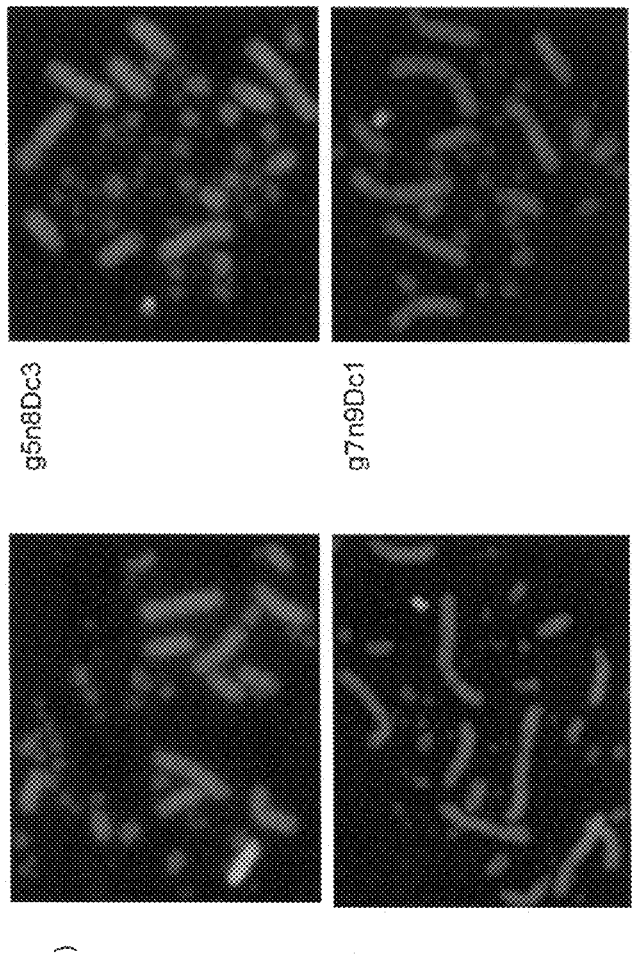
FIG. 50 shows the results of FISH analysis of the DT40 hybrid cell that carries 14gNΔqHAC.

FISH analysis was carried out in accordance with the method described in Matsubara et al. (FISH Experimental Protocol, Shujunsha Co. Ltd., 1994) using human-specific Cot1 (Invitrogen) probes. As a result of analysis of the 5 strains obtained in (3-3) above (i.e., g5n8Δc3, g5n8Δd1, g5n8Δd4, g7n9Δc1, and g7n9Δc3), all strains were were found to be of normal karyotypes and a copy of Cot1-stained signal were detected in most of the observed mitotic figures. Representative FISH images and the karyotype of the HAC vector are shown in FIG. 50A and FIG. 50B.

The experiments (3-1) to (3-4) demonstrated that the obtained hygromycin-resistant DT40 hybrid cells carry the human chromosome 14 fragment (14gNΔqHAC) with the deleted long-arm distal region, while maintaining a naturally-occurring telomeric region.

(4) Introduction of Cloning Site into the Long-Arm Proximal Region of 14gNΔqHAC (4-1) Construction of pSF(g+n1) Vector for Inserting loxP and 3'Neo Sequences As a basic plasmid for inserting the loxP and 3'neo sequences into the human artificial chromosome (HAC) prepared in Example 12 (3), pSF1③ prepared in Example 1 (2-1) was used. The 5'-target sequences for homologous recombination where loxP and 3'neo would be inserted were designed based on the sequence used for the ploxpPGK-14qtel2 vector obtained in Example 12 (1-1). The 3'-target sequences were designed based on the nucleotide sequence (Accession No. AL391156) of the long-arm proximal region of human chromosome 14 obtained from the GenBank database. Sequences of oligonucleotide primers for amplifying the same by PCR are shown below.

```
54023Flong2FseI:
                                      (SEQ ID NO: 93)
5'-GATGGCCGGCCTGGTTGGTAAAGATTGCTACACTTACGGCA 58830RlongSrfI:
                                      (SEQ ID NO: 94)
5'-GATGCCCGGGCCAATAGCCAGTCAATCGAGAAACCAAGCCC
```

Figure 51:
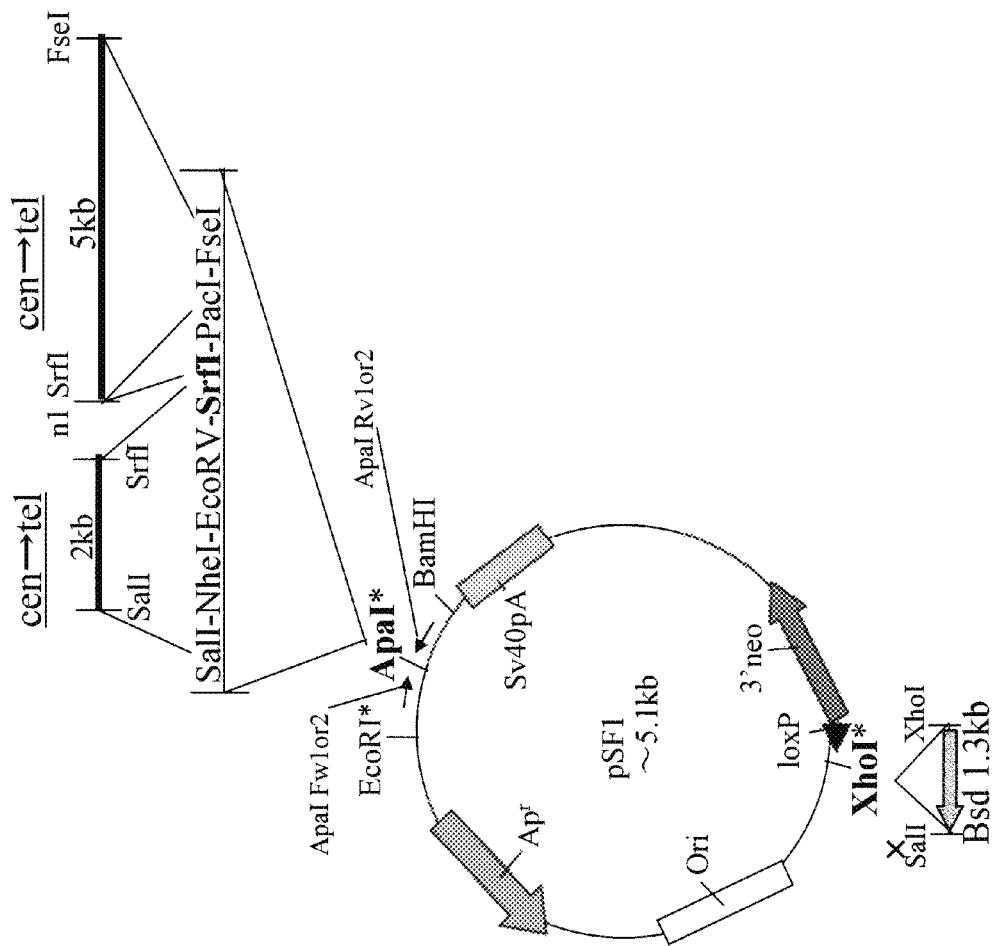
FIG. 51 shows the structure of the pSF1(g+n1) vector for insertion of loxP and 3'neo sequences.

The 5'-target sequence was cleaved from the ploxpPGK-14qtel2 vector by digestion with SalI and SrfI (Roche), separated and purified by agarose gel electrophoresis, and then cloned into the SalI-SrfI site of the pSF1③ plasmid. The 3'-target sequence was amplified by PCR using genomic DNA extracted from the A9c11-14chr cell carrying human chromosome 14 as a template. LA Taq polymerase (Takara Shuzo Co., Ltd.) was used, MgSO$_4$ (final concentration: 0.5 mM) was added, and reactions were carried out at 94° C. for 1 minute, followed by 3 cycles of denaturation at 98° C. for 5 seconds followed by annealing/extension at 72° C. for 8 minutes, 2 cycles of denaturation at 98° C. for 5 seconds followed by annealing/extension at 70° C. for 8 minutes, 30 cycles of denaturation at 98° C. for 5 seconds followed by annealing/extension at 68° C. for 8 minutes, and extension at 72° C. for 10 minutes. The DNA fragment (about 5.0 kb) was digested with restriction enzymes, FseI and SrfI (Roche), separated and purified by agarose gel electrophoresis, and then cloned into the FseI-SrfI site of the pSF1③ plasmid into which the 5'-target sequence had been inserted. The size of the final pSF1(g+n1) construct is about 13.2 kb. The targeting vector, the target sequence, and a chromosome allele resulting from homologous recombination are shown in FIG. 51 and in FIG. 34B.

(4-2) Introduction of pSF(g+n1) Vector into DT40 Cell Carrying 14gNΔqHAC

The pSF(g+n1) constructs were was linearized by digestion with the SrfI restriction enzyme (Roche) and then introduced into 3 types of DT40 hybrid cells carrying 14NΔqHAC with the deleted long-arm distal region (g5n8Δc3, g5n8Δd1, and g7n9Δc1) in accordance with the method of Example 1 (2-2). Blasticidin-resistant colonies developed 2 to 3 weeks thereafter. As a result of 3 transfection operations, a total of 154 drug-resistant colonies (i.e., 99 g5n8Δc3-derived colonies, 34 g5n8Δd1-derived colonies, and 21 g7n9Δc1-derived colonies) were isolated, and the subsequent analysis was performed.

(4-3) PCR Analysis

Genomic DNA of the blasticidin-resistant strain was used as a template, and the presence of two target sequences (i.e., the 5' target sequence and the 3' target sequence) was detected by PCR. By sandwiching these two target sequences, oligonucleotide primer pairs were designed on the chromosome and on the targeting vector, respectively. Such positions are indicated by arrows in FIG. 34B. The sequences of primers for detecting the 5'-target sequence are shown below.

```
AB01 37931F:
5'-AGCGGTACTGAGAGGCAATCTTTCATGGGC    (SEQ ID NO: 95)

ApaIlongFw2:
5'-ACCAAATATCCTGCTCAAACTGTAACCC      (SEQ ID NO: 96)
```

The method in accordance with Example 13 (4-1) was employed. The 5'-target sequence was detected under reaction conditions of 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 6 minutes, and extension at 72° C. for 10 minutes. Among the obtained blasticidin-resistant strains, 13 strains (i.e., 3 g5n8Δc3-derived strains, 8 g5n8Δd1-derived strains, and 2 g7n9Δc1-strains cells) were found to produce amplification products having sizes (5'-genome: about 2.0 kb; 3'-genome: about 5.0 kb) deduced from the nucleotide sequences.

(4-4) Southern Blot Analysis

Figure 52:
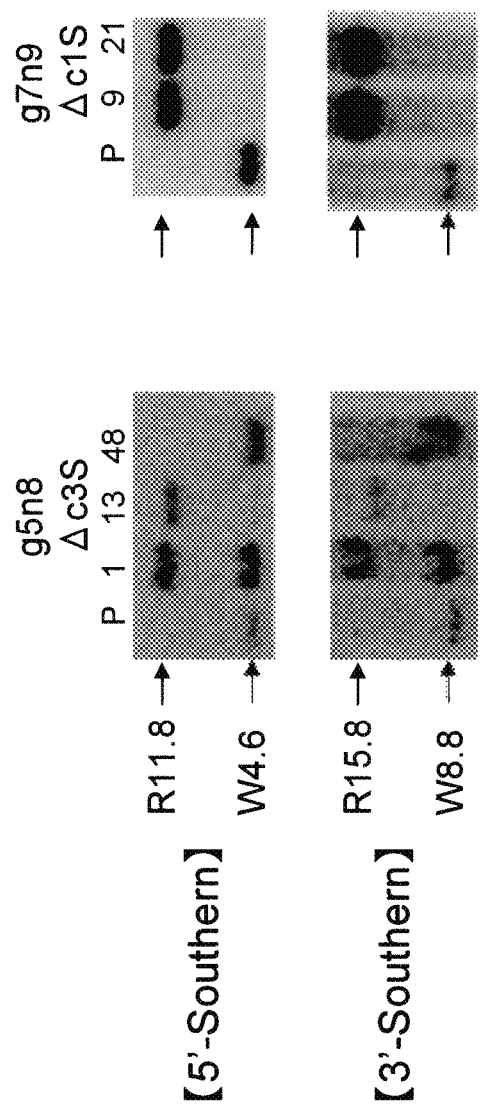
FIG. 52 shows the results of Southern analysis of the DT40 hybrid cell that carries the pSF1(g+n1) vector introduced into 14gNΔqHAC.

Southern blot analysis was carried out in order to select homologous recombinant. Probes g2-5'(i) (Example 12 (1-4)) and N3'(ii) (Example 6 (4-4)) were designated outside the target sequences of homologous recombination (FIG. 34B). Genomic DNA was extracted from the candidate drug-resistant strains obtained in Example 12 (4-3) in the same manner as in Example 12 (1-4). Digestion with restriction enzymes (Roche) involved the use of SphI (5'-side) or BstEII (3'-side). Representative results are shown in FIG. 52. The length of the restriction enzyme fragment deduced from the nucleotide sequence is 11.8 kb in the form of a homologous recombinant, and it is 4.6 kb in the form of a wild-type (i.e., a non-recombinant), for the 5'-genome target sequence. Such length is 15.8 kb in the form of a homologous recombinant, and it is 8.8 kb in the form of a wild-type (i.e., a non-recombinant), for the 3'-genome target sequence. From among the 13 candidate drug-resistant strains, a total of 9 strains of the homologous recombinants were identified.

Through experiments (4-1) to (4-4) above, the 9 strains of the DT40 hybrid cells (i.e., g5n8Δc3s13, g5n8Δd1s3, 4, 6, 8, 9, 10, g67n19Δc1s9, and 21) carrying 14gNΔqHAC vectors into which cloning sites (i.e., the loxP and 3'neo sequences) had been inserted by homologous recombination were obtained. Among them, two strains, g5n8Δc3s13 and g67n19Δc1s9, were subjected to the subsequent step.

(5) Introduction of 14gNΔqHAC Vector into CHO Cells (5-1) Introduction of 14gNΔqHAC Vector into CHO Cells by the Microcell Mediated Chromosome Transfer Method As chromosome donor cells, DT40 hybrid cells (g5n8Δc3s13 and g67n19Δc1s9) carrying the 14gNΔqHAC vector with the deleted long-arm distal region and with the cloning sites (i.e., the loxp and 3'neo sequences), which were obtained in Example 12 (4), inserted therein were used. As chromosome recipient cells, Chinese hamster-derived CHO-K1 strains (Accession No. JCRB9018) were used. The method in accordance with Example 1 (3-1) was employed. After selection culture had been carried out for about 2 weeks, developed blasticidin-resistant colonies were isolated, and the subsequent analysis was performed. As a result of 4 micronuclear cell fusion operations, a total of 55 strains of the blasticidin-resistant CHO strains (i.e., 32 g5n8Δc3s13-derived strains and 23 g67n19Δc1s9-derived strains) were obtained.

(5-2) PCR Analysis

Genomic DNA of a blasticidin-resistant strain was used as a template, and the presence of two target sequences (i.e., the 5' target sequence and the 3' target sequence) was detected by PCR. The method in accordance with Example 6 (5-2) was employed. Among the obtained blasticidin-resistant CHO cells, 52 strains (i.e., 29 g5n8Δc3s13-derived strains and 23 g67n19Δc1s9-derived strains) were found to produce amplification products having sizes (5'-genome: about 2.0 kb; 3'-genome: about 5.0 kb) deduced from the nucleotide sequence, and no inclusion of DT40 cells was detected.

(5-3) Southern Blot Analysis

Figure 53:
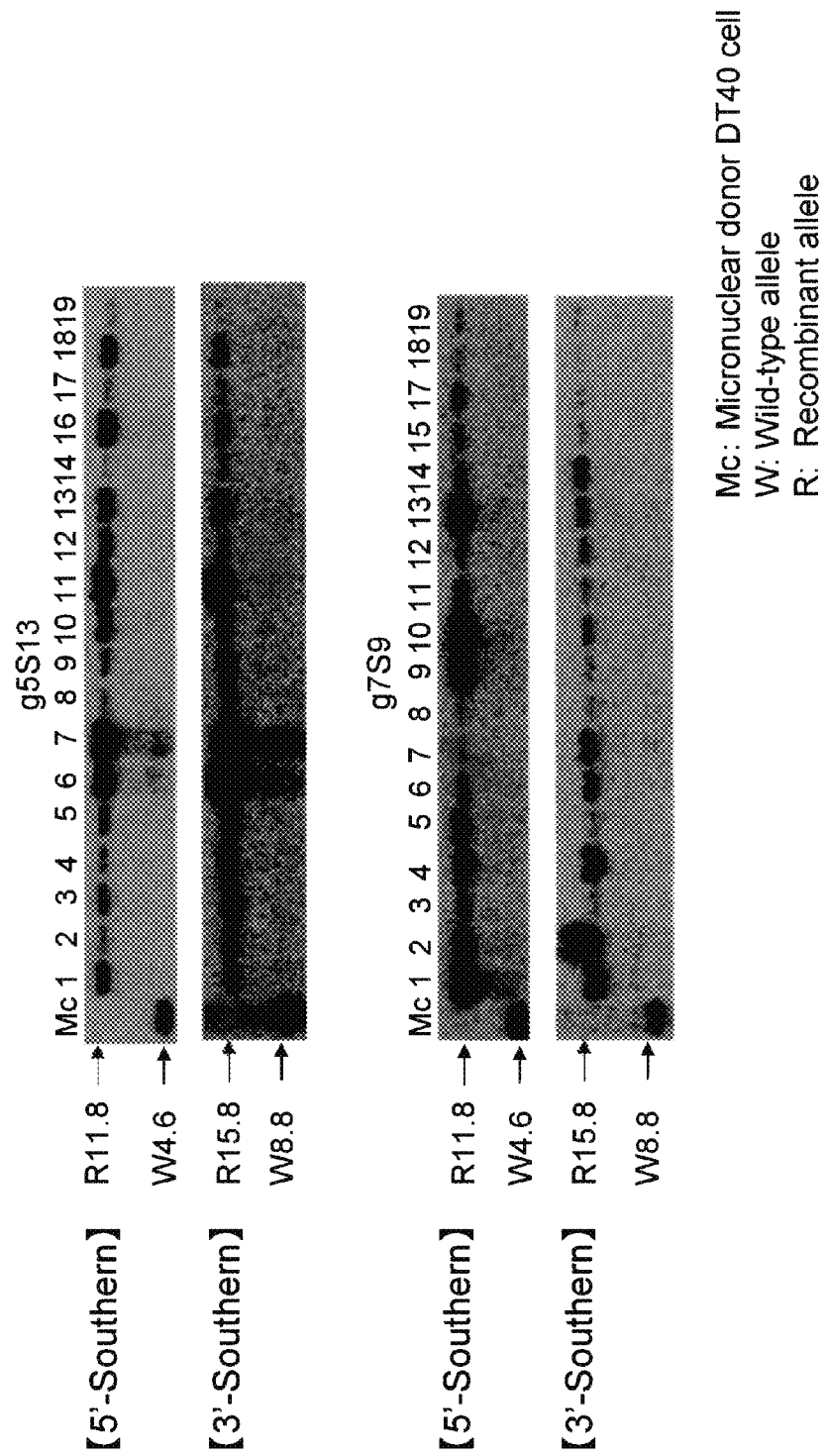
FIG. 53 shows the results of Southern analysis of the CHO hybrid cell into which the 14gNΔqHAC vector has been introduced.
Figure 54:
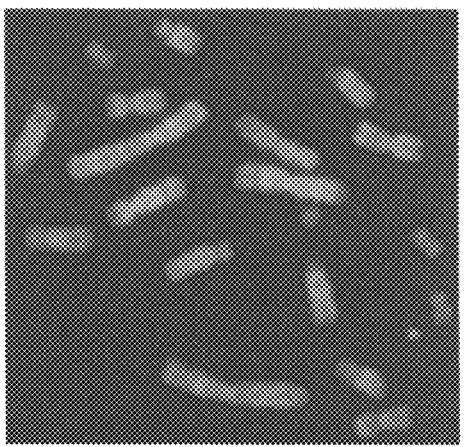
FIG. 54 shows the results of FISH analysis of the CHO hybrid cell into which the 14gNΔqHAC vector has been introduced.

Southern blot analysis was carried out in the same manner as in Example 12 (4-4), in order to identify the structure of the introduced 14gNΔqHAC vector. Representative results are shown in FIG. 53. The length of the restriction enzyme fragment deduced from the nucleotide sequence is 11.8 kb in the form of a homologous recombinant, and it is 4.6 kb in the form of a wild-type (i.e., a non-recombinant), for the 5'-genome target sequence. Such length is 15.8 kb in the form of a homologous recombinant, and it is 8.8 kb in the form of a wild-type (i.e., a non-recombinant), for the 3'-genome target sequence. From among the 36 candidate blasticidin-resistant strains, a total of 35 strains of the homologous recombinants (i.e., 17 g5n8Δc3s13-derived strains and 18 g67n19Δc1s9-derived strains) were identified. In FIG. 53 and FIG. 54, "g5S13" and "g7S9" represent g5n8Δc3s13-derived strains and g67n19Δc1s9-derived strains, respectively.

(5-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of 15 strains of the blasticidin-resistant CHO strains (i.e., 6 g5n8Δc3s13-derived strains and 9 g67n19Δc1s9-derived strains), a total of 5 strains (i.e., 2 g5n8Δc3s13-9 and 12 strains (hereafter referred to as g5S13-9 and g5S13-12) and 3 g67n19Δc1s9-11, 12, and 17 strains (hereafter referred to as g7S9-11, g7S9-12, and g7S9-17)) were found to be of normal karyotypes and a copy of Cot1-stained 14gNΔqHAC vector were detected in most of the observed mitotic figures. Representative FISH images and the karyotype of the 14gNΔqHAC vector are shown in FIG. 54A and in FIG. 54B.

The experiments (5-1) to (5-4) demonstrated that the obtained 5 strains of the blasticidin-resistant CHO strains have normal karyotypes and carry a copy of 14gNΔqHAC vector.

Example 13

Analysis of Long-Term Stability of 14gNΔqHAC Vector in CHO Hybrid Cell (1) Long-Term Subculture Under Non-Selective Culture Conditions In order to confirm stability of the 14gNΔqHAC vector in CHO cells, long-term subculture was carried out under non-selective culture conditions. Two strains of the CHO strains carrying the 14gNΔqHAC vectors described in Example 7 (g5S13-9 and g5S13-12) were used. A non-selection medium was F12 medium containing 10% FBS, and a selection medium comprised such F12 medium and blasticidin added thereto at 8 μg/ml. The 5.0×10⁵ CHO cells were plated in a 10-cm dish, the cells that had been cultured to a cell density of about 80 to 90% confluency were counted, the 5.0×10⁵ cells were plated again in a 10-cm dish, and subculture was continued up to the tenth passage. The number of cells was counted every passage to determine the population doubling level. The CHO strains were recovered after the tenth passage and FISH chromosome samples were prepared.

(2) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate and the average values were determined. The results regarding these two strains are shown in Table 5 and in FIG. 13. In FIG. 13, the results are shown in the item "14gΔqHAC(g)."

TABLE 5

Stability of 14gNΔqHAC vector in CHO cell

| HAC | Cell population Number of subculture | HAC retention (%) Without drug selection | With drug selection |
|---|---|---|---|
| G5S13-9 | At the initiation of culture | — | 100 |
|  | Ten passages | 99 | 98 |
| G5S13-12 | At the initiation of culture | — | 100 |
|  | Ten passages | 99 | 98 |

The 14gNΔqHAC vector was retained stably in CHO cells by the end of the tenth passage. As a result of observation of images of metaphase chromosomes, 1 or 2 signals were detected per cell.

The Experiments (1) and (2) demonstrated that the 14gNΔqHAC vector would be retained stably in CHO cells under non-selective culture conditions and that a copy number per cell would be maintained.

Example 14

Analysis of hEPO Gene Expression in CHO Cell Comprising hEPO-14gNΔqHAC Vector (1) Construction of hEPO-14gNΔqHAC Vector
(1-1) Introduction of hEPO Gene into 14gNΔqHAC Vector The hEPO gene expression unit was inserted into the 14gNΔqHAC vector constructed in Example 7. The hEPO expression plasmid containing the loxP sequence was prepared, and the Cre recombinase was expressed transiently to insert the gene expression unit into an artificial chromosome by site-directed recombination between the loxP sequences. A recombinant comprising an insert was selected using the acquisition of G418 resistance (i.e., reconstruction of the promoter-fragmented neo-resistant gene expression unit) as an indicator. Using the CHO cells carrying the 14gNΔqHAC vectors (i.e., g5S13-12 cells and g7S9-11 cells) prepared in Example 13, the hEPO gene expression unit was inserted in the same manner as in Example 3 (1-1). G418-resistant colonies developed 2 to 3 weeks thereafter, a total of 169 colonies (77 g5S13-12-derived colonies and 92 g7S9-11-derived colonies) were isolated, the isolated colonies were grown, and the subsequent analysis was performed.

(1-2) PCR Analysis

A recombinant comprising the hEPO gene expression unit inserted therein was selected by inspecting whether or not the hEPO gene expression unit had been inserted into a site of the loxP sequence of the 14gNΔqHAC vector by PCR using the SVpANp 1 and the Neo Rp2 primers, which had been designed on the pLN1-EPO vector and the 14gNΔqHAC vector, so as to sandwich the site of the loxP sequence. Also, it was selected by inspecting amplification of the inserted hEPO gene by PCR using the M13RV and the Neo Rp2 primers of the pBS226 plasmid vector. Primer sequences and PCR conditions were determined in accordance with the method of Kakeda et al. (Kakeda et al., Gene Therapy; 12: 852-856, 2005). In the case of a recombinant comprising an insert, amplification of about 1.0 kbp is deduced with the use of the SVpANp1 and the Neo Rp2 primers and that of about 2.7 kbp is deduced with the use of the M13RV and the Neo Rp2 primers. As a result, amplification as deduced was observed in a total of 69 strains of the G418-resistant CHO hybrid cells obtained in (1-1) above (i.e., 32 g5S13-12-derived strains and 37 g7S9-11-derived strains).

Thus, the above 69 strains of the G418-resistant CHO hybrid strains were found to be recombinants comprising the hEPO gene expression unit inserted into the loxP sequence.

(1-3) Southern Blot Analysis

Figure 55:
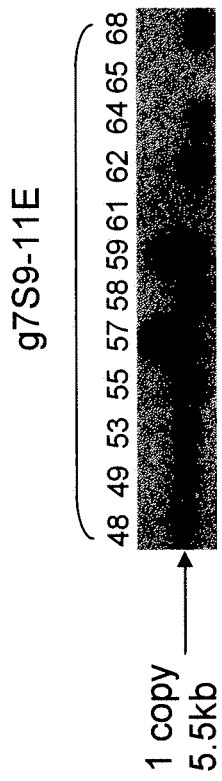
FIG. 55 shows the results of Southern analysis of the CHO hybrid cell into which the hEPO-introduced 14gNΔqHAC vector has been introduced.

Southern blot analysis was carried out in order to inspect whether or not the hEPO-14gNΔqHAC vector properly carries the hEPO expression unit. The method was carried out in accordance with Kakeda et al. (Gene Therapy; 12: 852-856, 2005). Representative results are shown in FIG. 55. The length of the restriction enzyme fragment resulting from digestion with XbaI deduced from the nucleotide sequence is 5.5 kb, including the hEPO expression unit. Bands having sizes as deduced were observed in a total of 32 strains (i.e., 10 g5S13-12-derived strains and 22 g7S9-11-derived strains) from among 65 strains of the candidate G418-resistant CHO hybrid cells obtained in (1-2) (i.e., 24 g5S13-12-derived strains and 41 g7S9-11 strains).

(1-4) FISH Analysis

Figure 56:
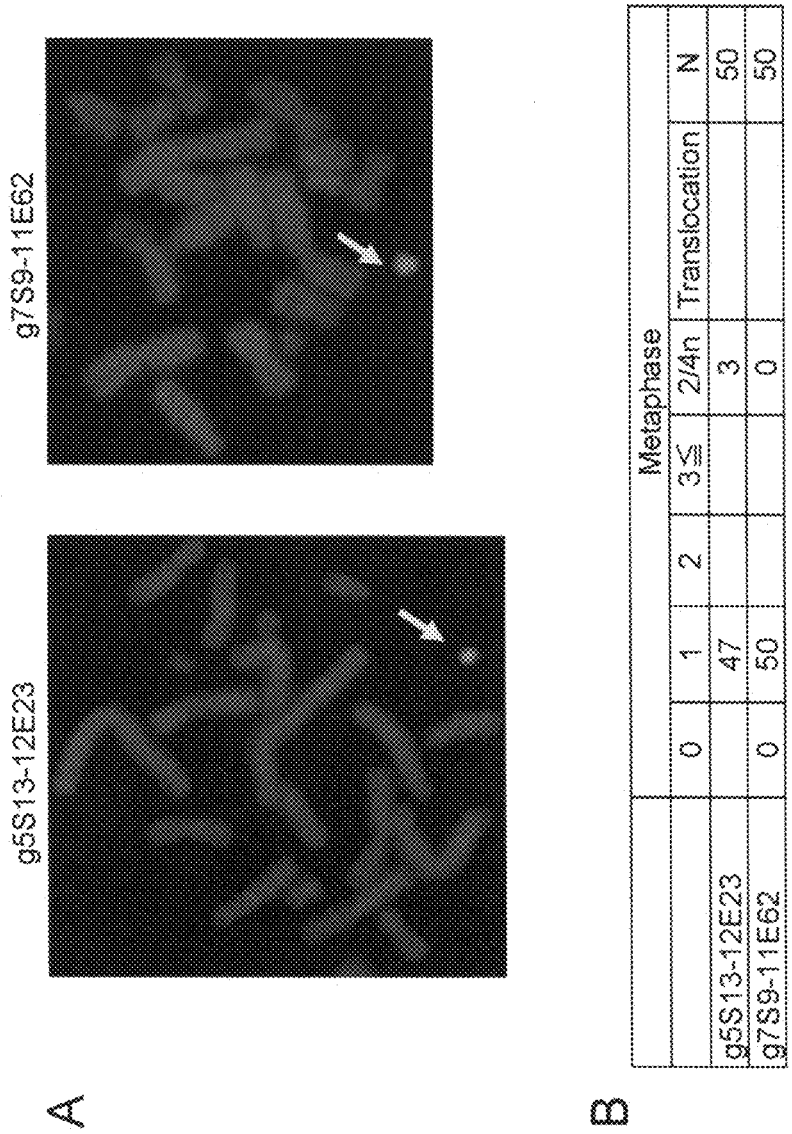
FIG. 56 shows the results of FISH analysis of the CHO hybrid cell that carries the hEPO-14gNΔqHAC vector.

FISH analysis was carried out in accordance with the method described in Matsubara et al. (FISH Experimental Protocol, Shujunsha Co. Ltd., 1994) using human-specific Cot1 (Invitrogen) probes. 17 strains of the G418-resistant CHO hybrid cells obtained in (1-3) were analyzed. As a result, a normal karyotype and a copy of Cot1-stained hEPO-14gNΔqHAC vector were detected in most of the observed mitotic figures of a total of 5 strains (a g5S13-12-derived strain (hereafter referred to as "g5S13-12E23;" 4 g7S9-11-derived strains (hereafter referred to as "g7S9-11E28, 48, 57, and 62"). Representative FISH images and the karyotype of the hEPO-14gNΔqHAC vector are shown in FIG. 56A and in 56B.

The experiments (1-1) to (1-4) demonstrated that the obtained 5 strains of the G418-resistant strains were CHO cells carrying the hEPO-14gNΔqHAC vector and having normal karyotypes.

(2) Expression of hEPO Genes Inserted into 14gNΔqHAC Vector

Expression of hEPO genes was quantified by enzyme-linked immunosorbent assay (ELISA) of hEPO proteins generated in the culture supernatant.

Figure 57:
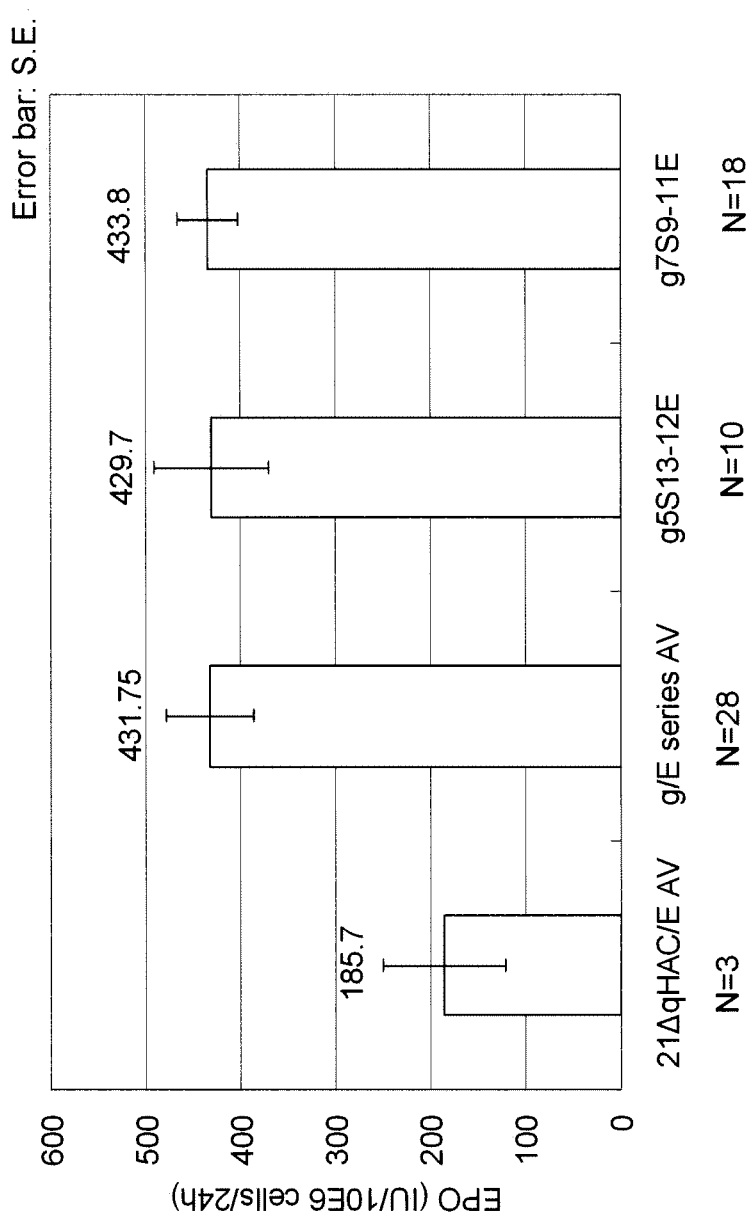
FIG. 57 shows expression of hEPO genes in the CHO hybrid cell that carries the hEPO-14gNΔqHAC vector.

28 strains of the G418-resistant CHO hybrid cells carrying the hEPO-14gNΔqHAC vectors (about $10^5$ cells), which had been isolated and subjected to Southern blot analysis in order to identify the presence and the structure of the hEPO gene expression unit in 1) above, were plated in 12-well tissue culture plastic petri-dishes (Falcon) comprising 2 ml of F12 medium containing 10% FBS and G418 at 0.8 mg/ml. After the cultured cells reached confluence, the medium was exchanged with 2 ml of F12 medium containing 10% FBS, culture was conducted for 7 days, the medium was exchanged with 1 ml of F12 medium containing 10% FBS, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in FIG. 57.

Thus, hEPO expression was observed in all the 28 strains of the G418-resistant CHO hybrid cells carrying the hEPO-14gNΔqHAC vectors.

Example 15

Analysis of Long-Term Stability of hEPO-14gNΔqHAC Vector in CHO Cells (1) Long-Term Subculture Under Non-Selective Culture Conditions In order to confirm stability of the hEPO-14gNΔqHAC vector in CHO cells, long-term subculture was carried out under non-selective culture conditions. 3 strains of the CHO hybrid cells obtained in Example 15 (g5S13-12E23, g7S9-11E28, and 62) were used. A non-selection medium was F12 medium containing 10% FBS, and a selection medium comprised such F12 medium and G418 added thereto at 0.8 mg/ml. The $5.0\times10^5$ CHO cells were plated in a 10-cm dish, the cells that had been cultured to a cell density of about 80 to 90% confluency were counted, the $5.0\times10^5$ cells were plated again in a 10-cm dish, and subculture was continued up to the tenth passage. The number of cells was counted every passage to determine the population doubling level. The CHO cells were recovered after the tenth passage, and hEPO gene expression analysis and FISH analysis were carried out.

(2) hEPO Gene Expression After Long-Term Subculture

Expression of hEPO genes was quantified by enzyme-linked immunosorbent assay (ELISA) of hEPO proteins generated in the culture supernatant.

The 3 strains of the CHO hybrid cells carrying the hEPO-14gNΔqHAC vectors (about $10^5$ cells) that had been subjected to long-term subculture in (1) above were plated in 12-well tissue culture plastic petri-dishes (Falcon) comprising 2 ml of F12 medium containing 10% FBS and G418 at 0.8 mg/ml. After the cultured cells reached confluence, the medium was exchanged with 2 ml of F12 medium containing 10% FBS, culture was conducted for 7 days, the medium was exchanged with 1 ml of F12 medium containing 10% FBS, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in FIG. 58.

Thus, hEPO expression was observed after long-term subculture in all the 3 strains of the CHO hybrid cells carrying the hEPO-14gNΔqHAC vectors.

(3) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate and the average values were determined. The results regarding the above 3 strains are shown in Table 6 and in FIG. 58.

TABLE 6

Stability of hEPO-14gNΔqHAC vector in CHO cell

| | | HAC retention (%) | |
|---|---|---|---|
| HAC | Cell population Number of subculture | Without drug selection | With drug selection |
| g5S13-12E23 | At the initiation of culture | — | 100 |
| | Ten passages | 90 | 100 |
| g7S9-11E28 | At the initiation of culture | — | 100 |
| | Ten passages | 90.4 | 97.9 |
| g7S9-11E62 | At the initiation of culture | — | 100 |
| | Ten passages | 93.5 | 98.8 |

The hEPO-14gNΔqHAC vector was retained stably in CHO cells by the end of the tenth passage. As a result of observation of images of metaphase chromosomes, 1 or 2 signals were detected per cell.

The above experiments (1) to (3) demonstrated that the hEPO-14gNΔqHAC vector would be retained stably in CHO cells after long-term subculture under non-selective culture conditions, that a copy number per cell would be maintained, and that hEPO gene expression would be maintained.

Example 16 hEPO Gene Expression in Human Normal Fibroblasts Comprising hEPO-14gNΔqHAC Vector (1) Preparation of hEPO-14gNΔqHAC Vector-Introduced Human Normal Fibroblasts (1-1) Introduction of hEPO-14gNΔqHAC Vector into Human Normal Fibroblasts, HFL-1, by the Microcell Mediated Chromosome Transfer Method Clones having the high capacity of forming micronucleus (g5S13-12E23, g7S9-11E28, and 62) were selected from among the CHO hybrid strains carrying the hEPO-14gNΔqHAC vectors obtained in Example 15 and used as chromosome donor cells. Human normal fibroblasts, HFL-1 (obtained from the Cell Engineering Division of the RIKEN BioResource Center; Accession No. RCB0521), were used as chromosome recipient cells. Micronuclear cell fusion was carried out in the same manner as in Example 5 (1). After selection culture had been carried out for about 4 weeks, the developed drug-resistant colonies were isolated and then subjected to the subsequent analysis. As a result of 24 micronuclear cell fusion operations, 51 drug-resistant colonies (i.e., 3 g5S13-12E23-derived colonies, 22 g7S9-11E28-derived colonies, and 26 g7S9-11E62-derived colonies) were obtained. Among the above colonies, cells obtained with the use of g5S13-12E23 cells as chromosome donor cells are hereafter referred to as the g23H cells, cells obtained with the use of g7S9-11E28 cells are hereafter referred to as the g28H cells, and cells obtained with the use of g7S9-11E62 cells are hereafter referred to as the g62H cells.

(1-2) PCR Analysis

Whether or not a human chromosome carries the hEPO-14gNΔqHAC vector was inspected by PCR amplification using the SVpANp1 and Neo Rp2 primers of Example 3 (1-2) and the STS marker, i.e., the D2S1334 primer, in accordance with the method of Kakeda et al. (Kakeda et al., Gene Therapy; 12: 852-856, 2005). Also, inclusion of chromosome donor CHO cells was inspected by PCR amplification using the CHO furin gene-specific primers, furin3'subF and furinEx6-28R. The method in accordance with Example 5 (1-2) was employed. When the HFL-1 cells carrying the hEPO-14gNΔqHAC vectors did not include the chromosome donor CHO cells, amplification of about 1.0 kbp is deduced with the use of the SVpANp1 and the Neo Rp2 primers, amplification of about 0.6 kbp is deduced with the use of the D2S1334 primer, and no amplification is deduced with the use of furin3'subF and furinEx6-28R. As a result, amplification as deduced was observed in a total of 6 strains from among 50 strains of the blasticidin-resistant strains obtained in (1-1) above (i.e., g23H1, 2, 3, g28H18, 22, and g62H26).

Thus, the above 6 strains of the blasticidin-resistant strains were found to be HFL-1 cells carrying the hEPO-14gNΔqHAC vectors.

(1-3) Southern Blot Analysis

In order to inspect whether or not the hEPO-14gNΔqHAC vector properly carries the hEPO expression unit, 4 strains (g23H1, 3, g28H18, and g62H26) from among the above 6 strains of the blasticidin-resistant strains were subjected to Southern blot analysis. The method was carried out in accordance with Kakeda et al. (Gene Therapy; 12: 852-856, 2005). Representative results are shown in FIG. 19C. The length of the restriction enzyme fragment resulting from digestion with XbaI deduced from the nucleotide sequence is 5.5 kb, including the hEPO expression unit. As a result, bands having sizes as deduced were observed in 3 strains of the blasticidin-resistant strains carrying the hEPO-14gNΔqHAC vectors obtained in (1-2) above (i.e., g23H1, 3, and g62H26).

(1-4) FISH Analysis

Figure 59:
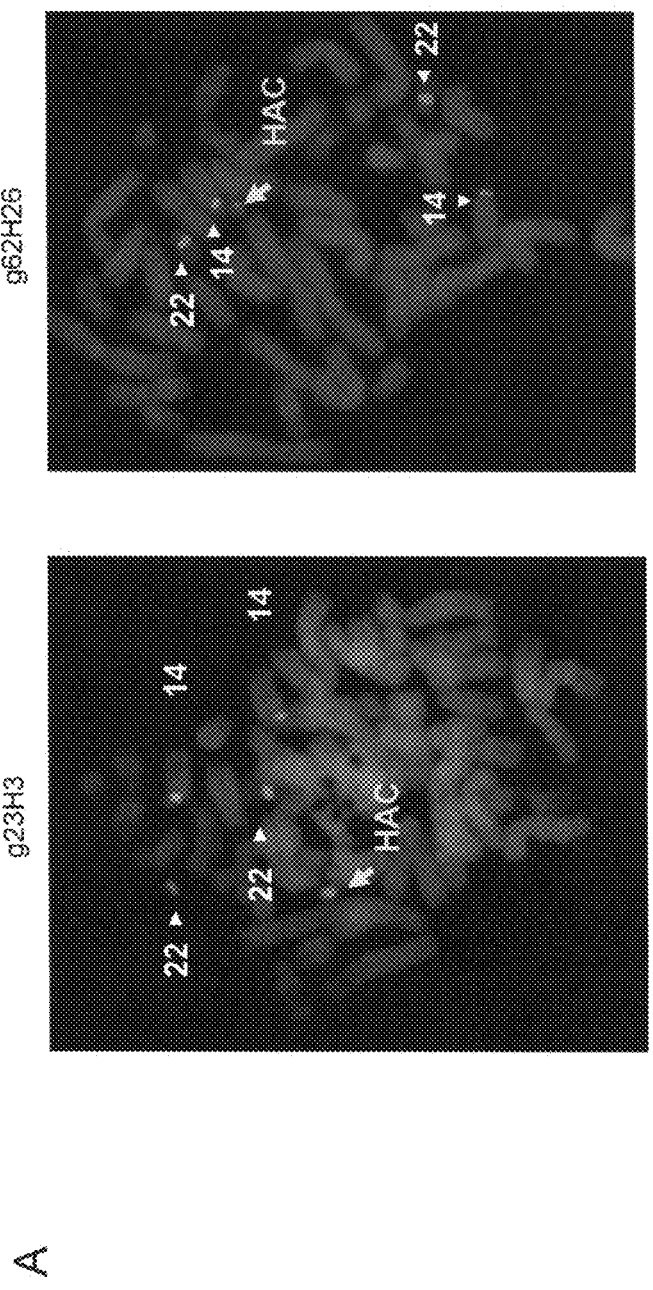
FIG. 59 shows the results of FISH analysis of the human normal fibroblast into which the hEPO-14gNΔqHAC vector has been introduced.

FISH analysis was carried out in accordance with the method described in Matsubara et al. (FISH Experimental Protocol, Shujunsha Co. Ltd., 1994). Human chromosome 14- and human chromosome 22-specific α-satellite DNA probe (Q-biogene, Funakoshi) were used. As a result of analysis of 3 strains of the blasticidin-resistant strains (g23H1, 3, and g62H26), 2 strains (g23H3 and g62H26) were found to be of normal karyotypes, and signals were detected in 4 sites in the centromeric regions of a pair of human chromosome 14 and human chromosome 22 derived from a host cell and in a site derived from a copy of 14gNΔqHAC vector in most of the observed mitotic figures. The results are shown in FIG. 59A and in FIG. 59B.

The experiments (1-1) to (1-4) demonstrated that the obtained 2 strains of the blasticidin-resistant strains were HFL-1 cells carrying the hEPO-14gNΔqHAC vector and having the normal karyotype.

(2) hEPO Gene Expression in hEPO-14gNΔqHAC Vector-Carrying HFL-1 Cells

Expression of hEPO genes was quantified by enzyme-linked immunosorbent assay (ELISA) of hEPO proteins generated in the culture supernatant.

The 3 strains of the blasticidin-resistant HFL-1 strains carrying the hEPO-14gNΔqHAC vectors (about $10^5$ cells), which had been isolated and subjected to Southern blot analysis in order to identify the hEPO gene expression unit in (1) above, were plated in collagen-I-coated 24-well tissue culture plastic petri-dishes (Falcon) comprising 1 ml of selection medium (DMEM containing 20% FBS) containing blasticidin (3 μg/ml). After the cultured cells reached confluence, culture was conducted for 7 days, the medium was exchanged with a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The results are shown in the item "14gN-HAC" of FIG. 21.

Thus, hEPO expression was observed in all the 3 strains of the HFL-1 cells carrying the hEPO-14gNΔqHAC vector and having the normal karyotype.

Example 17

Analysis of Long-Term Stability of hEPO-14gNΔqHAC Vector in Human Normal Fibroblasts (1) Long-Term Subculture Under Non-Selective Culture Conditions In order to confirm stability of the hEPO-14gNΔqHAC vector in human normal fibroblasts, HFL-1, long-term subculture was carried out under non-selective culture conditions. The 3 strains of the HFL-1 cells carrying the hEPO-14gNΔqHAC vectors obtained in Example 16 (g23H1, g23H3, and g62H26) were used. A non-selection medium was DMEM medium containing 20% FBS, and a selection medium comprised such DMEM medium and blasticidin added thereto at 3 μg/ml. The 1 to $3 \times 10^5$ HFL-1 cells carrying the hEPO-14gNΔqHAC vectors were plated in a collagen-I-coated T-25 flask (Falcon), the cells were cultured to a cell density of about 90% confluency, the 1 to $3 \times 10^5$ cells were plated again, and subculture was continued up to the fifth to the tenth passages. The number of cells was counted every passage to determine the population doubling level. The cells were recovered before and after the fifth passage and after the tenth passage, and hEPO gene expression analysis and FISH analysis were carried out.

(2) hEPO Gene Expression After Long-Term Subculture

Expression of hEPO genes was quantified by enzyme-linked immunosorbent assay (ELISA) of hEPO proteins generated in the culture supernatant.

The 2 strains of the hEPO-14gNΔqHAC vector-carrying HFL-1 cells, g23H1 and g62H26, that had been subjected to long-term subculture in (1) above, were plated in amounts of about $10^4$ cells in collagen-I-coated 24-well or 48-well tissue culture plastic petri-dishes (Falcon) comprising 2 ml of DMEM medium containing 20% FBS. After the cultured cells reached confluence, culture was conducted for 7 days, the medium was exchanged with a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in FIG. 43.

Thus, hEPO expression was observed after long-term subculture in all the 2 strains of the hEPO-14gNΔqHAC vector-carrying HFL-1 cells.

The experiment demonstrates that the hEPO-14gNΔqHAC vector would be retained stably in the HFL-1 cells after long-term subculture and that hEPO gene expression would be maintained.

Example 18

Figure 60:
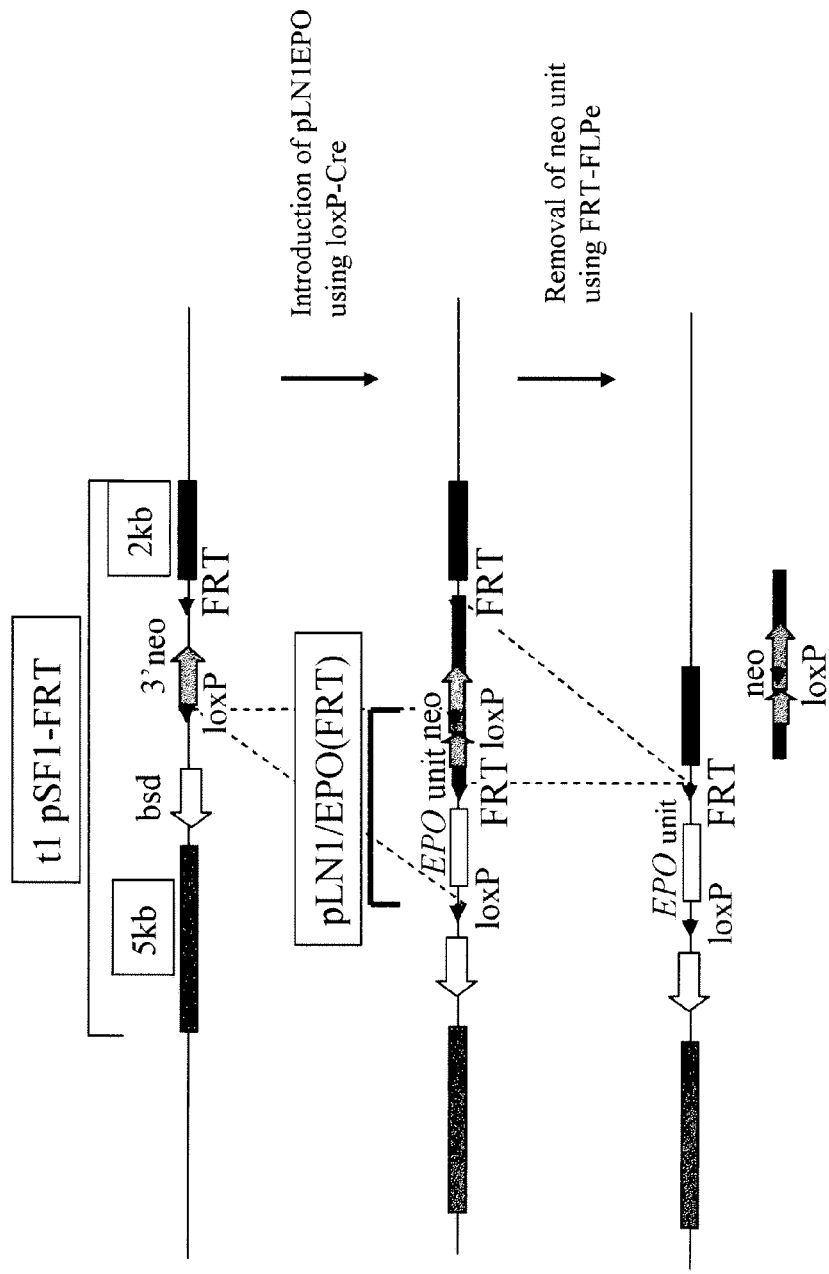
FIG. 60 schematically shows removal of the neo-resistant gene unit using FLP-FRT.

Construction of hEPO-14AΔqΔneo-HAC Vector from which Neo-Resistant Gene Unit has been Removed The FRT sequences are inserted into a site downstream of the hEPO expression unit of the 14AΔq-HAC vector and of the pLN1/EPO plasmid, and the neo-resistant gene expression unit is removed from the hEPO-14AΔq-HAC vector by the FRT/FLPe site-directed recombination system. The outline is shown in FIG. 60.
(1) Introduction of the FRT Sequence into Cloning Site of 14AΔqHAC
(1-1) Construction of t1pSF1-FRT Vector for Introducing the FRT Sequence
In order to insert the FRT sequence into the cloning site of 14AΔqHAC constructed in Example 1, oligo DNAs containing the FRT sequence were synthesized, and the resultants were cloned into the t1pSF vectors constructed in Example 1 (2-1). The sequences of the synthesized oligo DNAs containing the FRT sequences are shown below.

```
FRT linker S:
                                         (SEQ ID NO: 97)
5'-TGGACTAGTCCAGGCCGGCCACGCGTGAAGTTCCTATACTTTCTAGA
GAATAGGAACTTCGGAATAGGAACTTCGCTAGCGGCCGGCCTGGACTAGT
CCA FRT linker AS:
                                         (SEQ ID NO: 98)
5'-TGGACTAGTCCAGGCCGGCCGCTAGCGAAGTTCCTATTCCGAAGTTC
CTATTCTCTAGAAAGTATAGGAACTTCACGCGTGGCCGGCCTGGACTAGT
CCA
```

Figure 61:
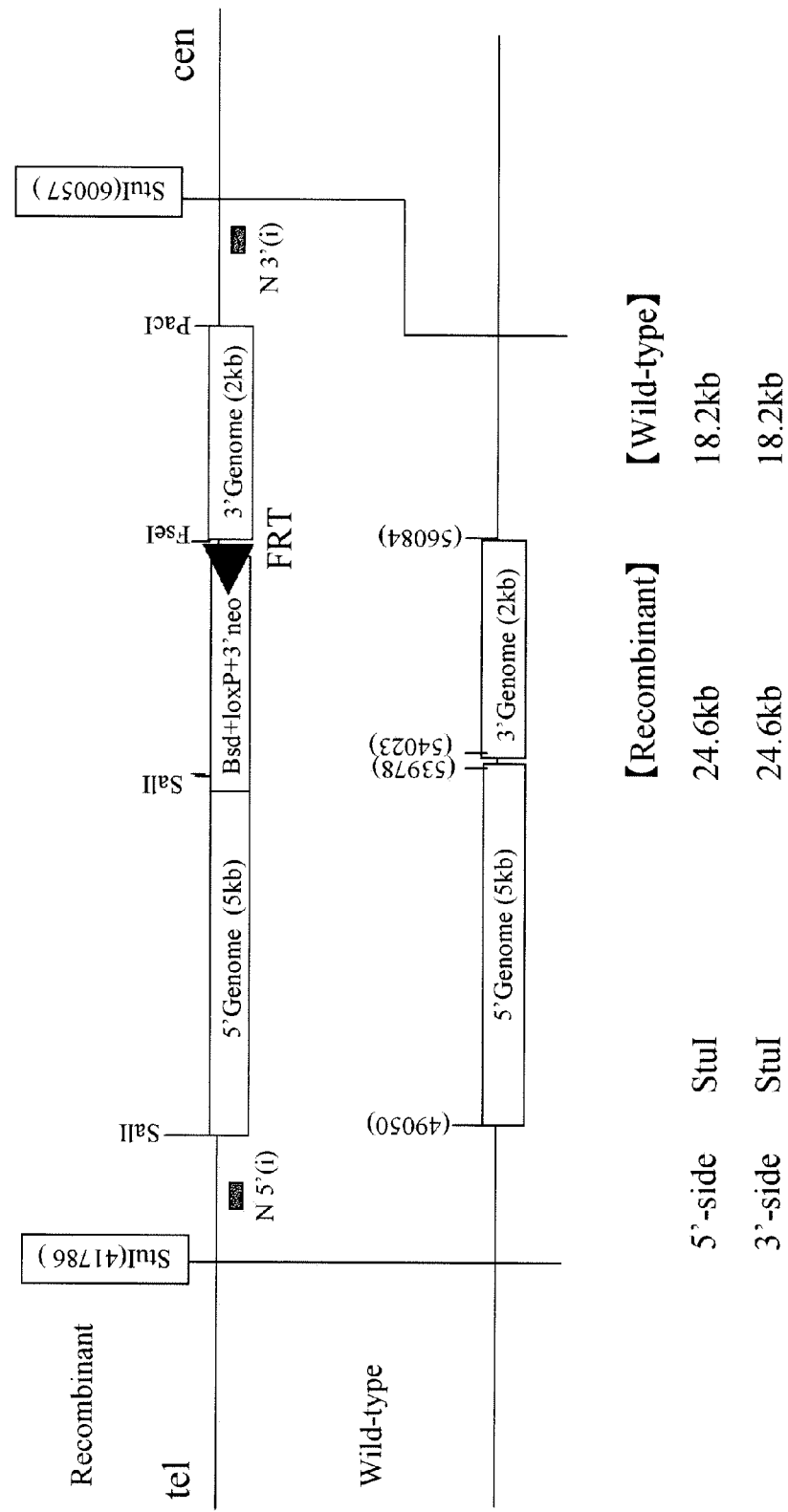
FIG. 61 shows an allele resulting from introduction of the t1pSF1-FRT vector into 14AΔqHAC.

The oligo DNAs containing the FRT sequences were double-stranded by annealing, cleaved with the FseI restriction enzyme, and then cloned into the FseI site of the t1pSF vector. The size of the final t1pSF1-FRT construct is about 13.5 kb. The targeting vector, the target sequence, and a chromosome allele resulting from homologous recombination are shown in FIG. 61.
(1-2) Introduction of t1pSF1-FRT Vector into 14AΔqHAC-Carrying DT40 Cell
The t1pSF1-FRT construct was linearized by digestion with the SrfI restriction enzyme (Roche), and the resultant was introduced into the DT40 hybrid cell with the deleted long-arm distal region while retaining 14AΔqHAC by electroporation. The method in accordance with Example 1 (2-2) was employed. Blasticidin-resistant colonies developed 2 to 3 weeks thereafter. A total of 12 drug-resistant colonies were isolated from 12t97sF through a single transfection operation and, a total of 94 drug-resistant colonies were isolated from 12t134sF through a single transfection operation. These isolated colonies were grown, and the subsequent analysis was performed.
(1-3) PCR Analysis
Genomic DNA of a blasticidin-resistant strain was used as a template, and the presence of two target sequences (i.e., the 5' target sequence and the 3' target sequence) was detected by PCR. The presence of 2 target sequences (indicated as "5'-genome" and "3'-genome" in FIG. 61) was analyzed. The method in accordance with Example 1 (2-3) was employed.

Figure 62:
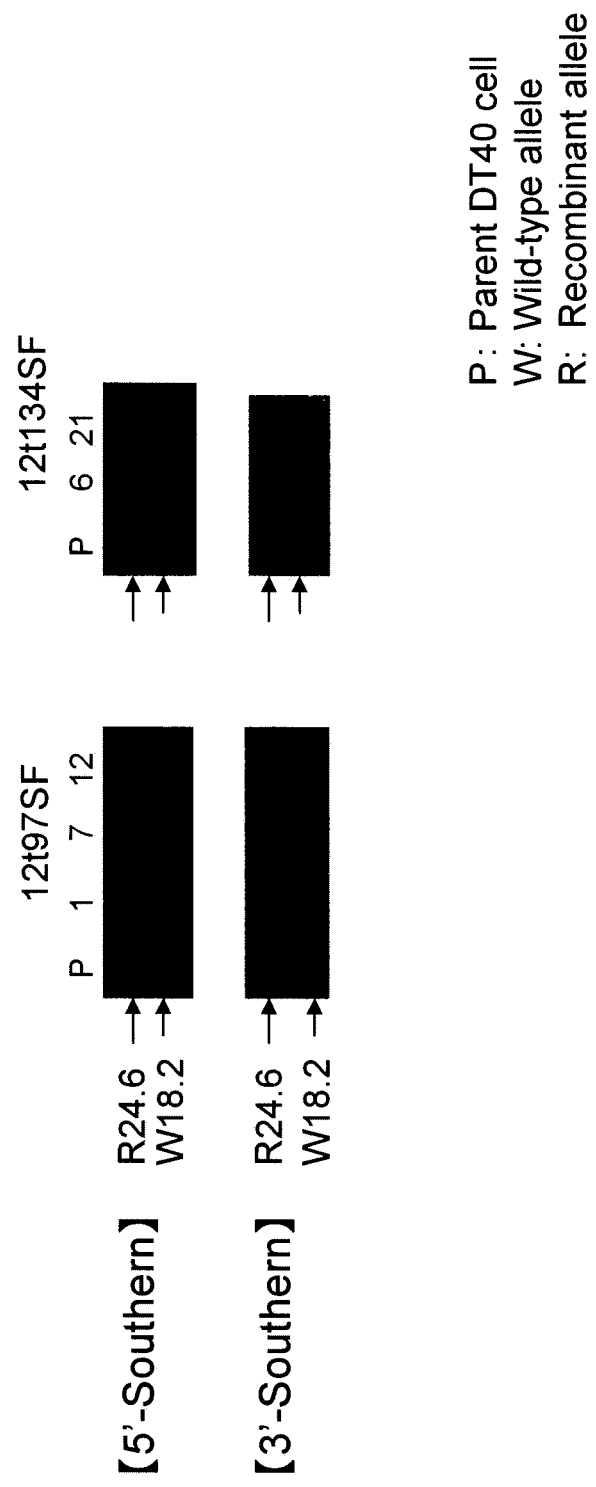
FIG. 62 shows the results of Southern analysis of the DT40 hybrid cell that carries the t1pSF1-FRT vector introduced into 14AΔqHAC.
Figure 63:
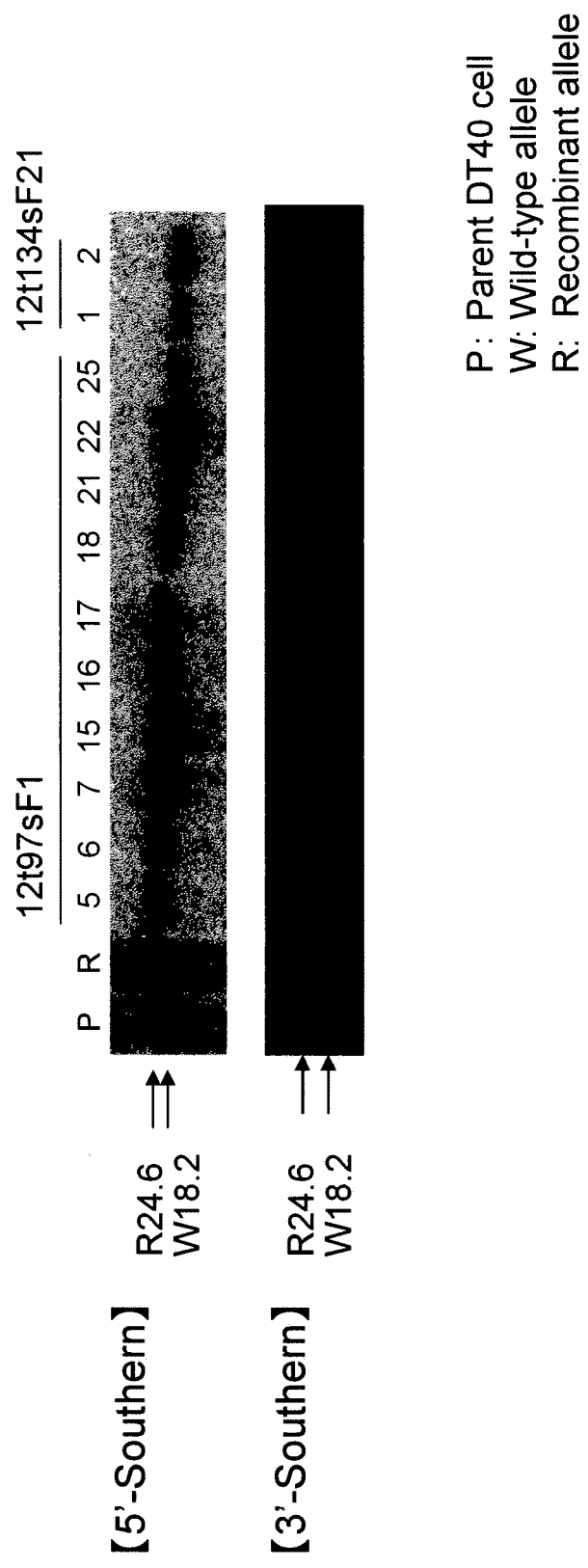
FIG. 63 shows the results of Southern analysis of the CHO hybrid cell into which the 14AΔqF-HAC vector has been introduced.
Figure 64:
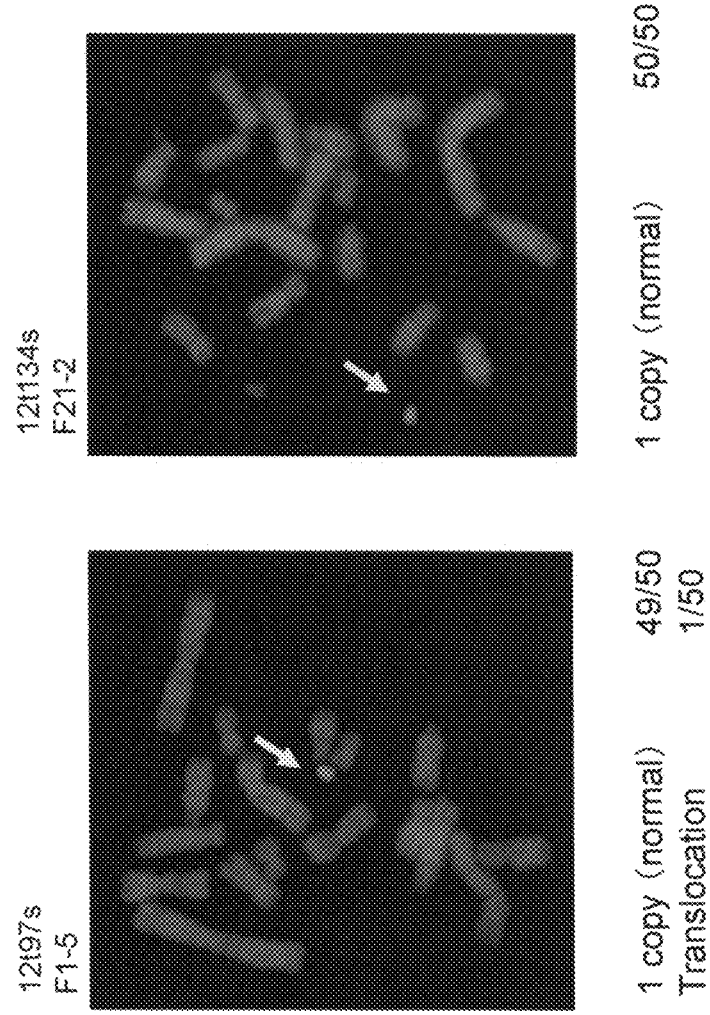
FIG. 64 shows the results of FISH analysis of the CHO hybrid cell into which the 14AΔqF-HAC vector has been introduced.

3 strains from among the obtained 12 strains of the 12t97SF-derived blasticidin-resistant DT40 strains, and 2 strains from among the 94 strains of the 12t134SF-derived blasticidin-resistant DT40 strains were found to produce amplification products having sizes deduced from the nucleotide sequence (5'-genome: about 5 kb; 3'-genome: about 2 kb).
(1-4) Southern Blot Analysis
As a screening method for selecting a homologous recombinant, Southern blot analysis was carried out. The presence of two target sequences for homologous recombination, i.e., the 5'-target sequence and the 3'-target sequence, was analyzed in accordance with the method of Example 1 (2-4). Representative results are shown in FIG. 62. The length of the restriction enzyme fragment deduced from the nucleotide sequence is 24.6 kb in the form of a homologous recombinant, and it is 18.2 kb in the form of a wild-type (i.e., a non-recombinant), as a result of the 5'-genome analysis and the 3'-genome analysis. Two strains of the homologous recombinants (12t97SF1 and 12) were identified from among the 3 12t97SF-derived candidate blasticidin-resistant strains, and two strains of the homologous recombinants (12t134SF6, 21) were identified from among the two strains of the 12t134sF 2 strains.
As a result of the experiments (1-1) to (1-4) above, two strains of the DT40 hybrid cells, 12t97SF, (−1, 12) and two strains of the 12t134SF cells (−6, 21), carrying the 14AΔqF-HAC vectors comprising the FRT sequence inserted in the cloning site by homologous recombination were obtained.
(2) Introduction of 14AΔqF-HAC Vector into CHO Cells
(2-1) Introduction of 14AΔqF-HAC Vector into CHO Cells by the Microcell Mediated Chromosome Transfer Method
The 14AΔqF-HAC vector-carrying DT40 hybrid cells (12t97sF1, 12t97sF12, and 12t134sF21) from which the long-arm distal region had been deleted and into which the FRT sequence had been inserted at the cloning site obtained in Example 18 (1) were used as chromosome donor cells. Chinese hamster-derived CHO-K1 cells (Accession No. JCRB9018) were used as chromosome recipient cells. The 14AΔqF-HAC vector was introduced into CHO cells by the microcell mediated chromosome transfer method in accordance with Example 1 (3).
After selection culture had been carried out for about 2 weeks, developed blasticidin-resistant colonies were isolated, and the subsequent analysis was performed. As a results of micronuclear cell fusion (3 strains×two times), a total of 36 blasticidin-resistant CHO strains (i.e., 25 12t97sF1-derived strains, 3 12t97sF12-derived strains, and 8 12t134sF21-derived strains) were obtained.
(2-2) PCR Analysis
In order to confirm that the cell of interest carries the 14AΔqF-HAC vector and that it does not include DT40, genomic DNA of the blasticidin-resistant CHO strain was used as a template to detect the presence of NEK2P(+), IGHV3(−), and Ggbeta-actin(−) by PCR. The methods in accordance with Example 1 (1-3) and Example 6 (5-2) were employed. The detection patterns deduced are NEK2P(+), IGHV3(−), and Ggbeta-actin (−). From among the 36 strains of the blasticidin-resistant CHO strains, 33 strains (i.e., 23 12t97sF1-derived strains, 3 12t97sF12-derived strains, and 7 12t134sF21-derived strains) were found to produce amplification products as deduced from the nucleotide sequences.
(2-3) Southern Blot Analysis
In order to identify the structure of the introduced 14AΔqF-HAC vector, Southern blot analysis was carried out in the same manner as in Example 1 (2-4). Representative results are shown in FIG. 63. The length of the restriction enzyme fragment deduced from the nucleotide sequence is 24.6 kb in the form of a homologous recombinant, and it is 18.2 kb in the form of a wild-type (i.e., a non-recombinant), as a result of the 5'-genome analysis and the 3'-genome analysis. A total of 26 strains of the homologous recombinants (i.e., 20 12t97sF1-derived strains, 2 12t97sF12-derived strains, and 4 12t134sF21-derived strains) were identified from among the 27 strains of the candidate blasticidin-resistant CHO strains.
(2-4) FISH Analysis FISH analysis was carried out in accordance with the method described in Matsubara et al. (FISH Experimental Protocol, Shujunsha Co. Ltd., 1994) using human-specific Cot1 (Invitrogen) probes. As a result of analysis of 14 strains of the blasticidin-resistant CHO strains (i.e., 11 12t97sF1-derived strains, a 12t97sF12-derived strain, and 2 12t134sF21-derived strains), a total of 6 strains (i.e., 5 12t97sF1-derived strains, 0 12t97sF12-derived strains, and a 12t134sF21-derived strain) were found to be of normal karyotypes, and a copy of Cot1-stained 14AΔqF-HAC vector were detected in most of the observed mitotic figures. Representative results are shown in FIG. 64.

The experiments (2-1) to (2-4) demonstrated that the obtained 6 strains of the blasticidin-resistant CHO strains (i.e., 12t97sF1-2, 5, 8, 17, 21, and 12t134sF21-2) carry the 14AΔqF-HAC vectors for removing the Neo-resistant gene unit. Among them, 12t97sF1-5 and 12t134sF21-2 (hereafter referred to as "F1-5" and "F21-2") were subjected to the experiment described below.
(3) Construction of hEPO-14AΔqF-HAC Vector
(3-1) Introduction of the FRT Sequence into hEPO Expression Plasmid, pLN1-EPO The synthesized oligo DNA comprising the FRT sequence used in Example 18 (1-1) is inserted into the hEPO expression plasmid, pLN1-EPO (Kakeda et al., Gene Therapy; 12: 852-856, 2005).

Figure 65:
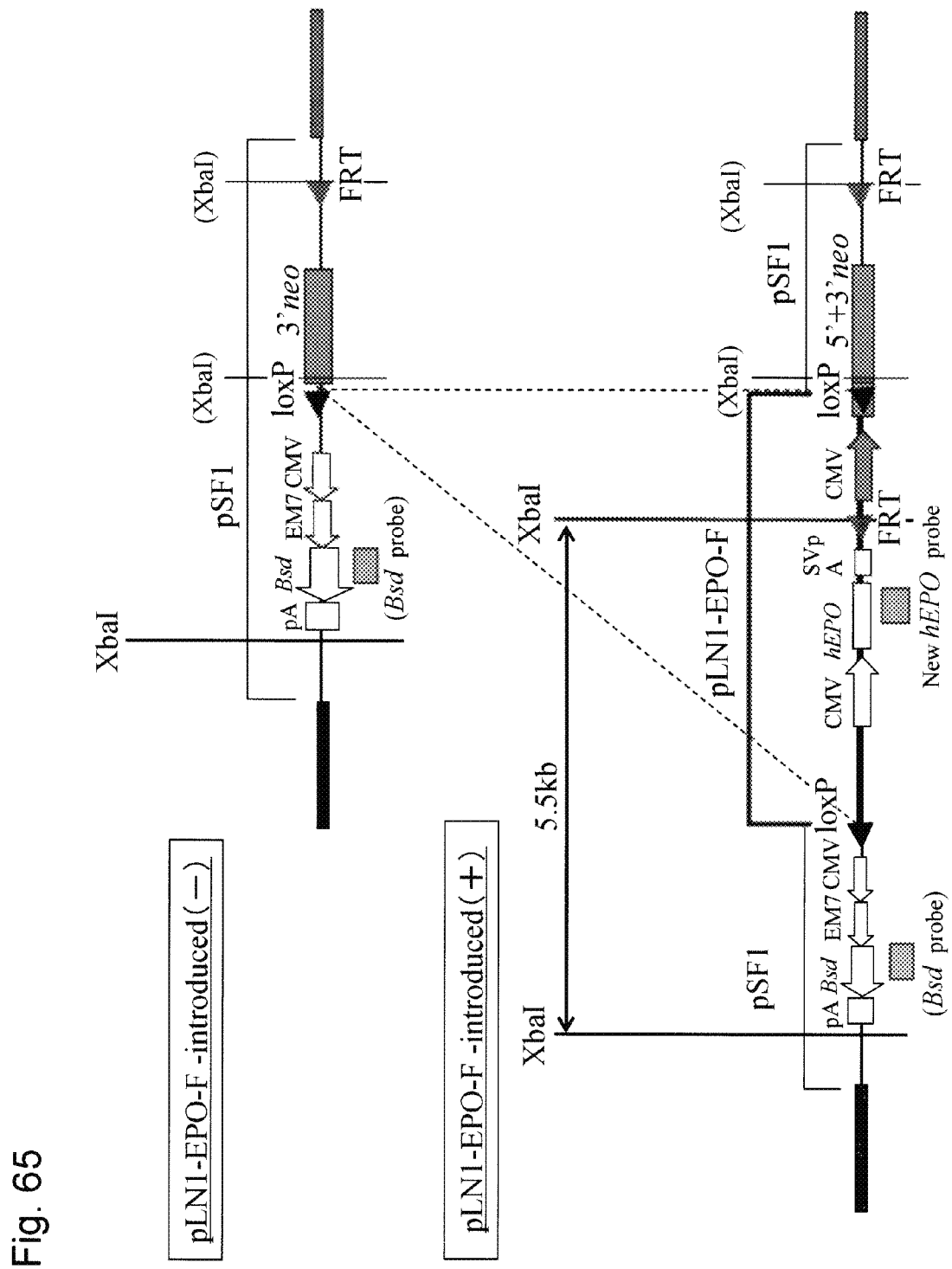
FIG. 65 shows an allele of the 14AΔqF-HAC vector resulting from introduction of the hEPO gene.
Figure 66:
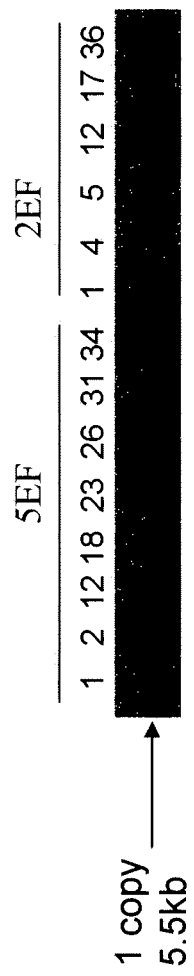
FIG. 66 shows the results of Southern analysis of the CHO hybrid cell into which the hEPO gene-introduced 14AΔqF-HAC vector has been introduced.
Figure 67:
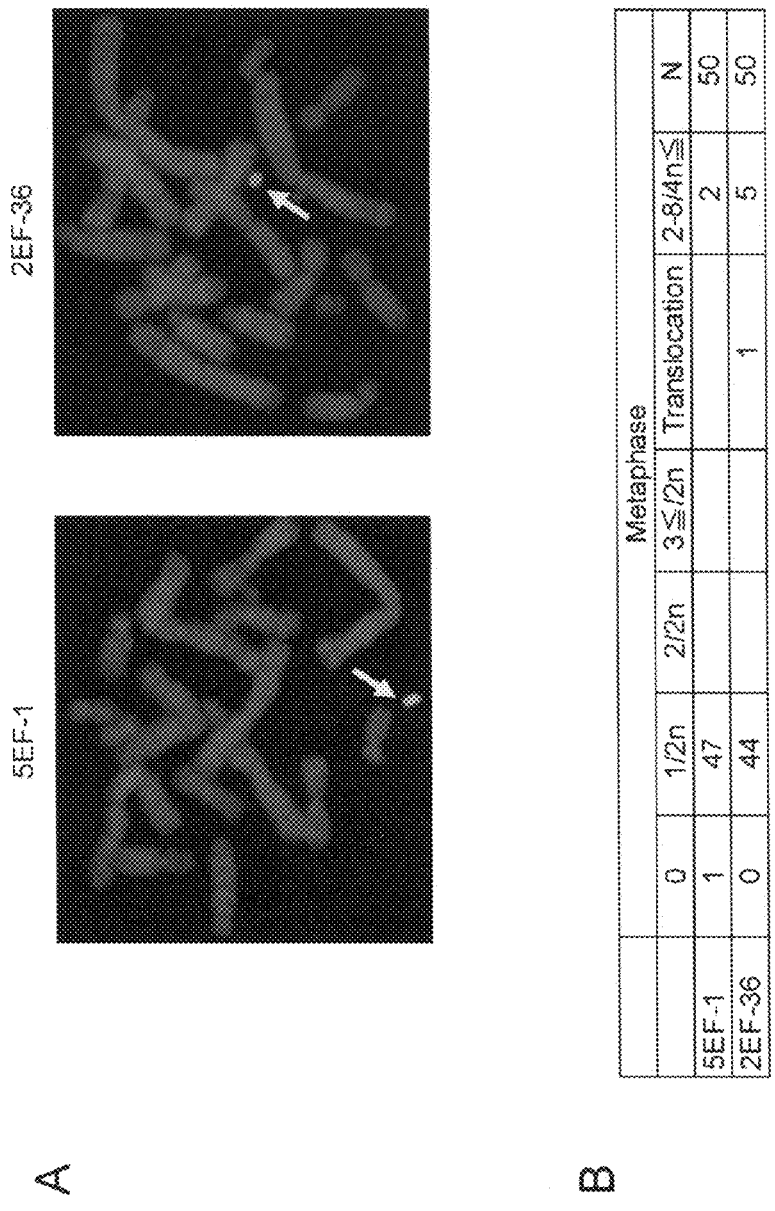
FIG. 67 shows the results of FISH analysis of the CHO hybrid cell that carries the hEPO-14AΔqF-HAC vector.

The oligo DNAs comprising the FRT sequence, i.e., FRT linker S and FRT linker AS, were double-stranded by annealing, digested with the SpeI restriction enzyme, and then cloned into the XbaI site, where the CMV promoter for driving the neo-resistant gene was removed by digestion with the XbaI restriction enzyme from the pLN1EPO vector. Further, the resultant was introduced again into the NheI site in the linker into which the CMV promoter for driving the neo-resistant gene had been introduced. The size of the final pLN1-EPOF construct is about 4.9 kb.
(3-2) Introduction of hEPO Gene into 14AΔqF-HAC Vector The hEPO gene expression unit comprising the FRT sequence is inserted into the 14AΔqF-HAC vector. The hEPO expression plasmid, pLN1-EPOF, comprising the loxP and the FRT sequences is prepared, and the Cre recombinase is expressed transiently to insert the gene expression unit into an artificial chromosome by site-directed recombination between the loxP sequences. A recombinant comprising an insert was selected using the acquisition of G418 resistance (i.e., reconstruction of the promoter-fragmented neo-resistant gene expression unit) as an indicator. The outline is shown in FIG. 65. With the use of the 14AΔqF-HAC vector-carrying CHO cells (F1-5 and F21-2) prepared in Example 18 (2), the method in accordance with Example 3 (1-1) was employed. G418-resistant colonies developed 2 to 3 weeks thereafter, a total of 92 colonies (45 F1-5-derived colonies and 47 F21-2-derived colonies; hereafter referred to as "5EF cells" and "2EF cells," respectively) were isolated, the isolated colonies were grown, and the subsequent analysis was performed.
(3-3) PCR Analysis A recombinant comprising the hEPO gene expression unit inserted therein was selected by inspecting whether or not the hEPO gene expression unit had been inserted into a site of the loxP sequence of the 14AΔqFHAC vector by PCR using the SVpANp1 and the Neo Rp2 primers, which had been designed on the pLN1-EPOF vector and the 14AΔqFHAC vector, so as to sandwich the site of the loxP sequence or amplifying the inserted hEPO gene by PCR using the M13RV and the Neo Rp2 primers on the pBS226 plasmid vector. Primer sequences and PCR conditions were determined in accordance with the method of Kakeda et al. (Kakeda et al., Gene Therapy; 12: 852-856, 2005). In the case of a recombinant comprising an insert, amplification of about 1.0 kbp is deduced with the use of the SVpANp1 and the Neo Rp2 primers and that of about 2.7 kbp is deduced with the use of the M13RV and the Neo Rp2 primers. As a result, amplification as deduced was observed in a total of 51 strains (i.e., 23 strains of the 5EF cells and 28 strains of the 2EF cells) from among the G418-resistant CHO hybrid cells obtained in (3-2) above. Thus, a total of 51 strains of the G418-resistant CHO hybrid cells above were found to be recombinants comprising the hEPO gene expression unit inserted into the loxP sequence.
(3-4) Southern Blot Analysis Southern blot analysis was carried out in order to inspect whether or not the hEPO-14AΔqF-HAC vector properly carries the hEPO expression unit. The method was carried out in accordance with Kakeda et al. (Gene Therapy; 12: 852-856, 2005). Representative results are shown in FIG. 66. The length of the restriction enzyme fragment resulting from digestion with XbaI deduced from the nucleotide sequence is 5.5 kb, including the hEPO expression unit. Bands having sizes as deduced were observed in a total of 23 strains (i.e., 8 strains of the 5EF cells and 15 strains of the 2EF cells) from among 65 strains of the candidate G418-resistant CHO hybrid cells obtained in (3-2) above.
(3-5) FISH Analysis FISH analysis was carried out in accordance with the method described in Matsubara et al. (FISH Experimental Protocol, Shujunsha Co. Ltd., 1994) using human-specific Cot1 (Invitrogen) probes. 16 strains from among the G418-resistant CHO hybrid cells obtained in (3-4) above (i.e., 5 strains of F1-5 cells and 11 strains of F21-2 cells) were analyzed. As a result, a normal karyotype and a copy of Cot1-stained hEPO-14AΔqHAC vector were detected in most of the observed mitotic figures of a total of 2 strains (5EF-1 and 2EF-36). Representative results are shown in FIG. 67A and FIG. 67B.

The experiments (3-1) to (3-5) demonstrated that the obtained 2 strains of the G418-resistant strains are CHO cells carrying the hEPO-14AΔqF-HAC vector and having the normal karyotype.
(4) hEPO Gene Expression in CHO Cells using hEPO-14AΔqF-HAC Vector Expression of hEPO genes was quantified by enzyme-linked immunosorbent assay (ELISA) of hEPO proteins generated in the culture supernatant.

The 2 strains of the hEPO-14AΔqFHAC vector-carrying G418-resistant CHO hybrid cells, 5EF-1 and 2EF-36 (about $10^5$ cells), which had been isolated in 1) above, were plated in 12-well tissue culture plastic petri-dishes (Falcon) comprising 2 ml of F12 medium containing 10% FBS and G418 at 0.8 mg/ml. After the cultured cells reached confluence, the medium was exchanged with 2 ml of F12 medium containing 10% FBS, culture was conducted for 2 days, the medium was exchanged with 1 ml of F12 medium containing 10% FBS, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in Table 7.

TABLE 7

| Clone No. | hEPO concentration in CM (IU/10E6 cells/24 h) |
|---|---|
| 5EF-1 | 539 |
| 2EF-36 | 316 |

Thus, hEPO expression was observed in all the 4 strains of the G418-resistant CHO hybrid cells carrying the hEPO-14AΔqFHAC vectors.

(5) Removal of Neo-Resistant Gene Unit from hEPO-14AΔqF-HAC Vector (5-1) Construction of FLPe Expression Vector, pOG44FLPe The FLP gene sequence of the pOG44 vector (Invitrogen) was modified by introducing mutations into 4 sites, i.e., L33S, L70F, Y108N, and S294P, of the FLPe gene sequence (Buchholz, F. et al., Nature Biotech. (USA), vol. 16, pp. 657-662) by PCR. FLPwt (D4G, L70F) was first prepared from FLP (D4, L70), and FLPe (D4•F70/L33S, Y108N, S294P) was then prepared using both FLP (D4, L70) and FLPwt (G4, F70). PCR was carried out using LA Taq polymerase (Takara Shuzo Co., Ltd.), and the reactions were carried out at 94° C. for 1 minute, followed by 35 cycles of denaturation at 98° C. for 30 seconds, annealing at 60° C. for 30 seconds, and extension at 72° C. for 30 seconds.

In order to perform amino acid substitution of D4G and L70F, nucleotide-substitution of A14G and G210C was carried out using the pOG44 vector as a template. Sequences of oligonucleotide primers used for PCR are shown below.

```
FLPFw(A14G)Ps:
                                         (SEQ ID NO: 99)
5'-AACTGCAGCCCAAGCTTCCACCATGCCACAATTTGG

FLPRv(G210C)Ps:
                                        (SEQ ID NO: 100)
5'-AACTGCAGTGACTTGTTGACAATATCGAAACTCAGC
```

The FLP gene sequence was cleaved from the pOG44 vector by digestion with PstI and then replaced with the PCR-amplified fragment digested with PstI (pOG44-FLPwt (D4G, L70F)).

Subsequently, in order to perform amino acid substitution of S294P, nucleotide-substitution of T880C was carried out by PCR using the pOG44 vector as a template. Sequences of oligonucleotide primers used are shown below.

```
FLPFw(T880C)Hd:
5'-CAAAGCTTTGAAGAAAAATGCGCCTTATCC   (SEQ ID NO: 101)

FLPRv Ns:
5'-GATCATATGCATAGTACCGAGAAACTAGTG   (SEQ ID NO: 102)
```

The EcoRV-NsiI region was removed from the pOG44 vector, a DNA fragment (EcoRV-HindIII: 0.5 kb) derived from the pOG44 vector and the above PCR-amplified fragment digested with HindIII and NsiI were cloned (pOG44-FLPe (D4•S294P).

Further, in order to perform amino acid substitution of L33S and Y108N, nucleotide-substitution of T109C and T322A was carried out by PCR. Sequences of oligonucleotide primers used are shown below.

```
FLPFw(T109C):
                                        (SEQ ID NO: 103)
5'-GACCTTCAGGTGAGAAAATAGCATCATGTG

FLPRv(T322A)Ev:
                                        (SEQ ID NO: 104)
5'-GTGATATCAGATTGATGTTTTTGTCCATTG

FLPFw(33-81)Bs36:
                                        (SEQ ID NO: 105)
5'-ACCTAAGGTGCTTGTTCGTCAGTTTGTGGAAAGGTTTGAAAGACCTT
CA
```

Nucleotide substitution was carried out by PCR using the pOG44-FLPwt (D4G, L70F) vector as a template and the primer, FLPFw(T109C)-FLPRv(T322A)Ev. Further, the resulting PCR product was used as a template, and the primer, FLPFw(33-81)Bs36-FLPRv(T322A)Ev, was used to add the restriction enzyme site, Bsu36I site, to the 5' end. The amplified DNA fragment was digested with the restriction enzymes, Bsu36I and EcoRV, and the resultant was replaced with the Bsu36I-EcoRV region of the pOG44-FLPe (D4•S294P) vector (pOG44-FLPe(D4•F70/L33S, Y108N, S294P). Thus, pOG44FLPe was obtained.

(5-2) Removal of Neo-Resistant Gene Unit using FLPe

The FLPe recombinases were expressed transiently in the CHO cells carrying the hEPO-14AΔqF-HAC vector prepared in Example 23 (3) to cleave and remove the Neo-resistant gene unit from the artificial chromosome by site-directed recombination between the FRT sequences. The recombinants comprising a insert were selected using deletion of the Neo-resistant gene unit as an indicator.

The CHO cells carrying the hEPO-14AΔqF-HAC vector prepared in Example 18 (3) (i.e., 5EF-1 and 21EF-36) were treated with trypsin, and the 5×10⁶ cells were suspended in 0.8 ml of the Hank's balanced salt solution (HBSS). In the presence of 20 to 100 μg of the FLPe enzyme expression vector, pOG44FLPe, electroporation was carried out using the Gene Pulser II (Bio-Rad). A voltage of 450 V was applied to a condenser having a capacity of 500 μF and then discharged using an electroporation cell having 4 mm of an interelectrode distance. The electroporated cells were plated in eight 96-well tissue culture plastic petri-dishes (Falcon) comprising F12 medium (Invitrogen) containing 10% FBS (i.e., 4 dishes of 1 cell/well; and 4 dishes of 0.1 cells/well). Blasticidin-resistant colonies developed 2 to 3 weeks thereafter, a total of 149 colonies (82 5EF-1-derived colonies and 67 21EF-36-derived colonies) were isolated, and the subsequent analysis was performed.

(5-3) PCR Analysis

Figure 68:
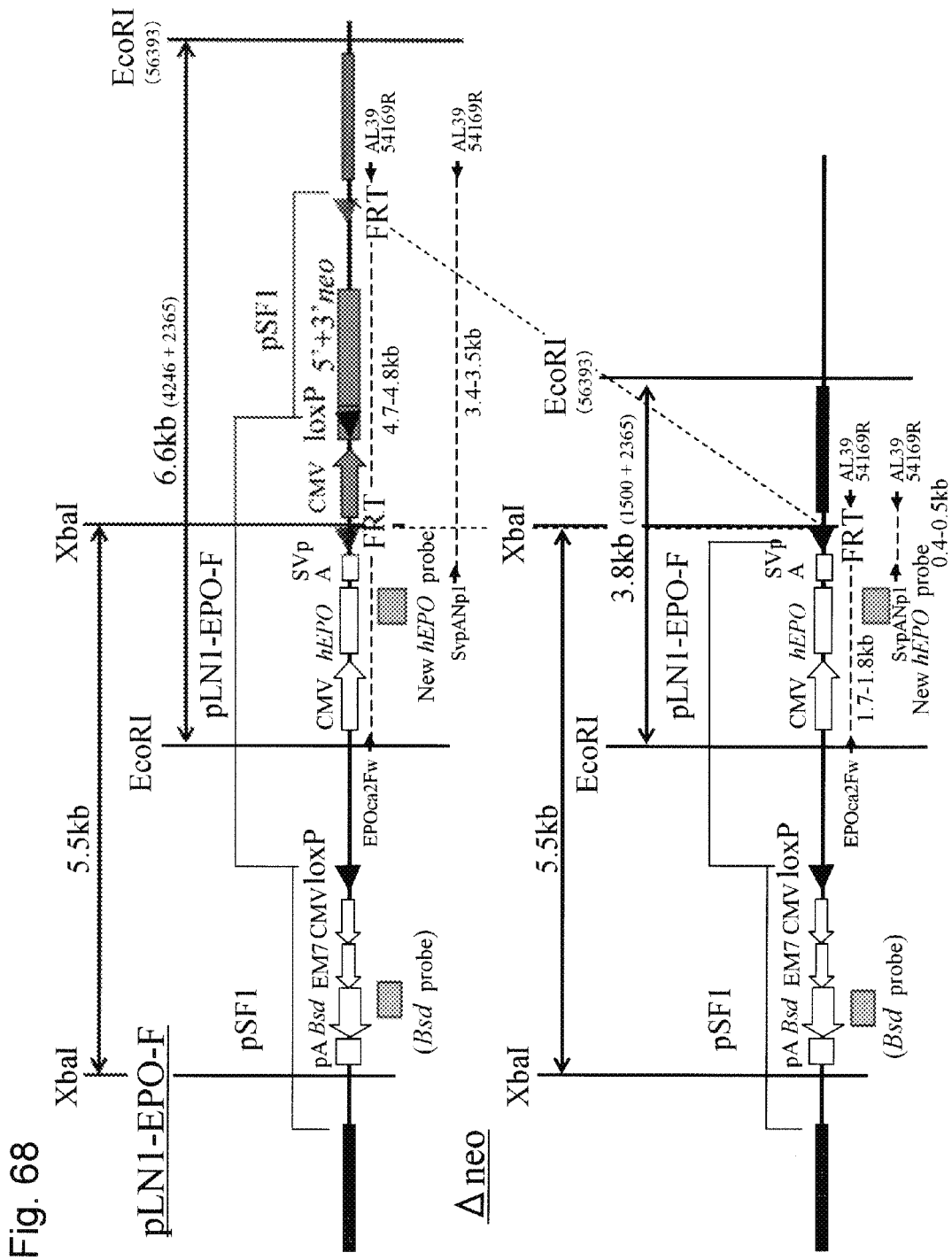
FIG. 68 shows an allele of the 14AΔqF-HAC vector resulting from removal of the neo-resistant gene unit.

In order to inspect whether or not the Neo-resistant gene unit had been removed from the hEPO-14AΔqF-HAC vector, primers were designed on the pLN1-EPOF vector and on the homologous recombinant region (FIG. 68), and PCR was carried out. Sequences of oligonucleotide primers are shown below.

```
SV40 polyA Np1(SvpANp1):
                                        (SEQ ID NO: 106)
5'-CGGGATCCCTCGAGCGAGACATGATAAGATACATTGATG AL39 54169R:
                                        (SEQ ID NO: 107)
5'-GATTTTCCACATACGTTCCCAAGCCACTCC
```

LA Taq polymerase (Takara Shuzo Co., Ltd.) was used, and the reactions were carried out at 94° C. for 1 minute, followed by 3 cycles of denaturation at 98° C. for 5 seconds followed by annealing/extension at 72° C. for 4.5 minutes, 2 cycles of denaturation at 98° C. for 5 seconds followed by annealing/extension at 70° C. for 4.5 minutes, 25 cycles of denaturation at 98° C. for 5 seconds followed by annealing/extension at 68° C. for 4.5 minutes, and extension at 72° C. for 10 minutes. When the Neo-resistant gene unit has been removed, amplification of about 0.4 kbp is deduced with the use of primers, SVpANp1 and AL39 54169F. As a result, amplification as deduced was observed in a total of 66 strains (34 5EF-1-derived strains and 32 21EF-36-derived strains) from among the Bsd-resistant CHO hybrid cells obtained in (5-2) above. This demonstrates that the Neo-resistant gene units had been removed in a total of 66 strains of the Bsd-resistant CHO hybrid cells above.

(5-4) Southern Blot Analysis

Figure 69:
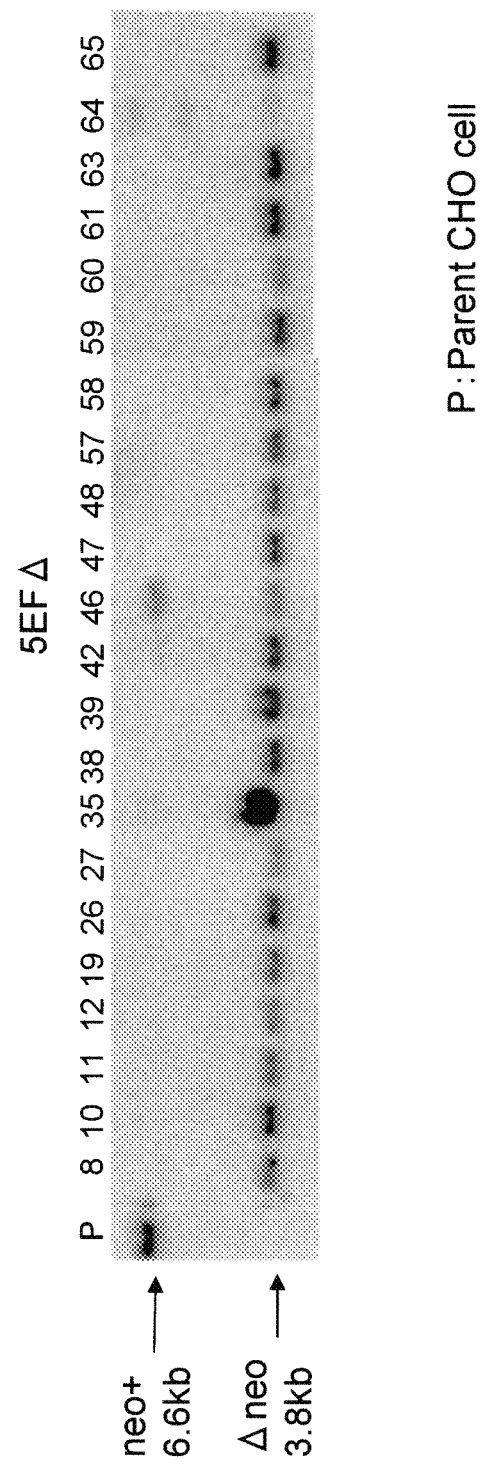
FIG. 69 shows the results of Southern analysis of the CHO hybrid cell that carries the hEPO-14AΔqΔneo-HAC vector.

Southern blot analysis was carried out in order to inspect whether or not the Neo-resistant gene unit had been removed from the hEPO-14AΔqF-HAC vector. The method was carried out in accordance with Kakeda et al. (Gene Therapy; 12: 852-856, 2005). Representative results are shown in FIG. 69. The length of the restriction enzyme fragment resulting from digestion with EcoRI deduced from the nucleotide sequence is 3.8 kb, when the fragment consists of the hEPO expression unit, while the Neo-resistant gene unit had been removed therefrom, and such length is 6.6 kb, when the fragment comprises both the Neo-resistant gene unit and the hEPO expression unit. Bands having sizes as deduced were detected in a total of 36 strains (18 5EF-1-derived strains and 18 2EF-2-derived strains) from among the 66 strains of the candidate CHO hybrid cells (34 5EF-1-derived strains and 32 21EF-2-derived strains) obtained in Example 23 (5-2). Thus, removal of the Neo-resistant gene unit was observed in the above 36 strains of the CHO hybrid cells. The hEPO-14AΔqF-HAC vector from which the Neo-resistant gene unit had been removed is hereafter referred to as the "hEPO-14AΔqneo-HAC vector."

(5-5) FISH Analysis

Figure 70:
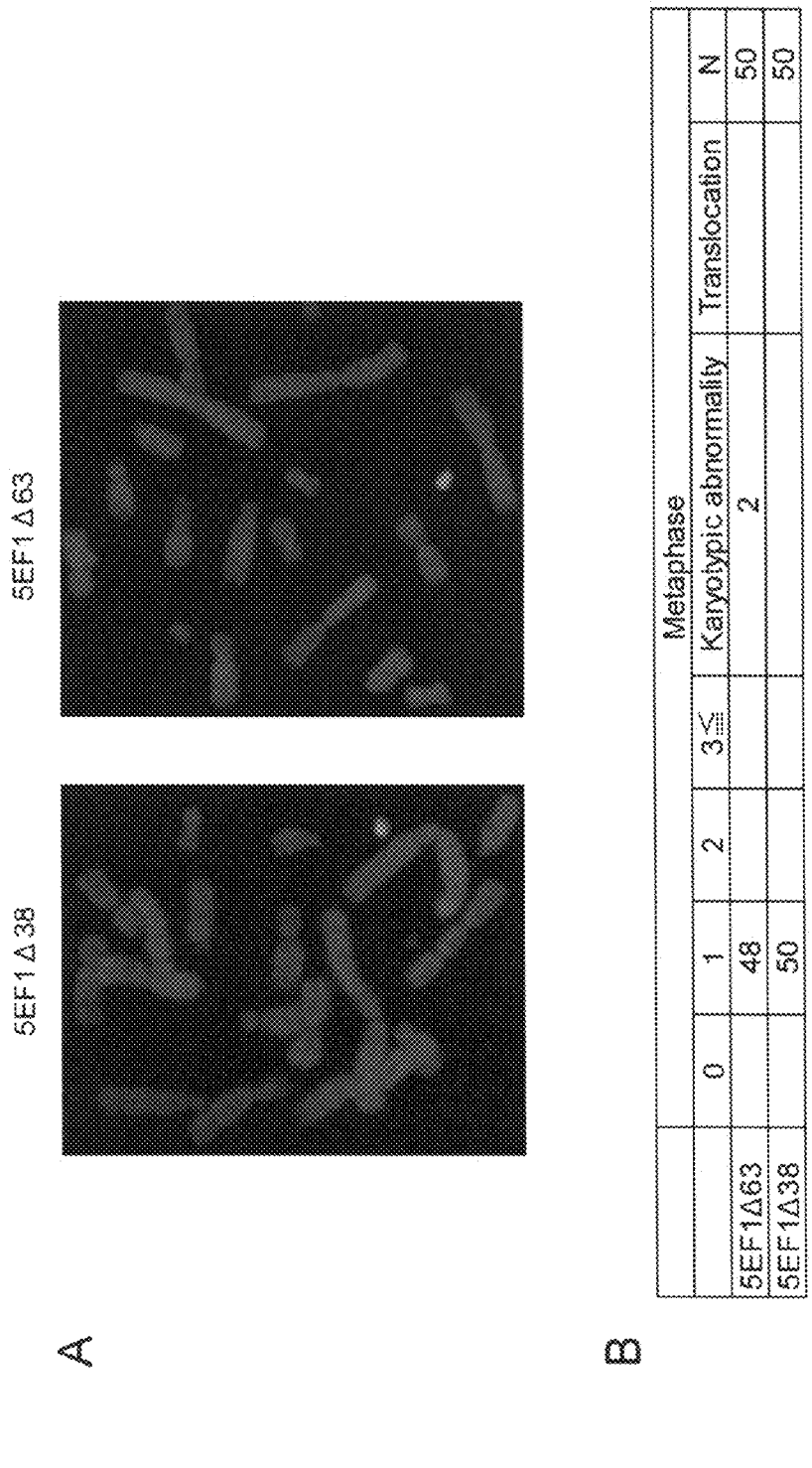
FIG. 70 shows the results of FISH analysis of the CHO hybrid cell that carries the hEPO-14AΔqΔneo-HAC vector.

FISH analysis was carried out in accordance with the method described in Matsubara et al. (FISH Experimental Protocol, Shujunsha Co. Ltd., 1994) using human-specific Cot1 (Invitrogen) probes. The 8 5EF-1-derived strains from among the candidate CHO hybrid cells obtained in (5-3) above were analyzed. As a result, a normal karyotype and a copy of Cot1-stained hEPO-14AΔqneo-HAC vector were detected in most of the observed mitotic figures of a total of 2 strains (5EF1Δ38 and 5EF1Δ63). Representative FISH images and the karyotype of the hEPO-14AΔqΔneo-HAC vector are shown in FIG. 70A and FIG. 70B.

The experiments (5-1) to (5-5) demonstrated that the 2 strains of the obtained CHO hybrid cells carry the hEPO-14AΔqΔneo-HAC vector and have the normal karyotypes.

(6) hEPO Gene Expression in CHO Cells Using hEPO-14AΔqΔNeo-HAC Vector from which Neo-Resistant Gene Unit has been Removed Expression of hEPO genes was quantified by enzyme-linked immunosorbent assay (ELISA) of hEPO proteins generated in the culture supernatant.

The 2 strains of the CHO hybrid cells (5EF1Δ38 and 5EF1Δ63) carrying the hEPO-14AΔqΔneoHAC vectors isolated in Example 23 (5) were plated in amounts of about 10⁵ cells in 12-well tissue culture plastic petri-dishes (Falcon) comprising 2 ml of F12 medium containing 10% FBS and G418 at 0.8 mg/ml. After the cultured cells reached confluence, the medium was exchanged with 2 ml of F12 medium containing 10% FBS, culture was conducted for 2 days, the medium was exchanged with 1 ml of F12 medium containing 10% FBS, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in Table 8.

TABLE 8

| Clone No. | hEPO concentration in CM (IU/10E6 cells/24 h) |
|---|---|
| 5EFΔ38 | 204 |
| 5EFΔ63 | 801 |

Thus, hEPO expression was observed in the 2 strains of the CHO hybrid cells carrying the hEPO-14AΔqΔneoHAC vector.

Example 19 hEPO Gene Expression in Human Normal Fibroblasts Comprising hEPO-14AΔqΔneoHAC Vector from which Neo-Resistant Gene Unit has been Removed (1) Preparation of hEPO-14AΔqΔneoHAC Vector-Introduced Human Normal Fibroblasts (1-1) Introduction of hEPO-14AΔqHAC Vector into Human Normal Fibroblasts, HFL-1, by the Microcell Mediated Chromosome Transfer Method The CHO hybrid cells carrying the hEPO-14AΔqΔneo-HAC vectors, 5EF1Δ38 and 5EF1Δ63, obtained in Example 18 were used as chromosome donor cells. Human normal fibroblasts, HFL-1 (obtained from the Cell Engineering Division of the RIKEN BioResource Center; Accession No. RCB0521), were used as chromosome recipient cells. The method in accordance with Example 5 (1-1) was employed. Selection culture was carried out for about 2 to 4 weeks, the developed blasticidin-resistant colonies were isolated, and the subsequent analysis was performed. As a result of 6 micronuclear cell fusion operations (two times for 5EF1Δ38 and 4 times for 5EF1Δ63), 56 drug-resistant colonies were obtained (8 clones from 5EF1Δ38 and 48 clones from 5EF1Δ63). Among the above colonies, cells obtained with the use of 5EF1Δ38 and 5EF1Δ63 as chromosome donor cells are hereafter referred to as tΔ38H cells and tΔ63H cells, respectively.

(1-2) PCR Analysis

Whether or not a human chromosome carries the hEPO-14AΔqΔneoHAC vector was inspected by PCR amplification using the SVpANp1 and the Neo Rp2 primers of Example 3 (1-2) and the STS marker, the D2S1334 primer, in accordance with the method of Kakeda et al. (Kakeda et al., Gene Therapy; 12: 852-856, 2005). Also, inclusion of chromosome donor CHO cells was inspected by PCR amplification using the CHO furin gene-specific primers, furin3'subF and furinEx6-28R. The sequences of the designed primers are shown below.

furin3'subF:
(SEQ ID NO: 108)
5'-ACTCAGAGATCCACTGCACCAGGATCCAAGGGAGG furinEx6-28R:
(SEQ ID NO: 109)
5'-CCGCTCGAGCGGCTACACCACAGACACCATTGTTGGCTACTGCTGCC The reactions were carried out at 94° C. for 5 minutes, followed by 32 cycles of denaturation at 94° C. for 20 seconds followed by annealing/extension at 68° C. for 3 minutes. When the HFL-1 cells carrying the hEPO-14AΔqΔneoHAC vector did not include the chromosome donor CHO cells, amplification of about 1.0 kbp is deduced with the use of the SVpANp1 and the Neo Rp2 primers, amplification of about 0.6 kbp is deduced with the use of the D2S1334 primer, and no amplification is deduced with the use of furin3'subF and furinEx6-28R. As a result, a band having a deduced size was observed in a total of 39 strains from among the 56 strains of the blasticidin-resistant strains obtained in (1-1) above (i.e., 4 strains of tΔ38H and 35 strains of tΔ63H).

Thus, the above 39 blasticidin-resistant strains were found to be HFL-1 cells carrying the hEPO-14AΔqΔneoHAC vectors.

(1-3) Southern Blot Analysis

Figure 71:
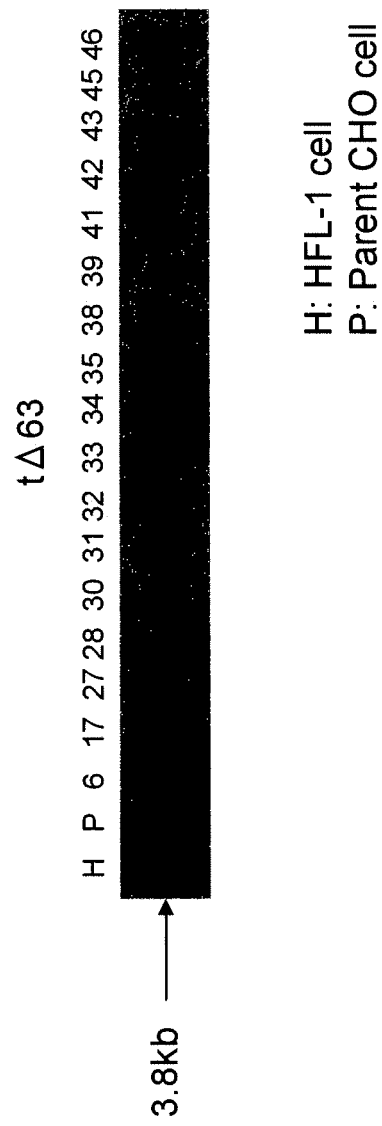
FIG. 71 shows the results of Southern analysis of the human normal fibroblast that carries the hEPO-14AΔqΔneo-HAC vector.

In order to inspect whether or not the hEPO-14AΔqΔneoHAC vector properly carries the hEPO expression unit, the 31 strains (i.e., 3 strains of tΔ38H and 28 strains of tΔ63H) from among the above 39 blasticidin-resistant strains were subjected to Southern blot analysis. The method was carried out in accordance with Kakeda et al. (Gene Therapy; 12: 852-856, 2005). Representative results are shown in FIG. 71. The length of the restriction enzyme fragment resulting from digestion with XbaI deduced from the nucleotide sequence is 5.5 kb, including the hEPO expression unit. As a result, bands having sizes as deduced were observed in the 28 blasticidin-resistant strains carrying the hEPO-14AΔqΔneoHAC vectors obtained in (1-2) above (3 strains of tΔ38H and 25 strains of tΔ63H).

(1-4) FISH Analysis

Figure 72:
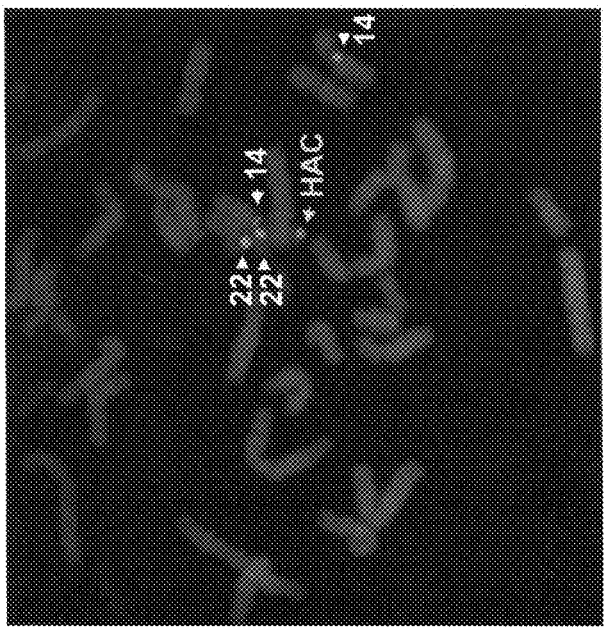
FIGS. 72A and 72B each show the results of FISH analysis of the human normal fibroblast that carries the hEPO-14AΔqΔneo-HAC vector.

FISH analysis was carried out in accordance with the method described in Matsubara et al. (FISH Experimental Protocol, Shujunsha Co. Ltd., 1994) using human chromosome 14- and human chromosome 22-specific α-satellite DNA probes (Q-biogene, Funakoshi). As a result of analysis of 8 strains from among the blasticidin-resistant strains obtained in (1-3) above, a total of 8 strains were found to be of normal karyotypes, and signals were detected in 4 sites in the centromeric regions of a pair of human chromosome 14 and human chromosome 22 derived from a host cell and in a site derived from a copy of 14AΔqΔneoHAC vector in most of the observed mitotic figure. The results are shown in FIG. 72A and in FIG. 72B.

The experiments (1-1) to (1-4) demonstrated that the obtained 8 blasticidin-resistant strains were HFL-1 cells carrying the hEPO-14AΔqΔneoHAC vectors and having the normal karyotype.

(2) hEPO Gene Expression by hEPO-14AΔqΔneoHAC Vector from which the Neo-Resistant Gene Unit has been Removed in HFL-1 Cells Expression of hEPO genes was quantified by enzyme-linked immunosorbent assay (ELISA) of hEPO proteins generated in the culture supernatant.

The 29 strains of the HFL-1 cells carrying the hEPO-14AΔqHAC vectors (tΔ38H4 strains and tΔ63H28 strains) that had been subjected to long-term subculture in (1) above were plated in amounts of about $10^4$ cells in collagen-I-coated 24-well tissue culture plastic petri-dishes (Falcon) comprising 1 ml of DMEM medium containing 20% FBS. After the cultured cells reached confluence, culture was conducted for 7 days, the medium was exchanged with 1 ml of a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in the item of "14AΔneo-HAC" in FIG. 21.

Thus, hEPO expression was observed in the 29 strains of the HFL-1 cells carrying the hEPO-14AΔqΔneoHAC vectors (i.e., 3 strains of tΔ38H and 26 strains of tΔ63H).

Example 20

Analysis of Long-Term EPO Expression of hEPO-14AΔqΔneoHAC Vector in Human Normal Fibroblasts (1) Long-Term Subculture Under Non-Selective Culture Conditions In order to confirm stability of the hEPO-14AΔqΔneoHAC vector in human normal fibroblasts, HFL-1, long-term subculture was carried out under non-selective culture conditions. The eleven strains of the HFL-1 cells carrying the hEPO-14AΔqΔneoHAC vectors obtained in Example 23 (3 strains of tΔ38H and 8 strains of tΔ63H) were used. A non-selection medium was DMEM medium containing 20% FBS, and a selection medium comprised such DMEM medium and blasticidin added thereto at 3 μg/ml. The 1 to $3 \times 10^5$ HFL-1 cells carrying the hEPO-14AΔqΔneoHAC vectors were plated in a collagen-I-coated T-25 flask (Falcon), the cells were cultured to a cell density of about 90% confluency, the 1 to $3 \times 10^5$ cells were plated again, and subculture was continued up to the tenth passage. The number of cells was counted every passage to determine the population doubling level. The cells were recovered before and after the fifth passage and after the tenth passage, and hEPO gene expression analysis and FISH analysis were carried out.

(2) hEPO Gene Expression After Long-Term Subculture

Expression of hEPO genes was quantified by enzyme-linked immunosorbent assay (ELISA) of hEPO proteins generated in the culture supernatant.

9 strains of the hEPO-14AΔqHAC vector-carrying HFL-1 cells that had been subjected to long-term subculture in (1) above were plated in amounts of about $10^4$ cells in collagen-I-coated 24-well tissue culture plastic petri-dishes (Falcon) comprising 1 ml of DMEM medium containing 20% FBS. After the cultured cells reached confluence, culture was conducted for 7 days, the medium was exchanged with 1 ml of a fresh medium, culture was conducted for an additional 24 hours, the supernatant was recovered, and the number of cells was then counted. hEPO in the culture supernatant was quantified using the hEPO ELISA kit (Quantikine IVD Human EPO Immunoassay, R&D System). The average values of the results of experiments conducted in duplicate are shown in the item of "14AΔneo" in FIG. 43.

Thus, hEPO expression was observed after long-term subculture in the above 8 strains of the HFL-1 cells carrying the hEPO-14AΔqΔneoHAC vectors.

The above experiment demonstrates that the hEPO-14AΔqΔneoHAC vector would be retained stably in the HFL-1 cells after long-term subculture under non-selective culture conditions, that a copy number per cell would be maintained, and that hEPO gene expression would be maintained.

Example 21

Figure 73:
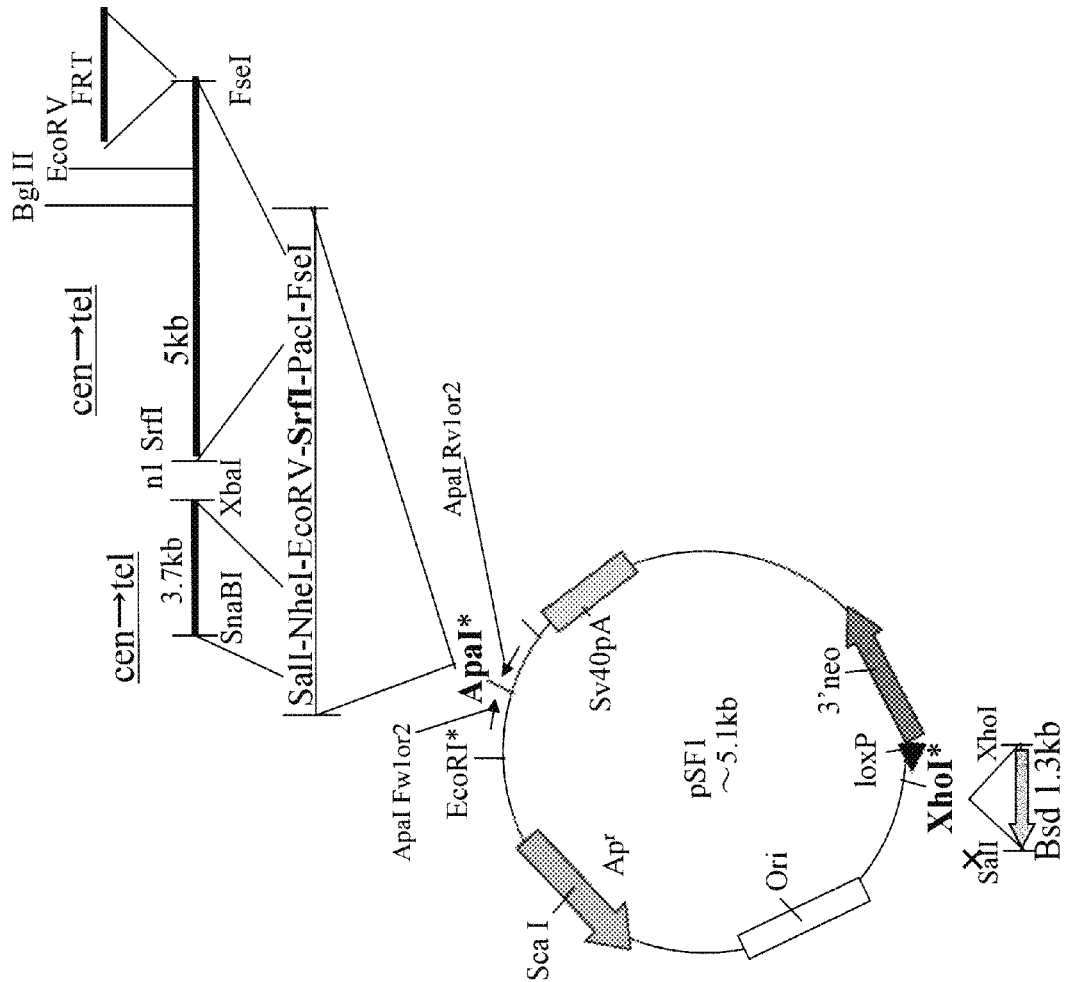
FIG. 73 shows the structure of the GnpSF1-FRT vector for introduction of the FRT sequence.

Construction of 14NΔqHAC Vector from which Neo-Resistant Gene Unit has been Removed (1) Introduction of FRT Sequence into 14NΔqHAC Cloning Site
(1-1) Construction of GnpSF1-FRT Vector for Introducing the FRT Sequence The t1pSF1-FRT vector constructed in Example 18 was digested with ScaI and EcoRV to prepare a 7.4-kb DNA fragment comprising the FRT sequence. The pSF1(G+n1)

vector constructed in Example 6 was digested with ScaI, BglII, and EcoRV to prepare a 7.0-kb ScaI-BglII DNA fragment and a 0.55 kb BglII-EcoRV DNA fragment, and the resultant DNA fragments were introduced into the 7.4-kb DNA fragment to prepare the GnpSFI-FRT vector comprising the FRT sequence. The outline is shown in FIG. 73. The size of the final GnpSF1-FRT construct is about 15.0 kb. FIG. 34A shows the targeting vector, the target sequence, and a chromosome allele resulting from homologous recombination.

(1-2) Introduction of GnpSFI(FRT) Vector into 14NΔqHAC-Carrying DT40 Cell

The GnpSF1(FRT) construct was linearized by digestion with the SrfI restriction enzyme (Roche), and the resultant was introduced by electroporation into the DT40 hybrid cell carrying 14NΔqHAC, from which the long-arm distal region had been deleted. The method in accordance with Example 1 (2-2) was employed. The blasticidin-resistant colonies developed 2 to 3 weeks thereafter. A total of 240 drug-resistant colonies were isolated from G4n6Δp25 through 2 transfection operations, and the subsequent analysis was performed.

(1-3) PCR Analysis

Genomic DNA of a blasticidin-resistant strain was used as a template, and the presence of two target sequences (i.e., the 5' target sequence and the 3' target sequence) was detected by PCR. The presence of the two target sequences (indicated as "5'-genome" and "3'-genome" in FIG. 34A) was analyzed in accordance with the method of Example 7 (4-3).

Among the obtained 96 strains of the blasticidin-resistant DT40 cells, i.e., G4n6Δp25sF, 52 strains were found to produce amplification products having sizes deduced from the sequences (5' genome: about 5 kb; 3' genome: about 2 kb).

(1-4) Southern Blot Analysis

Figure 74:
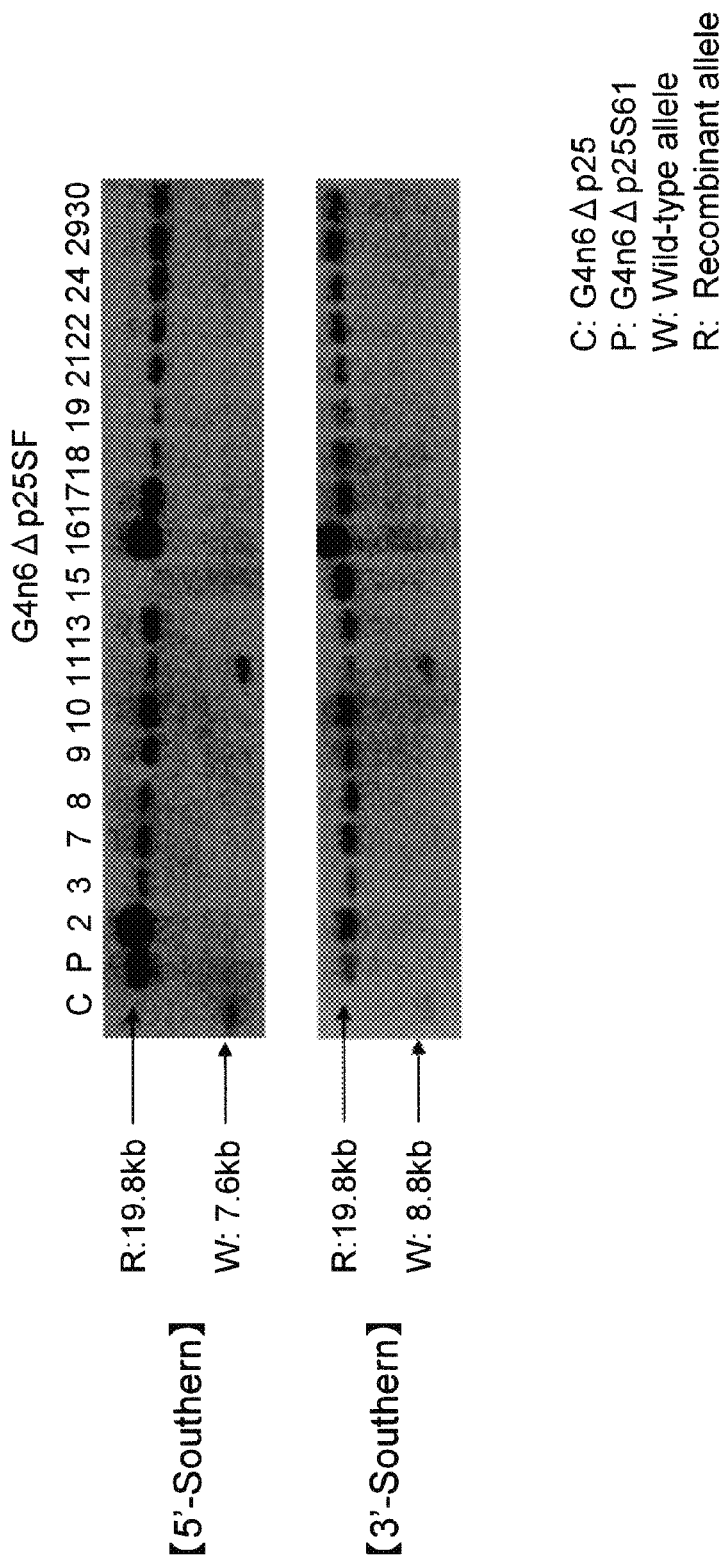
FIG. 74 shows the results of Southern analysis of the DT40 hybrid cell that carries the GnpSF1-FRT vector introduced into 14NΔqHAC.

As a screening method for selecting a homologous recombinant, Southern blot analysis was carried out. The presence of the two target sequences of homologous recombination, i.e., the 5'-target sequence and the 3'-target sequence, was analyzed in accordance with the method of Example 1 (2-4). Representative results are shown in FIG. 74.

The length of the restriction enzyme fragment deduced from the nucleotide sequence is 19.8 kb in the form of a homologous recombinant, and it is 7.6 kb in the form of a wild-type (i.e., a non-recombinant), as a result of the 5'-genome analysis. Such length is 19.8 kb in the form of a homologous recombinant, and it is 8.8 kb in the form of a wild-type (i.e., a non-recombinant), as a result of the 3'-genome analysis. From among 18 strains of the candidate blasticidin-resistant strains, G4n6Δp25sF, 16 strains of the homologous recombinants were identified.

The experiments (1-1) to (1-4) demonstrated that the 16 strains of the DT40 hybrid cells carrying the 14NΔqF-HAC vectors, G4n6Δp25sF, into which the FRT sequences had been inserted at the cloning sites by homologous recombination were obtained.

Example 22

Figure 75:
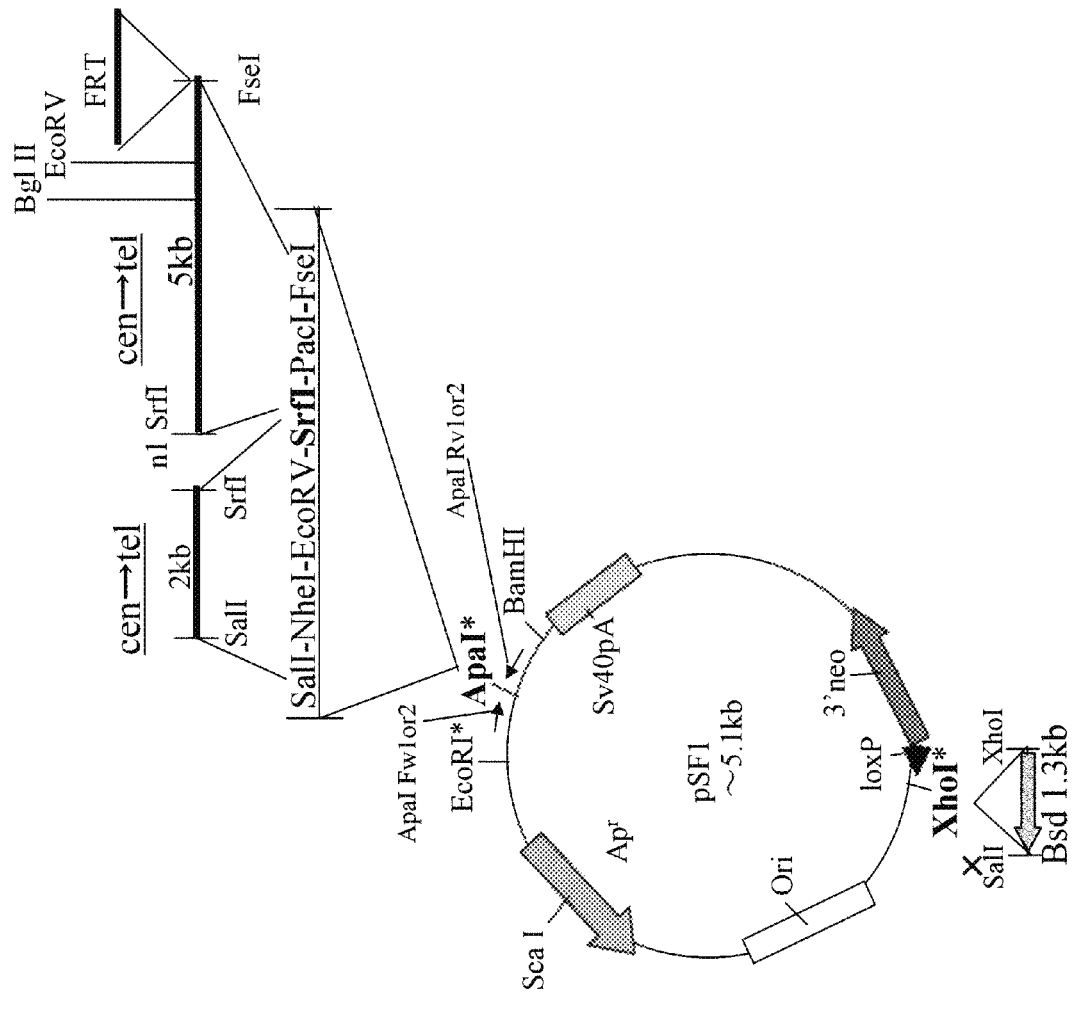
FIG. 75 shows the structure of the gnpSF1-FRT vector for introduction of the FRT sequence.

Construction of 14gNΔqHAC Vector from which Neo-Resistant Gene Unit had been Removed (1) Introduction of the FRT Sequence into 14gNΔqHAC Cloning Site
(1-1) Construction of gnpSF-FRT Vector for Introducing the FRT Sequence The t1pSF1-FRT vector constructed in Example 18 was digested with ScaI and EcoRV to prepare a 7.4 kb DNA fragment comprising the FRT sequence. The pSF1(g+n1) vector constructed in Example 6 was digested with ScaI, HindIII, and EcoRV to obtain a 5.4 kb ScaI-HindIII DNA fragment and a 0.45 kb DNA HindIII-EcoRV fragment. The resultant DNA fragments were introduced into the 7.4 kb DNA fragment to prepare the gnpSFI-FRT vector comprising the FRT sequence. The outline is shown in FIG. 75. The size of the final gnpSF1-FRT construct is about 13.3 kb. FIG. 34B shows the targeting vector, the target sequence, and a chromosome allele resulting from homologous recombination.

(1-2) Introduction of gnpSF(FRT) Vector into 14NΔqHAC-Carrying DT40

The gnpSF1(FRT) construct was linearized by digestion with the SrfI restriction enzyme (Roche), and the resultant was introduced by electroporation into the DT40 hybrid cell carrying 14NΔqHAC from which the long-arm distal region had been deleted. The method in accordance with Example 1 (2-2) was employed. Blasticidin-resistant colonies developed 2 to 3 weeks thereafter. A total of 116 drug-resistant colonies were isolated from g5n7Δc3 through 2 transfection operations, the isolated colonies were grown, and the subsequent analysis was performed.

(1-3) PCR Analysis

Genomic DNA of a blasticidin-resistant strain was used as a template, and the presence of two target sequences (i.e., the 5' target sequence and the 3' target sequence) was detected by PCR. The presence of the two target sequences (indicated as "5'-genome" and "3'-genome" in FIG. 34B) was analyzed. The method in accordance with Example 7 (4-3) was employed.

Among the obtained 116 strains of the blasticidin-resistant DT40 cells, i.e., g5n7Δc3sF, 54 strains were found to produce amplification products having sizes deduced from the sequence (5' genome: about 5 kb; 3' genome: about 2 kb).

(1-4) Southern Blot Analysis

Figure 76:
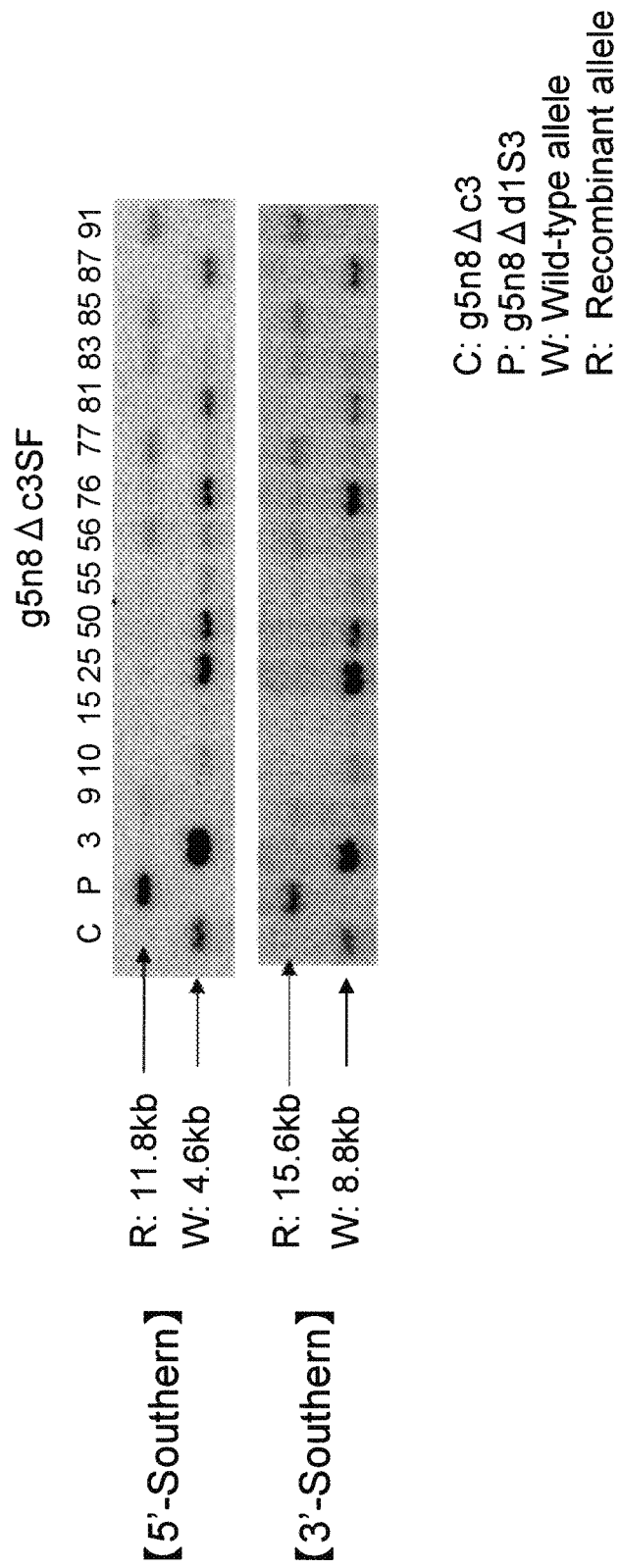
FIG. 76 shows the results of Southern analysis of the DT40 hybrid cell that carries the gnpSF1-FRT vector introduced into 14gNΔqHAC.

As a screening method for selecting a homologous recombinant, Southern blot analysis was carried out. The presence of the two target sequences of homologous recombination, i.e., the 5'-target sequence and the 3'-target sequence, was analyzed in accordance with the method of Example 1 (2-4). Representative results are shown in FIG. 76.

The length of the restriction enzyme fragment deduced from the nucleotide sequence is 11.8 kb in the form of a homologous recombinant, and it is 4.6 kb in the form of a wild-type (i.e., a non-recombinant), as a result of the 5'-genome analysis. Such length is 15.6 kb in the form of a homologous recombinant, and it is 8.8 kb in the form of a wild-type (i.e., a non-recombinant), as a result of the 3'-genome analysis. From among 36 strains of the candidate blasticidin-resistant strain, g5n7Δc3sF, 4 strains of the homologous recombinants were identified.

As a result of the experiments (1-1) to (1-4), the 4 strains of the DT40 hybrid cells carrying the 14NΔqF-HAC vectors, g5n7Δc3sF, into which the FRT sequences had been inserted at cloning sites by homologous recombination were obtained.

Example 23

Preparation of 21HAC (21AΔqHAC) Vector by Deletion of Long-Arm Distal Region from Human Chromosome 21

(1) Introduction of Cloning Site (HPRT-Reconstructing Site) into the Long-Arm Proximal Region of Human Chromosome 21 using HAC Vector
(1-1) Construction of kk Vector for Inserting loxP and 5'HPRT Sequences As a basic plasmid for inserting the loxP sequence into the long-arm proximal region of human chromosome 21, V901 (Lexicon genetics) was used. The DNA sequence of the proximal region of human chromosome 21 where loxP would be inserted was obtained from the GenBank database (AP001657). Sequences of oligonucleotide primers used for amplifying the two target sequences of homologous recombination are shown below.

```
#21CEN<1>1L:
acctggaatttcctaccatcccccataa      (SEQ ID NO: 110)

#21CEN<1>1R:
atctctccagagggacagcatcataccc      (SEQ ID NO: 111)

#21CEN<2>1L:
cctgcaagttatgaccactggggatttt      (SEQ ID NO: 112)

#21CEN<2>1R:
ctgcagtgagccgagatcataccactgt      (SEQ ID NO: 113)
```

Figure 78:
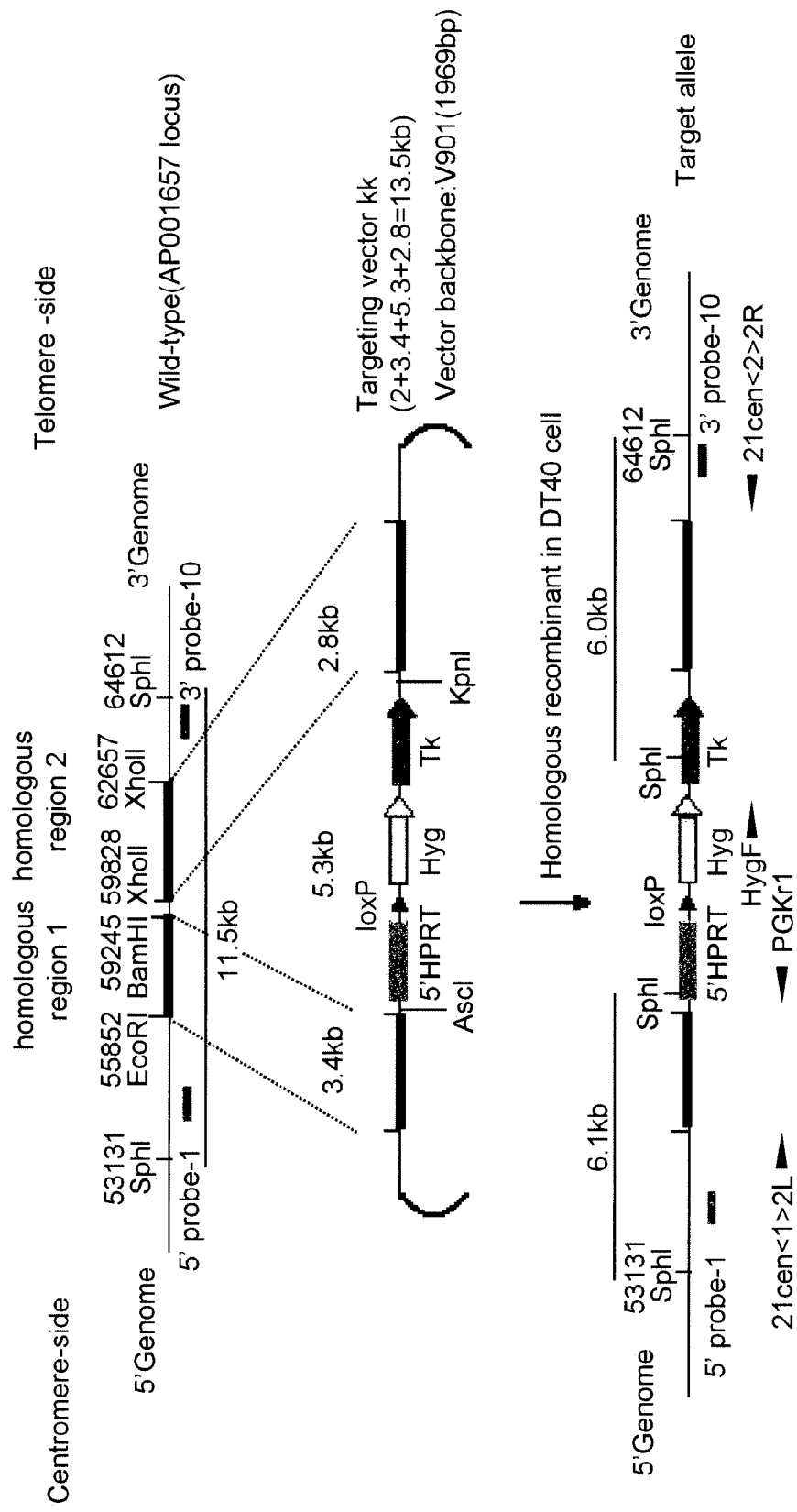
FIG. 78 schematically shows a method for inserting the loxP sequence into AP001657 of the long arm of human chromosome 21.

The MC1-TK sequence was cleaved from V830 (Lexicon genetics) using RsrII (NEB), and then cloned into the recognition site for the HindIII restriction enzyme of the V901 plasmid (V901T-1). Subsequently, mouse A9 hybrid cells (A9<21-2>, Shinohara et al., Hum Mol Genet, 10: 1163, 2001) carrying human chromosome 21 were cultured, and genomic DNA was extracted from the cells using the Puregene DNA isolation kit (Gentra System). The obtained genomic DNA was used as a template, and the target sequences to be recombined were amplified by PCR using the above primers. The reaction was conducted at 95° C. for 2 minutes followed by 30 cycles of denaturation at 95° C. for 15 seconds and annealing at 68° C. for 4 minutes. The DNA fragment (homologous region 1) amplified with the use of SEQ ID NOs: 110 and 111 was digested with the restriction enzymes, EcoRI (Nippon Gene) and BglII (Nippon Gene), the DNA fragment (homologous region 2) amplified with the use of SEQ ID NOs: 112 and 113 was digested with the restriction enzyme, XhoII (Promega), the resultants were separated and purified on agarose gel, and then cloned into the EcoRI site and the BamHI or BglII site of the V901 plasmid. Further, the 5'HPRT-loxP-hygromycin (hygromysin) cleaved with the use of AscI and KpnI was cloned into the AscI and KpnI sites of the V901 plasmid. The 5'HPRT-loxP-hygromycin was prepared by cloning the oligo-synthesized loxP sequence and PGK hygromycin (hygro) sequences (provided by Professor Lyons, I) into the XbaI site of V820 (Lexicon genetics). The size of the final loxP-inserted construct was 13.5 kb (hereafter designated as the "kk vector"). FIG. 78 shows the targeting vector, the target sequence, and a chromosome allele resulting from homologous recombination.

(1-2) Introduction of kk Vector into DT40 Cell Carrying Human Chromosome 21

DT40 hybrid cells carrying human chromosome 21 were prepared by the microcell mediated chromosome transfer method using the above A9<21-2> cells carrying human chromosome 21 as chromosome donor cells. The chromosome recipient DT40 cells are registered with the Japanese Collection of Research Bioresources (JCRB) under Accession No. JCRB2221 and such cells are available therefrom. The outline of the method for preparation is shown below.

At the outset, microcells were prepared from about $1 \times 10^8$ A9<21-2> cells. The A9<21-2> cells that had been cultured to a cell density of about 80% confluency in 12 25-cm$^2$ centrifuge flasks (Nunc) were cultured in a culture medium (DMEM containing 20% fetal bovine serum (FBS) and G418 at 0.8 mg/ml) containing colcemid (0.075 μg/ml, demecolcine, Wako Pure Chemical Industries Ltd.) for 48 hours to induce micronucleus formation. In Examples, DMEM manufactured by Nissui Pharmaceutical Co., Ltd. was used. After the medium was removed, the cytochalasin B (10 μg/ml in DMEM, Sigma) solution preheated to 34° C. was filled in centrifuge flasks, and centrifugation was carried out at 34° C. and 8,000 rpm for 1 hour. The microcells were suspended in serum-free medium (DMEM), recovered, and purified by filtration using SWINNEX-25 (Millipore) equipped with a filter (Whatman) having a pore size of 8 μm, 5 μm, or 3 μm. The purified microcells were resuspended in 6 ml of DMEM. DT40 cells were cultured in RPMI 1640 culture medium containing 10% FBS, 1% CS, and 0.1 mM 2-ME, the resultants were washed twice with DMEM, and $1 \times 10^7$ cells were resuspended in 5 ml of DMEM. The microcell suspension was centrifuged at room temperature and 1,500 rpm for 5 minutes, the DT40 cell suspension was superposed thereon, centrifugation was carried out at room temperature and 1,500 rpm for 5 minutes, and the supernatant was then removed. Cell fusion treatment was carried out in a polyethylene glycol (PEG) (1:1.4) solution (Tomizuka et al., Nature Genet., U.S.A., vol. 16, pp. 133-143, 1997) for 90 seconds. The fused cells were suspended in 60 ml of RPMI 1640 culture medium (Invitrogen) containing 10% FBS, 1% chicken serum (ChS), and 0.1 mM 2-mercaptoethanol (ME), the resulting suspension was plated in 6 96-well plates, culture was conducted for 24 hours, and selection culture was conducted in a medium containing G418 at 1.5 mg/ml for about 2 weeks. Drug-resistant colonies that had developed as a result of two microcell fusion experiments were isolated. The presence of the regions CBR, APP, TTC3, and PCP4 in human chromosome 21 was analyzed by PCR, and fluorescence in situ hybridization (FISH) analysis using a human-specific probe, Cot1, (Gibco BRL) was further carried out to examine and obtain a copy of human chromosome 21-carrying clones, DT40 (21-2-3).

Subsequently, the kk vector was linearized by digestion with the NotI restriction enzyme (Takara), and the resultant was introduced into the DT40 hybrid cell carrying human chromosome 21 from which the long-arm distal region had been deleted. The cells ($1 \times 10^7$ DT40 (21-2-3)) were suspended in 0.5 ml-RPMI medium. In the presence of 30 μg of DNA, the cells were allowed to stand at room temperature for 10 minutes, and electroporation was then carried out using the Gene Pulser II (Bio-Rad). A voltage of 550 V was applied to a condenser having a capacity of 25 μF and then discharged using an electroporation cell having 4 mm of an interelectrode distance. After the cells were allowed to stand at room temperature for 10 minutes, the electroporated cells were suspended in RPMI 1640 culture medium containing 10% FBS, 1% ChS, and 0.1 mM 2-ME, and the resulting suspension was plated in twenty 96-well plates (Falcon). Twenty four hours later, hygromycin B (WAKO) was added to a final concentration of 1.5 mg/ml, and resistant colonies developed 2 to 3 weeks thereafter. A total of 237 colonies obtained through 20 transfection operations were isolated, the isolated colonies were grown, and the subsequent analysis was carried out (clone name: DT40(kk)).

(1-3) PCR Analysis

Genomic DNA of hygromycin-resistant strains was used as a template to select recombinants, and the presence of the two target sequences, i.e., the 5'-target sequence and the 3'-target sequence, was detected by PCR using the primers shown below. The positions of the primers are shown in FIG. 78. The sequences are shown below.

```
#21CEN<1>2L:
5'-aaatgcatcaccattctcccagttaccc    (SEQ ID NO: 114)

PGKr1:
5'-ggagatgaggaagaggagaaca          (SEQ ID NO: 115)
```

-continued

```
#21CEN<2>2R:
5'-cctgttctatggttccagcctcacattg    (SEQ ID NO: 116)

hygF:
5'-GAATTCAGCGAGAGCCTGAC            (SEQ ID NO: 117)
```

LA Taq polymerase (Takara Shuzo Co., Ltd.) was used, and the reaction was carried out under the conditions shown below. The 5'-genome analysis (SEQ ID NOs: 114-115) was carried out at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 25 cycles of denaturation at 98° C. for 5 seconds followed by annealing/extension at 68° C. for 5 minutes, and extension at 72° C. for 10 minutes. The 3'-genome analysis (SEQ ID NOs: 116-117) was carried out at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 7 minutes, and extension at 72° C. for 10 minutes. To the PCR solution, $MgSO_4$ (final concentration: 0.5 mM) was added. A 4.5-kb band was detected on the 5'-side and a 6.5-kb band was detected on the 3'-side in only clones in which site-directed recombination had occurred. No band was detected in negative controls, DT40 and DT40 (21-2-3). The recombination frequency was about 20%, i.e., recombination had occurred in 46 clones among 237 clones.

(1-4) Southern Blot Analysis

As a screening method for selecting a homologous recombinant, Southern blot analysis was carried out. In order to prepare probes, PCR was carried out using oligonucleotide primer pairs shown below and genomic DNA of the A9<21-2> cell carrying human chromosome 21 as a template, and the resultants were isolated and purified.

Two types of probes, i.e., 5'probe-1 (SEQ ID NOs: 118-119) and 3'probe-10 (SEQ ID NOs: 120-121) were designated outside the target sequences of homologous recombination (FIG. 78).

```
21qA5-1L:
5'-caggcaactgtaacacagtggtaggta    (SEQ ID NO: 118)

21qA5-1R:
5'-aacagtagagcaatttcaggcaggtc     (SEQ ID NO: 119)

21qA3-3L:
5'-cgcagcttttagctgaactaaggaga     (SEQ ID NO: 120)

21qA3-3R:
5'-gtgacacagggatactctgtccaaaa     (SEQ ID NO: 121)
```

Genomic DNA (about 5 µg) extracted from 12 strains obtained by primary screening was digested with the SphI restriction enzyme (Roche), and Southern blot analysis was carried out by the method described in Ausubel et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). The length of the restriction enzyme fragment deduced from the nucleotide sequence is 6.1 kb in the form of a homologous recombinant, as a result of the 5'-genome analysis, it is 6.0 kb in the form of a homologous recombinant, as a result of the 3'-genome analysis, and it is 11.5 kb in the form of a wild-type (i.e., a non-recombinant), as a result of the 5'-genome analysis and the 3'-genome analysis. Homologous recombinants were identified in all the 12 analyzed strains.

(1-5) Fluorescence In Situ Hybridization (FISH) Analysis

FISH analysis was carried out in accordance with the method described in Matsubara et al. (FISH Experimental Protocol, Shujunsha Co. Ltd., 1994). Among the clones in which recombination was observed in (1-4) above, 6 clones were subjected to FISH analysis using human cot-1 DNA and hygromycin (prepared by cleaving from the kk vector) as probes, human chromosome 21 was not translocated to host chromosomes of all the clones, and a signal derived from hygromycin was detected in the long-arm proximal region. This demonstrates that site-directed recombination had occurred.

The above (1-1) to (1-5) demonstrated that 5'-HPRT-loxP-hygro-TK could be inserted into a proximal region of human chromosome 21, i.e., AP001657, by homologous recombination.

(2) Deletion of the Long Arm from Human Chromosome 21 by Telomere Truncation (2-1) Construction of pTELhisD-21q Vector for Telomere Truncation As a telomere truncation vector (i.e., a targeting vector) for deleting the long-arm distal region of human chromosome 21, pTELhisD (Kuroiwa et al., Nature Biotech., U.S.A., vol. 18, pp. 1086-1090, 2000) was used. Based on the nucleotide sequence of the long-arm distal region of human chromosome 21 obtained from the GenBank database (Accession No. AP001657), target sequences for insertion of the telomere truncation vector were designed. Sequences of oligonucleotide primers for amplifying the same by PCR are shown below.

```
q1L:
5'-ggagcaacaggacctctcattccttgtt   (SEQ ID NO: 122)

q1R:
5'-ccaatgtcaggcactcctgctctaaatg   (SEQ ID NO: 123)
```

Figure 79:
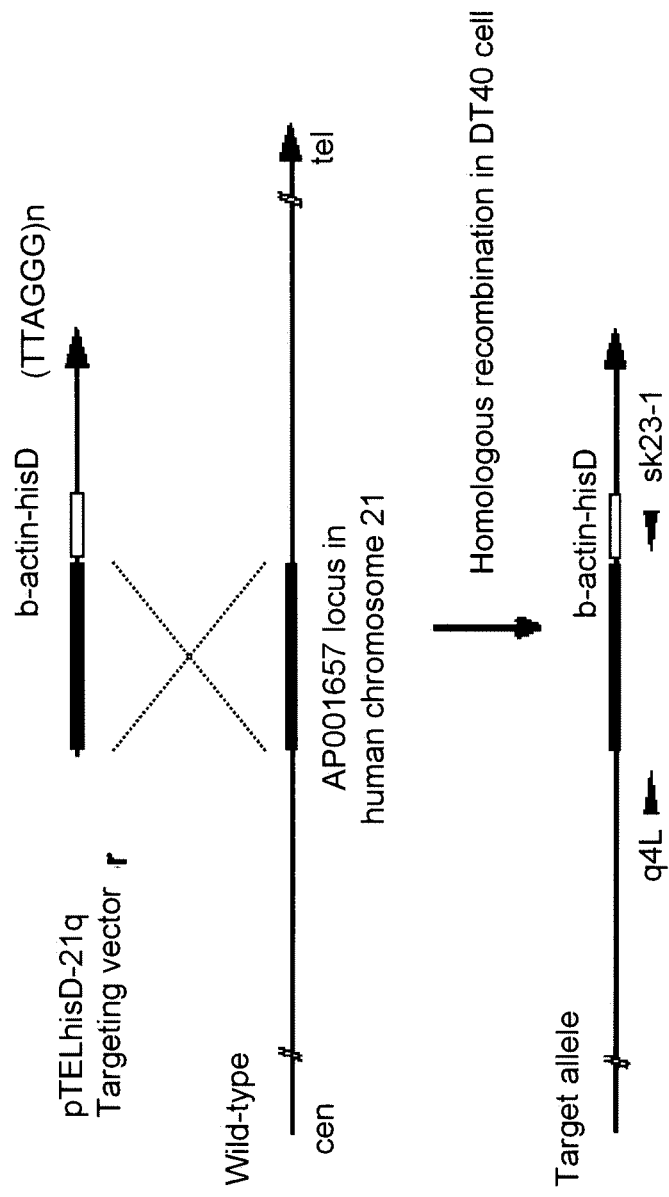
FIG. 79 schematically shows a method for performing site-directed cleavage at AP001657 of the long arm of human chromosome 21.

Mouse A9 hybrid cells (A9<21-2>, Shinohara et al., Hum Mol Genet, 10: 1163, 2001) carrying human chromosome 21 were cultured, and genomic DNA was extracted from the cells using the Puregene DNA isolation kit (Gentra System). The obtained genomic DNA was used as a template, and the target sequences to be recombined were amplified by PCR using the above primers. About 0.1 µg of Genomic DNA was used as a template, and PCR was carried out in accordance with Innis et al. (PCR Experimental Manual, HBJ Press, 1991) using a GeneAmp9700 thermal cycler (Applied Biosystems). LA Taq polymerase (Takara Shuzo Co., Ltd.) was used, and the reactions were carried out at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 25 cycles of denaturation at 98° C. for 5 seconds followed by annealing/extension at 68° C. for 10 minutes, and extension at 72° C. for 10 minutes. The 7.0-kb-amplification product was digested with the BamHI restriction enzyme (Roche), a DNA fragment having a cohesive end was separated by agarose gel electrophoresis, followed by purification. The resultant was then cloned into the BamHI site of the pTELhisD plasmid. The size of the final pTELhisD-21q construct is about 14.4 kb. FIG. 79 shows the telomere truncation vector, the target sequence, and a chromosome allele resulting from homologous recombination.

(2-2) Introduction of Telomere Truncation Vector into Human Chromosome 21-Carrying DT40 Cell The pTELhisD-21q construct was converted into linearized DNA by digestion with the SrfI restriction enzyme, and the resultant was introduced into a DT40 hybrid cell carrying human chromosome 21 comprising loxP introduced into the long-arm proximal region prepared in Example 23 (1). The 1×10⁷ DT40 (kk139) cells were suspended in 0.5 ml of RPMI medium, the resultant was allowed to stand at room temperature for 10 minutes in the presence of 30 μg of DNA, and electroporation was then carried out using the Gene Pulser II (Bio-Rad). A voltage of 550 V was applied to a condenser having a capacity of 25 μF and then discharged using an electroporation cell having 4 mm of an interelectrode distance. After the cells were allowed to stand at room temperature for 10 minutes, the electroporated cells were suspended in RPMI 1640 culture medium containing 10% FBS, 1% ChS, and 0.1 mM 2-ME, and the suspension was plated in twenty 96-well plates (Falcon). Twenty four hours later, histidinol (L-histidinol dihydrochloride, Sigma) was added to the final concentration of 0.5 μg/ml, and resistant colonies developed 2 to 3 weeks thereafter. A total of 105 drug-resistant colonies obtained through 5 transfection operations were isolated, the isolated colonies were grown, and the subsequent analysis was performed.

(2-3) PCR Analysis

Genomic DNA of a histidinol-resistant cell was used as a template to identify the presence of a genomic region of a gene on human chromosome 21 by PCR. Sequences of oligonucleotide primers of the genomic region are shown below.

```
CBR-L:
5'-gatcctcctgaatgcctg            (SEQ ID NO: 124)

CBR-R:
5'-gtaaatgccctttggacc            (SEQ ID NO: 125)

APP-L:
5'-ctgggcaatagagcaagacc          (SEQ ID NO: 126)

APP-R:
5'-acccatattatctatggacaattga     (SEQ ID NO: 127)

TTC3-L:
5'-tggacaaatataaggcatgttca       (SEQ ID NO: 128)

TTC3-R:
5'-gtcaccttcctctgcctttg          (SEQ ID NO: 129)

PCP4-L:
5'-gaattcactcatcgtaacttcattt     (SEQ ID NO: 130)

PCP4-R:
5'-ccttgtaggaaggtatagacaatgg     (SEQ ID NO: 131)
```

About 0.1 μg genomic DNA was used as a template, and the above 4 types of genomic regions were subjected to amplification by PCR (Innis et al., supra). Ex Taq polymerase (Takara Shuzo Co., Ltd.) was used, and the reactions were carried out at 94° C. for 5 minutes, followed by 35 cycles of denaturation at 94° C. for 15 seconds, annealing at 60° C. for 30 seconds, and extension at 72° C. for 30 seconds. When the long-arm distal region was deleted by telomere truncation, detection may not be achieved with the use of the above 4 types of primers. Subsequently, 10 clones that were not detected with the use of the above primers were inspected as to whether or not site-directed homologous recombination had occurred with the use of the primers shown below. The positions of the primers are shown in FIG. 79. The sequences are shown below.

```
q4L:
5'-ctgcaatctttacctccctggttcaagc  (SEQ ID NO: 132)

SK23:
5'-ggccgctctagaactagtggatc       (SEQ ID NO: 133)
```

From among the 10 clones, a 7.5-kb band was detected in only 2 clones in which site-directed recombination had occurred. No band was detected in negative controls, i.e., DT40 and DT40 (21-2-3).

(2-4) Fluorescence In Situ Hybridization (FISH) Analysis

FISH analysis was carried out in accordance with the method described in Matsubara et al. (FISH Experimental Protocol, Shujunsha Co. Ltd., 1994) using the human-specific Cot1 (Invitrogen) and FITC-labeled hisD fragment (prepared by cleaving from the pTELhisD vector) as probes. As a result, the shortened human chromosome 21 and 2 FITC signals at the end of the long arm of Cot1-stained shortened human chromosome 21 were detected in most of the observed mitotic figures. Based on a size relative to a host DT40 cell chromosome, human chromosome 21 was confirmed to have been shortened.

Thus, the obtained two histidinol-resistant strains were found to have the long arm being deleted from human chromosome 21.

(3) Introduction of Cloning Site (Neo Reconstructing Site) into Long-Arm Proximal Region of 21AΔqHAC (3-1) Construction of pSF1(FRT)-C Vector for Inserting loxP, 3'Neo, and FRT Sequences As the basic plasmid for inserting the loxP, 3'neo, and FRT sequences into the human artificial chromosome (HAC) prepared in Example 23 (2), t1pSF1(FRT) prepared in Example 18 (1) was used. The nucleotide sequence of the long-arm proximal region of human chromosome 21 where the loxP, 3'neo, and FRT sequences are to be inserted were obtained from the GenBank database (Accession No. AP001657). Sequences of oligonucleotide primers used for amplifying two target sequences for homologous recombination are shown below.

```
AP001657-55852F_PacI:
                                 (SEQ ID NO: 134)
5'-gcgTTAATTAAaccgattaactgttcttttccagta AP001657-59245R_NheI:
                                 (SEQ ID NO: 135)
5'-gcGCTAGCgAAGTCAAAAGAAGTAACTTCTTTCTCT AP001657-59828F_SalI:
                                 (SEQ ID NO: 136)
5'-gacagtGTCGACaagtcaaaagaagtaacttctatc AP001657-62657R_SrfI:
                                 (SEQ ID NO: 137)
5'-gatGCCCGGGCGTTTCCATGAAGGATATTAATCAGT
```

Genomic DNA extracted from A9<21-2> cells carrying human chromosome 21 was used as the template to amplify the two target sequences by PCR. A DNA fragment of about 3.4 kb (i.e., homologous region 1) amplified with the use of SEQ ID NOs: 134 and 135 was digested with PacI and NheI (Roche), a DNA fragment of about 2.8 kb (i.e., homologous region 2) amplified with the use of SEQ ID NOs: 136 and 137 was digested with restriction enzymes, SalI and SrfI (Roche), and DNA fragments having cohesive ends were separated by agarose gel electrophoresis, followed by purification. Subsequently, the following 3 DNA fragments, i.e., the DNA fragment of homologous region 1 digested with restriction enzymes, the t1pSF1(FRT) plasmid (prepared in Example 18

Figure 80:
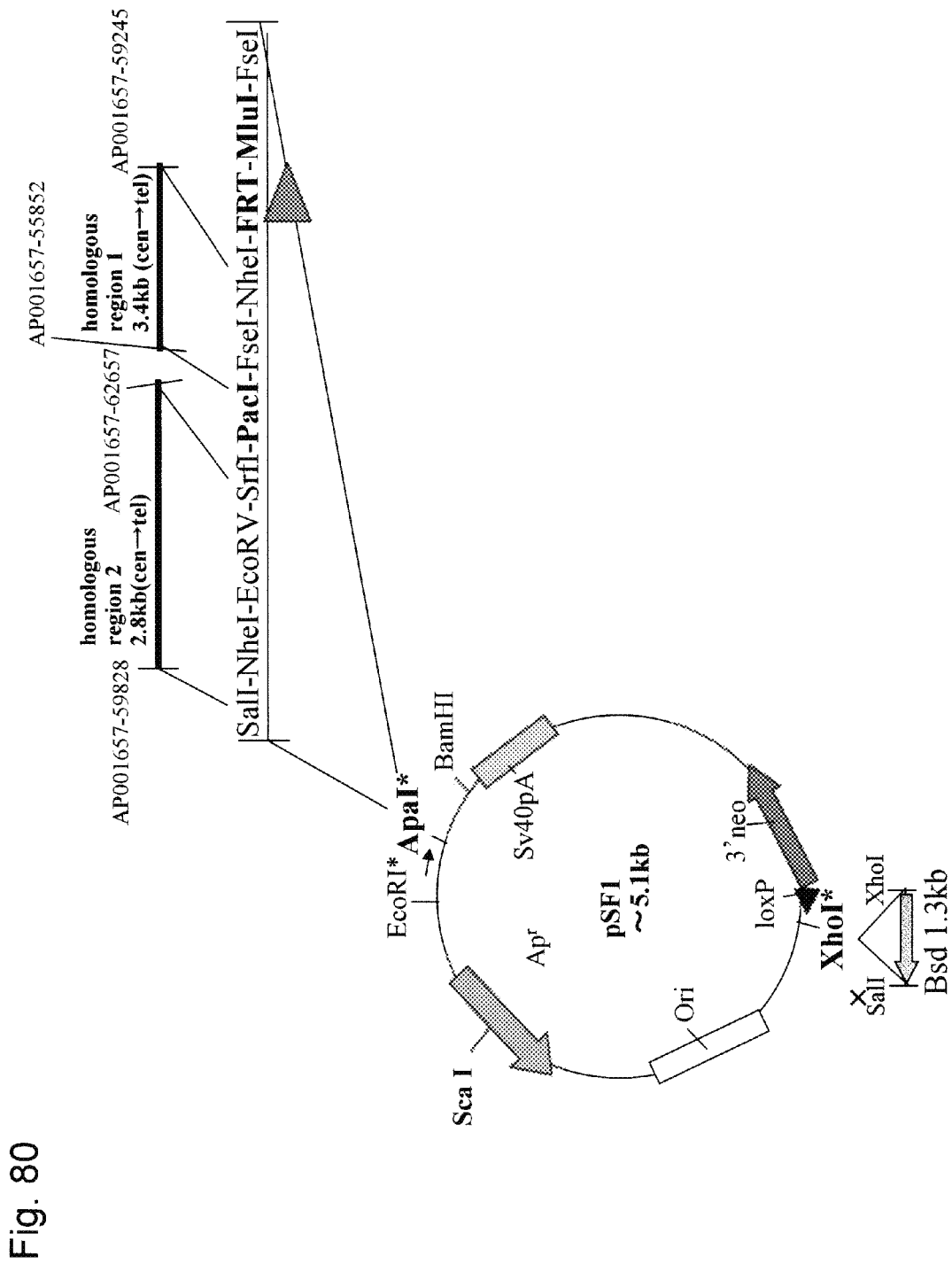
FIG. 80 shows the pSF1(FRT)-C vector for insertion of loxP, 3'neo, and FRT sequences.
Figure 81:
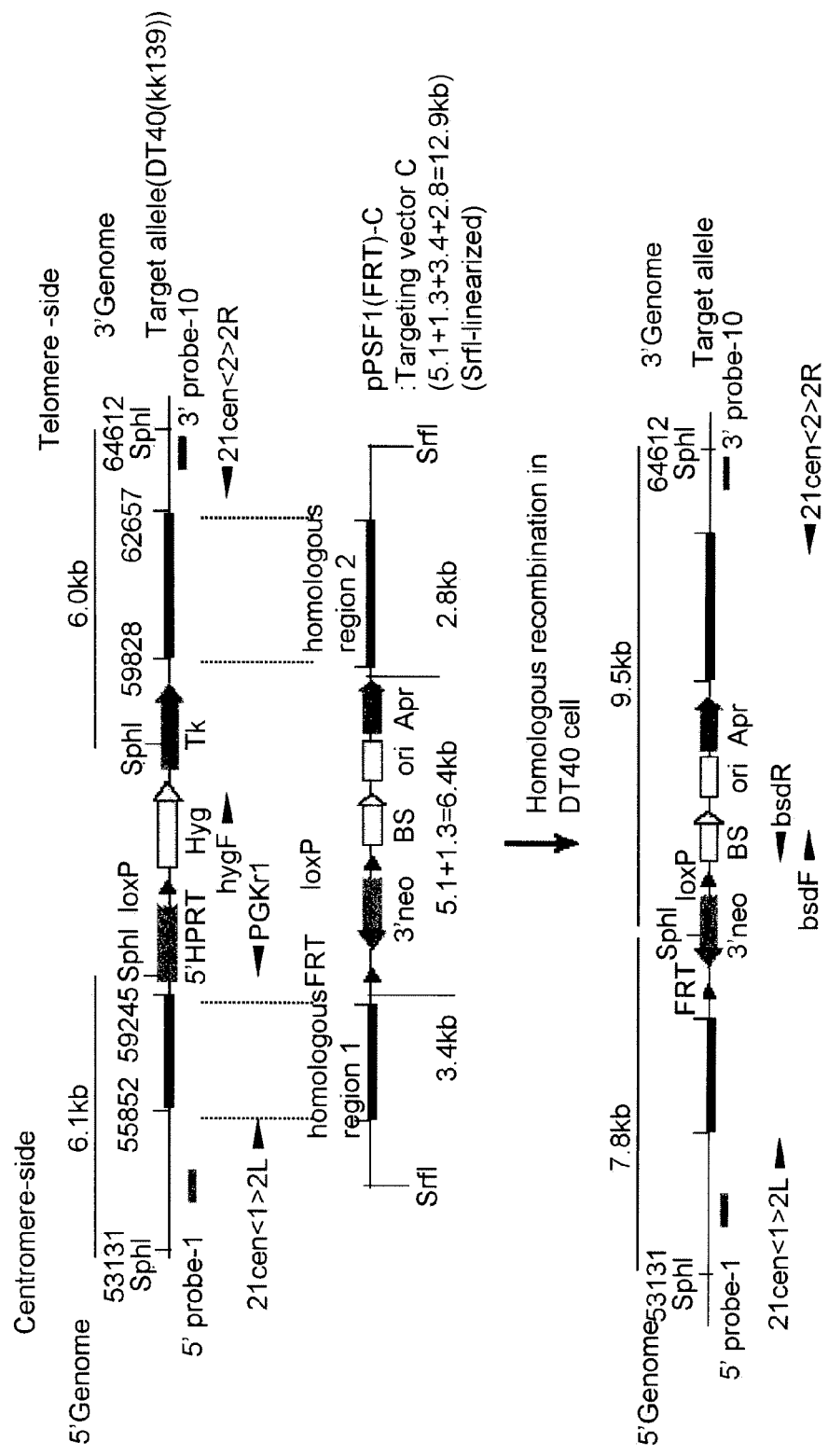
FIG. 81 shows an allele resulting from introduction of the pSF1(FRT)-C vector into 21AΔqHAC. In the figure, "5'HPRT" represents 5'-hypoxanthine-guanine phosphoribosyltransferase, "Hyg" represents a hygromycin gene, and "Tk" represents a thymidine kinase gene. "FRT" represents an FLP recombinase target, "BS" represents a blasticidin-resistant gene, and "Apr" represents an ampicillin resistant gene.

(1)) digested with NheI and ScaI, and pSF1③ obtained in Example 1 (2-1) digested with ScaI and PacI, were subjected to three-fragment ligation. The vector was digested with SalI and SrfI, and homologous region 2 digested with restriction enzymes was cloned therein to obtain pSF1(FRT)-C. The size of the final pSF1(FRT)-C construct is about 12.6 kb. FIG. 80 and FIG. 81 each show the targeting vector, the target sequence, and a chromosome allele resulting from homologous recombination.

(3-2) Introduction of pSF1(FRT)-C Vector into 21AΔqHAC-Carrying DT40 Cell

The pSF1(FRT)-C construct was linearized by digestion with the SrfI restriction enzyme (Roche), and the resultant was introduced into the DT40 hybrid cell carrying 21AΔqHAC from which the long-arm distal region had been deleted. The DT40 (kkq79) cells ($1 \times 10^7$ cells) were suspended in 0.5 ml of RPMI medium, the resulting suspension was allowed to stand at room temperature for 10 minutes in the presence of 30 µg of DNA, and electroporation was then carried out using the Gene Pulser II (Bio-Rad). A voltage of 550 V was applied to a condenser having a capacity of 25 µF and then discharged using an electroporation cell having 4 mm of an interelectrode distance. After the cells were allowed to stand at room temperature for 10 minutes, the electroporated cells were suspended in RPMI 1640 culture medium containing 10% FBS, 1% ChS, and 0.1 mM 2-ME, and the suspension was plated in twenty 96-well plates (Falcon). Twenty four hours later, blasticidin (blasticidin S hydrochloride, Funakoshi) was added to a final concentration of 8 µg/ml, and resistant colonies developed 2 to 3 weeks thereafter. A total of 51 drug-resistant colonies obtained through 4 transfection operations were isolated, the isolated colonies were grown, and the subsequent analysis was performed.

(3-3) PCR Analysis

Genomic DNA of a blasticidin-resistant strain was used as a template, and the presence of two target sequences, the 5'-target sequence and the 3'-target sequence, was detected by PCR. By sandwiching these two target sequences (indicated as "5'-genome" and "3'-genome" in FIG. 81), oligonucleotide primer pairs were designed on the chromosome and on the targeting vector, respectively. Such positions are indicated by arrows in FIG. 81. The sequences are shown below.

```
bsdF:
5'-caacagcatcccatctctg      (SEQ ID NO: 138)

bsdR:
5'-gctcaagatgcccctgttct     (SEQ ID NO: 139)
```

PCR was carried out using primer sets as shown in SEQ ID NOs: 138-116 (5'-genome) or as shown in SEQ ID NOs: 139-114 (3'-genome).

LA Taq polymerase (Takara Shuzo Co., Ltd.) was used, and the reaction was carried out at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 6 minutes, 30 cycles of denaturation at 98° C. for 5 seconds followed by annealing/extension at 68° C. for 7 minutes, and extension at 72° C. for 10 minutes. To the PCR solution, $MgSO_4$ (final concentration: 0.5 mM) was added.

Among 51 strains of the obtained blasticidin-resistant DT40 cells, 23 strains were found to produce amplification products of sizes deduced from the nucleotide sequences (5'-genome: about 6.7 kb; 3'-genome: about 6.1 kb).

(3-4) Southern Blot Analysis

As a screening method for selecting a homologous recombinant, Southern blot analysis was carried out. The 5' probe-1 and the 3' probe-10 used in Example 1 (1-4) were used.

Genomic DNA (about 5 µg) extracted from the 6 strains obtained by primary screening was digested with the SphI restriction enzyme (Roche), and Southern blot analysis was carried out by the method described in Ausubel et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). The length of the restriction enzyme fragment deduced from the nucleotide sequence is 7.8 kb in the form of a homologous recombinant, and it is 6.1 kb in the case of DT40 (kkq79) (a non-recombinant cell), as a result of the 5'-genome analysis. Such length is 9.5 kb in the form of a homologous recombinant, and it is 6.0 kb in the case of DT40 (kkq79) (a non-recombinant cell), as a result of the 3'-genome analysis. Homologous recombinants were identified in all the 6 analyzed strains.

(3-5) Fluorescence In Situ Hybridization (FISH) Analysis

FISH analysis was carried out in accordance with the method described in Matsubara et al. (FISH Experimental Protocol, Shujunsha Co. Ltd., 1994). The 6 clones in which recombination had been observed in (3-4) above were subjected to FISH analysis using human cot-1 DNA and blasticidin (prepared by cleaving from the pCMV/Bsd vector) as probes. As a result, human chromosome 21 was not translocated to host chromosomes of all the clones, and a signal derived from blasticidin was detected in the long-arm proximal region. This demonstrates that site-directed recombination had occurred.

As a result of the experiments (3-1) to (3-5), the 6 strains of the DT40 hybrid cells (DT40(21qAHAC)-2, 13, 16, 29, 39, and 51) carrying the 21AΔqHAC vectors into which the cloning sites (the loxP sequences), the 3'neo and FRT sequences had been inserted by homologous recombination were obtained.

(4) Introduction of 21AΔqHAC Vector into CHO Cells (4-1) Introduction of 21AΔqHAC Vector into CHO Cells by the Microcell Mediated Chromosome Transfer Method The DT40 hybrid cells (DT40(21qAHAC)-2, 39, and 51) carrying the 21AΔqHAC vectors obtained in Example 23 (3) by deleting the long-arm distal regions and inserting the cloning sites (the loxP, 3'neo, and FRT sequences) were used as chromosome donor cells. Chinese hamster-derived CHO-K1 cells (Accession No. JCRB9018) were used as chromosome recipient cells.

At the outset, microcells were prepared from about $10^9$ DT40 hybrid cells. The DT40 hybrid cells that had been cultured to a cell density of about 60 to 70% confluency were cultured in a culture medium (RPMI 1640 containing 10% FBS, 1% ChS, and 0.1 mM 2-mercaptoethanol) containing colcemid (0.05 µg/ml, Invitrogen) for 13 to 18 hours to induce micronucleus formation. The cells were recovered by centrifugation, resuspended in serum-free DMEM, and plated in twelve 25-cm² centrifuge flasks (Nunc), which had been coated with poly-L-lysine in advance. The resultants were allowed to stand at 37° C. for 1 hour, the culture medium was removed after the cells adhered, the cytochalasin B (10 µg/ml in DMEM, Sigma) solution preheated to 37° C. was filled in centrifuge flasks, the flasks were inserted into the centrifuge, and centrifugation was carried out at 34° C. and 8,000 rpm for 1 hour. The microcells were suspended in serum-free medium (DMEM), recovered, purified by filtration using the SWINNEX-25 (Millipore) equipped with a filter (Whatman) having a pore size of 8 µm, 5 µm, or 3 µm, and then suspended in 5 ml of DMEM. The microcell suspension was centrifuged at room temperature and 1,500 rpm for 5 minutes, about $10^7$ CHO-K1 cells, which had been washed twice with DMEM and then suspended in 5 ml of DMEM, were superposed thereon, centrifugation was carried out at room temperature and 1,500 rpm for 5 minutes, and the supernatant was then removed. The cells were subjected to fusion treatment for 120 seconds in a DMEM solution containing 45% polyethylene glycol 1500 (PEG1500, Roche) and 10% DMSO (Sigma), the resultant was suspended in 120 ml of F12 medium (Invitrogen) containing 10% FBS, the suspension was plated in 5 48-well plates (Falcon), and the resultant was cultured in a selection medium (F12 containing 10% FBS) containing blasticidin (8 μg/ml) 24 to 36 hours thereafter. After selection culture had been carried out for about 2 weeks, the developed drug-resistant colonies were isolated, and the subsequent analysis was performed. A total of 16 blasticidin-resistant CHO strains (i.e., 8 DT40 (21qAHAC)-2-derived strains, 3 DT40(21qAHAC)-39-derived strains, and 5 DT40 (21 qAHAC)-51-derived strains) were obtained through 3 micronuclear cell fusion operations.

(4-2) PCR Analysis

Genomic DNA of a blasticidin-resistant strain was used as a template, and the presence of two target sequences, the 5'-target sequence and the 3'-target sequence, was detected by PCR. The method in accordance with Example 1 (3-3) was employed. From among the obtained 16 strains of the blasticidin-resistant CHO cells, 11 strains were found to produce amplification products of sizes as deduced from the nucleotide sequences (5'-genome: about 6.7 kb; 3'-genome: about 6.1 kb).

(4-3) FISH Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of the 10 blasticidin-resistant CHO strains, a total of 3 strains (CHO (21qA-HAC)-5,6,17) were found to be of normal karyotypes, and a copy of Cot1-stained 21AΔqHAC vector were detected in most of the observed mitotic figures.

The experiments (4-1) to (4-3) above demonstrate that the obtained 3 blasticidin-resistant CHO strains carry the 21AΔqHAC vectors.

Example 24

Analysis of Long-Term Stability of 21AΔqHAC Vector in CHO Cells (1) Long-Term Subculture Under Non-Selective Culture Conditions In order to confirm stability of the 21AΔqHAC vector in CHO cells, long-term subculture was carried out under non-selective culture conditions. The 3 strains of the CHO cells described in Example 1 (CHO(21qA-HAC)-5, 6, and 17) were used. A non-selection medium was F12 medium containing 10% FBS, and a selection medium comprised such F12 medium and blasticidin added thereto at 8 μg/ml. The $5.0 \times 10^5$ CHO cells were plated in a 10-cm dish, the cells that had been cultured to a cell density of about 80 to 90% confluency were counted, the $5.0 \times 10^5$ cells were plated again in a 10-cm dish, and subculture was continued up to the tenth passage. The number of cells was counted every passage to determine the population doubling level. The CHO cells were recovered after the tenth passage and FISH chromosome samples were prepared.

(2) FISH Analysis

FISH analysis was carried out in accordance with the method described in Matsubara et al. (FISH Experimental Protocol, Shujunsha Co. Ltd., 1994) using human-specific Cot1 (Invitrogen) probes. The results are shown in Table 9.

TABLE 9

Stability of 21AΔqHAC vector in CHO cells

| | | HAC retention (%) | |
|---|---|---|---|
| HAC | Cell population Number of subculture | Without drug selection | With drug selection |
| CHO(21qA-HAC)-5 | At the initiation of culture | — | 98 |
| | 10 | 96 | 94 |
| CHO(21qA-HAC)-6 | At the initiation of culture | — | 100 |
| | 10 | 90 | 96 |
| CHO(21qA-HAC)-17 | At the initiation of culture | — | 100 |
| | 10 | 94 | 98 |

The 21AδqHAC vector was retained stably in CHO cells after long-term subculture. As a result of observation of images of metaphase chromosomes, 1 or 2 signals were detected per cell.

According to FIG. 13 shown in Example 2, 21δqhac disclosed in WO 2004/031385 exhibits the HAC retention (%) in CHO cells of 86% under the conditions of "with drug selection" at the initiation of culture. The HAC retention is 66.0% under the conditions of "without drug selection" and 86.0% under the conditions of "with drug selection," after culture had been conducted for 7 weeks. Accordingly, the novel HAC vector, 21AδqHAC, derived from chromosome 21 according to the present invention would undergo substantially no dropout after long-term culture, and it was found to be a significantly stable HAC vector compared with conventional HAC vectors.

The Experiments (1) and (2) demonstrated that the 21AδqHAC vector would be retained stably in CHO cells under non-selective culture conditions and that a copy number per cell would be maintained.

Example 25

Figure 77:
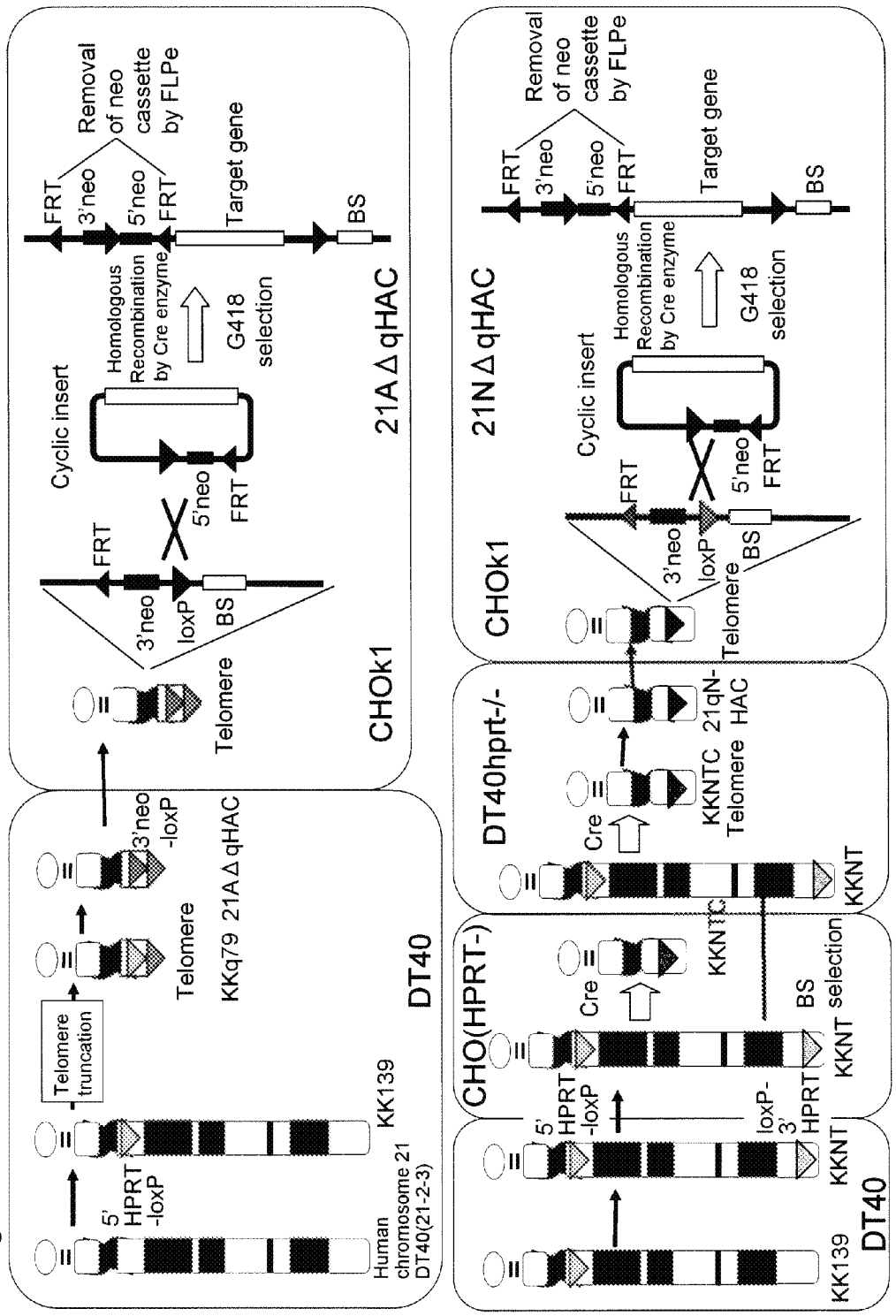
FIG. 77 shows the structure of the 21HAC vector. The upper figure shows a procedure for preparing 21AΔqHAC by telomere truncation, and the lower figure shows a procedure for preparing 21NΔqHAC utilizing deletion with Cre-loxP.

Hepo Gene Expression Analysis in CHO Hybrid Cell Using Hepo-21AδQhac Vector (1) Construction of hepo-21δqhac Vector
(1-1) Introduction of Hepo Gene into 21AδQhac Vector The hepo gene expression unit is inserted into the 21Aδqhac vector constructed in Example 23. The hepo expression plasmid containing the loxP sequence is prepared, and the Cre recombinase is expressed transiently to insert the gene expression unit into an artificial chromosome by site-directed recombination between the loxP sequences. A recombinant comprising an insert was selected using the acquisition of G418 resistance (i.e., reconstruction of the promoter-fragmented neo-resistant gene expression unit) as an indicator. The outline is shown in FIG. 77.

The 21Aδqhac vector-carrying CHO hybrid cells (CHO (21qa-HAC)-5 and 6) prepared in Example 1 were treated with trypsin, and the $5 \times 10^6$ cells were suspended in 0.8 ml of the Hank's balanced salt solution (HBSS). In the presence of 10 μg of the hepo expression plasmid, pln1-EPO, containing the loxP sequence (Kakeda et al., Gene Therapy; 12: 852-856, 2005) and 10 μg of the Cre enzyme expression vector, pbs185

(Life-Tech), electroporation was carried out using the Gene Pulser II (Bio-Rad). A voltage of 450 V was applied to a condenser having a capacity of 500 μF and then discharged using an electroporation cell having 4 mm of an interelectrode distance. The electroporated cells were plated in five 48-well tissue culture plastic petri-dishes (Falcon) containing F12 medium (Invitrogen) comprising 10% FBS. Two days later, the medium was exchanged with a medium containing G418 at 0.8 mg/ml (Geneticin, Invitrogen). G418-resistant colonies developed 2 to 3 weeks thereafter, a total of 48 colonies (20 CHO(21qa-HAC)-5-derived colonies and 28 CHO(21qa-HAC)-6-derived colonies) were isolated, the isolated colonies were grown, and the subsequent analysis was performed.

(1-2) PCR Analysis

A recombinant comprising the hEPO gene expression unit inserted therein was selected by inspecting whether or not the hEPO gene expression unit had been inserted into a site of the loxP sequence of the 21AδqHAC vector by PCR using the svpanp1 and the Neo Rp2 primers, which had been designed on the pln1-EPO vector and the 21Aδqhac vector, so as to sandwich the site of the loxP sequence. Also, it was selected by inspecting amplification of the inserted hepo gene by PCR using the M13RV and the Neo Rp2 primers of the pbs226 plasmid vector. Primer sequences and PCR conditions were determined in accordance with the method of Kakeda et al. (Kakeda et al., Gene Therapy; 12: 852-856, 2005). In the case of a recombinant comprising an insert, amplification of about 1.0 kbp is deduced with the use of the svpanp1 and the Neo Rp2 primers and that of about 2.7 kbp is deduced with the use of the M13RV and the Neo Rp2 primers. As a result, amplification as deduced was observed in a total of 40 strains from among the G418-resistant CHO hybrid cells obtained in (1-1) above. Thus, the above 40 G418-resistant CHO hybrid strains were found to comprise the hEPO gene expression units inserted into the loxP sequences by recombination.

(1-3) Southern Blot Analysis

In order to inspect whether or not the Hepo-21Aδqhac vector properly carries the hepo expression unit, Southern blot analysis was carried out. The method was carried out in accordance with Kakeda et al. (Gene Therapy; 12: 852-856, 2005). The length of the restriction enzyme fragment resulting from digestion with xbai, which is deduced from the nucleotide sequence, is 5.5 kb, including the hepo expression unit (FIG. 14). 6 strains from among the candidate G418-resistant CHO hybrid cells obtained in (1-2) were analyzed. As a result, bands having sizes as deduced were observed in a total of 3 strains (CHO(21qahace-13, 14, and 37).

(2) Expression of Hepo Gene Inserted into 21AδQhac Vector

Expression of Hepo genes was quantified by enzyme-linked immunosorbent assay (ELISA) of hepo proteins generated in the culture supernatant.

6 strains of the hepo-21Aδqhac vector-carrying G418-resistant CHO hybrid cells isolated in Example 103 (1-3) were plated in amounts of about $10^5$ cells in 12-well tissue culture plastic petri-dishes (Falcon) comprising 2 ml of F12 medium containing 10% FBS and G418 at 0.8 mg/ml. After the cultured cells reached confluence, the medium was exchanged with 2 ml of F12 medium containing 10% FBS, culture was conducted for 2 days, the medium was exchanged with 1 ml of F12 medium containing 10% FBS, culture was conducted for an additional 24 hours, the supernatant was recovered, and the number of cells were counted. hEPO in the culture supernatant was quantified using the Hepo ELISA kit (Quantikine IVD Human EPO Immunoassay, R&D System).

Thus, hEPO expression was observed in all 6 strains of the G418-resistant CHO hybrid cells carrying the hEPO-21AΔqHAC vectors.

(3) FISH Analysis

FISH analysis was carried out in accordance with the method described in Matsubara et al. (FISH Experimental Protocol, Shujunsha Co. Ltd., 1994) using human-specific Cot1 (Invitrogen) probes. The 6 strains of the G418-resistant CHO hybrid cells obtained in (1-3) above were analyzed. As a result, a normal karyotype and a copy of Cot1-stained hEPO-21AΔqHAC vector were detected in most of the observed mitotic figures of a total of 5 strains.

The above experiment (1) demonstrated that the obtained 5 G418-resistant strains were CHO cells carrying the hEPO-21AΔqHAC vectors and having the normal karyotypes.

Example 26

Analysis of Long-Term Stability of hEPO-21AΔqHAC Vector in CHO Hybrid Cell (1) Long-Term Subculture Under Non-Selective Culture Conditions In order to confirm stability of the hEPO-21AΔqHAC vector in CHO cells, long-term subculture was carried out under non-selective culture conditions and under selective conditions (the control group). The two strains of the CHO hybrid cells obtained in Example 25 (CHO(21qA-HACE)-13 and 14) were used. A non-selection medium was F12 medium containing 10% FBS, and a selection medium comprised such F12 medium and G418 added thereto at 0.8 mg/ml. The $5.0 \times 10^5$ CHO cells were plated in a 10-cm dish, the cells that had been cultured to a cell density of about 80 to 90% confluency were counted, the $5.0 \times 10^5$ cells were plated again in a 10-cm dish, and subculture was continued up to the tenth passage. The number of cells was counted every passage to determine the population doubling level. The CHO cells were recovered after the tenth passage, and hEPO gene expression analysis and FISH analysis were carried out.

(2) hEPO Gene Expression after Long-Term Subculture

Expression of hEPO genes was quantified by enzyme-linked immunosorbent assay (ELISA) of hEPO proteins generated in the culture supernatant. The two strains of the CHO hybrid cells carrying the hEPO-21AΔqHAC vectors that had been subjected to long-term subculture in (1) above were analyzed in accordance with the method of Example 3 (2). As a result, hEPO expression was observed after long-term subculture in both two strains of the CHO hybrid cells carrying the hEPO-21AΔqHAC vectors.

(3) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate, and the average value of the results thereof was determined. The results regarding the above two strains are shown in Table 10.

TABLE 10

Stability of hEPO-21AΔqHAC vector in CHO cells

| | | HAC retention (%) | |
| --- | --- | --- | --- |
| HAC | Cell population Number of subculture | Without drug selection | With drug selection |
| CHO(21qA-HACE)-13 | At the initiation of culture | — | 95 |
| | 10 | 90 | 92 |

TABLE 10-continued

Stability of hEPO-21AΔqHAC vector in CHO cells

| HAC | Cell population Number of subculture | HAC retention (%) | |
|---|---|---|---|
| | | Without drug selection | With drug selection |
| CHO(21qA-HACE)-14 | At the initiation of culture | — | 95 |
| | 10 | 92 | 96 |

The hEPO-21AΔqHAC vector was retained stably in CHO cells after long-term subculture. As a result of observation of images of metaphase chromosomes, 1 or 2 signals were detected per cell.

The above experiments (1) to (3) demonstrated that the hEPO-21AΔqHAC vector would be retained stably in CHO cells after long-term subculture under non-selective culture conditions, that a copy number per cell would be maintained, and that hEPO gene expression would be maintained.

Example 27

Figure 82:
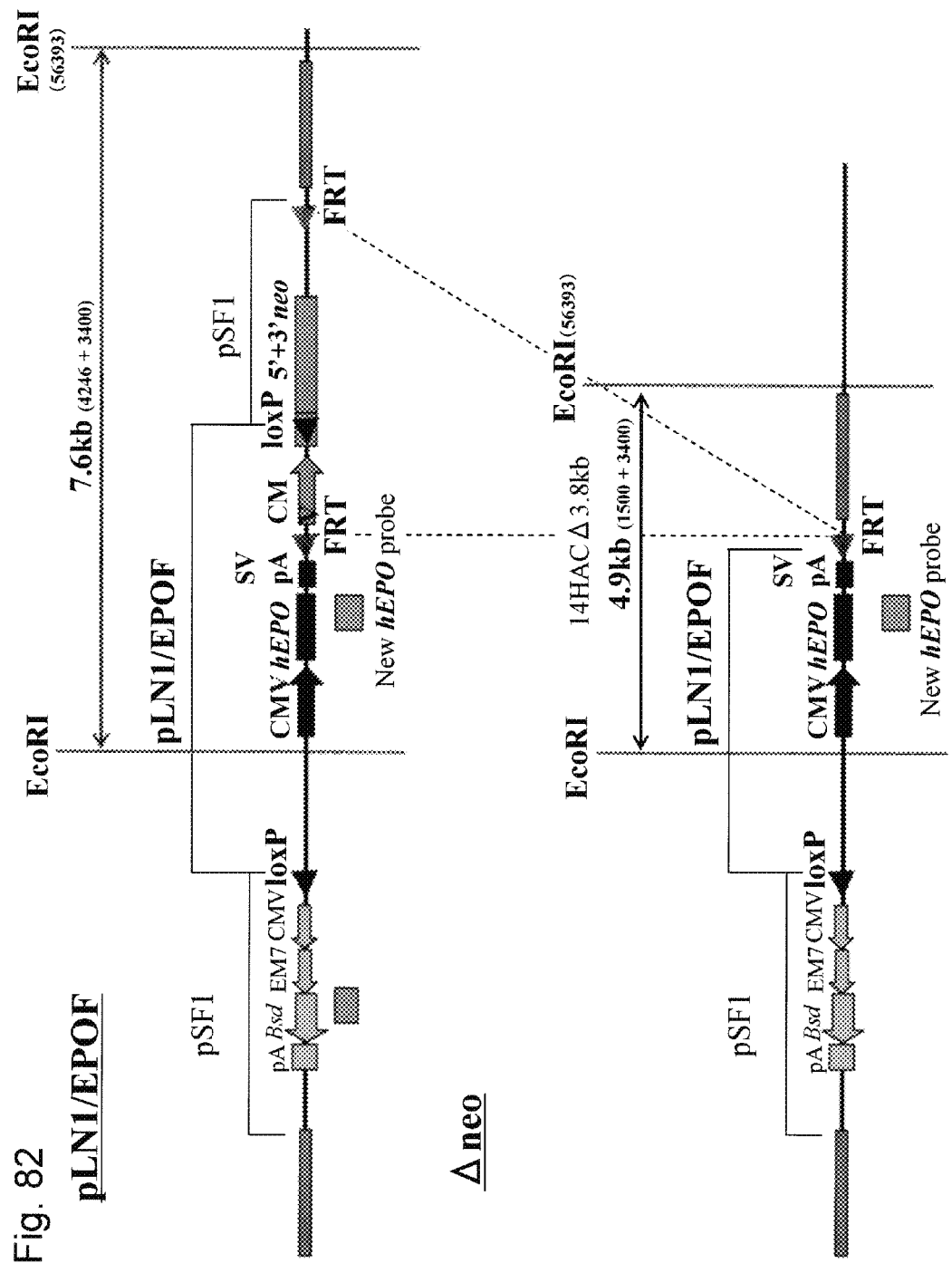
FIG. 82 shows removal of the neo-resistant gene unit using FLP-FRT.

Construction of hEPO-21AΔqΔneo-HAC Vector from which Neo-Resistant Gene Unit has been Removed The 21AΔq-HAC vector and the pLN1/EPOF plasmid (prepared in Example 18 (3)) each comprise the FRT sequence inserted into a site downstream of the hEPO expression unit. The neo-resistant gene expression unit is removed from the hEPO-21AΔq-HAC vector using the FRT/FLPe site-directed recombination system. The outline is shown in FIG. 82.

(1) Removal of Neo-Resistant Gene Unit from hEPO-21AΔq-HAC Vector (1-1) Removal of Neo-Resistant Gene Unit by FLPe The FLPe recombinase prepared in Example 18 (5-1) is expressed transiently in the CHO cells carrying the hEPO-21AΔqF-HAC vectors prepared in Example 25 to cleave and remove the Neo-resistant gene unit from the artificial chromosome by site-directed recombination between the FRT sequences. A recombinant comprising an insert was selected using deletion of the Neo-resistant gene unit as an indicator.

The CHO cells carrying the hEPO-21AΔq-HAC vectors (CHO(21qA-HACE)-13 and CHO(21 qA-HACE)-14) were treated with trypsin, and the 5×10⁶ cells were suspended in 0.8 ml of the Hank's balanced salt solution (HBSS). In the presence of 20 to 100 μg of FLPe enzyme expression vector, pOG44FLPe, electroporation was carried out using the Gene Pulser II (Bio-Rad). A voltage of 450 V was applied to a condenser having a capacity of 500 μF and then discharged using an electroporation cell having 4 mm of an interelectrode distance. The electroporated cells were plated in 8 96-well tissue culture plastic petri-dishes (Falcon) (4 plates of 1 cell/well; 4 plates of 0.1 cell/well) comprising F12 medium (Invitrogen) containing 10% FBS. Blasticidin-resistant colonies developed 2 to 3 weeks thereafter, a total of 120 colonies (60 CHO(21qA-HACE)-13-derived colonies and 60 CHO (21qA-HACE)-14-derived colonies) were isolated, the same clones were plated in two different 24-well plates, the clones in one plate were cultured in blasticidin, and the clones in the other plate were cultured in G418 and blasticidin. The clones, which died in wells containing G418, are considered to lack neo genes. The number of clones, which died because of G418, was 12 clones (i.e., 3 CHO(21qA-HACE)-13-derived clones and 9 CHO(21qA-HACE)-14-derived clones) out of 120 clones. These clones were subjected to the subsequent analysis.

(1-2) PCR Analysis

Primers, SVpANp1 and Neo Rp2, designed on the pLN1-EPOF vector and on the 21AΔqHAC vector were used in order to inspect whether or not the Neo-resistant gene unit has been removed from the hEPO-21AΔq-HAC vector. Also, the inserted hEPO gene was inspected using the primers, M13RV and Neo Rp2, on the pBS226 plasmid vector. The primer sequences and PCR conditions were determined in accordance with the method of Kakeda et al. (Kakeda et al., Gene Therapy; 12: 852-856, 2005). In the case of a recombinant comprising the Neo cassette inserted therein, amplification of about 1.0 kbp is deduced with the use of the SVpANp1 and the Neo Rp2 primers and that of about 2.7 kbp is deduced with the use of the M13RV and the Neo Rp2 primers. If the Neo-resistant gene unit has been removed, an amplification product cannot be detected with the use of the above two types of primers. As a result, the amplification product as deduced was not observed in a total of 10 strains from among the 12 strains of the non-G418-resistant CHO hybrid cells obtained in (1-1) above. This demonstrated that the Neo-resistant gene unit has been removed from each of a total of 10 strains of the Bsd-resistant and non-G418-resistant CHO hybrid cells above.

(1-3) Southern Blot Analysis

Southern blot analysis was carried out in order to inspect whether or not the Neo-resistant gene unit has been removed from the hEPO-21AΔq-HAC vector. The method was carried out in accordance with Kakeda et al. (Gene Therapy; 12: 852-856, 2005). The length of the restriction enzyme fragment resulting from digestion with EcoRI deduced from the nucleotide sequence is 4.9 kb, when the fragment comprises only the hEPO expression unit, while the Neo-resistant gene unit has been removed. Such length is 7.6 kb, when the fragment comprises both the Neo-resistant gene unit and the hEPO expression unit. Bands having sizes as deduced were detected in the 10 strains (i.e., 2 CHO(21qA-HACE)-13-derived strains and 8 CHO(21qA-HACE)-14-derived strains) from among the 12 strains of the candidate CHO hybrid cells obtained in Example 27 (1-1) (i.e., 3 CHO(21qA-HACE)-13-derived strains and 9 CHO(21qA-HACE)-14-derived strains). Thus, removal of the Neo-resistant gene unit was observed in the above 10 strains of CHO hybrid cells. The hEPO-21AΔqF-HAC vector from which the Neo-resistant gene unit has been removed is hereafter referred to as the hEPO-21AΔqΔneo-HAC vector.

(1-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. 10 strains of the candidate CHO hybrid cells obtained in (5-3) above were analyzed. As a result, a normal karyotype and a copy of Cot1-stained hEPO-21AΔqΔneo-HAC vector were detected in most of the observed mitotic figures of a total of 4 strains (CHO(21qA-HACEΔ)-4, 8, 10, and 11).

The experiments (1-1) to (1-4) demonstrated that the above 4 strains of the CHO hybrid cells carry the hEPO-21AΔqΔ-neo-HAC vectors and have normal karyotypes.

Example 28

Construction of 21HAC (21NΔqHAC) Vector Prepared by Deleting Long-Arm Distal Region from Human Chromosome 21 Using Cre-loxP The loxP sequences are inserted into the long-arm distal and proximal regions by homologous recombination, and a region between the two loxP sequences is cleaved and deleted by site-directed recombination using Cre enzyme, in such a manner that the HAC vector would comprise the telomere sequence and a short subtelomere sequence (about 8 kb) at the end of human chromosome 21. Thus, an artificial chromosome (21NΔqHAC) vector with the deleted long-arm distal region is constructed.

(1) Deletion of Long Arm from Human Chromosome 21 by Site-Directed Recombination (1-1) Construction of NT Vector for Inserting the loxP Sequence into Telomeric Long-Arm Distal Region of Human Chromosome 21

V901 (Lexicon genetics) was used as a basic plasmid for inserting the loxP sequence. The MC1-TK sequence was cleaved from V830 (Lexicon genetics) using RsrII (NEB) and then cloned into the recognition site for the BamHI restriction enzyme of the V901 plasmid (clone name: V901T-2). The nucleotide sequence of the distal region of human chromosome 21 where LoxP is to be inserted was obtained from the GenBank database (NT_011515). Sequences of oligonucleotide primers used for amplifying the two target sequences of homologous recombination are shown below.

```
#21NT1L:
                                      (SEQ ID NO: 140)
5'-gaatgtcccccattgtcacttcatgttc

#21NT1R:_
                                      (SEQ ID NO: 141)
5'-ggcaagcttagtccagttgggaaactgatgggttcat

#21NT3L:
                                      (SEQ ID NO: 142)
5'-ggcgaattcggattgagagacacacatagctggtca

#21NT3R:
                                      (SEQ ID NO: 143)
5'-ggcgaattctgtcaacctgccagttctcaggagttt
```

Figure 83:
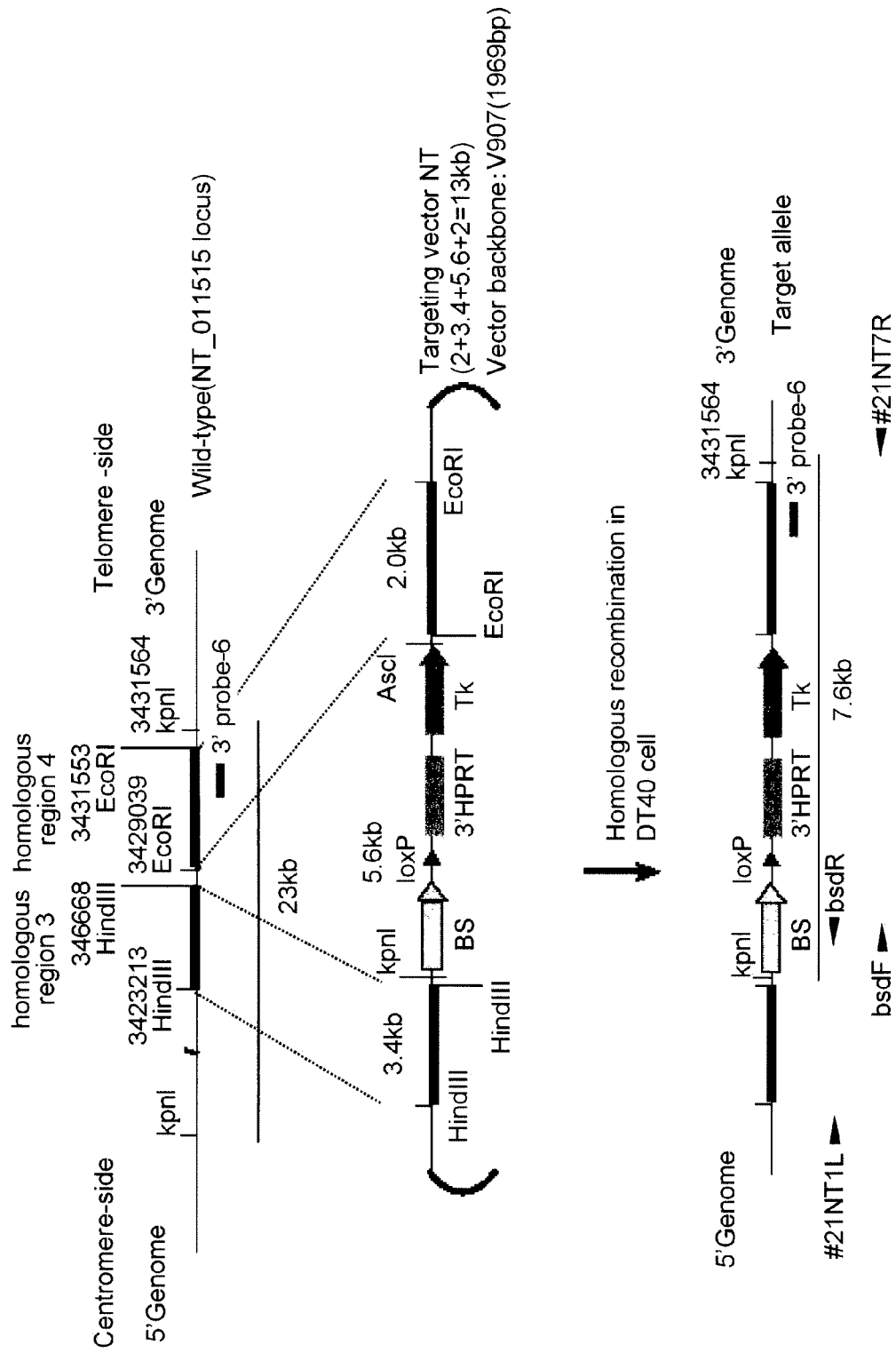
FIG. 83 schematically shows a method for inserting the loxP sequence into NT_011515 of the long arm of human chromosome 21.

Genomic DNA extracted from the A9<21-2> cell carrying human chromosome 21 was used as a template to amplify the target sequences by PCR. The reaction was carried out with the use of the above primers and LA Taq polymerase (Takara Shuzo Co., Ltd.) at 95° C. for 2 minutes, followed by 30 cycles of denaturation at 95° C. for 15 seconds and annealing at 68° C. for 4 minutes. The resultants were digested with the restriction enzyme, EcoRI (Nippon Gene) or HindIII (Nippon Gene), separated and purified on agarose gel, and then cloned into the EcoRI or HindIII site of the V901T-2 plasmid. Further, 3'HPRT-loxP-BS cleaved with the use of AscI and KpnI was cloned into the AscI and the KpnI sites of the V901T-2 plasmid. 3'HPRT-loxP-BS was prepared by cloning the oligo-synthesized loxP sequence and CMV-BS sequence (Invitrogen) into the XbaI site of V820 (Lexicon genetics). The size of the final construct comprising loxP inserted therein is 13 kb. FIG. 83 shows the targeting vector, the target sequence, and a chromosome allele resulting from homologous recombination.

(1-2) Introduction of NT Vector for Inserting loxP Sequence into Telomeric Long-Arm Distal Region of DT40 Cell Carrying Human Chromosome 21 Comprising loxP Inserted in Long-Arm Proximal Region In accordance with the method of Example 1 (1-2), the NT construct was converted into linearized DNA by digestion with the NotI restriction enzyme and then introduced into the DT40 hybrid cell DT40(kk139) carrying human chromosome 21 comprising loxP inserted in long-arm proximal region prepared in Example 23 (1). Selection culture was carried out using blasticidin (final concentration: 8 ug/ml), and drug-resistant colonies developed 2 to 3 weeks thereafter. A total of 12 blasticidin-resistant colonies obtained through 2 transfection operations were isolated, the isolated colonies were grown, and the subsequent analysis was then performed.

(1-3) PCR Analysis

Genomic DNA of a blasticidin-resistant strain was used as a template to detect the presence of the 5'-target sequence and the 3'-target sequence by PCR in accordance with the method of Example 6 (1-1). By sandwiching these two target sequences (indicated as "5'-genome" and "3'-genome" in FIG. 83), oligonucleotide primer pairs were designed on the chromosome and on the targeting vector, respectively. Such positions are indicated by arrows in FIG. 83. The sequences are shown below.

```
#21NT1L:
5'-CATTCATGGTAGTCATTGGTGCTGTTCTCC   (SEQ ID NO: 144)

#21NT7R:
5'-ACTTCCTGACTAGGGGAGGAGTAGAAGGTG   (SEQ ID NO: 145)
```

PCR was carried out using a primer pair of SEQ ID NOs: 138 and 145 (3'-genome sequences) or a primer pair of SEQ ID NOs: 139 and 144 (5'-genome sequences).

The presence of the 5'-target sequence and the 3'-target sequence was detected in 5 strains among the above 12 blasticidin-resistant strains.

(1-4) Southern Blot Analysis

As a screening method for selecting a homologous recombinant, Southern blot analysis was carried out. Probes were designated inside the 3'-target sequence of homologous recombination (FIG. 83). In order to prepare probes, PCR was carried out using oligonucleotide primer pairs shown below and genomic DNA of the A9<21-2> cell carrying human chromosome 21 as a template, and the resultants were isolated and purified (designated as 3'-probe-6).

```
21qN3-2L:
5'-ctggaagacactgagataaccatgacc    (SEQ ID NO: 146)

21qN3-2R:
5'-ctgagaagttccacaatagcctgtctc    (SEQ ID NO: 147)
```

Genomic DNA (about 5 μg) extracted from the 5 strains obtained by primary screening was digested with the KpnI restriction enzyme (Roche), and Southern blot analysis was carried out by the method described in Ausubel et al. (Current Protocols in Molecular Biology, John Wiley & Sons, Inc., 1994). The signal to which the labeled probe had hybridized was detected by the Typhoon9210 image analyzer (Molecular Dynamics). The length of the restriction enzyme fragment deduced from the nucleotide sequence is 7.6 kb in the form of a homologous recombinant, and it is 23 kb in the form of a wild-type (i.e., a non-recombinant). A total of 2 strains of homologous recombinants (DT40(kkNT)-7 and 11) were identified from among the candidate 5 strains. These two clones were subjected to the subsequent step (3).

(2) Introduction of Human Chromosome 21 Comprising loxP Introduced into Long-Arm Proximal and Distal Regions into CHO Cell (2-1) Introduction of Modified Human Chromosome 21 into CHO Cell by the Microcell Mediated Chromosome Transfer Method The DT40 hybrid cells (DT40(kkNT)-7,11) carrying human chromosome 21 comprising loxP introduced into the long-arm proximal and distal regions prepared in Example 28 (1) were used as chromosome donor cells. Chinese hamster-derived CHO hprt-deficient cells were used as chromosome recipient cells (obtained from the Health Science Research Resources Bank; Accession No. JCRB0218).

At the outset, microcells were prepared from about $10^9$ DT40 hybrid cells. DT40 hybrid cells that had been cultured to a cell density of about 60 to 70% confluency were cultured in a culture medium (RPMI 1640 comprising 10% FBS, 1% ChS, and 0.1 mM 2-mercaptoethanol) containing colcemid (0.05 µg/ml, Invitrogen) for 13 to 18 hours to induce micronucleus formation. The cells were recovered by centrifugation, resuspended in serum-free DMEM, and plated in twelve 25-cm² centrifuge flasks (Nunc), which had been coated with poly-L-lysine in advance. The resultant was allowed to stand at 37° C. for 1 hour, the culture medium was removed after the cells adhered, the cytochalasin B (10 µg/ml in DMEM, Sigma) solution preheated to 37° C. was filled in centrifuge flasks, the flasks were inserted into the centrifuge, and centrifugation was carried out at 34° C. and 8,000 rpm for 1 hour. The microcells were suspended in serum-free medium (DMEM), recovered, purified by filtration using the SWIN-NEX-25 (Millipore) equipped with a filter (Whatman) having a pore size of 8 µm, 5 µm, or 3 µm, and then suspended in 5 ml of DMEM. The microcell suspension was centrifuged at room temperature and 1,500 rpm for 5 minutes, about $10^7$ CHOhprt–/– cells, which had been washed twice with DMEM and then suspended in 5 ml of DMEM, were superposed thereon, and centrifugation was carried out at room temperature and 1,500 rpm for 5 minutes, and the supernatant was then removed. The cells were subjected to fusion treatment using a DMEM solution containing 45% polyethylene glycol 1500 (PEG1500, Roche) and 10% DMSO (Sigma) for 120 seconds, the resultant was suspended in 120 ml of F12 medium (Invitrogen) containing 10% FBS, the resulting suspension was plated in 5 48-well plates (Falcon), and the resultant was then cultured in a selection medium (F12 containing 10% FBS) containing blasticidin (8 µg/ml) 24 to 36 hours thereafter. After selection culture had been carried out for about 2 weeks, the developed drug-resistant colonies were isolated, and the subsequent analysis was performed. A total of 10 blasticidin-resistant CHOhprt–/– strains (i.e., 5 DT40 (kkNT)-7-derived strains and 5 DT40(kkNT)-11-derived strains) were obtained through 2 micronuclear cell fusion operations.

(2-2) PCR Analysis

Genomic DNA of a blasticidin-resistant strain was used as a template to identify the presence of the genomic region of the gene existing on human chromosome 21 by PCR described in Example 23 (1-3) and Example 28 (1-3). Amplification products were identified in all the 10 analyzed clones.

(2-3) Fluorescence In Situ Hybridization (FISH) Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of the 6 clones obtained in (2-2) above, all clones were found to be of normal karyotypes, and a copy of Cot1-stained signal was detected in most of the observed mitotic figures.

(3) Deletion of Long-Arm Distal Region by Cre-loxP Site-Directed Recombination (3-1) Introduction of Cre Expression Vector into CHO Hybrid Cell Carrying Human Chromosome 21 Comprising loxP Sequence Inserted into Long-Arm Distal and Proximal Region In accordance with the method of Example 1 (1-2), the Cre expression vectors, pCAGGS-Cre, were introduced into CHO(kkNT)-1, CHO(kkNT)-5, and CHO(kkNT)-6 cells obtained in Example 28 (2). Selection culture was carried out using HAT (SIGMA, final concentration: 1×), and drug-resistant colonies developed 2 to 3 weeks thereafter.

A total of 12 HAT-resistant colonies obtained through 3 transfection operations were isolated, the isolated colonies were grown, and the subsequent analysis was then carried out.

(3-2) PCR Analysis

Genomic DNA of a HAT-resistant strain was used as a template to identify deletion between the two loxP sequences by PCR. By sandwiching the loxP sequence remaining after deletion of the long-arm distal region, oligonucleotide primer pairs were designed on the chromosome and on the targeting vector. Such positions are indicated by arrows in FIG. 84. The sequences are shown below.

```
Trans L1:
5'-TGGAGGCCATAAACAAGAAGAC      (SEQ ID NO: 148)

Trans R1:
5'-CCCCTTGACCCAGAAATTCCA       (SEQ ID NO: 149)
```

The reactions were carried out using EX Taq polymerase (Takara Shuzo Co., Ltd.) at 94° C. for 1 minute, followed by 35 cycles of denaturation at 94° C. for 15 seconds, annealing at 60° C. for 30 seconds, and extension at 72° C. for 1 minute. When the long-arm distal region is removed by deletion of a region between the two loxP sequences, amplification of about 350 B is deduced. When a primer pair of SEQ ID NOs: 148 and 145, SEQ ID NOs: 114 and 149, or SEQ ID NOs: 114 and 145 is employed, amplification of 5.7 KB, 6.3 KB, or 12 KB is deduced. The reaction was carried out under the conditions shown below using LA Taq polymerase (Takara Shuzo Co., Ltd.). Analysis of SEQ ID NOs: 148 and 145 or SEQ ID NOs: 114 and 149 was carried out at 94° C. for 1 minute, followed by 3 cycles of denaturation at 98° C. for 5 seconds followed by annealing/extension at 72° C. for 10 minutes, 2 cycles of denaturation at 98° C. for 5 seconds followed by annealing/extension at 70° C. for 10 minutes, 25 cycles of denaturation at 98° C. for 5 seconds followed by annealing/extension at 68° C. for 6 minutes, and extension at 72° C. for 10 minutes. Analysis of SEQ ID NOs: 114 and 145 was carried out at 94° C. for 1 minute, followed by 3 cycles of denaturation at 98° C. for 5 seconds followed by annealing/extension at 72° C. for 6 minutes, 2 cycles of denaturation at 98° C. for 5 seconds followed by annealing/extension at 70° C. for 10 minutes, 30 cycles of denaturation at 98° C. for 5 seconds followed by annealing/extension at 68° C. for 6 minutes, and extension at 72° C. for 10 minutes. To the PCR solution, $MgSO_4$ (final concentration: 0.5 mM) was added.

As a result, amplification products as deduced were observed with the use of the primer pairs above in 6 strains among the above 12 HAT-resistant strains.

(3-3) Southern Blot Analysis

Figure 84:
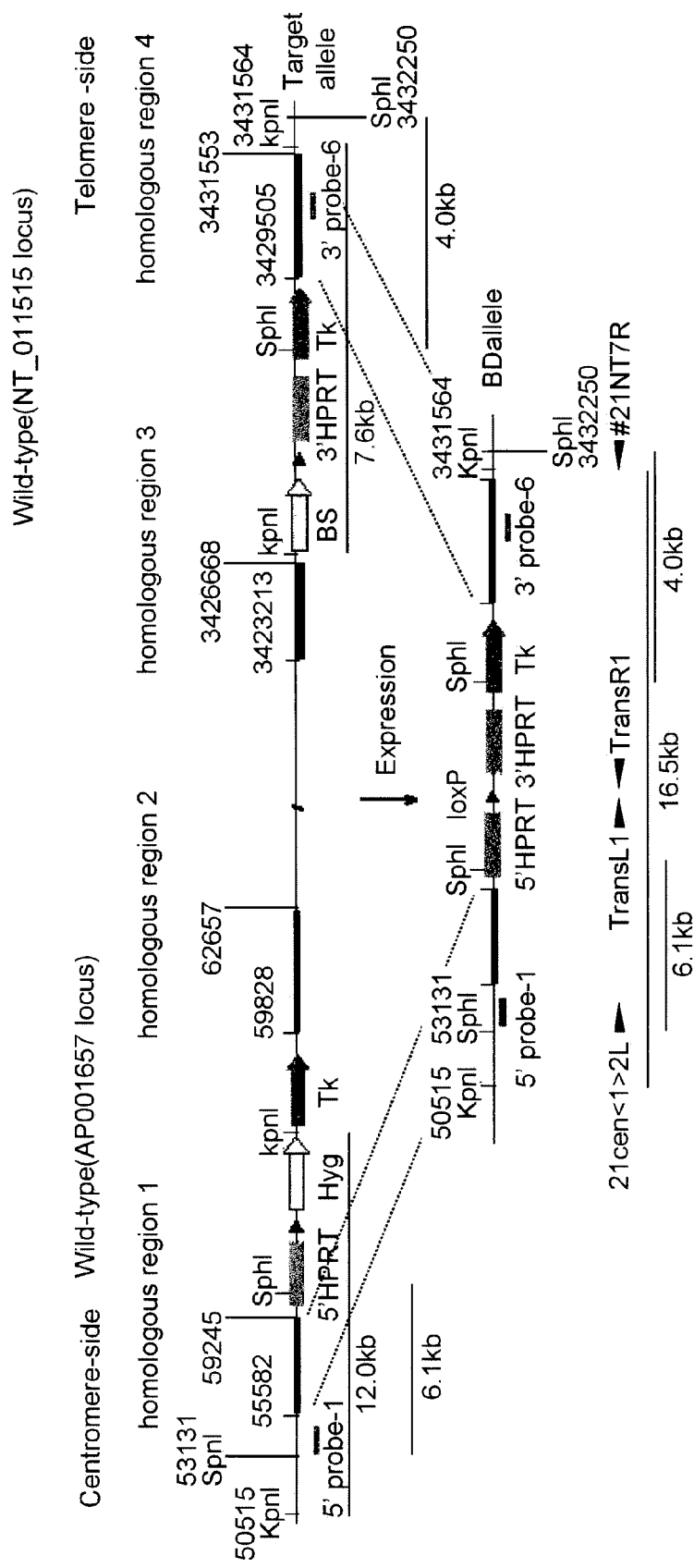
FIG. 84 shows an allele of human chromosome 21 from which the long arm resulting from introduction of the Cre vector has been deleted.

Southern blot analysis was carried out in order to identify the structure of a chromosome with the deleted long-arm distal region and select the chromosome with the deleted long-arm distal region. The positions of the target sequence, the chromosome allele, and the probe resulting from deletion of the long-arm distal region are shown in FIG. 84. 5'-PROBE-1 described in Example 1 (1-4) was used as the 5'-probe of homologous recombination, and 3'-PROBE-6 described in Example 28 (1-4) was used as the 3'-probe.

Genomic DNA (about 5 MG) obtained from the candidate 6 clones obtained by primary screening (PCR) was digested with the KPNI restriction enzyme (Roche), and Southern blot analysis was carried out in accordance with the method described in AUSUBEL et al. (Current Protocols in Molecular Biology, John Wiley & Sons, Inc., 1994). The signal to which the $^{32}$P-labeled probe had hybridized was detected by the Typhoon9210 image analyzer (Molecular Dynamics). The length of the restriction enzyme fragment deduced from the nucleotide sequence is 16.5 kb in the form of a homologous recombinant, and it is 12 kb in the form of a clone before recombination, for 5'-target sequence. Such length is 16.5 kb in the form of a homologous recombinant, and it is 7.6 kb in the form of a clone before recombination, for 3'-target sequence. As a result, chromosomes with the deleted long-arm distal regions were identified in all 6 strains.

(3-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of the 6 clones obtained in (3-3), the 4 clones were found to be of normal karyotypes, and human chromosome 21 fragments with the deleted long-arm distal regions were stained with Cot1 and a copy of signal was detected in most of the observed mitotic figures.

The experiments (3-1) to (3-4) demonstrated that the obtained HAT-resistant CHO hybrid cells carry the human chromosome 21 fragment (21NΔqHAC) with the deleted long-arm distal region, while maintaining the telomere and subtelomere sequences.

Example 29

Analysis of Long-Term Stability of 21NΔqHAC Vector in CHO Hybrid Cell (1) Long-Term Subculture Under Non-Selective Culture Conditions In order to confirm stability of the 21NΔqHAC vector in CHO hybrid cells, long-term subculture was carried out under non-selective culture conditions. The two strains of the CHO cells carrying the 21NΔqHAC vectors described in Example 28 (CHO(21qN-HAC)17 and 18) were used. A non-selection medium was F12 medium containing 10% FBS, and a selection medium comprised such F12 medium and 1×HAT added thereto. The 5.0×10$^5$ CHO cells were plated in a 10-cm dish, the cells that had been cultured to a cell density of about 80 to 90% confluency were counted, the 5.0×10$^5$ cells were plated again in a 10-cm dish, and subculture was continued up to the tenth passage. The number of cells was counted every passage to determine the population doubling level. The CHO cells were recovered after the tenth passage and FISH chromosome samples were prepared.

(2) FISH Analysis

FISH analysis was carried out in accordance with the method described in Matsubara et al. (FISH Experimental Protocol, Shujunsha Co. Ltd., 1994) using human-specific Cot1 (Invitrogen) probes. The population doubling level and the HAC retention were measured in duplicate, and the average of the results was determined. The results regarding the above 2 strains are shown in Table 11.

TABLE 11

Stability of 21NΔqHAC vector in CHO cells

| | | HAC retention (%) | |
|---|---|---|---|
| HAC | Cell population Number of subculture | Without drug selection | With drug selection |
| CHO(21qN-HAC)17 | At the initiation of culture | — | 100 |
| | 10 | 94 | 100 |

TABLE 11-continued

Stability of 21NΔqHAC vector in CHO cells

| | | HAC retention (%) | |
|---|---|---|---|
| HAC | Cell population Number of subculture | Without drug selection | With drug selection |
| CHO(21qN-HAC)18 | At the initiation of culture | — | 100 |
| | 10 | 98 | 100 |

The 21NΔqHAC vector was retained stably in CHO cells by the end of the tenth passage. As a result of observation of images of metaphase chromosomes, 1 or 2 signals were detected per cell.

The Experiments (1) and (2) demonstrated that the 21NΔqHAC vector would be retained stably in CHO cells under non-selective culture conditions and that a copy number per cell would be maintained.

Example 30

Analysis of hEPO Gene Expression in CHO Hybrid Cell Using hEPO-21NΔqHAC Vector (1) Introduction of Cloning Site into Long-Arm Proximal Region of 21NΔqHAC (1-1) Construction of pSF1(FRT)-D Vector for Inserting loxP, 3'neo, and FRT Sequences t1pSF1(FRT) prepared in Example 18 (1) was used as a basic plasmid for inserting the loxP, 3'neo, and FRT sequences into the human artificial chromosome (21NΔqHAC). The nucleotide sequence of the long-arm proximal region of human chromosome 21 where the loxP, 3'neo, and FRT sequences would be inserted was obtained from the GenBank database (Accession No. NT_011515). Sequences of oligonucleotide primers used for amplifying two target sequences for homologous recombination are shown below.

```
NT011515-3429039F_SalI:
                              (SEQ ID NO: 150)
5'-gacagtGTCGACcggattgagagacacacatagctg NT011515-3431553R_SrfI:
                              (SEQ ID NO: 151)
5'-gatGCCCGGGCCTGTCAACCTGCCAGTTCTCAGGAG
```

Figure 85:
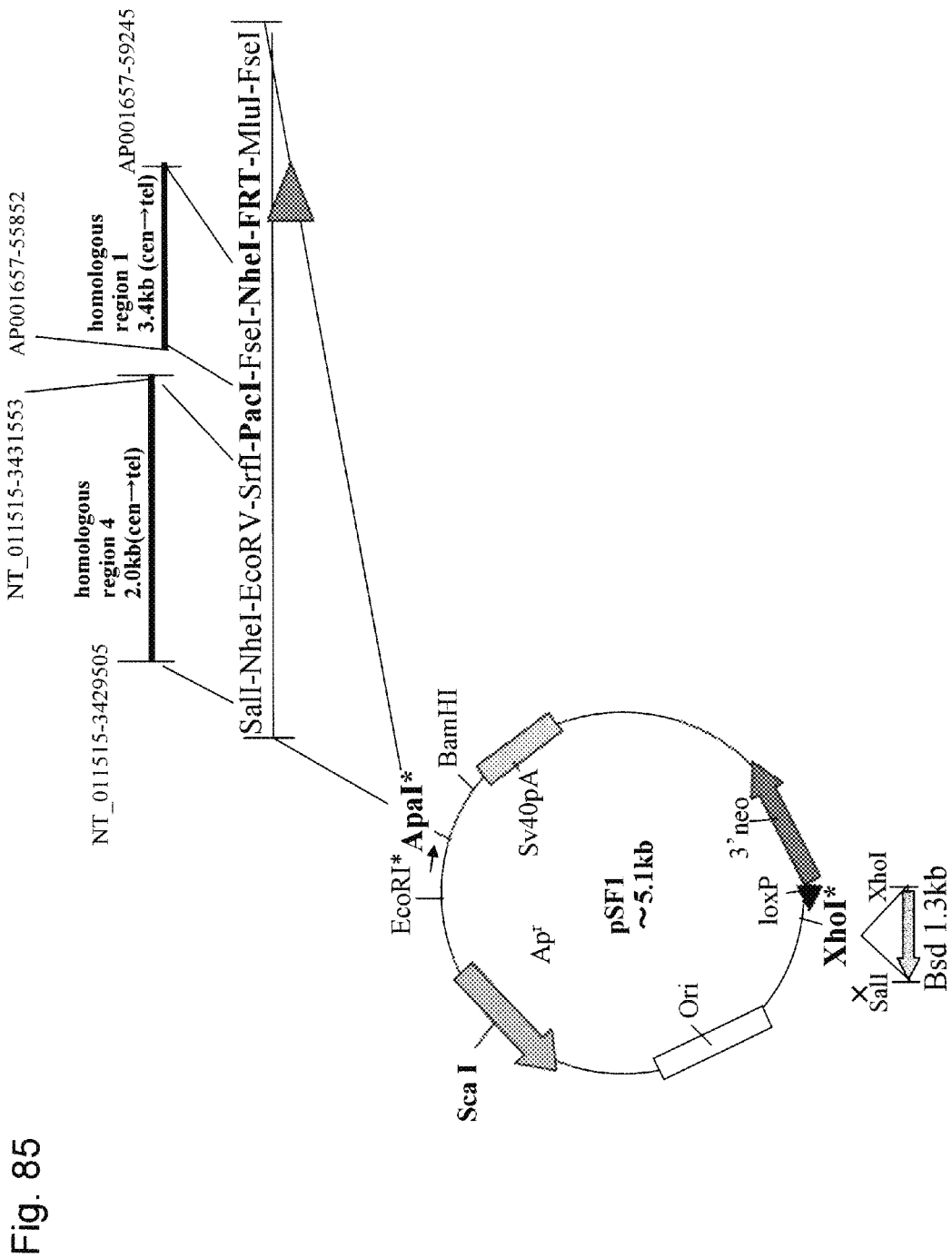
FIG. 85 shows the pSF1(FRT)-D vector for insertion of loxP, 3'neo, and FRT sequences.
Figure 86:
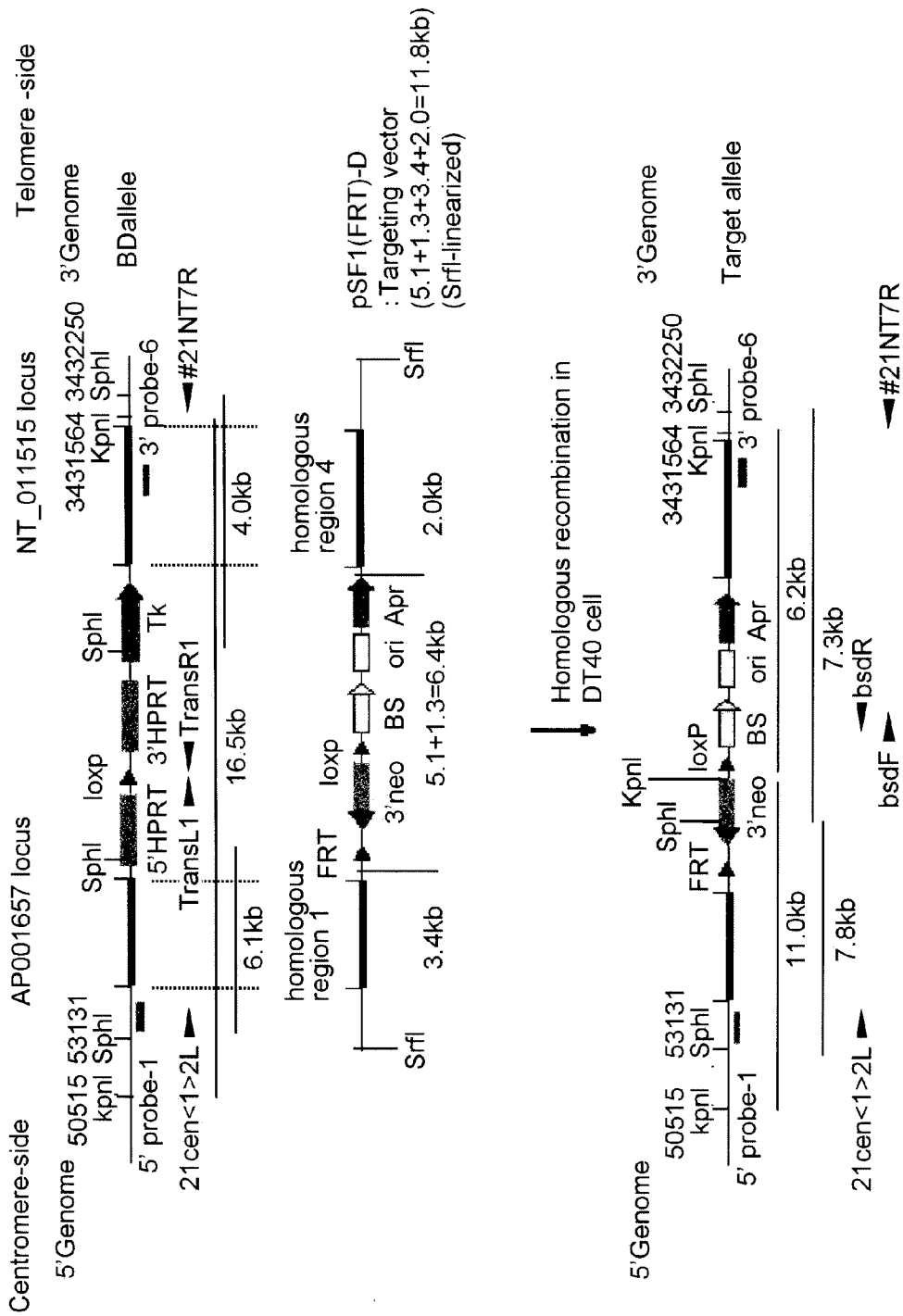
FIG. 86 shows an allele resulting from introduction of the pSF1(FRT)-D vector into 21NΔqHAC.

Genomic DNA extracted from the A9<21-2> cell carrying human chromosome 21 was used as a template to amplify the two target sequences by PCR. A DNA fragment of about 3.4 kb (i.e., homologous region 1) amplified with the use of SEQ ID NOs: 134 and 135 was digested with PacI and NheI (Roche), a DNA fragment of about 2.0 kb (i.e., homologous region 4) amplified with the use of SEQ ID NOs: 150 and 151 was digested with restriction enzymes, SalI and SrfI (Roche), and DNA fragments having cohesive ends were separated by agarose gel electrophoresis, followed by purification. Subsequently, the following 3 DNA fragments, i.e., the DNA fragment of homologous region 1 digested with restriction enzymes, the t1pSF1(FRT) plasmid (prepared in Example 18 (1)) digested with NheI and ScaI, and pSF1③ obtained in Example 1 (2-1) digested with ScaI and PacI, were subjected to three-fragment ligation. The vector was digested with SalI and SrfI, and homologous region 4 digested with restriction enzymes was cloned therein to obtain pSF1(FRT)-D. The size of the final pSF1(FRT)-D construct is about 11.8 kb. FIG. 85 and FIG. 86 each show the targeting vector, the target sequence, and a chromosome allele resulting from homologous recombination.

(1-2) Introduction of Human Chromosome 21 Comprising loxP Introduced into Long-Arm Proximal and Distal Regions into hprt-Deficient DT40 Cell The hprt-deficient DT40 hybrid cells carrying human chromosome 21 comprising loxP introduced into the long-arm proximal and distal regions were prepared by the microcell mediated chromosome transfer method using the CHO (kkNT)6 cells carrying human chromosome 21 prepared in Example 28 (2) as chromosome donor cells. DT4032 strains (Fukagawa et al. Nucleic Acids Research, 1996) were used as chromosome recipient hprt-deficient DT40 cells. The outline of the preparation method is described below.

At the outset, microcells were prepared from about $1 \times 10^8$ CHO(kkNT)6 cells. The CHO(kkNT)6 cells that had been cultured to a cell density of about 80% confluency in 12 25-cm$^2$ centrifuge flasks (Nunc) were cultured in a culture medium (F12 containing 20% fetal bovine serum (FBS) and 0.8 mg/ml G418) containing colcemid (0.1 µg/ml, demecolcine, Wako Pure Chemical Industries Ltd.) for 72 hours to induce micronucleus formation. In Examples, DMEM manufactured by Nissui Pharmaceutical Co., Ltd. was used. After the medium was removed, the cytochalasin B (10 µg/ml in DMEM, Sigma) solution preheated to 34° C. was filled in centrifuge flasks, and centrifugation was carried out at 34° C. and 8,000 rpm for 1 hour. The microcells were suspended in serum-free medium (DMEM), recovered, and purified by filtration using the SWINNEX-25 (Millipore) equipped with a filter (Whatman) having a pore size of 8 µm, 5 µm, or 3 µm. The purified microcells were resuspended in 6 ml of DMEM. DT4032 cells were cultured in RPMI 1640 culture medium containing 10% FBS, 1% CS, and 0.1 mM 2-ME, the cells were washed twice with DMEM, and $1 \times 10^7$ cells were resuspended in 5 ml of DMEM. The microcell suspension was centrifuged at room temperature and 1,500 rpm for 5 minutes, the DT4032 cell suspension was superposed thereon, centrifugation was then carried out at room temperature and 1,500 rpm for 5 minutes, and the supernatant was then removed. The cells were subjected to fusion treatment using a polyethylene glycol (PEG) 1:1.4 solution (Tomizuka et al., Nature Genet., U.S.A., vol. 16, pp. 133-143, 1997) for 90 seconds. The fused cells were suspended in 60 ml of RPMI 1640 culture medium (Invitrogen) containing 10% FBS, 1% chicken serum (ChS), and 0.1 mM 2-mercaptoethanol (ME), the resulting suspension was plated in 6 96-well plates, culture was conducted for 24 hours, and selection culture was carried out in a medium containing 1 mg/ml G418 for about 2 weeks. Drug-resistant colonies that had developed as a result of two microcell fusion experiments were isolated. Genomic DNA of the G418-resistant strain was used as a template to inspect the presence of the genomic region of the gene existing on human chromosome 21 by PCR described in Example 28 (2-2), and fluorescence in situ hybridization (FISH) analysis using a human-specific probe, Cot1, (Gibco BRL) was further carried out to examine and obtain a copy of human chromosome 21-carrying clones DT4032(KKNT)8 and 9.

(1-3) Deletion of Long-Arm Distal Region by Cre-loxP Site-Directed Recombination (1-3-1) Introduction of Cre Expression Vector into Human Chromosome 21-Carrying DT4032 Hybrid Cell Comprising loxP Sequences Inserted into Long-Arm Distal and Proximal Regions In accordance with the method of Example 1 (1-2), the Cre expression vectors, pCAGGS-Cre, were introduced into the DT4032(kkNT)-8 and the DT4032(kkNT)-9 cells obtained in Example 30 (1-2). Selection culture was carried out using HAT (SIGMA, final concentration: 1×), and drug-resistant colonies developed 2 to 3 weeks thereafter.

A total of 43 HAT-resistant colonies obtained through 4 transfection operations were isolated, grown, and then subjected to the subsequent analysis.

(1-3-2) PCR Analysis

Genomic DNA of the HAT-resistant strain was used as a template to identify deletion between two loxP sequences by PCR in the same manner as in Example 30 (3-2).

As a result, amplification products as deduced were observed with the use of the primer pairs above in 40 strains among the 43 above HAT-resistant strains.

(1-3-3) Southern Blot Analysis

Genomic DNA was extracted from the 25 clones from among the candidate clones obtained by primary screening (PCR), and Southern blot analysis was carried out in the same manner as in Example 30 (3-3). As a result, chromosomes with the deleted long-arm distal regions were identified in 5 clones from among the 25 clones.

(1-3-4) FISH Analysis

FISH analysis was carried out in accordance with the method described in Matsubara et al. (FISH Experimental Protocol, Shujunsha Co. Ltd., 1994) using human-specific Cot1 (Invitrogen) probes. As a result of analysis of the 5 clones obtained in (1-3-3) above, a 4 clones were found to be of normal karyotypes, and a Cot1-stained human chromosome 21 fragment with the deleted long-arm distal region and a copy of signal were detected in most of the observed mitotic figures.

The experiments (1-3-1) to (1-3-4) demonstrated that the obtained HAT-resistant DT4032 hybrid cell carries a human chromosome 21 fragment (21NΔqHAC) with the deleted long-arm distal region, while maintaining the telomere and the subtelomere sequences.

(1-4) Introduction of pSF1(FRT)-D Vector into 21NΔqHAC-Carrying DT4032 Cell

The pSF1(FRT)-D construct was linearized by digestion with the SrfI restriction enzyme (Roche), and the resultant was introduced into 3 types of DT4032 hybrid cells (DT4032 (kkNTC)15, 17, and 22) carrying 21NΔqHAC with the deleted long-arm distal region. The method in accordance with Example 1 (2-2) was employed. Blasticidin-resistant colonies developed 2 to 3 weeks thereafter. A total of 125 drug-resistant colonies obtained through 2 transfection operations were isolated with the use of DT4032(kkNTC)15, a total of 110 drug-resistant colonies obtained through 2 transfection operations were isolated with the use of DT4032 (kkNTC)17, a total of 124 drug-resistant colonies obtained through 2 transfection operations were isolated with the use of DT4032(kkNTC)22, and the isolated colonies were subjected to the subsequent analysis.

(1-5) PCR Analysis

Genomic DNA of the blasticidin-resistant strain may be used as a template to detect the presence of the 5'-target sequence and the 3'-target sequence by PCR using a primer set of SEQ ID NOs: 114 and 139 and a primer set of SEQ ID NOs: 145 and 138. Such positions are indicated by arrows in FIG. 86. LA Taq polymerase (Takara Shuzo Co., Ltd.) was used, and MgSO$_4$ (final concentration: 0.5 mM) was added to the PCR solution. The reaction may be conducted at 94° C. for 1 minute, followed by 3 cycles of denaturation at 98° C. for 5 seconds followed by annealing/extension at 72° C. for 8 minutes, 2 cycles of denaturation at 98° C. for 5 seconds followed by annealing/extension at 70° C. for 8 minutes, 30 cycles of denaturation at 98° C. for 5 seconds followed by annealing/extension at 68° C. for 8 minutes, and extension at 72° C. for 10 minutes.

(1-6) Southern Blot Analysis

Southern blot analysis can be carried out in order to identify the structure of a chromosome with the deleted long-arm distal region and select a chromosome with the deleted long-arm distal region. FIG. 86 shows positions of the target sequences, chromosome alleles, and probes resulting from deletion of the long-arm distal region. The 5'probe-1 described in Example 23 (1-4) is used as the 5' probe for homologous recombination and the 3'probe-6 described in Example 28 (1-4) is used as the 3' probe.

Genomic DNA (about 5 μg) extracted from the strains obtained by primary screening (PCR) can be digested with the KpnI restriction enzyme (Roche), and Southern blot analysis can be carried out in accordance with the method described in Ausubel et al. (Current Protocols in Molecular Biology, John Wiley & Sons, Inc., 1994). The signal to which the $^{32}$P-labeled probe had hybridized can be detected by the Typhoon9210 image analyzer (Molecular Dynamics). The length of the restriction enzyme fragment deduced from the nucleotide sequence is 11 kb in the form of a homologous recombinant and it is 16.5 kb in the form of a clone before recombination, for 5'-target sequence. Such length is 6.2 kb in the form of a homologous recombinant and it is 16.5 kb in the form of a clone before recombination, for 3'-target sequence.

The experiments (1-1) to (1-6) enable preparation of a DT4032 hybrid cell carrying the 21NΔqHAC vector comprising the cloning sites (loxP, 3'neo, and FRT sequences) inserted therein by homologous recombination.

(2) Introduction of 21NΔqHAC Vector into CHO Cell (2-1) Introduction of 21NΔqHAC Vector into CHO Cells by the Microcell Mediated Chromosome Transfer Method DT4032 hybrid cells carrying the 21NΔqHAC vectors obtained in Example 30 (2) with the deleted long-arm distal region and with the cloning site (the loxP, 3'neo, or FRT sequence) inserted therein are used as chromosome donor cells. Chinese hamster-derived CHO-K1 strains (Accession No. JCRB9018) are used as chromosome recipient cells. The method in accordance with Example 1 (3-1) can be employed.

(2-2) PCR Analysis

Genomic DNA of a blasticidin-resistant strain can be used as a template to detect the presence of the 5'-target sequence and the 3'-target sequence by PCR in accordance with the method of Example 30 (1-5). Amplification products having sizes deduced from the nucleotide sequences (5'-genome: about 7.5 kb; 3'-genome: about 5.3 kb) can be produced.

(2-3) Southern Blot Analysis

In order to identify the structure of the introduced 21NΔqHAC vector, Southern blot analysis can be carried out in the same manner as in Example 30 (1-6). The length of the restriction enzyme fragment deduced from the nucleotide sequence is 11 kb in the form of a homologous recombinant and it is 16.5 kb in the form of a clone before recombination, for 5'-target sequence. Such length is 6.2 kb in the form of a homologous recombinant and it is 16.5 kb in the form of a clone before recombination, for 3'-target sequence.

(2-4) FISH Analysis

FISH analysis can be carried out in accordance with the method described in Matsubara et al. (FISH Experimental Protocol, Shujunsha Co. Ltd., 1994) using human-specific Cot1 (Invitrogen) probes.

The experiments (2-1) to (2-4) can demonstrate that the obtained blasticidin-resistant CHO strain carries the 21NΔqHAC vector.

(3) Construction of hEPO-21NΔqHAC Vector (3-1) Introduction of hEPO Gene into 21NΔqHAC Vector The hEPO gene expression unit is inserted into the 21NΔqHAC vector constructed in Example 30 (2). The hEPO expression plasmid containing the loxP sequence is prepared, and the Cre recombinase is expressed transiently to insert the gene expression unit into an artificial chromosome by site-directed recombination between the loxP sequences. A recombinant comprising an insert is selected using the acquisition of G418 resistance (i.e., reconstruction of the promoter-fragmented neo-resistant gene expression unit) as an indicator. With the use of the CHO hybrid cell carrying the 21NΔqHAC vector prepared in Example 30 (2), the hEPO gene expression unit was inserted in the same manner as in Example 3 (1-1). G418-resistant colonies can be isolated and they can then be grown 2 to 3 weeks thereafter.

(3-2) PCR Analysis

A recombinant comprising the hEPO gene expression unit inserted therein can be selected by inspecting whether or not the hEPO gene expression unit had been inserted into a site of the loxP sequence of the 21NΔqHAC vector by PCR using the SVpANp1 and the Neo Rp2 primers, which had been designed on the pLN1-EPO vector and the 14AΔqHAC vector, so as to sandwich the site of the loxP sequence. Alternatively, it was selected by inspecting amplification of the inserted hepo gene by PCR using the M13RV and the Neo Rp2 primers of the pBS226 plasmid vector.

Primer sequences and PCR conditions are determined in accordance with the method of Kakeda et al. (Kakeda et al., Gene Therapy; 12: 852-856, 2005). In the case of a recombinant comprising an insert, amplification of about 1.0 kbp is deduced with the use of the SVpANp1 and the Neo Rp2 primers and that of about 2.7 kbp is deduced with the use of the M13RV and the Neo Rp2 primers. Thus, the G418-resistant CHO hybrid cell can be identified as a recombinant comprising the hEPO gene expression unit inserted in the loxP sequence.

(3-3) Southern Blot Analysis

Southern blot analysis can be carried out in order to inspect whether or not the hEPO-21NΔqHAC vector properly carries the hEPO expression unit in accordance with the method of Kakeda et al. (Gene Therapy; 12: 852-856, 2005). The length of the restriction enzyme fragment resulting from digestion with XbaI deduced from the nucleotide sequence is 5.5 kb, including the hEPO expression unit.

(3-4) FISH Analysis

FISH analysis can be carried out in accordance with the method described in Matsubara et al. (FISH Experimental Protocol, Shujunsha Co. Ltd., 1994) using human-specific Cot1 (Invitrogen) probes. The experiments (3-1) to (3-4) can demonstrate that the G418-resistant CHO hybrid cell ** carries the hEPO-21NΔqHAC vector and has a normal karyotype.

(4) Expression of hEPO Genes Inserted into 21NΔqHAC Vector

Expression of hEPO genes can be quantified by enzyme-linked immunosorbent assay (ELISA) of hEPO proteins generated in the culture supernatant.

The G418-resistant CHO hybrid cells carrying the hEPO-21NΔqHAC vector (about $10^5$ cells) isolated in (3) above may be plated in 12-well tissue culture plastic petri-dishes (Falcon) comprising 2 ml of F12 medium containing 10% FBS and G418 added at 0.8 mg/ml. After the cultured cells reach confluence, the medium may be exchanged with 2 ml of F12 medium containing 10% FBS, culture may be conducted for 2 days, the medium may be exchanged with 1 ml of F12 medium containing 10% FBS, culture may be conducted for an additional 24 hours, the supernatant may be recovered, and the number of cells may then be counted. hEPO expression can be detected in the G418-resistant CHO hybrid cells carrying the hEPO-21NΔqHAC vectors that are capable of quantifying hEPO in the culture supernatant with the use of the hEPO ELISA kit (Quantikine IVD Human EPO Immunoassay, R&D Systems).

INDUSTRIAL APPLICABILITY

The present invention provides a human artificial chromosome (HAC) vector and a method for preparing thereof Such HAC vector is retained stably in a cell and it is capable of expressing the inserted foreign DNA at a high level. Accordingly, such HAC vector is useful for a wide variety of applications, such as gene expression analysis, gene therapy, gene introduction, and protein production.

All publications, patents, and patent applications cited herein are incorporated herein by reference in their entirety.

Sequence Listing Free Text

SEQ ID NO: 1 to 109: Synthesized oligonucleotides
SEQ ID NO: 110 to 117: Primers
SEQ ID NO: 118 to 121: Probes
SEQ ID NO: 122 to 177: Primers
SEQ ID NO: 178 to 179: Linkers

The invention claimed is:

1. A human artificial chromosome (HAC) vector comprising a human chromosome 14 fragment with deletion of a long-arm distal region at AL391156, wherein the human chromosome 14 fragment comprises a human chromosome 14-derived centromere, a telomere sequence, and a subtelomere sequence,
   wherein the telomere sequence and the subtelomere sequence represent a region from a site within the 14q32 region to the 14q-tel region of human chromosome 14 and are added to the long-arm distal region that is deleted, and wherein the subtelomere sequence is approximately 5 to 60 Kb.

2. The HAC vector according to claim 1, wherein the human chromosome 14 fragment has a size of approximately 19 Mb or smaller.

3. The HAC vector according to claim 1, wherein said HAC vector further comprises a foreign DNA encoding a protein.

4. The HAC vector according to claim 3, wherein the foreign DNA is inserted into a more proximal region than the position where the long-arm distal region is deleted from the human chromosome 14 fragment.

5. The HAC vector according to claim 3, wherein the foreign DNA is inserted into a region 1 to 500 kb away from the telomere sequence.

6. The HAC vector according to claim 1, wherein the human chromosome 14 fragment further comprises the short-arm of human chromosome 14.

7. The HAC vector according to claim 1, wherein the human chromosome 14 fragment lacks the short-arm distal region due to deletion and comprises a short-arm proximal region of human chromosome 14.

8. The HAC vector according to claim 1, wherein the human chromosome 14 fragment lacks the long-arm and short-arm distal regions due to deletion and comprises long-arm and short-arm proximal regions of human chromosome 14.

9. The HAC vector according to claim 1, wherein the short-arm distal region of the human chromosome 14 fragment is deleted within the p11 region or between the p11 region and the p12 region of the short arm of human chromosome 14.

10. The HAC vector according to claim 1, wherein the human chromosome 14 fragment further comprises: (iv) at least one recognition site for a site-directed recombinant enzyme.

11. The HAC vector according to claim 10, wherein the human chromosome 14 fragment comprises at least two types of recognition sites for site-directed recombinant enzymes.

12. The HAC vector according to claim 10, wherein the recognition site for the site-directed recombinant enzyme is inserted into the long-arm proximal region and/or the short-arm proximal region of the human chromosome 14 fragment.

13. The HAC vector according to claim 10, wherein the site-directed recombinant enzyme is the enzyme Cre, and the recognition site for the site-directed recombinant enzyme is the loxP sequence.

14. The HAC vector according to claim 10, wherein the site-directed recombinant enzyme is the FLPe enzyme, and the recognition site for the site-directed recombinant enzyme is the FRT sequence.

15. A method for preparing a human artificial chromosome (HAC) vector containing foreign DNA, comprising the following steps:
(a) obtaining a cell that carries a human chromosome 14 or a human chromosome 14 fragment;
(b) deleting the long-arm distal region of the human chromosome 14 or the human chromosome 14 fragment;
(c) adding a telomere sequence or a telomere sequence in combination with a subtelomere sequence at a site(s) where the long-arm region is deleted;
(d) inserting at least one recognition site for a site-directed recombinant enzyme into the human chromosome 14 or the human chromosome 14 fragment; and
(e) inserting foreign DNA into the human chromosome 14 or the human chromosome 14 fragment in the presence of a site-directed recombinant enzyme,
wherein the deletion in step (b) is deletion of a long-arm distal region at AL391156, wherein the telomere sequence and the subtelomere sequence represent a region from a site within the 14q32 region to the 14q-tel region of human chromosome 14 and are added to the long-arm distal region that is deleted, and wherein the subtelomere sequence is approximately 5 to 60 Kb.

16. A method for preparing a human artificial chromosome (HAC) vector containing foreign DNA, comprising the following steps:
(a) obtaining a cell that carries a human chromosome 14 or a human chromosome 14 fragment;
(b) deleting the long-arm distal region of the human chromosome 14 or the human chromosome 14 fragment;
(c) adding a telomere sequence or a telomere sequence in combination with a subtelomere sequence at a site(s) where the long-arm region is deleted;
(d) inserting at least two types of recognition sites for site-directed recombinant enzymes into the human chromosome 14 or the human chromosome 14 fragment;
(e) inserting foreign DNA comprising a drug-resistance gene expression unit or fragment thereof into the human chromosome 14 or the human chromosome 14 fragment in the presence of a site-directed recombinant enzyme; and
(f) removing said drug-resistance gene expression unit or fragment thereof from the human chromosome 14 or the human chromosome 14 fragment in the presence of a site-directed recombinant enzyme different from the recombinant enzyme used in step (e),
wherein the deletion in step (b) is deletion of a long-arm distal region at AL391156, wherein the telomere sequence and the subtelomere sequence represent a region from a site within the 14q32 region to the 14q-tel region of human chromosome 14 and are added to the long-arm distal region that is deleted, and wherein the subtelomere sequence is approximately 5 to 60 Kb.

17. The method according to claim 16, wherein the drug-resistant gene is a neomycin-resistant gene.

18. A HAC vector containing a foreign DNA, which is obtained by the method according to claim 15.

* * * * *